(12) United States Patent
Lazar et al.

(10) Patent No.: US 10,095,829 B2
(45) Date of Patent: Oct. 9, 2018

(54) COMPUTER IMPLEMENTED METHODS OF TREATING LUNG CANCER

(75) Inventors: Vladimir Lazar, Villejuif (FR); Jean-Charles Soria, Igny (FR); Michel Ducreux, Vanves (FR); Thomas Tursz, Paris (FR)

(73) Assignee: WORLDWIDE INNOVATIVE NETWORK, Villejuif (FR)

( * ) Notice: Subject to any disclaimer, the term of this patent is extended or adjusted under 35 U.S.C. 154(b) by 0 days.

(21) Appl. No.: 13/382,585

(22) PCT Filed: Jul. 6, 2010

(86) PCT No.: PCT/EP2010/059648
§ 371 (c)(1),
(2), (4) Date: Feb. 8, 2012

(87) PCT Pub. No.: WO2011/003911
PCT Pub. Date: Jan. 13, 2011

(65) Prior Publication Data
US 2012/0136583 A1 May 31, 2012

Related U.S. Application Data

(60) Provisional application No. 61/223,798, filed on Jul. 8, 2009.

(51) Int. Cl.
*G06F 19/18* (2011.01)
*G06F 19/00* (2018.01)
*G06F 19/20* (2011.01)

(52) U.S. Cl.
CPC ............ *G06F 19/18* (2013.01); *G06F 19/326* (2013.01); *G06F 19/3456* (2013.01); *G06F 19/20* (2013.01); *Y02A 90/26* (2018.01)

(58) Field of Classification Search
None
See application file for complete search history.

(56) References Cited

U.S. PATENT DOCUMENTS

| | | |
|---|---|---|
| 2005/0260572 A1 | 11/2005 | Kato et al. |
| 2006/0275747 A1 | 12/2006 | Hardy et al. |
| 2008/0118576 A1 | 5/2008 | Theodorecu et al. |
| 2008/0221932 A1 | 9/2008 | Kane et al. |
| 2009/0171697 A1 | 7/2009 | Glauser et al. |

FOREIGN PATENT DOCUMENTS

| | | |
|---|---|---|
| JP | 2009/131287 | 6/2009 |
| WO | WO 03/076660 | 9/2003 |

OTHER PUBLICATIONS

Subramanian, "Gene set enrichment analysis: A knowledge-based approach for interpreting genome-wide expression profiles," PNAS, vol. 102, pp. 15545-15550, 2005.*
Ebert, "Identification of RPS14 as a 5q2 syndrome gene by RNA interference screen," Nature, vol. 451, pp. 335-340, 2008.*
Bull, "Identification of potential diagnostic markers of prostate cancer and prostatic intraepithelial neoplasia using cDNA microarray," British Journal of Cancer, vol. 84, pp. 1512-1519, 2001.*
Simon, "Pitfalls in the Use of DNA Microarray Data for Diagnostic and Prognostic Classification," Journal of the National Cancer Institute, vol. 95, pp. 14-18, 2003.*
Nirmala, "Genomic Data Mining and Its Impact on Drug Discovery," Annual Reports in Medicinal Chemistry, vol. 41, pp. 319-330, 2006.*
Braxton, "The integration of microarray information in the drug development process," Current Opinion in Biotechnology, vol. 9, pp. 643-649, 1998.*
Huang, "Bioinformatics enrichment tools: paths toward the comprehensive functional analysis of large gene lists," Nucleic Acids Research, vol. 37, pp. 1-13, 2008.*
Kutalik, "A modular approach for integrative analysis of large-scale gene-expression and drug-response data," Nature Biotechnology, vol. 26, pp. 531-538, 2008.*
Armstrong, "MLL translocations specify a distinct gene expression profile that distinguishes a unique leukemia," Nature Genetics, vol. 30, pp. 41-47, 2002.*
Beer, "Gene-expression profiles predict survival of patients with lung adenocarcinoma," Nature Medicine, vol. 8, pp. 816-824, 2002.*
Sasaki, "Expression of CD44 splicing isoforms in lung cancers: Dominant expression of CD44v8-10 in non-small cell lung carcinomas," Int'l J Oncology, vol. 12, p. 525-533, 1998.*
Kihara, C. et al. "Prediction of Sensitivity of Esophageal Tumors to Adjuvant Chemotherapy by cDNA Microarray Analysis of Gene-Expression Profiles" *Cancer Research*, Sep. 1, 2001, pp. 6474-6479, vol. 61.
Written Opinion in International Application No. PCT/EP2010/059648, dated Oct. 12, 2010, pp. 1-7.
U.S. Appl. No. 60/388,046, filed Jun. 12, 2002, pp. 1-101.
Dunckley, T. et al., "Gene expression correlates of neurofibrillary tangles in Alzheimer's disease," *Neurobiology of Aging*, 2006, pp. 1359-1371, vol. 27.
Mendeloshn, J. "The Era of Precision Cancer Medicine: A worldwide effort and challenge Introduction to WIN Consortium" *WIN Worldwide innovative networking in personalized cancer medicine*, Jun. 29, 2015, pp. 1-27.
Rodon, J. et al. "Challenges in initiating and conducting personalized cancer therapy trials: perspectives from WINTHER, a Worldwide Innovative Network (WIN) Consortium trial" *Annals of Oncology*, 2015, pp. 1-8.
WINTHER Report Summary, "Final Report Summary—WINTHER (WINTHERapeutics: development of a systems biology method to predict efficacy of cancer drugs to optimize individualized therapeutic decision and improve clinical outcome for cancer patients.)" pp. 1-9, last updated Dec. 18, 2015, Project ID: 306125, retrieved on Jul. 27, 2017 from http://cordis.europa.eu/result/rcn/174135_en.html.
WINTHER: A Study to Select Rational Therapeutics Based on the Analysis of Matched Tumor and Normal Biopsies in Subjects With Advanced Malignancies, *ClinicalTrials.gov Protocol Registration and Results System (PRS) Receipt*, Aug. 25, 2016, pp. 1-4, ClinicalTrials.gov ID: NCT01856296.
Soria, J.-C. et al. "WINTHER: An international study to select rational therapeutics based on the analysis of matched tumor and normal biopsies in subjects with advanced malignancies", Jun. 3, 2017, 2017 ASCO Annual Meeting, p. 1, Abstract Only, Abstract No. TPS11625.
Lazar, V. et al. "Initial perspectives from WINTHER, an international precision medicine trial using both DNA and RNA data to guide treatment" ClinicalTrials.gov Identifier: NCT01856296, p. 1, Abstract Only, 2017.

\* cited by examiner

*Primary Examiner* — G Steven Vanni
(74) *Attorney, Agent, or Firm* — Saliwanchik, Lloyd & Eisenschenk

(57) ABSTRACT

The present invention concerns a method for predicting the relative efficacy of a plurality of drugs for treating a tumor in an individual comprising the molecular characterization of the tumor, and the calculation of a score for the plurality of drugs essentially based on the percentage of deregulated target genes.

32 Claims, 5 Drawing Sheets

Mediastinal lymph node (C1) = 32 mm

Adrenal node (C2) = 26 mm

Mediastinal lymph node (C1) = 32 mm

Adrenal node (C2) = 58  Disease Progression
New sublclavious metastasis

Mediastinal lymph node (C1) = 32 mm

Adrenal node (C2) = 62 mm

Mediastinal lymph node (C1) = 32 mm

Adrenal node (C2) = 62 mm

COMPUTER IMPLEMENTED METHODS OF TREATING LUNG CANCER

CROSS-REFERENCE TO RELATED APPLICATIONS

This application is the U.S. national stage application of International Patent Application No. PCT/EP2010/059648, filed Jul. 6, 2010, which claims the benefit of U.S. Provisional Patent Application No. 61/223,798, filed Jul. 8, 2009.

FIELD OF INVENTION

The present invention relates to the field of medicine, in particular personalized medicine in cancer therapy.

BACKGROUND OF THE INVENTION

The therapeutic care of the patients having cancer is primarily based on surgery, radiotherapy and chemotherapy which have to be used according to standard protocols. The curative surgery consists in removal of all the tumoral mass. However, this is not always possible to guarantee the absence of any residual disease after the ablation of the observable part of the tumour, even by experienced surgeons. This is why the surgery is generally used in combination is with radiotherapy and/or chemotherapy. Chemotherapy and/or radiotherapy can be used as neoadjuvant therapy or auxiliary or adjuvant therapy, or alone when the surgery is impossible. Neoadjuvant therapy is usually used when the tumoral mass is too important and requires a reduction before surgery. Auxiliary or adjuvant chemotherapy is used to treat the residual tumoral diseases and to limit the local recurrences or the metastatic relapses. When a tumour is detected at an inoperable stage, then the therapeutic care is only based on chemotherapy and/or radiotherapy. Surgery is marginally used in this context and has palliative objectives.

In any case, the choice of chemotherapy always raises the following questions: Which drug or combination of drugs is adapted to this type of cancer? What is the most adapted therapeutic strategy for this patient? What are the chances for observing a therapeutic benefit with the selected drugs?

The current medical practice consists in treating the patients according to the existing therapeutic protocols. In the majority of the cases, the choice of the therapeutic protocol is based on the anatomo-pathological and clinical data. These protocols apply in first, second, even third therapeutic line. When there is therapeutic failure, or for the metastatic stages, certain patient are included in clinical trials generally using broad selection criteria defining primarily, the location of the primitive tumour, the extension of the disease, the situation of the vital functions of the patient and certain specific contraindications of the drug under trial. Whatever the therapeutic approach (standard or clinical trial), only part of the treated population profits from the treatment whereas the remainder of the patients do not respond and show a progressing disease even under treatment.

To improve this situation, since many years, physicians and researchers are trying to identify markers for predicting the efficacy of the treatments for a given patient and to be able to adapt the treatment of each patient. Thus the concept of personalized medicine consists in adapting the therapeutic decision according to the anatomo-pathological, clinical characteristics but especially of the biological characteristics of the tumour.

Several examples are known without representing a solution useful for any patient having a cancer.

A first approach was the so-called "test-companion" assay, used for the first time for the trastuzumab (Herceptin®), a monoclonal antibody targeting the Her2/Neu receptor. In breast cancers, this drug is administered only when an amplification/overexpression of this receptor is observed. However, this overexpression does not guarantee a therapeutic response. Some resistances to Herceptin® can be explained by an activation of the Akt pathway, for instance. The association of an mTOR inhibitor (targeting the Akt pathway) can restore the sensitivity to Herceptin. Nevertheless, for some patients, the therapeutic benefit was observed in the absence of an amplification of the receptor.

The measurement of the expression level of the Her2 receptor is the first example of test companion and the majority of pharmaceutical companies or researchers are trying to reproduce this model considered as the first example of personalized medicine. The following examples are relevant to illustrate the concept of selection of the patients who could profit from a given drug:
  Mutation or amplification of EGFR receptor and erlotinib/gefitinib;
  Mutations c-Kit/PDGFRa and imatinib;
  Translocation of Bcr-Abl and imatinib;
  Amplification of HER2 and HER2 inhibitors;
  Amplification of TOP2A and anthracyclines;
  Deletion of PTEN and mTOR inhibitors;
  Amplification of FGFR1 and FGFR1 inhibitors;
  ERCC1 negative-treatment and platinum salts;
  RAS mutations and treatment of colon cancer
  etc.

In the case of breast cancer, prognostic molecular signatures, such as the tests Mamaprint® (developed by the Agendia company) or OncotypeDX® (company Genomic Health) are available. These signatures are used to determine if an auxiliary chemotherapy is necessary or not. But, although these tests make it possible to conclude on the need from an auxiliary chemotherapy, they do not make it possible to select the optimal therapy.

In short, the concept of personalized medicine corresponds to a selection of patients on biological criteria to increase the chances of response to a given therapy. Currently, these tests companion are rather used for the treatments by targeted therapies and make it possible to select the patients likely to profit from a given therapy but not to select the best therapy for a given patient. This is a major conceptual difference which constitutes the main interest of the present invention compared to the other markers proposed to date.

The anomalies of strong amplitude of the gene copy number (amplifications or deletions) modify the levels of gene expression. This mechanism of genomic deregulation is involved in the ontogenesis of many cancers. Amplifications of the EGFR gene are found in approximately 30% of lung cancers. The inhibition of EGFR in case of amplification is associated with a significant benefit in this same pathology. Similarly, MYCN is amplified in approximately 25% of the neuroblastoma and several studies showed the prognostic value of this anomaly in this pathology. Other oncogenes/anti-oncogenes (tumour suppressor genes) are frequently amplified/deleted in other types of tumours such HER, PTEN, PUTS, and the like.

Breast cancer presents an important frequency of chromosomal aberrations. Gene HER2 (ErbB2) is amplified in 10 to 20% of the cases. This amplification is associated with a hyper-expression of the Her2 protein and is involved in the tumoral transformation. A therapeutic strategy based on the targeting of this anomaly showed a benefit in the patients having HER2-positive breast cancer. In addition, the gene coding for the topoisomerase II is amplified in approximately 7% of breast cancers. This amplification is correlated with a good sensitivity to the anthracyclines, a class of drugs targeting the topoisomerase II. Other anomalies have often been observed in breast cancer. A1B1 gene is amplified in 10% of the cases, and leads to ontogenesis via the activation of AKT by the IGFR. FGF1R gene is amplified in 10% of case. The targeting of this protein by a tyrosine kinase inhibitor leads in vitro to a reduction of the cell multiplication. Similarly, amplifications of the genes EGFR, IGF1R or the deletions of PTEN can be treated by molecules targeting EGFR, IGF1R or mTOR, respectively.

In the scientific literature, certain works, among which those of A. Potti et al., propose a prediction of the drug's efficacy, primarily cytotoxicity, based on the analysis of the expression of genes selected from experiments on well-established cell lines (panel NCI60). These data allow the identification of expression profiles associated with the response for each tested molecule and this prediction is transposed to the human tumours. However, if this approach allows a molecule by molecule prediction, it does not allow the comparison of the efficacy of each molecule for a given patient in order to select the best drug. In addition, the one skilled in the art knows the limitations of in vitro model to perform in vivo predictions. These approaches tend to enrich the patient cohort for a given chemotherapy rather than to select a targeted individual therapy for a given patient on the basis of the intrinsic tumoral characteristics.

However, the choice of the appropriate chemotherapy in cancer treatment is a crucial issue. Indeed, most of the chemotherapies have very significant adverse effects and an erroneous choice (i.e., treatment without any therapeutic benefit) could lead to a cancer progression.

Up today, there is no marker efficient to select the most optimal therapeutic strategy for a given individual having a cancer. Accordingly, there is a strong need to methods of personalized medicine in the field of cancer treatment allowing the selection for a given individual of the most appropriate chemotherapy strategy.

SUMMARY OF THE INVENTION

The present invention concerns a method for predicting the relative efficacy of a plurality of drugs for treating a cancer in a patient comprising:
- characterizing molecular anomalies of a tumour or metastase sample from the patient in comparison to a normal sample from the same patient, thereby determining the deregulated genes in the tumour;
- providing a database comprising the target genes for each drug of the plurality of drugs;
- determining a score for each drug of the plurality of drugs essentially based on the percentage of deregulated genes among the target genes for each drug in the tumour sample from the patient, thereby a higher score is predictive of a higher relative efficacy of the drug for treating the tumour in the patient. Preferably, the normal sample is the normal histologic counterpart to the primary tumor.

In particular, the step of characterizing molecular anomalies of a tumour sample comprises determining the genes differentially expressed in the tumour in comparison to the normal sample, and/or determining the gain or loss of gene copy number and/or detecting the presence of a mutation in a gene. Preferably, the step of characterizing molecular anomalies of a tumour sample comprises determining a fold change (F) for the differentially expressed genes and/or for the gain or loss of gene copy number and, optionally, further determining the intensity of the gene transcription (Int) for the differentially expressed genes.

Preferably, the target genes for each drug are classified in the database into the major target genes (CM), the minor target genes (Cm) and the resistance genes (CR).

In a first embodiment, the score (W) for a given drug is determined by the following algorithm:

$$W = Pz \frac{(\Sigma_C F_{c>2})}{n_C F_{c>2}}$$

wherein
W is the score for the given drug;
P is the percentage of target genes for the given drug which are deregulated in the tumour of the patient;
z is an optional multiplication coefficient associated to the presence of a mutation in a target gene of the given drug;
$\Sigma$ is sum;
$F_{c>2}$ is the fold change of each deregulated target gene for the given drug with a Fold Change higher than 2;
$nC_{Fc>2}$ refers to the number of target genes for the given drug with a Fold Change higher than 2.

Preferably, $F_{c>2}$ is the Fold Change of each over-expressed target gene for the given drug with a Fold Change higher than 2 and $nC_{Fc>2}$ is either the number of target genes for the given drug with a Fold Change higher than 2, or the number of over-expressed target genes for the given drug with a Fold Change higher than 2.

In a second embodiment, the score (W) for a given drug is determined by the following algorithm:

$$W = P\left(\frac{(\Sigma_{CM} F_{CM})}{n_1 CM} q_1 z_1 + \frac{(\Sigma_{Cm} F_{Cm})}{n_2 Cm} q_2 z_2 - \frac{(\Sigma_{CR} F_{CR})}{n_3 CR} q_3 z_3\right)$$

wherein
W is the score for the given drug;
P is the percentage of target genes for the given drug which are deregulated in the tumour of the patient;
$\Sigma$ is sum;
CM refers to major target genes for the given drug;
Cm refers to minor target genes for the given drug;
CR refers to resistance genes for the given drug;
$n_1CM$, $n_2Cm$ and $n_3CR$ are respectively the number of deregulated target genes with a defined threshold for major target genes, minor target genes and resistance genes;
$F_{CM}$, $F_{Cm}$ and $F_{CR}$ are the Fold change of each gene higher than the defined threshold for major target genes, minor target genes and resistance genes, respectively;
$q_1$, $q_2$ and $q_3$ are optional multiplication coefficients for major target genes, minor target genes and resistance genes, respectively;
$z_1$, $z_2$ and $z_3$ are optional multiplication coefficients associated to the presence of a mutation in a major target gene, a minor target gene and a resistance gene, respectively.

In a third embodiment, the score (W) for a given drug is determined by the following algorithm:

$$W = \frac{P_{CM}(\Sigma_{CM} F_{CM})}{n_1 CM} q_1 z_1 + \frac{P_{Cm}(\Sigma_{Cm} F_{Cm})}{n_2 Cm} q_2 z_2 - \frac{P_{CR}(\Sigma_{CR} F_{CR})}{n_3 CR} q_3 z_3$$

wherein the meaning of W, $\Sigma$, CM, Cm, CR, $F_{CM}$, $F_{Cm}$, $F_{CR}$, $q_1$, $q_2$, $q_3$, $z_1$, $z_2$ and $z_3$ are the same than the previous algorithm and $P_{CM}$, $P_{Cm}$ and $P_{CR}$ are the percentage of genes for the given drug which are deregulated in the tumour of the individual for major target genes, minor target genes and resistance genes, respectively In a fourth embodiment, the score (W) for a given drug is determined by one of the following algorithms:

$$W = P\left(\frac{(\Sigma_{CM} F_{CM} \times Int_{CM})}{n_1 CM} q_1 z_1 + \frac{(\Sigma_{Cm} F_{Cm} \times Int_{Cm})}{n_2 Cm} q_2 z_2 - \frac{(\Sigma_{CR} F_{CR} \times Int_{CR})}{n_3 CR} q_3 z_3\right)$$

or $$W = \frac{P_{CM}(\Sigma_{CM} F_{CM} \times Int_{CM})}{n_1 CM} q_1 z_1 + \frac{P_{Cm}(\Sigma_{Cm} F_{Cm} \times Int_{Cm})}{n_2 Cm} q_2 z_2 - \frac{P_{CR}(\Sigma_{CR} F_{CR} \times Int_{CR})}{n_3 CR} q_3 z_3$$

wherein the meaning of W, Σ, CM, Cm, CR, $F_{CM}$, $F_{Cm}$, $F_{CR}$, $q_1$, $q_2$, $q_3$, $z_1$, $z_2$ and $z_3$, and if present $P_{CM}$, $P_{Cm}$ and $P_{CR}$, are the same than the previous algorithm and $Int_{CM}$, $Int_{Cm}$ and $Int_{CR}$ are the intensity for major target genes, minor target genes and resistance genes, respectively.

In a fifth embodiment, the score (W) for a given drug is determined by one of the following algorithms:

$$W = P\left(\frac{(\Sigma_{CM} F_{CM})}{n_1 CM} q_1 z_1 - \frac{(\Sigma_{CR} F_{CR})}{n_3 CR} q_3 z_3\right)$$

or $$W = \frac{P_{CM}(\Sigma_{CM} F_{CM})}{n_1 CM} q_1 z_1 - \frac{P_{CR}(\Sigma_{CR} F_{CR})}{n_3 CR} q_3 z_3$$

or $$W = P\left(\frac{(\Sigma_{CM} F_{CM} \times Int_{CM})}{n_1 CM} q_1 z_1 - \frac{(\Sigma_{CR} F_{CR} \times Int_{CR})}{n_3 CR} q_3 z_3\right)$$

or $$W = \frac{P_{CM}(\Sigma_{CM} F_{CM} \times Int_{CM})}{n_1 CM} q_1 z_1 - \frac{P_{CR}(\Sigma_{CR} F_{CR} \times Int_{CR})}{n_3 CR} q_3 z_3$$

wherein the meaning of W, Σ, CM, CR, $F_{CM}$, $F_{CR}$, $q_1$, $q_3$, $z_1$ and $z_3$, and if present $P_{CM}$, $P_{CR}$, $Int_{CM}$ and $Int_{CR}$ are the same as the previous algorithms.

Preferably, in the second to fifth embodiment, $F_{CM}$, $F_{Cm}$ and $F_{CR}$ are the Fold Change of each over-expressed target gene for the given drug with the defined threshold and $n_1 CM$, $n_2 Cm$ and $n_3 CR$ are either the number of target genes for the given drug with the defined threshold, or the number of over-expressed target genes for the given drug with the defined threshold. More preferably, the defined threshold is a Fold change of at least 2 or higher than 2.

In addition, in the second to fifth embodiment, multiplication coefficients for the target genes can be comprised between 10 and 1,000 for major target genes ($q_1$), 0.1 and 10 for minor target genes ($q_2$) and 10 to 1,000 for resistance genes ($q_3$).

Furthermore, in the second to fifth embodiment, multiplication coefficients associated to a mutation $z_1$, $z_2$ and $z_3$ are 1 when no mutation exists and, depending on the functional impact of the mutation, can be comprised between 10 and 1,000.

DETAILED DESCRIPTION OF THE INVENTION

Figure 1:
FIG. 1: Thoracic scanner in October 2005 of the patient of Example 1.
Figure 1:
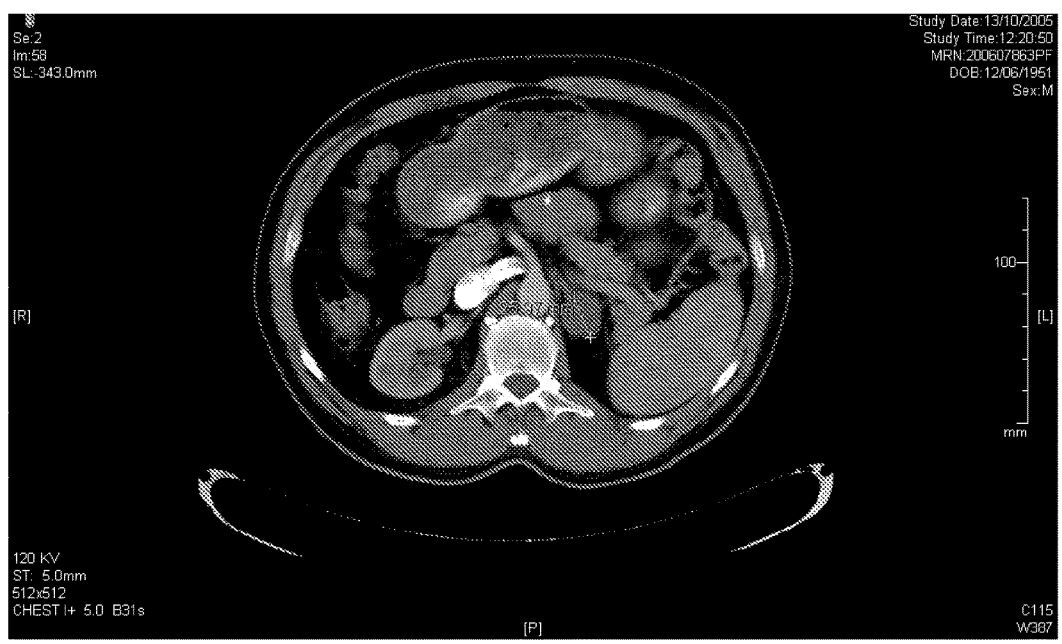

The present invention provides a new concept for selecting the most appropriate therapy at the individual level. The drug selection is based on the biologic characteristics of the tumor of the individual to be treated in comparison to a normal sample from the same individual. Based on a score essentially based on the percentage of deregulated target genes or microRNAs for each drug, the relative efficacy of the drugs can be predicted for the individual in order to treat the specific tumour.

General Concept

It is at the level of the optimal therapeutic strategy choice that applies the object of the present invention. For selecting the most appropriate therapeutic strategy, the method of the present invention is taking into account of, on one hand, the biological data of the tumor to be treated as a whole and, on the other hand, a plurality of drugs, preferably all existing drugs (either registered or in development). A score is determined for each drug based on the biological characteristics of the specific tumour to be treated for a given subject. This score makes it possible to order the various drugs in decreasing order for their potential efficacy. The physician can use these scores to select the optimal drug or combination of drugs for the given subject. This approach, allowing the association of each drug with a score depending on the biological characteristics of the tumour, constitutes the basis of this invention. Therefore, this invention is likely to meet the present needs for personalized medicine.

The method can be used both for registered drugs and for developed drugs (e.g., temporary authorization of use or clinical trials).

This concept thus consists in considering the choice of the therapy for the patient at the level of the individual depending on the intrinsic characteristics of his tumour and not on global results obtained from large groups of individuals.

The present invention is based on the combination of three fundamental points, detailed below, and which are combined together to optimize the choice of the strategy for each individual having a cancer:

The first point corresponds to the analysis, as exhaustive as possible, of the biological or gene anomalies (amplification, deletions, mutations, gene expression, microRNAs expression and the like) which characterize a given tumour for an individual.

The second point consists in the identification of genes known to be in relation with a drug.

The third point corresponds to the establishment of the connection between each drug and the anomalies detected in the tumour to be treated in an individual. An algorithm has been identified for calculating a score for each drug in consideration of the tumour characteristics and the genes known to be in relation with a drug.

The method of the invention will allow guiding the therapeutic choice because the available drugs will be ordered on their score basis, reflecting their potential therapeutic efficacy for the given tumour in an individual.

One advantage of the present method is that the relative efficacy of a plurality of drugs can be predicted for an individual without exposing the individual to drugs. By a plurality of drugs is intended at least or about 10, 20, 30, 40, 50 or 100 different drugs. Indeed, when a panel of drugs is available for treatment, one cannot be envisaged to try the treatment by each drug on the patient. The present method allows the consideration of all potential therapeutic strategy and the selection of the most appropriate for the patient.

Indeed, the scores for the plurality of drugs allow the determination of the relative efficacy of the plurality of drugs for treating the tumour of the considered individual. Indeed, a drug having a higher score than another drug is predicted to have a higher efficacy for treating the tumour. By treating is intended that the drug allows to stop or slow down the growth of the tumour, and/or to decrease the size of tumour even up to its disappearance. By treating is also intended to avoid the metastasis, the recurrence or the relapse.

Another advantage is that the method does not depend on a cancer type. The method of the invention can be used for any type of cancer including haematological tumour (e.g. leukemia, lymphoma) and bladder, breast, stomach, thyroid, prostate, testis, liver, pancreatic, bone, pancreatic, kidney, endometrial, melanoma, lung, gastric, colorectal, prostate, head or neck tumours, brain, neuroblastoma, and ovarian cancer.

In a preferred embodiment, the patient or individual is a human being.

Tumour Characterization

Tumour characterization corresponds to the analysis, as exhaustive as possible, of the biological or gene anomalies (amplification, deletions, mutations, gene expression and the like) which characterize a given tumour for an individual. In particular, the anomalies are determined in a tumour from the patient in comparison with a normal tissue of the same patient. Preferably, the tumour sample and the normal sample provides from the same type of tissue. For the tumour characterization, several technologies are available and can be combined.

The first technology is the gene analysis. This analysis can be carried out by CGH (Comparative Genomic Hybridization) which makes it possible to compare the tumoral DNA with the normal DNA of the same individual to detect chromosomal aberrations, i.e. the chromosomal losses or gains. This technology is well-known by the man skilled in the art. As an illustration of this knowledge, the following reviews or reference books can be cited: Davies et al. (2005, *Chromosome Research*, 13, 237-248). This technology can also help to identify translocations. It can be easily carried out with frozen biopsies or tumoral paraffin-included material. CGH results are expressed as the ratios of copy numbers in the tumoral material and in normal tissue. A threshold of 0.5 is been acknowledged to describe a gain or a loss. More this ratio is high, more the amplitude of the anomaly is important. Thus, an important anomaly is likely to have a real impact at the biological level. However, the chromosomal aberrations only represent a weak part of the origins of gene expression deregulation. This is why other technologies are necessary. CGH have another advantage, to certify presence of tumoral samples in the tumoral biopsy or biospecimen, and this whenever an aberration can be detected.

The second technology allowing a functional genomic analysis corresponds to the measurement of mRNA and microRNA. The determination of the expression level variation for these RNA is carried out by comparing the expression levels in a tumoral tissue and in the corresponding normal tissue. For instance, in case of colon adenocarcinoma, the corresponding normal tissue is the normal colic mucosal tissue. The gene expression analysis allows the study of the independent deregulations or deregulations due to chromosomal aberrations. Indeed, the regulation of the transformational activity of genes is complex and involves many levels of regulation: trans/cis transcription factors, promoters, chromatin regulation, and the like. Generally, all deregulations (over-expression or under-expression) are considered with a ratio tumour/normal of at least 2. This threshold called "fold change" can thus have a positive value >2 or a negative value <−2. The same concept applies to the microRNAs which play an important role in the post-transcriptional regulation of genes, therefore for the proteins expression. Technologies that can be used comprise northern analysis, mRNA or cDNA microarrays, RT-PCT (in particular quantitative RT-PCR) and the like. The level of transcription can be determined at the mRNA level or at the encoded protein level. Protein expression can be assessed by Western blotting, immunoassay, proteomics tools or mass spectrometry.

These two types of analyses, CGH and RNA expression determination can be supplemented by an analysis of the mutational status of genes. Indeed, the presence of mutation leading to a functional gain or loss has an important effect on biology of the tumour without being always connected to variations of gene expression or of gene copy number. Many mutations are known to have a direct effect on the activity of a treatment by inducing increased sensitivities or resistances. For example, the mutations in the tyrosine kinase domain of EGFR are often associated with sensitivity to the small molecules inhibiting EGFR, the mutations in KRAS gene are associated with resistance to the treatment by monoclonal antibodies targeting EGFR. In addition to mutational status, some SNP can also be detected. Indeed, SNP can be also associated to a functional gain or loss, a resistance or a toxicity for a drug. The mutational status can be determined by any method known in the art, for instance by sequencing, microsequencing or hybridization.

In short, high throughput genomic technologies can be used to characterize in the most exhaustive possible way the biological anomalies of a given tumour from an individual to be treated. The experimental data for each tumour are compiled in basic files being used for the application of the algorithms allowing calculation of a score for each drug. These files comprise the copy number of genes, the mutations, the fold-changes or the intensities of signals (proportional to the number of transcripts or to the number of gene copy) for normal tissue (Intensity 1 or I1) and for tumoral tissue (intensity 2 or I2). The functional genomic analysis allows the simultaneous measurement of 44,000 or more (for example 244,000) RNA sequences covering all the genome. Preferably, a filtration can be applied to retain only the probes having a ratio or fold-changes higher or lower than 2 and whose average of the intensities I1 and I2 is higher than 100 units of fluorescence (arbitrary units).

The term "molecular anomalies" refers herein to the gene expression differences (either mRNA, microRNA or protein expression), to a gain or loss of gene copy number, or to a mutation presence.

In a particular embodiment of the invention, the exhaustive characterization of the tumour is replaced by the characterization of the target genes of the drug database. In this embodiment, specific array can be prepared to determine the gene expression level of all the target genes of the database.

Drug Database

For the method of the invention, it is necessary to provide a database with a list of target genes for each drug of the database. As explained before, a target gene for a drug can be, without being limited thereto, any gene documented to be involved in the drug mechanism of action, to be involved in the drug metabolism, to have a modified gene expression in presence of the drug, to be associated with a drug resistance, to be associated with a drug toxicity. The database can be prepared based on the search in the public databases (such as CTD, DrugBank, PubMed, and the like) in order to identify the genes associated with each drug. For instance, the database can be built based on the CTD (The Comparative Toxicogenomics Database, See Worldwide Website: ctd.mdibl.org) data for a selection of drugs and their molecular targets (genes), restricted to the human species (ID 9606). These data can be crossed with genes' information from LocusLink (gene symbol, RefSeq NM, gene description). Finally, each drug/gene interaction in the database can be qualified from the available publications, to determine the type of interactions: some positive interactions (target, sensitivity, drug activator, drug carrier, toxicity reverser), some negative interactions (resistance, toxicity, drug metabolism, apoptosis, death).

The identified genes can have different roles and significances. Therefore, in a preferred embodiment, the target genes are classified into three categories: the major target genes, the minor target genes and the resistance genes. The identification of these genes from the public data (public literatures and data banks) and their classification in the three categories form an integral part of this invention. The major target genes are those which have been demonstrated to have a clear cause and effect link with the drug mechanism of action. For example, HER2 gene is regarded as major target gene for trastuzumab, VEGFA gene is regarded as major target gene for bevacizumab, and the like. A given drug can have one or more major target genes. This category also includes the genes known to be involved in the drug metabolization when drugs are known to become active only when an active metabolite is generated. The minor target genes are those which are found to be those whose level of regulation is modified in the presence of the drug, without a direct link with the drug mechanism of action. The resistance genes comprise genes known to induce a direct resistance to the drug but also genes associated with a major toxicity. For example, ERCC1 gene is a target gene of resistance for the use of platinum salts. For example, some cytochrome P450 isoforms are associated with a major toxicity.

In a particular embodiment of the invention, the considered target genes can only belong to the two following categories: the major target genes and the resistance genes.

A first drug database has been established by the inventors and is disclosed in Table 1. For some drugs, the target genes have been categorized.

The drug database can be incremented over the time, by categorizing target genes for a drug, and/or by adding new drug, new target genes and/or by including combination data (e.g. combination of drugs with radiotherapy or combination of drugs).

More complete is the drug database, more accurate is the prediction. However, the method for predicting the relative efficacy of drugs can be carried out as soon as a preliminary database is ready.

Algorithm

An algorithm has been identified for calculating a score for each drug in consideration of the tumour characteristics and the genes known to be in relation with a drug. This calculation can be carried out by specific softwares by using of the scripts developed under R for instance, and allowing the determination of the frequencies and the association links between the file of target genes for the drugs and the file integrating the data of the genomic analysis resulting from the biological investigation from the tumour of the individual.

The algorithm can take into account the following parameter:

1) the whole percentage of deregulation of target genes of a drug. Therefore, the list of target genes for a given drug is compared with the list of deregulated genes in order to determine the percentage of deregulated genes for this drug. For instance, if 10 target genes have been identified for a given drug and, for a given tumour, 4 of the 10 target genes are found to be deregulated, then the percentage of deregulated genes for this drug is 40%.

2) the deregulation extent and sense (e.g., over- or under-expression) of the target genes defined by a Fold Change (Fc) and an average intensity (AvgInt). These parameters can be defined either as a whole for the target genes or by each category (e.g., major target genes, minor target genes and resistance target genes).

3) the presence of mutations in target genes known to have an effect on the given drug.

An algorithm is used to calculate a score for each drug of the database in consideration of the tumour characterization for the subject to be treated.

A first basic algorithm that can be used in the method is the following:

$$W = Pz \frac{(\Sigma_C F_{c>2})}{n_C F_{c>2}}$$

wherein

W is the score for a given drug;

P is the percentage of target genes for the given drug which are deregulated in the tumour of the individual;

z is an optional multiplication coefficient associated to the presence of a mutation in a target gene;

Σ is sum;

Fc>2 is the Fold Change of each deregulated target gene for a given drug with a Fold Change higher than 2;

$nC_{Fc>2}$ refers to the number of target genes for the given drug with a Fold Change higher than 2.

In a particular embodiment of this algorithm, Fc>2 is the Fold Change of each over-expressed target gene for a given drug with a Fold Change higher than 2 and $nC_{Fc>2}$ can refer to the number of target genes for the given drug with a Fold Change higher than 2, or the number of over-expressed target genes for the given drug with a Fold Change higher than 2.

Of course, the algorithm can be more complex in order to take into account the category of the target genes (e.g., major target gene, minor target gene or resistance target gene), for instance by introducing a multiplication coefficient.

Such a more complex algorithm can be the following:

$$W = P\left(\frac{(\Sigma_{CM} F_{CM})}{n_1 CM} q_1 z_1 + \frac{(\Sigma_{Cm} F_{Cm})}{n_2 Cm} q_2 z_2 - \frac{(\Sigma_{CR} F_{CR})}{n_3 CR} q_3 z_3\right)$$

wherein

W is the score for a given drug;

P is the percentage of target genes for the given drug which are deregulated in the tumour of the individual;

Σ is sum;

CM refers to major target gene for the given drug;

Cm refers to minor target gene for the given drug;

CR refers to resistance gene for the given drug;

$n_1CM$, $n_2Cm$ and $n_3CR$ respectively are the number of deregulated target genes with a defined threshold for major target genes, minor target genes and resistance genes;

$F_{CM}$, $F_{Cm}$ and $F_{CR}$ are the Fold change of each gene higher than the defined threshold for major target genes, minor target genes and resistance genes, respectively;

$q_1$, $q_2$ and $q_3$ are multiplication coefficients for major target genes, minor target genes and resistance genes, respectively;

$z_1$, $z_2$ and $z_3$ are optional multiplication coefficients associated to the presence of a mutation in a major target gene, a minor target gene and a resistance gene, respectively.

For instance, multiplication coefficients for the target genes can be comprised between 10 and 1,000 for major target genes, 0.1 and 10 for minor target genes and 10 to 1,000 for resistance genes. Other values for multiplication coefficients are not excluded.

The multiplication coefficients associated to a mutation are 1 when no mutation exists. Depending on the functional impact of the mutation, the coefficient z can be comprised between 10 and 1,000, for instance. Other values for multiplication coefficients associated to a mutation are not excluded.

In a preferred embodiment, the defined threshold is a Fold change of at least 2 or higher than 2. However, the consideration of a lower threshold is not excluded in the present method since a fold change of 1.5 can be significant for some genes.

In a particular embodiment, $F_{CM}$, $F_{Cm}$ and $F_{CR}$ can be the Fold Change of each over-expressed target gene for the given drug with the defined threshold and $n_1CM$, $n_2Cm$ and $n_3CR$ can refer to the number of target genes for the given drug with the defined threshold, or the number of over-expressed target genes for the given drug with the defined threshold.

In an alternative complex algorithm, the formulae can be the following:

$$W = \frac{P_{CM}(\Sigma_{CM}F_{CM})}{n_1CM}q_1z_1 + \frac{P_{Cm}(\Sigma_{Cm}F_{Cm})}{n_2Cm}q_2z_2 - \frac{P_{CR}(\Sigma_{CR}F_{CR})}{n_3CR}q_3z_3$$

wherein the meaning of W, Σ, CM, Cm, CR, $F_{CM}$, $F_{Cm}$, $F_{CR}$, $q_1$, $q_2$, $q_3$, $z_1$, $z_2$ and $z_3$ are the same than the previous algorithm and $P_{CM}$, $P_{Cm}$ and $P_{CR}$ are the percentage of genes for the given drug which are deregulated in the tumour of the individual for major target genes, minor target genes and resistance genes, respectively.

Similarly, in a preferred embodiment, the defined threshold is a Fold change of at least 2 or higher than 2. However, the consideration of a lower threshold is not excluded in the present method since a fold change of 1.5 can be significant for some genes.

In a particular embodiment, $F_{CM}$, $F_{Cm}$ and $F_{CR}$ can be the Fold Change of each over-expressed target gene for the given drug with the defined threshold and $n_1CM$, $n_2Cm$ and $n_3CR$ can refer to the number of target genes for the given drug with the defined threshold, or the number of over-expressed target genes for the given drug with the defined threshold.

In a particular embodiment, the algorithm can take into account the average intensity or intensity variation. This parameter is indicative of the transcription level of genes. Indeed, it can be considered that for a same Fold Change of 2, a gene deregulation can have a different weight depending on the intensity of the transcription, for instance 200/100 in comparison to 200,000/100,000.

Accordingly, a still more complex algorithm can be one of the followings:

$$W = P\left(\frac{(\Sigma_{CM}F_{CM} \times Int_{CM})}{n_1CM}q_1z_1 + \frac{(\Sigma_{Cm}F_{Cm} \times Int_{Cm})}{n_2Cm}q_2z_2 - \frac{(\Sigma_{CR}F_{CR} \times Int_{CR})}{n_3CR}q_3z_3\right)$$

$$W = \frac{P_{CM}(\Sigma_{CM}F_{CM} \times Int_{CM})}{n_1CM}q_1z_1 + \frac{P_{Cm}(\Sigma_{Cm}F_{Cm} \times Int_{Cm})}{n_2Cm}q_2z_2 - \frac{P_{CR}(\Sigma_{CR}F_{CR} \times Int_{CR})}{n_3CR}q_3z_3$$

wherein the meaning of W, Σ, CM, Cm, CR, $F_{CM}$, $F_{Cm}$, $F_{CR}$, $q_1$, $q_2$, $q_3$, $z_1$, $z_2$ and $z_3$, and if present $P_{CM}$, $P_{Cm}$ and $P_{CR}$, are the same than the previous algorithm and $Int_{CM}$, $Int_{Cm}$ and $Int_{CR}$ are the intensity for major target genes, minor target genes and resistance genes, respectively. "Int" can be the intensity of the gene transcription in the tumour sample, the difference of the gene transcription between the tumour sample and the normal sample from the individual.

In an additional embodiment, the method can be focused on the major target genes and the resistance genes, without taking into account of the minor target genes. In this embodiment, the algorithm could be one of the followings:

$$W = P\left(\frac{(\Sigma_{CM}F_{CM})}{n_1CM}q_1z_1 - \frac{(\Sigma_{CR}F_{CR})}{n_3CR}q_3z_3\right)$$

$$W = \frac{P_{CM}(\Sigma_{CM}F_{CM})}{n_1CM}q_1z_1 - \frac{P_{CR}(\Sigma_{CR}F_{CR})}{n_3CR}q_3z_3$$

$$W = P\left(\frac{(\Sigma_{CM}F_{CM} \times Int_{CM})}{n_1CM}q_1z_1 - \frac{(\Sigma_{CR}F_{CR} \times Int_{CR})}{n_3CR}q_3z_3\right)$$

$$W = \frac{P_{CM}(\Sigma_{CM}F_{CM} \times Int_{CM})}{n_1CM}q_1z_1 - \frac{P_{CR}(\Sigma_{CR}F_{CR} \times Int_{CR})}{n_3CR}q_3z_3$$

wherein the meaning of W, Σ, CM, CR, $F_{CM}$, $F_{CR}$, $q_1$, $q_3$, $z_1$ and $z_3$, and if present $P_{CM}$, $P_{CR}$, $Int_{CM}$ and $Int_{CR}$ are the same than the previous algorithms.

Preferably, the selected algorithm is validated with two models: a retrospective model (e.g., tumours for which chemotherapies have been performed and for which the response to treatments is known); and a prospective model allowing the evaluation of the efficacy of a particular treatment in relation with the score.

During the algorithm validation tests, some variables can be refined, in particular the multiplication coefficients, the consideration of the average intensity or not, the threshold of the fold change. In addition, during this step, one can determine if it is preferable to use CGH or functional genomic analysis or both.

The method also considers other variants of the algorithm that could be proposed, the final objective staying to calculate a score for each drug based on the characteristic of the tumour of the individual to be treated, in particular on the biologic and genetic anomalies of the tumour.

Further aspects and advantages of this invention will be disclosed in the following examples, which should be regarded as illustrative and not limiting the scope of this invention.

EXAMPLES

Example 1

At diagnosis, 70% of lung cancers are in late stages. They are non operable with a poor clinical outcome.

The method of the present invention has been used in a patient case to help the practitioner to choose the most appropriate treatment.

The patient was a male Caucasian of 58 years old. He suffered of a non-small cell lung carcinoma (NSCLC), cT4, N0, M1. Nine therapeutic lines have been used, namely cisplatin-Gemzar, taxotere, navelbine, taxol-carboplatin, mediastinal radiotherapy, IRESSA, alimta, tarceva and HKI 272 (pan Her inhibitor). For HKI 272, the patient has been included in a clinical trial.

Figure 2:
FIG. 2: Thoracic scanner in November 2008 of the patient of Example 1.
Figure 2:
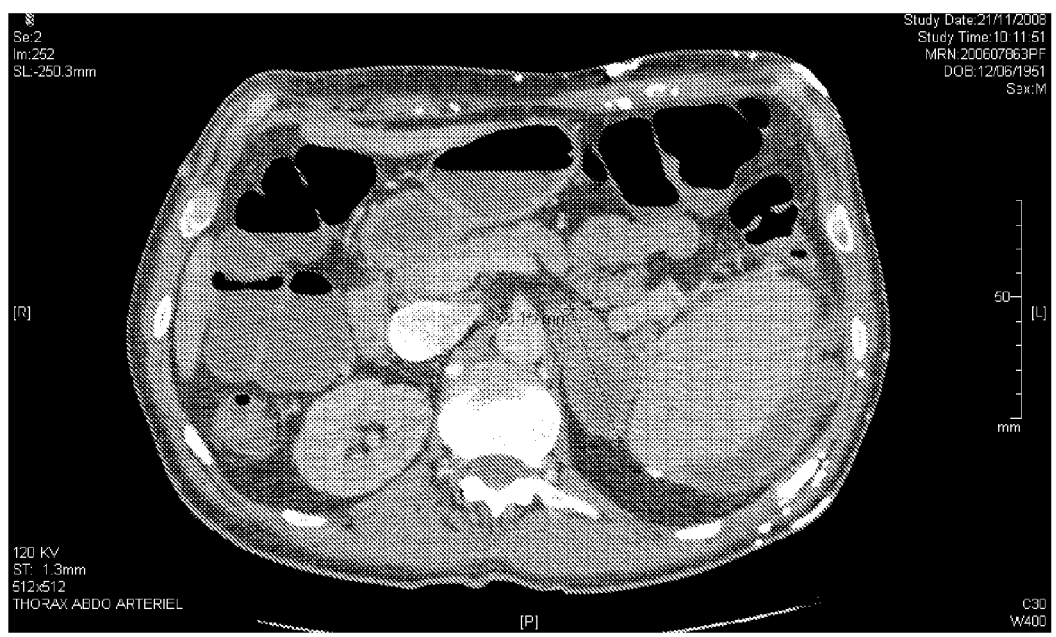

HKI 272 began in October 2005. FIG. 1 show NMR of mediastinal lymph node (C1) and adrenal node (C2). HKI was efficient; the patient remained in the study almost three years. However, after 37 months of HKI 272, a disease progression was observed (FIG. 2). New subclavious metastasis appeared. This is one of the biggest problems in oncology today; even if there is initial response, a secondary resistance to treatment often occurs. Accordingly, the decision to stop HKI 272 treatment was taken since new metastasis occurred. It is important to mention that practitioners considered at that time that HKI 272 was the last therapeutic line available for this patient.

Subclavious metastasis was resected and used for complete molecular profiling. The features of the profiling were:
1—comparison tumoral tissue versus normal lung tissue (T vs N);
2—Comparative genome hybridzation (CGH) (T vs N);
3—Gene expression (GE) comparison (T vs N);
4—microRNA (miRNA) profiling (T vs N);
5—Sequencing of genes including EGFR, p53, CTNNB1, AKT1, BRAF, KRAS, HRAS, NRAS, PIK3CA, FBXW7, EGFR, ERBB2, KIT, NOTCH1, PTEN, STK11, TP53, APC, MET, RB1, FGFR2, FGFR3, JAK2, TSC1, TSC2, CDKN2A, CDKN2A, TOP1, TOP2A, PDGFRA, VHL, CDK4, JAK1, TYK.
6—No relevant mutations were found in any of these genes (for example no mutation of EGFR or other genes). Therefore mutations did not impact algorithm for this patient. Only relevant results obtained with gene expression were used.

Then, the algorithm of the present invention was applied on these data in order to predict the drug efficacy. A score for each drug was calculated based on the collected data. The algorithm used was the following:

$$W = P z \frac{(\Sigma_c F_{c>2})}{n_c F_{c>2}}$$

wherein
W is the score for a given drug;
P is the percentage of target genes for the given drug which are deregulated in the tumour of the individual;
z is 1 because, in this example, no mutation was detected;
Σ is sum;

Fc>2 is the Fold Change of each deregulated target gene for a given drug with a Fold Change higher than 2;
nCFc>2 refers to the number of target genes for the given drug with a Fold Change higher than 2.

Table 2 shows the calculated scores. It can be observed that the drugs used in the previous therapeutic lines were associated with low scores, namely 108 for cisplatine, 70 for gemzar, 77 for taxotere, 147 for taxol, 82 for carboplatin, 66 for Iressa, and 73 for Alimta.

On December 2008, HKI 272 was stopped and a treatment with a combination of Xeloda (3600 mg/day, from Day 1 to Day 14, every 21 days) and Lapatinib (1250 mg/day) began. At the beginning of this treatment, the patient showed a rapid disease progression and demonstrated a degraded health. Lapatinib, an anti-HER1 and -HER2 inhibitor, was justified, even if no mutation was detected in EGFR, because EGF overexpressed 15 folds in the patient and it was needed to continue HKI 272. Indeed, overexpression of EGF in the tumor induces a constant activation of EGFR, that is why it appeared logic to assure the transition from HKI272 to another anti EGFR in order to cover the same spectra. Xeloda (score 555) was selected based on algorithm's score.

Figure 3:
FIG. 3: Thoracic scanner in April 2009 of the patient of Example 1.
Figure 3:
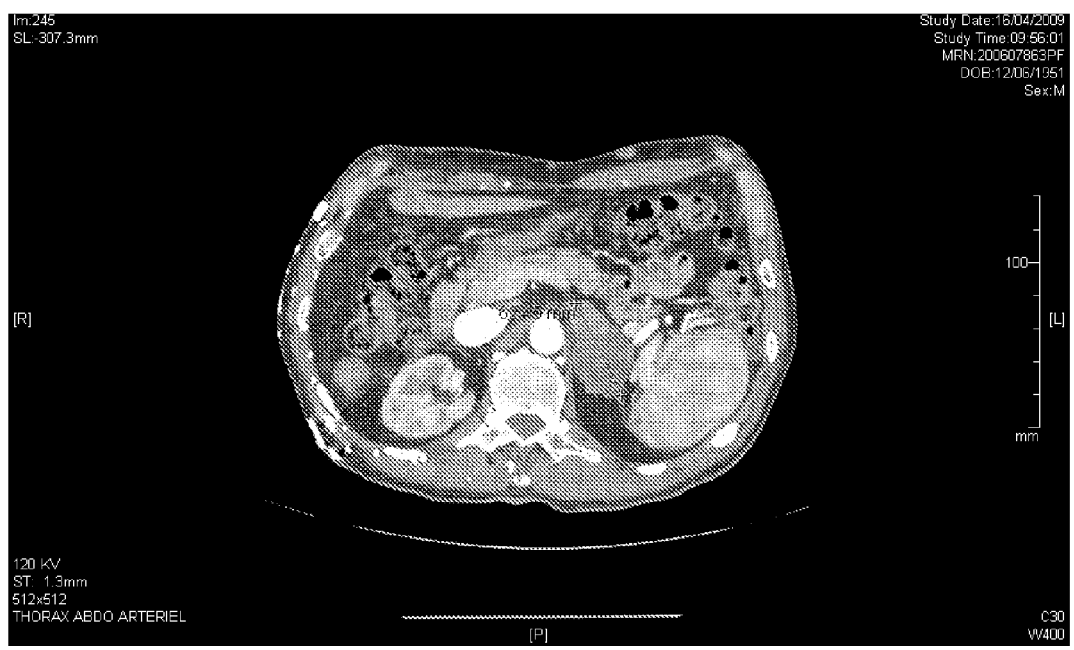
Figure 4:
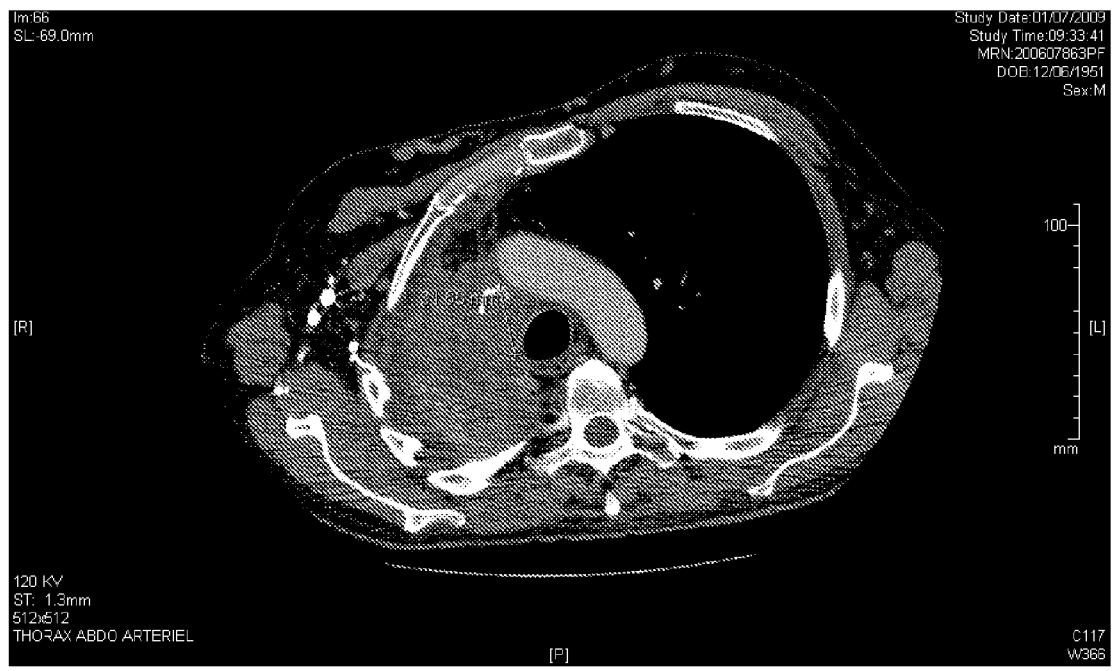
FIG. 4: Thoracic scanner in July 2009 of the patient of Example 1.
Figure 4:
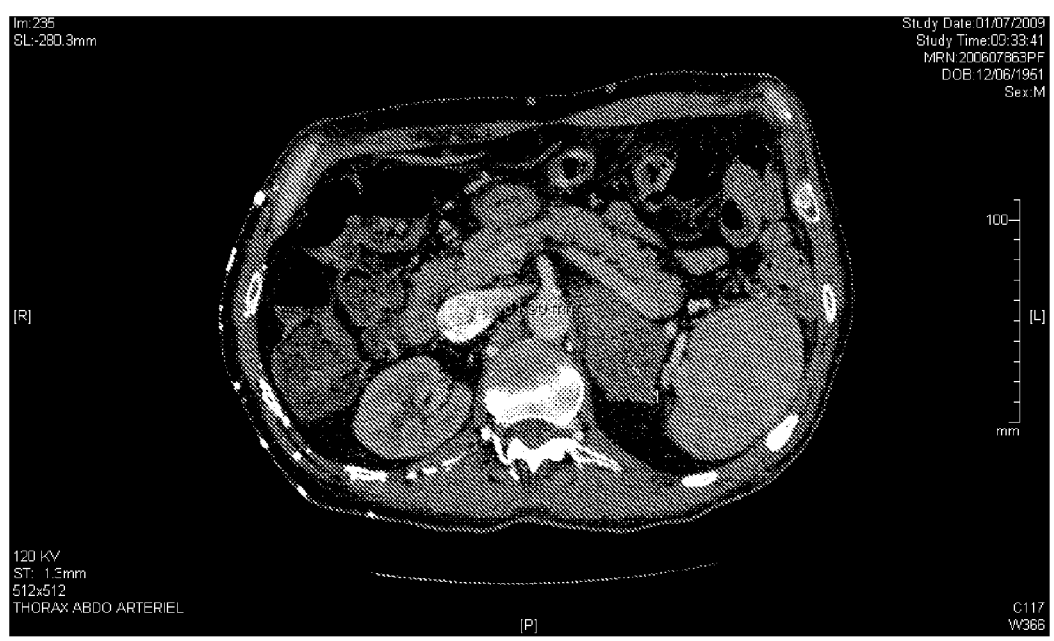

The disease was stable but recurrential paralysis was observed. Accordingly, in February 2009, it was decided to add Thiotepa which showed the highest algorithm score (score 713). After two months of treatment with the combination Xeloda (3600 mg/day, 5 days by week, 3 weeks on 4 weeks), Lapatinib (1250 mg/day) and Thiotepa (15-30 mg/day, Days 1 and 2, every 4 weeks), the disease was stable (FIG. 3). The disease was still stable for eleven months (FIG. 4), no more recurrential paralysis occurred and the patient showed a good general status.

In addition, the present method allows the determination of future therapeutic combinations. Indeed, during cancer treatment, resistance often appears. At least three others drugs showed high scores and can be used in case of resistance to the combination Xeloda, Lapatinib and Thiotepa, namely fotemustine (score 627), rituximab (score 761) and trabectidin (score 376).

By using the present method for selecting drugs, unexpected results were obtained. Indeed, without the score predicting the potential efficacy of a drug for a particular patient, the practitioner would not select both Xeloda and Thiotepa. Indeed, there is no indication for these drugs in lung cancer, in particular NSCLC. The present method allowed reaching fourteen months of stability with a good general status for the patient, whereas the vital prognosis was only of few weeks at the initiation of the treatment with the combination of Xeloda and Thiotepa.

In conclusion, the present example proves the value of the method of the present invention to help the practitioner to select appropriate drugs based on the individual data.

Retrospectively, the use of the new predicting method clearly demonstrated that all previous therapeutic lines, totally inefficient, were associated with a very low predictive score, as described. This is exactly the purpose of this innovative method, to be able to provide a predictive determination of the efficacy of drugs, and in this example, there is perfect validation of the concept, since all used inefficient drugs are linked with low score.

Other patients experiment the new procedure, and the high added value of the present method is to demonstrate that each patient needs a unique combination of drugs. The method appears therefore extremely relevant in the area of individualized selection of treatments.

Example 2

The patient was 64 years old. He suffered of a bronchial adenocarcinoma T4 with bones and pleural metastases. Two therapeutic lines have been used, namely cisplatin-Alimta and Tarceva. The first therapeutic line was associated with disease progression and the second was inefficient and led to a rapid progression.

A biopsy of normal bronchial mucosa and a tumoral biopsy were carried out and used for mutational analysis by sequencing, CGH, microRNAs analysis and Genome expression analysis.

CGH profile comprised numerous alteration (loss or gain), proving the tumoral status of the biopsy.

Mutational analysis including the genes as listed in Example 1 results in the identification of a mutation G464V in BRAF gene (B-Raf proto-oncogene serine/threonine-protein kinase, GeneID 673). This mutation is postulated to be activating with intrinsic mitotic signalisation. Therefore, a treatment with sorafenib could be contemplated.

Based on Genome Expression analysis, scores have been calculated as detailed in Example 1 and are shown in the following table only for some relevant drugs.

| Chemical | Target Genes | Target Genes List | Found Targets | Found Targets List (with fold-changes) | Avg Abs(FC) | Avg Abs(FC) UP-REG | Score |
|---|---|---|---|---|---|---|---|
| TIPIFARNIB (Zamestra) | 4 | ABCB1 CYP3A4 CYP3A5 UGT1A1 | 2 (2 + 0) (50.0%) | CYP3A4 (17.99) CYP3A5 (23.46) | 20.73 | 20.73 | 1036 |
| BEVACIZUMAB (Avastin) | 1 | VEGFA | 1 (1 + 0) (100.0%) | VEGFA (2.30, 7.27, 4.15) | 4.58 | 4.58 | 457 |
| AFLIBERCEPT (VEGF Trap) | 1 | VEGFA | 1 (1 + 0) (100.0%) | VEGFA (2.30, 7.27, 4.15) | 4.58 | 4.58 | 457 |
| IFOSFAMIDE (Cyfos, Holoxan, 1000, IFEX, Ifex/Mesnex Kit, Ifosfamide/Mesna Kit Isoendoxan, Mitoxana, Naxamide) | 11 | BCL2, CASP9, CYP2A6, CYP2B6, CYP3A4, CYP3A5, DNMT1, GSTM1, GSTP1, GSTT1, SLC34A1 | 4 (2 + 2) (36.4%) | CYP3A4 (17.99) CYP3A5 (23.46) BCL2 (−4.42) CYP2B6 (−13.41) | 14.82 | 20.73 | 376 |
| ECTEINASCIDIN 743 (Trabectedin, ET-743, Yondelis) | 4 | CCNA2 CCNB1 CCNB2 E2F1 | 3 (3 + 0) (75.0%) | CCNA2 (4.55) CCNB1 (2.95) CCNB2 (5.21) | 4.24 | 4.24 | 317 |
| VINORELBINE (Navelbine, Navelbine Base) | 7 | CASP3 CDKN2A PTGS2 RALBP1 RBM17 SLC29A1 TUBB2A | 3 (2 + 1) (42.9%) | PTGS2 (17.97) SLC29A1 (2.36) TUBB2A (−2.05) | 7.46 | 10.16 | 290 |
| --- | --- | --- | --- | --- | --- | --- | --- |
| PEMETREXED (Alimta) | 10 | DHFR FAS FPGS GART GGH RBM17 SLC19A1 TP53 TYMP TYMS | 4 (4 + 0) (40.0%) | DHFR (2.40, 2.26) CART (3.29) SLC19A1 (4.68) TYMS (5.32) | 3.91 | 3.91 | 156 |
| --- | --- | --- | --- | --- | --- | --- | --- |
| GEFITINIB (Iressa, Irressat, Tarceva) | 57 | ABCG2 ADORA1 AKT1 AREG AVEN CASP3 CGRRF1 COL4A3BP CORO1C CYP1A2 CYP2C19 CYP2C9 CYP2D6 CYP2F1 CYP3A4 CYP3A5 DUSP3 DUSP9 E2F1 EGF EGFR EPOR EPS15 ERBB2 EREG ESR1 FGF6 GADD45A GADD45G GARS GCLC GNB2 GUCY2D HBEGF IFI6 IGFBP3 IL8 LEPR MAPK1 MAPK3 MLH1 NFKB1 NPTX2 NRL OSMR PARP1 PHLDA2 PLBD1 PTEN QSOX1 RBM7 RPA1 SFN SKI TGFA TNFRSF1B TYMS | 18 (11 + 7) (31.6%) | AREG (6.94) CYP3A4 (17.99) CYP3A5 (23.46) DUSP3 (3.18) EPOR (2.02, 2.11) IFI6 (3.79) NPTX2 (2.77) PHLDA2 (5.98) PLBD1 (8.04) SKI (2.09) TYMS (5.32) CYP2C9 (−2.94) CYP2F1 (−27.19, −7.80) EGF (−2.04) EGFR (−3.99) GADD45G (−3.12) GCLC (−2.59) LEPR (−6.56) | 6.69 | 7.42 | 143 |
| --- | --- | --- | --- | --- | --- | --- | --- |
| CISPLATIN (Abiplatin, Biocisplatinum, Briplatin, Carboquone, Cis Pt II, Cismaplat, Cisplatine, Cisplatyl, Citoplationo, Lederplatin, Neoplatin, Plastin, Platamine, Platiblastin, Platidiam, Platinex, Platinol, Platinol-AQ, Platinoxan, Randa) | 403 | A2M ABCB1 ABCC1 ABCC2 ABCC5 ABHD11 ABHD2 ABR ACSL3 ADAM10 ADFP ADORA2B AHCYL1 AKAP12 AKR1B1 AKT1 AKT2 AKT3 ALB ANXA1 APEX1 ARF6 ARHGEF6 ARID5B ARMCX2 ASS1 ASTN1 ATP6V1G2 AXL B3GALT4 BACH1 BAX BBC3 BCAM BCAS4 BCL2 BCL2L1 BCL2L12 BIRC2 BIRC3 BIRC5 BMP7 BTG2 C11ORF68 C11ORF9 C19ORF2 C4ORF29 C7ORF16 CA2 CALCB CASP2 CASP3 CASP8 CASP9 CAT CAV1 CCDC85B CCNE1 CCNG2 CD151 CD55 CDC40 CDH3 CDKL5 CDKN1A CDKN2AIP CELSR2 CES2 CFHR1 CFLAR CIAPIN1 CIDEB CILP CKMT1B CLU CNTF CNTNAP2 COL11A2 COL4A5 CORO1C CREBBP | 137 (63 + 71 + 3) (34.0%) | ABHD2 (2.30, 2.58) ADAM10 (2.01) BACH1 (2.09) BAX (2.02) BBC3 (2.35) BCAM (2.00) BIRC2 (2.06) BIRC3 (4.00) BIRC5 (12.70) CCNE1 (3.18) CDKN1A (2.33) CILP (4.39) CNTNAP2 (20.81) CYP3A4 (17.99) DAB2 (2.33) DKK1 (51.55) ETV4 (2.96) FADS1 (2.31, 2.17) FANCC (2.05) FEN1 (2.99, 3.13) FOS (32.01) GDF15 (14.33) GLRX2 (2.53) GSTM3 (2.04) HHEX (3.59) HPCAL1 (2.96) IFI30 (2.79) JUN (2.41) KLK3 (2.11) LANCL1 (2.60) LAPTM4B (3.54, 3.75) MAP2K6 (2.32) | 5.94 | 5.17 | 80 |

| Chemical | Target Genes | Target Genes List | Found Targets | Found Targets List (with fold-changes) | Avg Abs(FC) | Avg Abs(FC) UP-REG | Score |
|---|---|---|---|---|---|---|---|
| | | CTAGE4 CTDSP1 CTH CTNNAL1 CYCS CYP2C9 CYP3A4 D6S2723E DAB2 DDIT3 DDR1 DENND4A DEPDC6 DIABLO DKK1 DMBT1 DPYD DRAP1 DST EDN2 EDNRA EGFR ELMO2 EMP3 ENPP2 EP300 ERBB2 ERCC1 ERCC2 ETV4 F8A3 FADD FADS1 FAM129A FAM13A1 FAM46A FANCC FANCG FAS FASLG FASN FEN1 FGF7 FGF9 FGFR2 FGFR3 FKBP2 FMOD FOS FOSL1 FOXC1 FTLL1 GADD45A GALNT7 GARS GAS1 GCLC GCLM GCNT1 GCNT2 GDF15 GLRX2 GMPPA GOLGA8A GOLGA8B GOLSYN GPAA1 GPX3 GSTM1 GSTM2 GSTM3 GSTO1 GSTP1 GSTT1 GUCY1B3 GUK1 HERV-FRD HHEX HIF1A HLA-A HLA-DPA3 HLA-G HNRNPA1 HPCAL1 HSD17B8 HSPB1 HSPE1 HTRA2 ICAM1 ID4 IFI30 IFITM1 IGFBP3 IGFBP5 IL13RA1 IL1B IL1R1 IL4R IL6 ITGA9 ITGAE ITGB4 ITPA JUN KCNA5 KCNK1 KLF2 KLK1 KLK10 KLK11 KLK12 KLK15 KLK2 KLK3 KLK4 KLK5 KLK6 KLK7 KLK8 KLK9 KRT17 KRT19 KRT4 LANCL1 LAPTM4B LASS4 LEPREL1 LIMCH1 LOH11CR2A LTBP1 M6PRBP1 MACF1 MAD2L2 MAGED2 MAL MAP2K6 MCM2 MED1 MED21 MEST MGMT MLL MMP10 MMP15 MMP16 MMP3 MPO MPP2 MRPS27 MT1A MT1F MT2A MT3 MVP MYC NAB1 NAIP NCOA3 NDUFS8 NEAT1 NEDD9 NMI NMU NOTCH2 NOTCH4 NR1I2 NR4A1 NTHL1 NUDT1 OPTN P4HA2 PAFAH1B3 PAPPA2 PARD6A PARP1 PAX8 PBX1 PCNA PDIA3 PDXK PFDN5 PFKFB4 PFKP PGK1 PHIP PHLDA1 PLP2 PMAIP1 PMPCA PMS2L11 POLA1 POP4 PPIE PPP1R1B PPP3CB PRKCI PRKDC PRNP PRODH PROS1 PSMB10 PTEN PTGS1 PTGS2 PTK2 PXDN QSOX1 RAB40B RAD21 RALB RALBP1 RASSF1 RB1 RBCK1 RBM9 RBP1 RELA RHOC RING1 RNASET2 RNF34 RPL21 RPL36 RPL6 RPS14 RPS18 RPS4Y2 RPS5 RRAGD RUNX3 RXRB SCRN1 SDC2 SERPINB4 SERPINE2 SFN SH2B3 SH3BGRL3 SLC15A1 SLC20A1 SLC29A1 SLC2A1 SLC31A1 SLC39A7 SLC6A12 SLC7A11 SLC7A8 SLPI SNAP29 SNAPC3 SNRPA SOCS1 SOCS2 SOD2 SOD3 SP1 SP100 SP110 SPINT2 SPON1 SPTLC2 STEAP1 STYX SULT1A1 SULT1A2 SWAP70 SYNJ2 TANK TERT TF TFAP2A TFB1M TGFA TGFB1 TLR2 TMSL6 TNF TNFAIP3 TNFSF10 TNFSF13 TP53 TP53I3 TP73 TPI1 TRADD TRAM1 TRAP1 | | MED21 (2.11) MEST (8.01) MMP15 (3.00) MMP16 (3.26) NCOA3 (2.54) NMI (2.13) NMU (2.49) NR4A1 (3.47) NUDT1 (2.01) PDXK (3.48, 2.73, 2.41) PMAIP1 (3.68) PRKCI (2.83, 2.64) PTGS2 (17.97) PXDN (3.61, 4.00) RNASET2 (2.15) RNF34 (2.28) SDC2 (3.25) SLC29A1 (2.36) SP1 (2.15, 2.24) SPON1 (2.57) STEAP1 (2.90, 3.34, 2.83) STYX (2.41) TANK (2.02) TERT (2.54) TP53I3 (3.40) TPI1 (2.88) TRAM1 (2.56) TRIB3 (2.05, 2.13) TYMS (5.32) UPK1B (2.08) VEGFA (2.30, 7.27, 4.15) A2M (−7.98) ABCC5 (−2.30, −2.38) ANXA1 (−2.14) ARHGEF6 (−2.10) ARID5B (−2.58, −2.20, −2.04) BCL2 (−4.42) BTG2 (−2.33) CA2 (−3.62) CDH3 (−4.12) CELSR2 (−2.39) CES2 (−2.61) CIDEB (−2.19) CLU (−8.31) COL4A5 (−2.74) CTNNAL1 (−4.41) CYP2C9 (−2.94) DDR1 (−2.50, −2.46) DMBT1 (−31.82) DPYD (−4.02, −3.55) DST (−3.08, −14.93) EGFR (−3.99) FAM129A (−11.54, −14.34) FGF7 (−6.10, −6.45, −2.30) FGF9 (−2.12) FGFR2 (−15.60, −8.81) FGFR3 (−3.11, −7.43) FMOD (−2.27) FOXC1 (−3.90, −4.46) GAS1 (−2.36) GCLC (−2.59) GCLM (−3.92) GOLGA8A (−3.47, −2.17) GOLSYN (−3.18) GSTM2 (−3.53) HLA-A (−2.18) ID4 (−2.25) ITGA9 (−2.61) KLK10 (−5.32, −12.20) KLK11 (−51.60) KLK12 (−21.92) KRT19 (−2.14) KRT4 (−11.12) LASS4 (−2.24) LIMCH1 (−2.87) LTBP1 (−2.35) MACF1 (−2.02) MAL (−12.81) MMP10 (−62.97) MT3 (−13.83, −2.32) NAIP (−2.67) PBX1 (−3.32, −3.26) PHIP (−2.01) PHLDA1 (−3.12, −2.49) PPP1R1B (−3.30) PTGS1 (−4.87) RRAGD (−2.48) RUNX3 (−4.02) SERPINB4 (−7.72) SLC31A1 (−2.78, −2.75, −2.79) SLPI (−10.90, −12.82) SOD3 (−5.07) SWAP70 (−2.00) TF (−4.25, −4.55) TNFSF10 (−3.01) TUBB2A (−2.05) UCP2 (−2.53) UGT1A6 (−16.01, −24.90) VAV3 (−7.76) WFDC2 (−14.33, −12.71) | | | |

-continued

| Chemical | Target Genes | Target Genes List | Found Targets | Found Targets List (with fold-changes) | Avg Abs(FC) | Avg Abs(FC) UP-REG | Score |
|---|---|---|---|---|---|---|---|
| | | TRIB3 TRIP13 TSPAN12 TUBA1A TUBB2A TXN TXNDC13 TXNRD1 TYMP TYMS UCP2 UGDH UGT1A1 UGT1A3 UGT1A6 UMPS UPK1B USP14 VAPA VAV3 VEGFA VPS52 WDR46 WFDC2 WWC1 XIAP XPA XRCC1 XRCC5 XRCC6 YARS ZFP36L1 ZFP36L2 ZNF192 ZNRD1 | | XPA (−2.62) XRCC1 (−2.80) BCAS4 (2.21, −2.07) CYCS (−2.70, 2.03) PRNP (−4.40, 2.43) | | | |

Accordingly, it can be observed that the drugs used in the two therapeutic lines, which did not provide therapeutic efficacy are associated with low scores, namely 80 for cisplatine, 156 for alimta and 143 for Tarceva. Accordingly, the method of the invention should avoid the choice of such treatments.

Since January 2010, Vinorelbine, associated with a score of 290, has been selected for treating the patient. At the beginning, the patient has a very worsened general status. Three months later, the disease was stable, then progressed. In conclusion, although the drug associated with the best score has not been selected, the selected drug showed efficacy, conferring three months survival.

Example 3

A patient was diagnosed in May 2007 for a primary bronchial adenocarcinoma with bilateral pulmonary metastases and asymptomatic cerebral metastases. A surgical treatment has been carried out in November 2008 and two therapeutic lines have been used, namely thirteen cycles of cisplatin-gemcitabin for the first line and Alimta for the second one. The first line was associated with a partial response followed by a disease progression and the second line was only associated with a disease progression.

A normal bronchial biopsy and a pulmonary metastasis biopsy were carried out and used for mutational analysis by sequencing, CGH, microRNAs analysis and Genome expression analysis.

CGH profile comprised numerous aberrations (loss and gain throughout the genome) demonstrating the tumoral status of the biopsy.

Mutational analysis including the genes as listed in Example 1 did not lead to the identification of any mutation.

Based on Genome Expression analysis, scores have been calculated as detailed in Example 1 and are shown in the following table only for some relevant drugs.

| Chemical | Target Genes | Target Genes List | Found Targets | Found Targets List (with fold-changes) | Avg Abs(FC) | Avg Abs(FC) UP-REG | Score |
|---|---|---|---|---|---|---|---|
| CARBOPLATIN (Paraplatin, Paraplatin-AQ) | 16 | ALB BAX BCL2 BCL2L12 BIRC2 CASP3 CASP9 DCT DPYD ERBB2 FAS PARP1 PCNA PTGS2 RBM17 TYMS | 6 (3 + 3) (37.5%) | ALB (84.71) BAX (2.03) PTGS2 (2.81) CASP3 (−2.56) DPYD (−2.07) FAS (−2.69) | 16.14 | 29.85 | 559 |
| BEVACIZUMAB (Avastin) | 1 | VEGFA | 1 (1 + 0) (100.0%) | VEGFA (3.18, 3.55, 4.81, 3.82) | 3.84 | 3.84 | 384 |
| AFLIBERCEPT (VEGF Trap) | 1 | VEGFA | 1 (1 + 0) (100.0%) | VEGFA (3.18, 3.55, 4.81, 3.82) | 3.84 | 3.84 | 384 |
| CEDIRANIB (Recentin) | 2 | FLT1 FLT4 | 1 (1 + 0) (50.0%) | FLT1 (4.36, 5.59) | 4.98 | 4.98 | 248 |
| AXITINIB | 6 | FLT1 FLT4 KDR KIT PDGFRA PDGFRB | 3 (3 + 0) (50.0%) | FLT1 (4.36, 5.59) PDGFRA (4.21, 3.56) PDGFRB (5.18) | 4.68 | 4.68 | 234 |
| CAMPTOTHECIN | 57 | ABCB1 AGRN ALB ANXA4 BAX BCL2 BID BIRC5 BRCA1 BRCA2 CAB39 CASP2 CASP3 CCNB1 CDK2 CDKN1A CEACAM1 CEBPZ CTSB CYCS DPYD EI24 EP300 EPM2AIP1 FDXR GSTP1 HNRNPC IL1B IL8 JUN LGALS1 MAP2K3 MAP3K5 MAPK9 MAPT MDM2 NCK2 PARP1 PLK3 PPP1R1B PRC1 RAD51 RB1 RBL1 RBL2 SDC1 TAP1 TAX1BP3 THBS1 TNFSF9 TOP1 TP53 TP53I3 TP53TG1 TYMS VEGFA XIAP | 16 (8 + 8) (28.1%) | AGRN (2.26, 2.29, 2.11) ALB (84.71) BAX (2.03) LGALS1 (3.09) PLK3 (2.10) PPP1R1B (5.31) THBS1 (10.46, 9.80) VEGFA (3.18, 3.55, 4.81, 3.82) ABCB1 (−2.74) CASP3 (−2.56) DPYD (−2.07) FDXR (−4.08) GSTP1 (−2.04) MDM2 (−2.46) TAP1 (−2.71) TP53TG1 (−2.28) | 8.40 | 14.18 | 199 |
| VINORELBINE (Navelbine, Navelbine Base) | 7 | CASP3 CDKN2A PTGS2 RALBP1 RBM17 SLC29A1 TUBB2A | 4 (3 + 1) (57.1%) | CDKN2A (9.83, 6.61) PTGS2 (2.81) TUBB2A (2.88) CASP3 (−2.56) | 4.12 | 4.64 | 198 |

-continued

| Chemical | Target Genes | Target Genes List | Found Targets | Found Targets List (with fold-changes) | Avg Abs(FC) | Avg Abs(FC) UP-REG | Score |
|---|---|---|---|---|---|---|---|
| GEMCITABINE (DDFC, DFDC, GEO, Gemcin, Gemcitabina, Gemcitabine, HCl, Gemcitabine hydrochloride, Gemcitabinum, Gemtro, Gemzar) | 158 | AGPAT2 ALDH1A3 ALDH6A1 ANAPC1 ANK3 ANKRD1 ANTXR1 ARF1 ATF3 BAIAP1 BAX BCL2 BCL2L1 BCL2L11 BCL6 BIRC2 BIRC3 BIRC5 BNIP3L C15ORF15 C1ORF144 C4ORF18 CASP3 CCL20 CCND1 CCNG2 CD40 CDA CDH1 CDKN1A CEBPB CKB CLIC4 CMPK COX3 CSRP2 CTHRC1 CXCL1 CXCL2 CXCL3 CYP24A1 DDIT4 DHX9 DLG2 DNCH1 DPYD EDN2 EGFR EGR1 ETV1 EVI2B FBXO25 FGG FOSL2 FXYD3 GAL3ST1 GAS1 GLRX GPC3 GTF2A1 HDAC9 HIF1A HIST1H4B HIST1H4C HOXB2 HSPA1L HSPA5 IFIT1 IL6 INSIG1 IQGAP1 IRAK2 IRF3 ITSN2 JAM3 KCTD12 KLF8 KRT8 LARP5 LIFR LRRC28 LYZ MAF MAGEA10 MAGEC1 MAP17 MARCKS MARS MDM2 MGMT MXI1 MYB NCBP1 NEDD9 NEU1 NFKB2 NFKBIE NNMT NPEPPS NR4A3 NRG1 NRP1 P2RY5 PAQR8 PARP1 PCSK9 PDPK1 PJA2 PLAU PPFIA4 PPP1R15A PSAT1 PTEN PTGS1 PTPN11 RAB8A RBM17 RELA RGS2 RNF149 RPL37 RRAGD RRM1 SAT SCD SLC25A29 SLC29A1 SLC2A14 SLC2A3 SLC43A3 SLITRK2 SPP1 SYNCRIP TCOF1 TERT TGFB2 TNF TNFAIP3 TNFRSF11B TP53 TP53BP1 TP53INP1 TRAF1 TUBE1 TYMP TYMS TYRP1 UBE2C UGGT2 VEGFA VGF VLDLR WBP5 WNT5A XIAP ZNF274 ZNF449 ZNF521 | 48 (31 + 17) (30.4%) | ANTXR1 (2.23, 2.64, 3.53) BAX (2.03) CLIC4 (2.63, 2.54, 2.54) CTHRC1 (19.05) DLG2 (3.80) ETV1 (3.09, 3.19) GAL3ST1 (5.88) GAS1 (2.17) GPC3 (3.00) HOXB2 (2.95, 2.38) IFIT1 (2.11) IL6 (2.67) JAM3 (2.13, 2.01) KLF8 (3.81) KRT8 (2.56, 2.55) MAF (2.66, 2.91) NEDD9 (3.66) NEU1 (2.80) NNMT (3.15) NRP1 (2.03, 3.00, 2.60) PLAU (9.25) RGS2 (3.75) SCD (3.76, 3.04, 3.90) SLC2A3 (4.22, 7.94) SPP1 (70.93) TNFRSF11B (12.11, 8.17) TYRP1 (13.30) VEGFA (3.18, 3.55, 4.81, 3.82) WBP5 (2.13) ZNF274 (3.73) ZNF521 (2.79) ANK3 (−3.59, −3.38, −3.62) BIRC3 (−2.27) CASP3 (−2.56) CCL20 (−10.90) CD40 (−2.36) CXCL1 (−47.43) CXCL2 (−2.14, −5.83) CXCL3 (−4.04) CYP24A1 (−2.10) DPYD (−2.07) FXYD3 (−2.79) HDAC9 (−4.09) LYZ (−7.83) MDM2 (−2.46) MGMT (−2.34) MYB (−8.21) NRG1 (−2.47, −3.36) | 6.60 | 6.60 | 129 |
| CISPLATIN (Abiplatin, Biocisplatinum, Briplatin, Carboquone, Cis Pt II, Cismaplat, Cisplatine, Cisplatyl, Citoplationo, Lederplatin, Neoplatin, Plastin, Platamine, Platiblastin, Platidiam, Platinex, Platinol, Platinol-AQ, Platinoxan, Randa) | 403 | A2M ABCB1 ABCC1 ABCC2 ABCC5 ABHD11 ABHD2 ABR ACSL3 ADAM10 ADFP ADORA2B AHCYL1 AKAP12 AKR1B1 AKT1 AKT2 AKT3 ALB ANXA1 APEX1 ARF6 ARHGEF6 ARID5B ARMCX2 ASS1 ASTN1 ATP6V1G2 AXL B3GALT4 BACH1 BAX BBC3 BCAM BCAS4 BCL2 BCL2L1 BCL2L12 BIRC2 BIRC3 BIRC5 BMP7 BTG2 C11ORF68 C11ORF9 C19ORF2 C4ORF29 C7ORF16 CA2 CALCB CASP2 CASP3 CASP8 CASP9 CAT CAV1 CCDC85B CCNE1 CCNG2 CD151 CD55 CDC40 CDH3 CDKL5 CDKN1A CDKN2AIP CELSR2 CES2 CFHR1 CFLAR CIAPIN1 CIDEB CILP CKMT1B CLU CNTF CNTNAP2 COL11A2 COL4A5 CORO1C CREBBP CTAGE4 CTDSP1 CTH CTNNAL1 CYCS CYP2C9 CYP3A4 D6S2723E DAB2 DDIT3 DDR1 DENND4A DEPDC6 DIABLO DKK1 DMBT1 DPYD DRAP1 DST EDN2 EDNRA EGFR ELMO2 EMP3 ENPP2 EP300 ERBB2 ERCC1 ERCC2 ETV4 F8A3 FADD FADS1 FAM129A FAM13A1 FAM46A FANCC FANCG FAS FASLG FASN FEN1 FGF7 FGF9 FGFR2 FGFR3 FKBP2 FMOD FOS FOSL1 FOXC1 FTLL1 GADD45A GALNT7 GARS GAS1 GCLC GCLM GCNT1 GCNT2 GDF15 GLRX2 GMPPA GOLGA8A GOLGA8B GOLSYN GPAA1 GPX3 GSTM1 GSTM2 GSTM3 GSTO1 GSTP1 GSTT1 GUCY1B3 GUK1 HERV-FRD HHEX HIF1A HLA-A HLA-DPA3 HLA-G HNRNPA1 HPCAL1 HSD17B8 HSPB1 HSPE1 HTRA2 ICAM1 ID4 IFI30 IFITM1 IGFBP3 IGFBP5 IL13RA1 IL1B IL1R1 IL4R IL6 ITGA9 ITGAE ITGB4 ITPA JUN KCNA5 KCNK1 KLF2 KLK1 KLK10 KLK11 | 112 (68 + 43 + 1) (27.8%) | A2M (2.45) ABCC2 (4.03, 3.37) AKAP12 (2.40) AKT3 (3.10) ALB (84.71) BAX (2.03) CA2 (2.50) CCNE1 (3.72) CILP (3.81) COL11A2 (21.07) DAB2 (2.64) DKK1 (6.38) EDNRA (2.53, 2.37) ENPP2 (2.36) ERCC2 (2.03) FADS1 (3.44, 3.92) FANCC (2.22) FASN (2.36) FGF7 (2.19, 3.31, 2.06, 2.66) FMOD (2.38) GARS (2.10) GAS1 (2.17) GCNT1 (2.06) GDF15 (3.10) GPX3 (2.08) GSTM1 (4.71) GSTM3 (5.35, 5.57) GUCY1B3 (2.65) HHEX (2.27) HPCAL1 (2.54) ICAM1 (5.72) ID4 (2.59) IGFBP3 (2.97, 2.56) IGFBP5 (3.91, 2.60, 2.94) IL13RA1 (2.10, 2.42) IL1R1 (2.41, 2.24) IL6 (2.67) ITGA9 (3.20, 4.54) KLK8 (4.87) LIMCH1 (2.71, 2.26) LTBP1 (2.86) MACF1 (3.18, 3.43) MAL (2.83) MEST (5.64) MMP15 (3.05) MMP16 (3.43) NEDD9 (3.66) PAFAH1B3 (2.04) PAX8 (2.17) PFKFB4 (2.76) PPP1R1B (5.31) PRKCI (2.31, 2.39) PRODH (3.77) PTGS2 (2.81) PXDN (10.10, 19.71) SCRN1 (2.76) SDC2 (3.16) SERPINE2 (2.63) SLC39A7 (3.59) SPINT2 (2.47) SPON1 (2.80) | 5.94 | 4.76 | 80 |

-continued

| Chemical | Target Genes | Target Genes List | Found Targets | Found Targets List (with fold-changes) | Avg Abs(FC) | Avg Abs(FC) UP-REG | Score |
|---|---|---|---|---|---|---|---|
| | | KLK12 KLK15 KLK2 KLK3 KLK4 KLK5 KLK6 KLK7 KLK8 KLK9 KRT17 KRT19 KRT4 LANCL1 LAPTM4B LASS4 LEPREL1 LIMCH1 LOH11CR2A LTBP1 M6PRBP1 MACF1 MAD2L2 MAGED2 MAL MAP2K6 MCM2 MED1 MED21 MEST MGMT MLL MMP10 MMP15 MMP16 MMP3 MPO MPP2 MRPS27 MT1A MT1F MT2A MT3 MVP MYC NAB1 NAIP NCOA3 NDUFS8 NEAT1 NEDD9 NMI NMU NOTCH2 NOTCH4 NR1I2 NR4A1 NTHL1 NUDT1 OPTN P4HA2 PAFAH1B3 PAPPA2 PARD6A PARP1 PAX8 PBX1 PCNA PDIA3 PDXK PFDN5 PFKFB4 PFKP PGK1 PHIP PHLDA1 PLP2 PMAIP1 PMPCA PMS2L11 POLA1 POP4 PPIE PPP1R1B PPP3CB PRKCI PRKDC PRNP PRODH PROS1 PSMB10 PTEN PTGS1 PTGS2 PTK2 PXDN QSOX1 RAB40B RAD21 RALB RALBP1 RASSF1 RB1 RBCK1 RBM9 RBP1 RELA RHOC RING1 RNASET2 RNF34 RPL21 RPL36 RPL6 RPS14 RPS18 RPS4Y2 RPS5 RRAGD RUNX3 RXRB SCRN1 SDC2 SERPINB4 SERPINE2 SFN SH2B3 SH3BGRL3 SLC15A1 SLC20A1 SLC29A1 SLC2A1 SLC31A1 SLC39A7 SLC6A12 SLC7A11 SLC7A8 SLPI SNAP29 SNAPC3 SNRPA SOCS1 SOCS2 SOD2 SOD3 SP1 SP100 SP110 SPINT2 SPON1 SPTLC2 STEAP1 STYX SULT1A1 SULT1A2 SWAP70 SYNJ2 TANK TERT TF TFAP2A TFB1M TGFA TGFB1 TLR2 TMSL6 TNF TNFAIP3 TNFSF10 TNFSF13 TP53 TP53I3 TP73 TPI1 TRADD TRAM1 TRAP1 TRIB3 TRIP13 TSPAN12 TUBA1A TUBB2A TXN TXNDC13 TXNRD1 TYMP TYMS UCP2 UGDH UGT1A1 UGT1A3 UGT1A6 UMPS UPK1B USP14 VAPA VAV3 VEGFA VPS52 WDR46 WFDC2 WWC1 XIAP XPA XRCC1 XRCC5 XRCC6 YARS ZFP36L1 ZFP36L2 ZNF192 ZNRD1 | | STYX (2.12) SWAP70 (2.36) TGFB1 (2.40) TRIB3 (8.75) TUBB2A (2.88) VEGFA (3.18, 3.55, 4.81, 3.82) WWC1 (2.43) ABCB1 (−2.74) ABHD2 (−2.82, −2.33, −2.55) ADORA2B (−4.27) BIRC3 (−2.27) CASP3 (−2.56) CES2 (−2.08) CLU (−4.24) COL4A5 (−3.24) DMBT1 (−34.95) DPYD (−2.07) FAS (−2.69) FGFR2 (−4.25, −4.25) FGFR3 (−2.10, −2.89) FOXC1 (−2.51, −3.13) GCLC (−2.03) GCLM (−3.16, −2.98) GOLSYN (−3.36) GSTP1 (−2.04) HLA-A (−2.16, −2.37) HLA-G (−2.84) KLK10 (−3.75, −5.35) KLK11 (−10.49) KLK3 (−9.01) KRT17 (−3.10) KRT4 (−4.61) MGMT (−2.34) MMP10 (−12.00) MT3 (−8.76) NAB1 (−2.03) NEAT1 (−2.29, −2.02) NMU (−7.07) PMAIP1 (−3.07) PSMB10 (−3.25) SERPINB4 (−71.70) SLC31A1 (−2.06) SLPI (−17.09, −28.09) SOD2 (−2.54) TF (−15.98, −17.72) TNFSF10 (−3.33) UGT1A6 (−8.88, −8.56) UPK1B (−28.60) VAV3 (−4.99, −3.12) WFDC2 (−20.20, −15.05) DST (2.30, 2.14, 2.36, −2.86) | | | |
| PEMETREXED (Alimta) | 10 | DHFR FAS FPGS GART GGH RBM17 SLC19A1 TP53 TYMP TYMS | 1 (0 + 1) (10.0%) | FAS (−2.69) | 2.69 | 0.00 | 0 |

First of all, the scores associated with the drugs used in the first and second therapeutic lines are low (Gemcitabin=129; cisplatine=80 and Alimta=0). Those scores are consistent with the observed clinical data.

Figure 5:
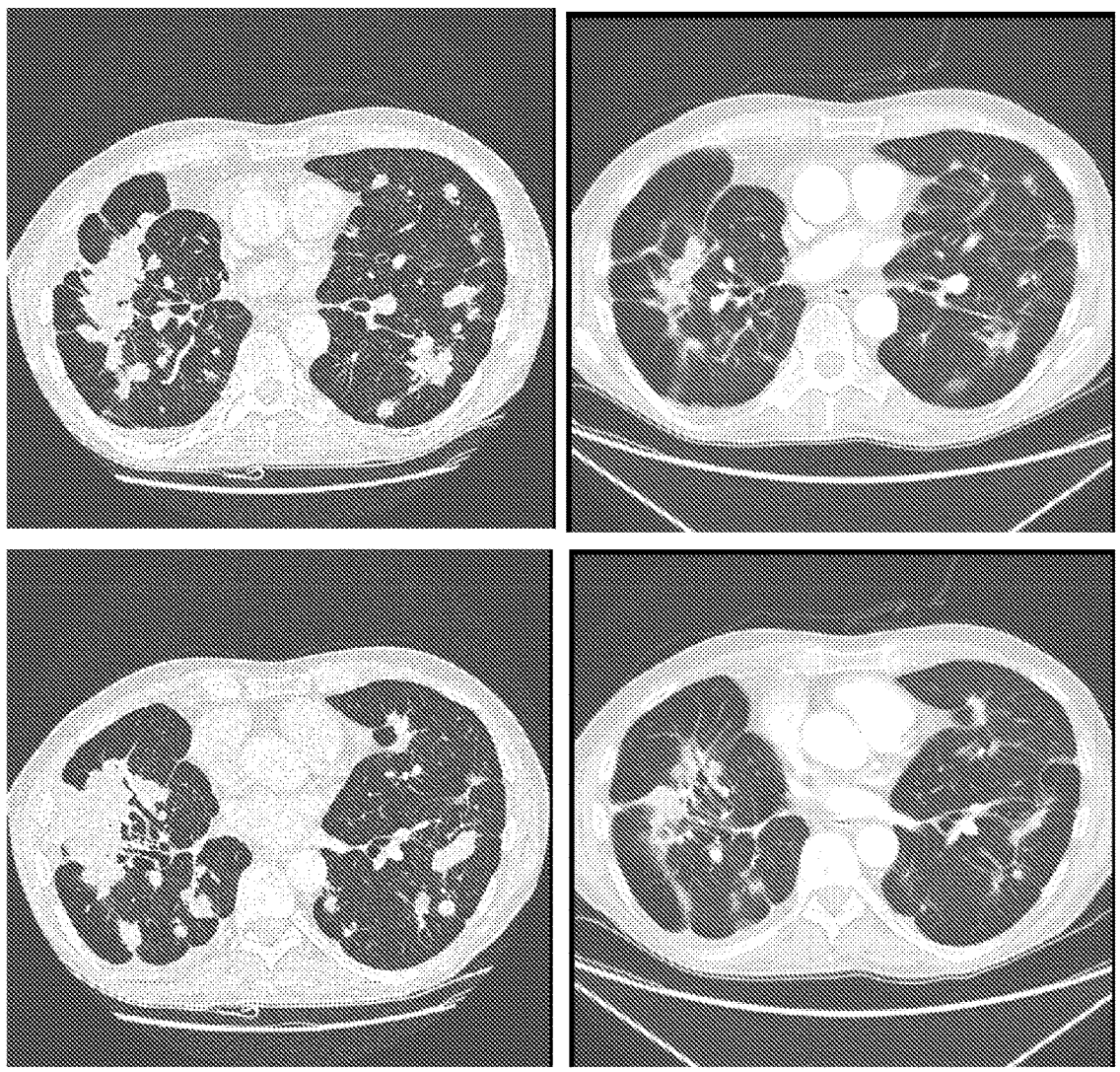
FIG. 5: Thoracic scanners in January and March 2010 of the patient of Example 3.

However, based on this score table, avastin associated with a score of 384 has been selected. The treatment has begun in January 2010 and a major response has been observed after two treatment cycles, as showed with the scanners of FIG. 5. This major response validates the present method and the unquestionable benefit for the patient.

Example 4

The patient was 59 years old. He suffered of a non small cell bronchial carcinoma with adrenal metastases. Two therapeutic lines have been used, namely three cycles of cisplatin-Alimta and three cycles of taxotere-cisplatine-avastin. These therapeutic lines were associated with a first step of stabilization and then a step of disease progression.

Normal and tumoral bronchial biopsies were carried out and used for mutational analysis by sequencing, CGH, microRNAs analysis and Genome expression analysis.

CGH profile is shown in FIG. 6 and comprises chromosomal aberrations in chromosome 11.

Mutational analysis including the genes as listed in Example 1 did not lead to the identification of any mutation.

Based on Genome Expression analysis, scores have been calculated as detailed in Example 1 and are shown in the following table only for some relevant drugs.

| Chemical | Target Genes | Target Genes List | Found Targets |
|---|---|---|---|
| ECTEINASCIDIN 743 (Trabectedin, ET-743, Yondelis) | 4 | CCNA2 CCNB1 CCNB2 E2F1 | 4 (4 + 0) (100.0%) |

-continued

| | | | |
|---|---|---|---|
| GEMTUZUMAB (Mylotarg) | 1 | CD33 | 1 (1 + 0) (100.0%) |
| HYDROXYUREA (Biosupressin, Droxia, Hidrix, Hydrea, Hydreia, Hydura, Hydurea, Litaler, Litalir, Onco-Carbide, Oxyurea, Ureaphil) | 26 | BAX C13ORF34 CASP3 CCNA2 CCNB1 CCND1 CCND2 CCND3 CCNE1 CCNG1 CDC25C CDCA8 CDKN1A CKS2 EDN3 FAS KPNA2 MECOM PRC1 PSRC1 RRM1 RRM2 RUNX1 SNCA TP53 UBE2C | 11 (10 + 1) (42.3%) |
| - - - | - - - | - - - | - - - |
| DOCETAXEL (Taxotere) | 43 | ABCB1 ABCC1 ABCC2 BAX BCL2 BCL2L1 BIRC5 BUB1B CASP3 CCNB1 CFLAR CSF2 CYP19A1 CYP1B1 CYP3A4 DPYD ERBB2 F2R GSTP1 HIF1A HRAS IL6 MAD2L1 MAPK1 MAPK3 MDM2 PARP1 PGR POR PTGS2 RAF1 RB1 SKP2 TNF TNFRSF10B TP53 TUBB TUBB1 TYMP TYMS UMPS VEGFA XIAP | 15 (12 + 3) (34.9%) |
| - - - | - - - | - - - | - - - |
| PEMETREXED (Alimta) | 10 | DHFR FAS FPGS GART GGH RBM17 SLC19A1 TP53 TYMP TYMS | 3 (3 + 0) (30.0%) |
| - - - | - - - | - - - | - - - |
| VINORELBINE (Navelbine, Navelbine Base) | 7 | CASP3 CDKN2A PTGS2 RALBP1 RBM17 SLC29A1 TUBB2A | 2 (2 + 0) (28.6%) |
| - - - | - - - | - - - | - - - |
| CISPLATIN (Abiplatin, Biocisplatinum, Briplatin, Carboquone, Cis Pt II, Cismaplat, Cisplatine, Cisplatyl Citoplationo, Lederplatin, Neoplatin, Plastin, Platamine, Platiblastin, Platidiam, Platinex Platinol Platinol-AQ, Platinoxan, Randa) | 403 | A2M ABCB1 ABCC1 ABCC2 ABCC5 ABHD11 ABHD2 ABR ACSL3 ADAM10 ADFP ADORA2B AHCYL1 AKAP12 AKR1B1 AKT1 AKT2 AKT3 ALB ANXA1 APEX1 ARF6 ARHGEF6 ARID5B ARMCX2 ASS1 ASTN1 ATP6V1G2 AXL B3GALT4 BACH1 BAX BBC3 BCAM BCAS4 BCL2 BCL2L1 BCL2L12 BIRC2 BIRC3 BIRC5 BMP7 BTG2 C11ORF68 C11ORF9 C19ORF2 C4ORF29 C7ORF16 CA2 CALCB CASP2 CASP3 CASP8 CASP9 CAT CAV1 CCDC85B CCNE1 CCNG2 CD151 CD55 CDC40 CDH3 CDKL5 CDKN1A CDKN2AIP CELSR2 CES2 CFHR1 CFLAR CIAPIN1 CIDEB CILP CKMT1B CLU CNTF CNTNAP2 COL11A2 COL4A5 CORO1C CREBBP CTAGE4 CTDSP1 CTH CTNNAL1 CYCS CYP2C9 CYP3A4 D6S2723E DAB2 DDIT3 DDR1 DENND4A DEPDC6 DIABLO DKK1 DMBT1 DPYD DRAP1 DST EDN2 EDNRA EGFR ELMO2 EMP3 ENPP2 EP300 ERBB2 ERCC1 ERCC2 ETV4 F8A3 FADD FADS1 FAM129A FAM13A1 FAM46A FANCC FANCG FAS FASLG FASN FEN1 FGF7 FGF9 FGFR2 FGFR3 FKBP2 FMOD FOS FOSL1 FOXC1 FTLL1 GADD45A GALNT7 GARS GAS1 GCLC GCLM GCNT1 GCNT2 GDF15 GLRX2 GMPPA GOLGA8A GOLGA8B GOLSYN GPAA1 GPX3 GSTM1 GSTM2 GSTM3 GSTO1 GSTP1 GSTT1 GUCY1B3 GUK1 HERV-FRD HHEX HIF1A HLA-A HLA-DPA3 HLA-G HNRNPA1 HPCAL1 HSD17B8 HSPB1 HSPE1 HTRA2 ICAM1 ID4 IFI30 IFITM1 IGFBP3 IGFBP5 IL13RA1 IL1B IL1R1 IL4R IL6 ITGA9 ITGAE ITGB4 ITPA JUN KCNA5 KCNK1 KLF2 KLK1 KLK10 KLK11 KLK12 KLK15 KLK2 KLK3 KLK4 KLK5 KLK6 KLK7 KLK8 KLK9 KRT17 KRT19 KRT4 LANCL1 LAPTM4B LASS4 LEPREL1 LIMCH1 LOH11CR2A LTBP1 M6PRBP1 MACF1 MAD2L2 MAGED2 MAL MAP2K6 MCM2 MED1 MED21 MEST MGMT MLL MMP10 MMP15 MMP16 MMP3 MPO MPP2 MRPS27 MT1A MT1F MT2A MT3 MVP MYC NAB1 NAIP NCOA3 NDUFS8 NEAT1 NEDD9 NMI NMU NOTCH2 NOTCH4 NR1I2 NR4A1 NTHL1 NUDT1 OPTN P4HA2 PAFAH1B3 PAPPA2 PARD6A PARP1 PAX8 PBX1 PCNA PDIA3 PDXK PFDN5 PFKFB4 PFKP PGK1 PHIP | 59 (39 + 19 + 1) (14.6%) |

PHLDA1 PLP2 PMAIP1 PMPCA PMS2L11
POLA1 POP4 PPIE PPP1R1B PPP3CB
PRKCI PRKDC PRNP PRODH PROS1
PSMB10 PTEN PTGS1 PTGS2 PTK2 PXDN
QSOX1 RAB40B RAD21 RALB RALBP1
RASSF1 RB1 RBCK1 RBM9 RBP1 RELA
RHOC RING1 RNASET2 RNF34 RPL21
RPL36 RPL6 RPS14 RPS18 RPS4Y2 RPS5
RRAGD RUNX3 RXRB SCRN1 SDC2
SERPINB4 SERPINE2 SFN SH2B3
SH3BGRL3 SLC15A1 SLC20A1 SLC29A1
SLC2A1 SLC31A1 SLC39A7 SLC6A12
SLC7A11 SLC7A8 SLPI SNAP29 SNAPC3
SNRPA SOCS1 SOCS2 SOD2 SOD3 SP1
SP100 SP110 SPINT2 SPON1 SPTLC2
STEAP1 STYX SULT1A1 SULT1A2
SWAP70 SYNJ2 TANK TERT TF TFAP2A
TFB1M TGFA TGFB1 TLR2 TMSL6 TNF
TNFAIP3 TNFSF10 TNFSF13 TP53 TP53I3
TP73 TPI1 TRADD TRAM1 TRAP1 TRIB3
TRIP13 TSPAN12 TUBA1A TUBB2A TXN
TXNDC13 TXNRD1 TYMP TYMS UCP2
UGDH UGT1A1 UGT1A3 UGT1A6 UMPS
UPK1B USP14 VAPA VAV3 VEGFA VPS52
WDR46 WFDC2 WWC1 XIAP XPA XRCC1
XRCC5 XRCC6 YARS ZFP36L1 ZFP36L2
ZNF192 ZNRD1

| | | | | |
|---|---|---|---|---|
| --- | --- | --- | | --- |
| BEVACIZUMAB (Avastin) | 1 | VEGFA | | 1 (0 + 1) (100.0%) |

| Chemical | Found Targets List (with fold-changes) | Avg Abs(FC) | Avg Abs(FC) UP-REG | Score |
|---|---|---|---|---|
| ECTEINASCIDIN 743 (Trabectedin, ET-743, Yondelis) | CCNA2 (7.13) CCNB1 (4.52) CCNB2 (4.00) E2F1 (4.85) | 5.13 | 5.13 | 512 |
| GEMTUZUMAB (Mylotarg) | CD33 (2.02, 2.63) | 2.33 | 2.33 | 232 |
| HYDROXYUREA (Biosupressin, Droxia, Hidrix, Hydrea, Hydreia, Hydura, Hydurea, Litaler, Litalir, Onco-Carbide, Oxyurea, Ureaphil) | CCNA2 (7.13) CCNB1 (4.52) CCNE1 (2.56) CDCA8 (4.40) CDKN1A (2.35) KPNA2 (2.00) PRC1 (3.28) PSRC1 (2.71) RRM2 (14.29, 5.77) UBE2C (7.67) BAX (−2.32) | 4.45 | 4.67 | 179 |
| --- | --- | --- | --- | --- |
| DOCETAXEL (Taxotere) | ABCC1 (2.14) ABCC2 (2.58, 3.19) BIRC5 (8.83) BUB1B (8.66) CCNB1 (4.52) CYP1B1 (2.39) IL6 (2.79) MAD2L1 (2.68) PTGS2 (3.78, 2.77) SKP2 (2.18) TNFRSF10B (2.35) TYMS (3.72) BAX (−2.32) BCL2 (−2.35) VEGFA (−2.35) | 3.56 | 3.87 | 107 |
| --- | --- | --- | --- | --- |
| PEMETREXED (Alimta) | DHFR (2.02, 2.20, 2.69, 3.12) SLC19A1 (2.59) TYMS (3.72) | 2.94 | 2.94 | 88 |
| --- | --- | --- | --- | --- |
| VINORELBINE (Navelbine, Navelbine Base) | CDKN2A (2.42, 2.51) PTGS2 (3.78, 2.77) | 2.87 | 2.87 | 81 |
| --- | --- | --- | --- | --- |
| CISPLATIN (Abiplatin, Biocisplatinum, | ABCC1 (2.14) ABCC2 (2.58, 3.19) BIRC3 (4.02) BIRC5 | 4.23 | 5.04 | 48 |

| | | | | |
|---|---|---|---|---|
| Briplatin, Carboquone, Cis Pt II, Cismaplat, Cisplatine, Cisplatyl Citoplationo, Lederplatin, Neoplatin, Plastin, Platamine, Platiblastin, Platidiam, Platinex Platinol Platinol-AQ, Platinoxan, Randa) | (8.83) CA2 (2.25) CCNE1 (2.56) CDH3 (2.23) CDKN1A (2.35) CREBBP (2.16) CYP2C9 (2.09) DDIT3 (2.09) DKK1 (14.15) ETV4 (2.22) FADS1 (2.84, 3.87) FEN1 (2.52, 2.70) FGFR3 (2.26, 3.09) ICAM1 (3.90) IGFBP5 (2.04) IL1B (4.60) IL6 (2.79) KRT17 (3.17) MAP2K6 (3.28) MCM2 (3.84) MEST (2.74) MMP10 (70.58) MYC (2.42) PAFAH1B3 (2.10) PHLDA1 (2.20) PTGS2 (3.78, 2.77) PXDN (2.31) SERPINB4 (2.63) SFN (2.66) SLC7A11 (2.22) SOD2 (3.28) SPON1 (2.86) TRIB3 (6.70) TXNRD1 (2.49) TYMS (3.72) UGT1A6 (2.26, 2.11) BAX (−2.32) BBC3 (−2.27) BCAM (−2.07) BCL2 (−2.35) CASP8 (−3.17) CD55 (−4.47) CILP (−2.53) FOS (−2.24) KLK3 (−2.46) KRT4 (−4.87) LEPREL1 (−2.15) LIMCH1 (−2.07) MLL (−2.34) PRNP (−2.27) PTGS1 (−2.24) SLPI (−2.68, −2.32) SOD3 (−2.54) SP100 (−2.51, −2.24) VEGFA (−2.35) DST (−3.26, 3.55) | | | |
| --- | --- | --- | --- | --- |
| BEVACIZUMAB (Avastin) | VEGFA (−2.35) | 2.35 | 0.00 | 0 |

Accordingly, the following scores are associated with the drugs of the first and second therapeutic lines: cisplatine (48), Alimta (88), taxotere (107) and avastin (0). Those scores are consistent with the clinical data.

However, other drugs are associated with better scores, for instance Trabectedin (512), Gemtuzumab (232) and hydroxyuea (179).

Example 5

The patient suffered of a rhabdomyosarcoma with pulmonary metastases, proving that the present method is efficient to predict the therapeutic efficacy in any type of tumors. This is an evolutive metastatic disease derived from a fibromixoid sarcoma of a buttock muscle. This initial tumor has been resected by curative surgery in 2006. Subsequently, the patient developed pleural mesothelial metastases in 2007. After six cycles of treatment with a combination of Alimta and cisplatine, with a really poor response, the patient was subjected to a pleuralectomy. A novel pulmonary metastatic lesion was then detected with complex location prohibiting any surgery.

Normal muscle biopsy and pulmonary metastasis biopsy were carried out and used for mutational analysis by sequencing, CGH and Genome expression analysis.

CGH profile showed an important amplification of chromosome 16. It corresponds to an amplification of the PDGA locus.

Mutational analysis including the genes as listed in Example 1 did not lead to the identification of any mutation.

Based on Genome Expression analysis, scores have been calculated as detailed in Example 1 and are shown in the following table only for some relevant drugs.

| Chemical | Target Genes | Target Genes List | Found Targets | Found Targets List (with fold-changes) | Avg Abs(FC) | Avg Abs(FC) UP-REG | Score |
|---|---|---|---|---|---|---|---|
| VINORELBINE (Navelbine, Navelbine Base) | 6 | CDKN2A PTGS2 RALBP1 RBM17 SLC29A1 TUBB2A | 1 (1 + 0) (16.7%) | CDKN2A (48.68) | 48.68 | 48.68 | 811 |
| TEGAFUR (UFT) | 5 | CDA CYP2A6 DPYD TP53 TYMS | 1 (1 + 0) (20.0%) | TYMS (16.61) | 16.61 | 16.61 | 332 |
| NILOTINIB (Ketek) | 5 | ABL1 BCR KIT PDGFRA PDGFRB | 2 (2 + 0) (40.0%) | BCR (5.91) PDGFRA (11.97, 10.80, 8.13) | 8.10 | 8.10 | 324 |

Remarkably, Nilotinib is associated with a high score of 324 and is known to be active on the pathway of PDGFRA and PDGFRB. Accordingly, the inventors studied more precisely the PDGF pathway and obtained the following results.

| Primary seq. name | Sequence Description | Fold Change | Intensity 1 | Intensity 2 | Accession # |
|---|---|---|---|---|---|
| PDGFD | Platelet derived growth factor D | 18.6 | 114.8 | 2142.4 | NM_025208 |
| PDGFRA | Platelet derived growth factor receptor, alpha | 12.0 | 2072.6 | 24849.8 | NM_006206 |
| PDGFRA | Platelet derived growth factor receptor, alpha | 10.8 | 819.6 | 8964.0 | AA559881 |
| PDGFRA | Platelet derived growth factor receptor, alpha | 8.1 | 21.3 | 182.3 | BC015186 |
| PDGFA | Platelet derived growth factor alpha | 7.7 | 591.2 | 4576.5 | NM_002607 |
| PDGFRL | Platelet derived growth factor receptor like | 4.7 | 5397.2 | 25269.9 | NM_006207 |
| PDGFRB | Platelet derived growth factor receptor beta | 3.2 | 3327.0 | 10558.3 | NM_002609 |
| PDGFC | Platelet derived growth factor C | 1.1 | 23.1 | 23.7 | NM_016205 |
| PDGFC | Platelet derived growth factor C | −1.6 | 1028.7 | 615.7 | NM_016205 |
| PDGFB | Platelet derived growth factor beta | −3.7 | 375.2 | 101.8 | NM_002608 |

A very significant activation can be observed.

CGH and Gene expression profiles corroborate to designate the PDGF pathway as an important driver of tumorogenesis for this lesion. Indeed, PDGF D is overexpressed 18 fold in tumor versus noram tissue and will activate receptor beta-beta. It is worthwhile to mention that PDGFRB is also overexpressed 3 fold. PDFGA is overexpressed 8 fold and receptor PDGFRA is overexpressed 10 fold.

Taken together, Nilotinib appears a good candidate of targeted therapies because it inhibits both receptors.

The patient is awaiting for regulatory authorization for Nilotinib treatment. His attending physician acknowledged this therapeutic choice.

In conclusion, the studied patients were all in therapeutic failure. For all of them, there was no more therapeutic choice, and their general status was prohibiting entering into clinical trials. Based upon written consentment and upon request of oncology doctors, this method was applied. The present method allows the association of low scores for the drugs used in the previous therapeutic lines, illustrating the good correlation between low scores and therapeutic efficiency. Retrospectively, experts may envision that use of inefficient drugs may have been avoided if such strategy would have been applied, saving time for the patient. It is important to note that the studied patients showed quite unique profiles, proving the potency of the concept for personalized medicine. Method can apply to any type of tumors as far as normal cells and tumoral cells of same histologic type can be compared for a patient. Another advantage is that the method can provide a solution with potential therapeutic benefit for all patients, whereas current methods based on companion tests can apply only for limited number of patients which harbour a given abnormality.

TABLE 1

| Molecule | RefSeq | Description | Symbol | PMID | Interaction |
|---|---|---|---|---|---|
| METHOTREXATE | NM_000927 | ATP-binding cassette, sub-family B (MDR/TAP), member 1 | ABCB1 | 12576456, 15239124 | drug efflux |
| METHOTREXATE | NM_004996; NM_019862; NM_019898; NM_019899; NM_019900 | ATP-binding cassette, sub-family C (CFTR/MRP), member 1 | ABCC1 | 15718312 | drug efflux |
| METHOTREXATE | NM_000392 | ATP-binding cassette, sub-family C (CFTR/MRP), member 2 | ABCC2 | 11500505, 15864128 | drug efflux |
| METHOTREXATE | NM_001105515; NM_005845 | ATP-binding cassette, sub-family C (CFTR/MRP), member 4 | ABCC4 | 15454390 | drug efflux |
| METHOTREXATE | NM_004827 | ATP-binding cassette, sub-family G (WHITE), member 2 | ABCG2 | 17032904 | drug efflux |
| METHOTREXATE | NM_000477 | albumin | ALB | — | used as drug carrier |
| METHOTREXATE | NM_001631 | alkaline phosphatase, intestinal | ALPI | 16598758 | mesure drug toxicity |
| METHOTREXATE | NM_004044 | 5-aminoimidazole-4-carboxamide ribonucleotide formyltransferase/IMP cyclohydrolase | ATIC | 17410198 | target |
| METHOTREXATE | NM_000616 | CD4 molecule | CD4 | 15476228 | altered by MTX |
| METHOTREXATE | NM_001040059; NM_001251 | CD68 molecule | CD68 | 15476228 | altered by MTX |
| METHOTREXATE | NM_001145873; NM_001768; NM_171827 | CD8a molecule | CD8A | 15476228 | altered by MTX |
| METHOTREXATE | NM_017460 | cytochrome P450, family 3, subfamily A, polypeptide 4 | CYP3A4 | 12065438, 16837568 | drug metabolism |
| METHOTREXATE | NM_000791 | dihydrofolate reductase | DHFR | 14679136 | resistance |
| METHOTREXATE | NM_012242 | dickkopf homolog 1 (Xenopus laevis) | DKK1 | 17320366 | unrelated |
| METHOTREXATE | NM_000561; NM_146421 | glutathione S-transferase mu 1 | GSTM1 | 15713801 | hepatotoxicity |
| METHOTREXATE | NM_000201 | intercellular adhesion molecule 1 | ICAM1 | 15476228 | altered by MTX |
| METHOTREXATE | NM_000584 | interleukin 8 | IL8 | 15476228 | altered by MTX |
| METHOTREXATE | NM_002422 | matrix metallopeptidase 3 (stromelysin 1, progelatinase) | MMP3 | 15476228 | altered by MTX |
| METHOTREXATE | NM_005957 | 5,10-methylenetetrahydrofolate reductase (NADPH) | MTHFR | 17488658 | polymorphisms |
| METHOTREXATE | NM_000254 | 5-methyltetrahydrofolate-homocysteine methyltransferase | MTR | 16598758 | polymorphisms |
| METHOTREXATE | NM_000662 | N-acetyltransferase 1 (arylamine N-acetyltransferase) | NAT1 | 16003948 | target |
| METHOTREXATE | NM_003889; NM_022002; NM_033013 | nuclear receptor subfamily 1, group I, member 2 | NR1I2 | 12065438 | resistance |
| METHOTREXATE | NM_002539 | ornithine decarboxylase 1 | ODC1 | 16598758 | apoptosis |
| METHOTREXATE | NM_001618 | poly (ADP-ribose) polymerase 1 | PARP1 | 17286800 | marker |
| METHOTREXATE | NM_003981; NM_199413; NM_199414 | protein regulator of cytokinesis 1 | PRC1 | 17374387 | resistance |
| METHOTREXATE | NM_000321 | retinoblastoma 1 | RB1 | 12972956, 14534726, 14679136 | altered by MTX |
| METHOTREXATE | NM_000450 | selectin E | SELE | 15476228 | altered by MTX |
| METHOTREXATE | NM_194255 | solute carrier family 19 (folate transporter), member 1 | SLC19A1 | 14679136, 16505119, 17034785, 17410198 | drug uptake |
| METHOTREXATE | NM_080669 | solute carrier family 46 (folate transporter), member 1 | SLC46A1 | 17475902 | drug uptake |
| METHOTREXATE | NM_001001522; NM_003186 | transgelin | TAGLN | 17320366 | unrelated |
| METHOTREXATE | NM_003254 | TIMP metallopeptidase inhibitor 1 | TIMP1 | 15476228 | altered by MTX |
| METHOTREXATE | NM_001071 | thymidylate synthetase | TYMS | 15713801, 17410198 | resistance |
| METHOTREXATE | NM_007019; NM_181799; NM_181800; NM_181801; NM_181802; NM_181803 | ubiquitin-conjugating enzyme E2C | UBE2C | 17374387 | |
| METHOTREXATE | NM_000376; NM_001017535 | vitamin D (1,25-dihydroxyvitamin D3) receptor | VDR | 15713801 | |
| METHOTREXATE | NM_003882; NM_080838 | WNT1 inducible signaling pathway protein 1 | WISP1 | 17320366 | unrelated |

TABLE 1-continued

| Molecule | RefSeq | Description | Symbol | PMID | Interaction |
|---|---|---|---|---|---|
| METHOTREXATE | NM_003392 | wingless-type MMTV integration site family, member 5A | WNT5A | 17320366 | unrelated |
| PEMETREXED | NM_000791 | dihydrofolate reductase | DHFR | — | target |
| PEMETREXED | NM_001018078; NM_004957 | folylpolyglutamate synthase | FPGS | 17575230 | drug activation |
| PEMETREXED | NM_000819; NM_001136005; NM_001136006; NM_175085 | phosphoribosylglycinamide formyltransferase, phosphoribosylglycinamide synthetase, phosphoribosylaminoimidazole synthetase | GART | — | target |
| PEMETREXED | NM_003878 | gamma-glutamyl hydrolase (conjugase, folylpolygammaglutamyl hydrolase) | GGH | 17575230 | |
| PEMETREXED | NM_001145547; NM_032905 | RNA binding motif protein 17 | RBM17 | 16061639 | resistance |
| PEMETREXED | NM_194255 | solute carrier family 19 (folate transporter), member 1 | SLC19A1 | 16505119 | drug uptake |
| PEMETREXED | NM_001113755; NM_001113756; NM_001953 | thymidine phosphorylase | TYMP | 17575230 | resistance |
| PEMETREXED | NM_001071 | thymidylate synthetase | TYMS | — | unrelated |
| PEMETREXED | NM_000022 | adenosine deaminase | ADA | — | resistance |
| FLUDARABINE | NM_001014431; NM_001014432; NM_005163 | v-akt murine thymoma viral oncogene homolog 1 | AKT1 | 15059916; 15213310 | |
| FLUDARABINE | NM_001668; NM_178426; NM_178427 | aryl hydrocarbon receptor nuclear translocator | ARNT | 15213310 | |
| FLUDARABINE | NM_001127240; NM_001127241; NM_001127242; NM_014417 | BCL2 binding component 3 | BBC3 | 16439685 | |
| FLUDARABINE | NM_000633; NM_000657 | B-cell CLL/lymphoma 2 | BCL2 | — | |
| FLUDARABINE | NM_004346; NM_032991 | caspase 3, apoptosis-related cysteine peptidase | CASP3 | 11675354 | |
| FLUDARABINE | NM_001080124; NM_001080125; NM_001228; NM_033355; NM_033356; NM_033358 | caspase 8, apoptosis-related cysteine peptidase | CASP8 | 11675354 | |
| FLUDARABINE | NM_001237 | cyclin A2 | CCNA2 | 15059916 | altered by F-ara-A |
| FLUDARABINE | NM_053056 | cyclin D1 | CCND1 | 15059916 | |
| FLUDARABINE | NM_001238; NM_057182 | cyclin E1 | CCNE1 | 15059916 | |
| FLUDARABINE | NM_000389; NM_078467 | cyclin-dependent kinase inhibitor 1A (p21, Cip1) | CDKN1A | 16439685, 16 | altered by F-ara-A |
| FLUDARABINE | NM_004064 | cyclin-dependent kinase inhibitor 1B (p27, Kip1) | CDKN1B | 15059916 | |
| FLUDARABINE | NM_018947 | cytochrome c, somatic | CYCS | 15059916 | death pathway |
| FLUDARABINE | NM_019887; NM_138929 | diablo homolog (Drosophila) | DIABLO | 15059916 | death pathway |
| FLUDARABINE | — | | ERK | 15059916 | resistance |
| FLUDARABINE | NM_000043; NM_152871; NM_152872; NM_152873; NM_152874; NM_152875; NM_152876; NM_152877 | Fas (TNF receptor superfamily, member 6) | FAS | 11675354 | |
| FLUDARABINE | NM_004864 | growth differentiation factor 15 | GDF15 | 16439677 | altered by F-ara-A |
| FLUDARABINE | NM_001530; NM_181054 | hypoxia inducible factor 1, alpha subunit (basic helix-loop-helix transcription factor) | HIF1A | 15213310 | |
| FLUDARABINE | NM_003493 | histone cluster 3, H3 | HIST3H3 | 15059916 | unrelated |
| FLUDARABINE | NM_175054 | histone cluster 4, H4 | HIST4H4 | 15059916 | unrelated |
| FLUDARABINE | NM_002755 | mitogen-activated protein kinase kinase 1 | MAP2K1 | 15059916 | resistance |
| FLUDARABINE | NM_030662 | mitogen-activated protein kinase kinase 2 | MAP2K2 | 15059916 | |
| FLUDARABINE | NM_002745; NM_138957 | mitogen-activated protein kinase 1 | MAPK1 | 15213310 | resistance |
| FLUDARABINE | NM_001040056; NM_001109891; NM_002746 | mitogen-activated protein kinase 3 | MAPK3 | 15213310 | resistance |
| FLUDARABINE | NM_021960; NM_182763 | myeloid cell leukemia sequence 1 (BCL2-related) | MCL1 | 15059916 | resistance |
| FLUDARABINE | NM_002592; NM_182649 | proliferating cell nuclear antigen | PCNA | 16439677 | |
| FLUDARABINE | — | | PDCD8 | 15059916 | |
| FLUDARABINE | NM_016937 | polymerase (DNA directed), alpha 1, catalytic subunit | POLA1 | — | target |
| FLUDARABINE | NM_001033 | ribonucleotide reductase M1 | RRM1 | — | target |
| FLUDARABINE | NM_007315; NM_139266 | signal transducer and activator of transcription 1, 91 kDa | STAT1 | — | altered by F-ara-A |

TABLE 1-continued

| Molecule | RefSeq | Description | Symbol | PMID | Interaction |
|---|---|---|---|---|---|
| FLUDARABINE | NM_003844 | tumor necrosis factor receptor superfamily, member 10a | TNFRSF10A | 14614459 | |
| FLUDARABINE | NM_003842; NM_147187 | tumor necrosis factor receptor superfamily, member 10b | TNFRSF10B | 14614459, 18092340 | |
| FLUDARABINE | NM_000546; NM_001126112; NM_001126113; NM_001126114; NM_001126115; NM_001126116; NM_001126117 | tumor protein p53 | TP53 | 16439677, 17226861, 18092340 | |
| FLUDARABINE | NM_001025366; NM_001025367; NM_001025368; NM_001025369; NM_001025370; NM_001033756; NM_003376 | vascular endothelial growth factor A | VEGFA | 15213310 | altered by F-ara-A |
| FLUDARABINE | NM_001167 | X-linked inhibitor of apoptosis | XLAP | 15059916 | altered by F-ara-A |
| FLUDARABINE | NM_022470; NM_152240 | zinc finger, matrin type 3 | ZMAT3 | 16439685 | |
| FLUOROURACIL | NM_000927 | ATP-binding cassette, sub-family B (MDR/TAP), member 1 | ABCB1 | 12576456, 15239124 | resistance |
| FLUOROURACIL | NM_004996; NM_019862; NM_019898; NM_019899; NM_019900 | ATP-binding cassette, sub-family C (CFTR/MRP), member 1 | ABCC1 | 12576456 | resistance |
| FLUOROURACIL | NM_032583; NM_033151; NM_145186 | ATP-binding cassette, sub-family C (CFTR/MRP), member 11 | ABCC11 | 18310281 | |
| FLUOROURACIL | NM_001023587; NM_005688 | ATP-binding cassette, sub-family C (CFTR/MRP), member 5 | ABCC5 | 19077464 | resistance |
| FLUOROURACIL | NM_004827 | ATP-binding cassette, sub-family G (WHITE), member 2 | ABCG2 | 12576456 | |
| FLUOROURACIL | NM_001608 | acyl-Coenzyme A dehydrogenase, long chain | ACADL | 15585135 | |
| FLUOROURACIL | NM_001116 | adenylate cyclase 9 | ADCY9 | 19219653 | |
| FLUOROURACIL | NM_001126 | adenylosuccinate synthase | ADSS | 15585135 | |
| FLUOROURACIL | NM_001130846; NM_001130847; NM_004208; NM_145812; NM_145813 | apoptosis-inducing factor, mitochondrion-associated, 1 | AIFM1 | 16168113 | death pathway |
| FLUOROURACIL | NM_001014431; NM_001014432; NM_005163 | v-akt murine thymoma viral oncogene homolog 1 | AKT1 | 18794807 | |
| FLUOROURACIL | NM_001144 | autocrine motility factor receptor | AMFR | 16896004 | |
| FLUOROURACIL | NM_004037; NM_139156; NM_203404 | adenosine monophosphate deaminase 2 (isoform L) | AMPD2 | 19219653 | |
| FLUOROURACIL | NM_000481 | aminomethyltransferase | AMT | 15585135 | |
| FLUOROURACIL | NM_012098 | angiopoietin-like 2 | ANGPTL2 | 17327601 | altered by 5FU |
| FLUOROURACIL | NM_001657 | amphiregulin | AREG | 15067352 | sensitivity |
| FLUOROURACIL | NM_001024226; NM_001024227; NM_001024228; NM_001658 | ADP-ribosylation factor 1 | ARF1 | 18927307 | |
| FLUOROURACIL | NM_001697 | ATP synthase, H+ transporting, mitochondrial F1 complex, O subunit | ATP5O | 17327601 | sensitivity |
| FLUOROURACIL | NM_000053; NM_001005918 | ATPase, Cu++ transporting, beta polypeptide | ATP7B | 18593893 | |
| FLUOROURACIL | NM_001188 | BCL2-antagonist/killer 1 | BAK1 | 18593893 | |
| FLUOROURACIL | NM_003658 | BARX homeobox 2 | BARX2 | 15585135 | |
| FLUOROURACIL | NM_004324; NM_138761; NM_138765 | BCL2-associated X protein | BAX | 11062132, 15986848, 15996812, 16168113, 18834353, 19015929 | death pathway |
| FLUOROURACIL | NM_033028 | Bardet-Biedl syndrome 4 | BBS4 | 16896004 | |
| FLUOROURACIL | NM_000633; NM_000657 | B-cell CLL/lymphoma 2 | BCL2 | 14503796, 15940066, 15996812, 18949393, 19015929, 19084572 | resistance |
| FLUOROURACIL | NM_001040668; NM_138639 | BCL2-like 12 (proline rich) | BCL2L12 | 19015929 | |
| FLUOROURACIL | NM_004051; NM_203314; NM_203315 | 3-hydroxybutyrate dehydrogenase, type 1 | BDH1 | 15585135 | |
| FLUOROURACIL | NM_003766 | beclin 1, autophagy related | BECN1 | 16896004 | altered by 5FU |
| FLUOROURACIL | NM_001012270; NM_001012271; NM_001168 | baculoviral IAP repeat-containing 5 | BIRC5 | 15067352, 18714155 | resistance |
| FLUOROURACIL | NM_016252 | baculoviral IAP repeat-containing 6 | BIRC6 | 18239605 | |
| FLUOROURACIL | NM_004052 | BCL2/adenovirus E1B 19 kDa interacting protein 3 | BNIP3 | 15067352 | sensitivity |

TABLE 1-continued

| Molecule | RefSeq | Description | Symbol | PMID | Interaction |
|---|---|---|---|---|---|
| FLUOROURACIL | NM_004331 | BCL2/adenovirus E1B 19 kDa interacting protein 3-like | BNIP3L | 15067352 | sensitivity |
| FLUOROURACIL | NM_033030; NM_197970 | bol, boule-like (Drosophila) | BOLL | 17327601 | |
| FLUOROURACIL | NM_001130914; NM_006806 | BTG family, member 3 | BTG3 | 16896004 | |
| FLUOROURACIL | NM_001007793; NM_004725 | budding uninhibited by benzimidazoles 3 homolog (yeast) | BUB3 | 15585135 | altered by 5FU |
| FLUOROURACIL | — | | C13ORF34 | 17374387 | |
| FLUOROURACIL | NM_001218; NM_206925 | carbonic anhydrase XII | CA12 | 16896004 | |
| FLUOROURACIL | NM_001024649; NM_001746 | calnexin | CANX | 18678097 | |
| FLUOROURACIL | NM_032982; NM_032983 | caspase 2, apoptosis-related cysteine peptidase | CASP2 | 14757846 | death pathway |
| FLUOROURACIL | NM_004346; NM_032991 | caspase 3, apoptosis-related cysteine peptidase | CASP3 | 12414664, 14503796, 18608205, 18772588, 19084572 | death pathway |
| FLUOROURACIL | NM_001227; NM_033338; NM_033339; NM_033340 | caspase 7, apoptosis-related cysteine peptidase | CASP7 | 16168113 | death pathway |
| FLUOROURACIL | NM_001080124; NM_001080125; NM_001228; NM_033355; NM_033356; NM_033358 | caspase 8, apoptosis-related cysteine peptidase | CASP8 | 12414664, 18830594, 15585135, 16168113 | death pathway |
| FLUOROURACIL | NM_001229; NM_032996 | caspase 9, apoptosis-related cysteine peptidase | CASP9 | 12414664, 15996812, 16168113, 19015929 | death pathway |
| FLUOROURACIL | NM_001237 | cyclin A2 | CCNA2 | 18383818 | |
| FLUOROURACIL | NM_053056 | cyclin D1 | CCND1 | 18930000 | |
| FLUOROURACIL | NM_001136017; NM_001136125; NM_001136126; NM_001760 | cyclin D3 | CCND3 | 15067352, 18383818 | resistance |
| FLUOROURACIL | NM_001238; NM_057182 | cyclin E1 | CCNE1 | 18930000 | resistance |
| FLUOROURACIL | NM_057749 | cyclin E2 | CCNE2 | 15067352 | |
| FLUOROURACIL | NM_001761 | cyclin F | CCNF | 15067352 | resistance |
| FLUOROURACIL | NM_004354 | cyclin G2 | CCNG2 | 15067352, 18754885 | sensitivity |
| FLUOROURACIL | NM_001790; NM_022809 | cell division cycle 25 homolog C (S. pombe) | CDC25C | 19074854 | |
| FLUOROURACIL | NM_018101 | cell division cycle associated 8 | CDCA8 | 17374387 | |
| FLUOROURACIL | NM_001798; NM_052827 | cyclin-dependent kinase 2 | CDK2 | 18383818 | |
| FLUOROURACIL | NM_000389; NM_078467 | cyclin-dependent kinase inhibitor 1A (p21, Cip1) | CDKN1A | 15067352, 16168113, 18834353 | sensitivity |
| FLUOROURACIL | NM_004064 | cyclin-dependent kinase inhibitor 1B (p27, Kip1) | CDKN1B | 18930000 | |
| FLUOROURACIL | NM_000076; NM_001122630; NM_001122631 | cyclin-dependent kinase inhibitor 1C (p57, Kip2) | CDKN1C | 15067352 | sensitivity |
| FLUOROURACIL | NM_001114121; NM_001114122; NM_001274 | CHK1 checkpoint homolog (S. pombe) | CHEK1 | 18698031 | |
| FLUOROURACIL | NM_020313 | cytokine induced apoptosis inhibitor 1 | CIAPIN1 | 18389626 | |
| FLUOROURACIL | NM_014430 | cell death-inducing DFFA-like effector b | CIDEB | 15585135 | altered by 5FU |
| FLUOROURACIL | NM_001827 | CDC28 protein kinase regulatory subunit 2 | CKS2 | 17374387 | |
| FLUOROURACIL | NM_004859 | clathrin, heavy chain (Hc) | CLTC | 18927307 | |
| FLUOROURACIL | NM_001083914; NM_001329; NM_022802 | C-terminal binding protein 2 | CTBP2 | 18927307 | |
| FLUOROURACIL | NM_001332 | catenin (cadherin-associated protein), delta 2 (neural plakophilin-related arm-repeat protein) | CTNND2 | 16896004 | |
| FLUOROURACIL | NM_001905 | CTP synthase | CTPS | 19219653 | |
| FLUOROURACIL | NM_005231; NM_138565 | cortactin | CTTN | 15585135 | altered by 5FU |
| FLUOROURACIL | NM_000762 | cytochrome P450, family 2, subfamily A, polypeptide 6 | CYP2A6 | 11376561 | |
| FLUOROURACIL | NM_001554 | cysteine-rich, angiogenic inducer, 61 | CYR61 | 15067352 | resistance |
| FLUOROURACIL | NM_001098424; NM_004087 | discs, large homolog 1 (Drosophila) | DLG1 | 18927307 | |

TABLE 1-continued

| Molecule | RefSeq | Description | Symbol | PMID | Interaction |
|---|---|---|---|---|---|
| FLUOROURACIL | NM_000110 | dihydropyrimidine dehydrogenase | DPYD | 15239142, 15737843, 15858133, 15930747, 18600527, 16761622, 18383874, 18443386, 18443386, 18299612, 18986760, 18846242, 19093184, 19104657, 19105824, 19219653 | drug metabolism |
| FLUOROURACIL | NM_000798 | dopamine receptor D5 | DRD5 | 17327601 | drug |
| FLUOROURACIL | NM_012145 | deoxythymidylate kinase (thymidylate kinase) | DTYMK | 15067352 | metabolism |
| FLUOROURACIL | NM_001025248; NM_001025249; NM_001948 | deoxyuridine triphosphatase | DUT | 19015155 | sensitivity |
| FLUOROURACIL | NM_001949 | E2F transcription factor 3 | E2F3 | 16896004 | resistance |
| FLUOROURACIL | NM_005228; NM_201282; NM_201283; NM_201284 | epidermal growth factor receptor (erythroblastic leukemia viral (v-erb-b) oncogene homolog, avian) | EGFR | 15723263, 15737843, 15981280, 16098254, 18794807, 19217205 | |
| FLUOROURACIL | NM_001964 | early growth response 1 | EGR1 | 18757417 | |
| FLUOROURACIL | NM_014239 | eukaryotic translation initiation factor 2B, subunit 2 beta, 39 kDa | EIF2B2 | 15585135 | |
| FLUOROURACIL | — | | EIF3S3 | 15585135 | |
| FLUOROURACIL | NM_012155 | echinoderm microtubule associated protein like 2 | EML2 | 17327601 | |
| FLUOROURACIL | NM_001126123; NM_017512; NM_202758 | enolase superfamily member 1 | ENOSF1 | 18357371 | |
| FLUOROURACIL | NM_001098175; NM_001776 | ectonucleoside triphosphate diphosphohydrolase 1 | ENTPD1 | 19219653 | |
| FLUOROURACIL | NM_001005862; NM_004448 | v-erb-b2 erythroblastic leukemia viral oncogene homolog 2, neuro/glioblastoma derived oncogene homolog (avian) | ERBB2 | 15737843, 15940066, 18337622 | resistance |
| FLUOROURACIL | NM_001042599; NM_005235 | v-erb-a erythroblastic leukemia viral oncogene homolog 4 (avian) | ERBB4 | 16896004 | |
| FLUOROURACIL | NM_001983; NM_202001 | excision repair cross-complementing rodent repair deficiency, complementation group 1 (includes overlapping antisense sequence) | ERCC1 | 15737843, 17401013, 18448328, 15213713 | resistance |
| FLUOROURACIL | NM_000400; NM_001130867 | excision repair cross-complementing rodent repair deficiency, complementation group 2 | ERCC2 | 15213713, 17401013 | |
| FLUOROURACIL | NM_001034025; NM_006817 | endoplasmic reticulum protein 29 | ERP29 | 15585135 | |
| FLUOROURACIL | NM_001001998; NM_002685 | exosome component 10 | EXOSC10 | 18567802 | |
| FLUOROURACIL | NM_001993 | coagulation factor III (thromboplastin, tissue factor) | F3 | 15067352 | resistance |
| FLUOROURACIL | NM_000132; NM_019863 | coagulation factor VIII, procoagulant component | F8 | 17327601 | marker microvessels |
| FLUOROURACIL | NM_004629 | Fanconi anemia, complementation group G | FANCG | 15067352 | resistance |
| FLUOROURACIL | NM_000043; NM_152871; NM_152872; NM_152873; NM_152874; NM_152875; NM_152876; NM_152877 | Fas (TNF receptor superfamily, member 6) | FAS | 15034078, 15585135, 19015929 | death pathway |
| FLUOROURACIL | NM_004111 | flap structure-specific endonuclease 1 | FEN1 | 15067352 | resistance |
| FLUOROURACIL | NM_002009 | fibroblast growth factor 7 (keratinocyte growth factor) | FGF7 | 18575591, 18708365, 15375550 | resistance |
| FLUOROURACIL | NM_000141; NM_001144913; NM_001144914; NM_001144915; NM_001144916; NM_001144917; NM_001144918; NM_001144919; NM_022970 | fibroblast growth factor receptor 2 | FGFR2 | 18575591 | |
| FLUOROURACIL | NM_022110 | FK506 binding protein like | FKBPL | 14503796 | |
| FLUOROURACIL | NM_001455; NM_201559 | forkhead box O3 | FOXO3 | 15067352 | sensitivity |
| FLUOROURACIL | NM_001924 | growth arrest and DNA-damage-inducible, alpha | GADD45A | 15067352, 19003803 | sensitivity |
| FLUOROURACIL | NM_000156; NM_138924 | guanidinoacetate N-methyltransferase | GAMT | 16896004 | |

TABLE 1-continued

| Molecule | RefSeq | Description | Symbol | PMID | Interaction |
|---|---|---|---|---|---|
| FLUOROURACIL | NM_000819; NM_001136005; NM_001136006; NM_175085 | phosphoribosylglycinamide formyltransferase, phosphoribosylglycinamide synthetase, phosphoribosylaminoimidazole synthetase | GART | 19219653 | |
| FLUOROURACIL | NM_001145453; NM_005264; NM_145793 | GDNF family receptor alpha 1 | GFRA1 | 16896004 | resistance |
| FLUOROURACIL | NM_005269 | GLI family zinc finger 1 | GLI1 | 18776995 | |
| FLUOROURACIL | NM_181077 | golgi autoantigen, golgin subfamily a, 8A | GOLGA8A | 17327601 | |
| FLUOROURACIL | NM_000852 | glutathione S-transferase pi 1 | GSTP1 | 15213713, 15737843 | |
| FLUOROURACIL | NM_000853 | glutathione S-transferase theta 1 | GSTT1 | 15585135 | |
| FLUOROURACIL | NM_005524 | guanylate cyclase 1, soluble, beta 3 | GUCY1B3 | 19219653 | |
| FLUOROURACIL | NM_005340 | hairy and enhancer of split 1, (Drosophila) | HES1 | 19147571 | |
| FLUOROURACIL | NM_005320 | histidine triad nucleotide binding protein 1 | HINT1 | 15585135 | |
| FLUOROURACIL | NM_000189 | histone cluster 1, H1d | HIST1H1D | 15585135 | |
| FLUOROURACIL | — | hexokinase 2 | HK2 | 18772588 | |
| FLUOROURACIL | NM_001540 | heat shock 27 kDa protein 1 | HNRPC | 15585135 | |
| FLUOROURACIL | NM_001541 | heat shock 27 kDa protein 2 | HSPB1 | 18949417, 19088045 | |
| FLUOROURACIL | NM_002176 | interferon, beta 1, fibroblast | HSPB2 | 18757417 | |
| FLUOROURACIL | NM_000875 | insulin-like growth factor 1 receptor | IFNB1 | 18608205, 18695887 | |
| FLUOROURACIL | NM_001552 | insulin-like growth factor binding protein 4 | IGF1R | 15499378 | |
| FLUOROURACIL | NM_000634 | interleukin 8 receptor, alpha | IGFBP4 | 16896004 | |
| FLUOROURACIL | NM_001025242; NM_001102524; NM_001569 | interleukin-1 receptor-associated kinase 1 | IL8RA | 16098254 | |
| FLUOROURACIL | | | IRAK1 | 15067352 | resistance |
| FLUOROURACIL | — | | JMJD2B | 16896004 | death pathway |
| FLUOROURACIL | NM_002229 | jun B proto-oncogene | JUNB | 18678097 | |
| FLUOROURACIL | NM_012289; NM_203500 | kelch-like ECH-associated protein 1 | KEAP1 | 18692501 | |
| FLUOROURACIL | NM_015443 | KIAA1267 | KIAA1267 | 18927307 | |
| FLUOROURACIL | NM_020853 | KIAA1467 | KIAA1467 | 16896004 | |
| FLUOROURACIL | NM_007054 | kinesin family member 3A | KIF3A | 16896004 | |
| FLUOROURACIL | NM_002266 | karyopherin alpha 2 (RAG cohort 1, importin alpha 1) | KPNA2 | 17374387 | |
| FLUOROURACIL | NM_004985; NM_033360 | v-Ki-ras2 Kirsten rat sarcoma viral oncogene homolog | KRAS | 15585135 | |
| FLUOROURACIL | NM_006499; NM_201543; NM_201544; NM_201545 | lectin, galactoside-binding, soluble, 8 | LGALS8 | 17327601 | |
| FLUOROURACIL | NM_005573 | lamin B1 | LMNB1 | 15067352 | resistance |
| FLUOROURACIL | NM_002355 | mannose-6-phosphate receptor (cation dependent) | M6PR | 15585135 | |
| FLUOROURACIL | NR_002819; NR_002819; NR_002819; NR_002819; NR_002819; NR_002819 | metastasis associated lung adenocarcinoma transcript 1 (non-protein coding) | MALAT1 | 18927307 | |
| FLUOROURACIL | NM_006785; NM_173844 | mucosa associated lymphoid tissue lymphoma translocation gene 1 | MALT1 | 15067352 | resistance |
| FLUOROURACIL | NM_002754 | mitogen-activated protein kinase 13 | MAPK13 | 15585135 | |
| FLUOROURACIL | NM_001230066; NM_001123067; NM_005910; NM_016834; NM_016835; NM_016841 | microtubule-associated protein tau | MAPT | 16896004 | |
| FLUOROURACIL | NM_022132 | methylcrotonoyl-Coenzyme A carboxylase 2 (beta) | MCCC2 | 18927307 | |
| FLUOROURACIL | NM_002393 | Mdm4 p53 binding protein homolog (mouse) | MDM4 | 18678097 | |
| FLUOROURACIL | NM_015335 | mediator complex subunit 13-like | MED13L | 16896004 | |
| FLUOROURACIL | NM_014791 | maternal embryonic leucine zipper kinase | MELK | 16896004 | |
| FLUOROURACIL | NM_024042 | meteorin, glial cell differentiation regulator | METRN | 16896004 | |
| FLUOROURACIL | NM_002417 | antigen identified by monoclonal antibody Ki-67 | MKI67 | 15940066 | |
| FLUOROURACIL | NM_000249 | mutL homolog 1, colon cancer, nonpolyposis type 2 (E. coli) | MLH1 | 18497967, 18949393 | sensitivity |
| FLUOROURACIL | NM_001127891; NM_004530 | matrix metallopeptidase 2 (gelatinase A, 72 kDa gelatinase, 72 kDa type IV collagenase) | MMP2 | 18678097 | |

TABLE 1-continued

| Molecule | RefSeq | Description | Symbol | PMID | Interaction |
|---|---|---|---|---|---|
| FLUOROURACIL | NM_001142418; NM_001142419; NM_001142420; NM_001142421; NM_001142422; NM_001142423; NM_001142424; NM_001142425; NM_001142426; NM_001142427; NM_001142428; NM_001142429; NM_001142430; NM_001142431; NM_001142432; NM_012286 | mortality factor 4 like 2 | MORF4L2 | 18593893 | |
| FLUOROURACIL | NM_000251 | mutS homolog 2, colon cancer, nonpolyposis type 1 (E. coli) | MSH2 | 18949393 | |
| FLUOROURACIL | NM_005957 | 5,10-methylenetetrahydrofolate reductase (NADPH) | MTHFR | 18633250, 19203896 | resistance |
| FLUOROURACIL | NM_002467 | v-myc myelocytomatosis viral oncogene homolog (avian) | MYC | 15585135, 18802399 | |
| FLUOROURACIL | NM_006311 | nuclear receptor co-repressor 1 | NCOR1 | 18927307 | |
| FLUOROURACIL | NM_004544 | NADH dehydrogenase (ubiquinone) 1 alpha subcomplex, 10, 42 kDa | NDUFA10 | 15585135 | |
| FLUOROURACIL | NM_001145412; NM_001145413; NM_006164 | nuclear factor (erythroid-derived 2)-like 2 | NFE2L2 | 18692501 | |
| FLUOROURACIL | NM_024522 | Na+/K+ transporting ATPase interacting 1 | NKAIN1 | 16896004 | |
| FLUOROURACIL | NM_020201 | 5',3'-nucleotidase, mitochondrial | NT5M | 19219653 | |
| FLUOROURACIL | NM_022731 | nuclear casein kinase and cyclin-dependent kinase substrate 1 | NUCKS1 | 15585135 | |
| FLUOROURACIL | NM_001079524; NM_001079525; NM_006452 | phosphoribosylaminoimidazole carboxylase, phosphoribosylaminoimidazole succinocarboxamide synthetase | PAICS | 19219653 | |
| FLUOROURACIL | NM_001618 | poly (ADP-ribose) polymerase 1 | PARP1 | 15996812, 16525653, 19084572 | apoptosis marker |
| FLUOROURACIL | NM_018908; NM_031501 | protocadherin alpha 5 | PCDHA5 | 15585135 | |
| FLUOROURACIL | NM_014891 | PDGFA associated protein 1 | PDAP1 | 15585135 | |
| FLUOROURACIL | NM_000926 | progesterone receptor | PGR | 15940066 | |
| FLUOROURACIL | NM_000944; NM_001130691; NM_001130692 | protein phosphatase 3 (formerly 2B), catalytic subunit, alpha isoform | PPP3CA | 15585135, 18927307 | |
| FLUOROURACIL | NM_003981; NM_199413; NM_199414 | protein regulator of cytokinesis 1 | PRC1 | 17374387 | altered by 5FU |
| FLUOROURACIL | NM_001081640; NM_006904 | protein kinase, DNA-activated, catalytic polypeptide | PRKDC | 18546291 | unrelated |
| FLUOROURACIL | NM_000311; NM_001080121; NM_001080122; NM_001080123; NM_183079 | prion protein | PRNP | 15386405 | |
| FLUOROURACIL | — | — | PSCD3 | 15585135 | |
| FLUOROURACIL | NM_002784 | pregnancy specific beta-1-glycoprotein 9 | PSG9 | 17327601 | |
| FLUOROURACIL | NM_001005290; NM_001032290; NM_001032291; NM_032636 | proline/serine-rich coiled-coil 1 | PSRC1 | 17374387 | unrelated |
| FLUOROURACIL | NM_000264; NM_001083602; NM_001083603; NM_001083604; NM_001083605; NM_001083606; NM_001083607 | patched homolog 1 (Drosophila) | PTCH1 | 18776995 | |
| FLUOROURACIL | NM_012212 | prostaglandin reductase 1 | PTGR1 | 15585135 | |
| FLUOROURACIL | NM_000963 | prostaglandin-endoperoxide synthase 2 (prostaglandin G/H synthase and cyclooxygenase) | PTGS2 | 12414664, 18695918 | resistance |
| FLUOROURACIL | NM_002874 | RAD23 homolog B (S. cerevisiae) | RAD23B | 15067352 | |
| FLUOROURACIL | NM_005855 | receptor (G protein-coupled) activity modifying protein 1 | RAMP1 | 16896004 | |
| FLUOROURACIL | NM_000321 | retinoblastoma 1 | RB1 | 18383818, 18678097 | |
| FLUOROURACIL | NM_001135255; NM_001135256; NM_005610 | retinoblastoma binding protein 4 | RBBP4 | 18678097 | |
| FLUOROURACIL | NM_001145138; NM_021975 | v-rel reticuloendotheliosis viral oncogene homolog A (avian) | RELA | 19003803 | |
| FLUOROURACIL | NM_001128617; NM_031922 | RALBP1 associated Eps domain containing 1 | REPS1 | 18927307 | |

TABLE 1-continued

| Molecule | RefSeq | Description | Symbol | PMID | Interaction |
|---|---|---|---|---|---|
| FLUOROURACIL | NM_025126; NM_194271 | ring finger protein 34 | RNF34 | 16270526 | resistance |
| FLUOROURACIL | NM_000967; NM_001033853 | ribosomal protein L3 | RPL3 | 15585135 | |
| FLUOROURACIL | NM_001034 | ribonucleotide reductase M2 polypeptide | RRM2 | 16896004 | target |
| FLUOROURACIL | NM_001015055; NM_001015056; NM_033046 | rhotekin | RTKN | 15480428 | resistance |
| FLUOROURACIL | NM_005980 | S100 calcium binding protein P | S100P | 18636193 | |
| FLUOROURACIL | NM_020974 | signal peptide, CUB domain, EGF-like 2 | SCUBE2 | 16896004 | |
| FLUOROURACIL | NM_001136528; NM_001136529; NM_001136530; NM_006216 | serpin peptidase inhibitor, clade E (nexin, plasminogen activator inhibitor type 1), member 2 | SERPINE2 | 17327601 | unrelated |
| FLUOROURACIL | NM_006142 | stratifin | SFN | 15999354 | |
| FLUOROURACIL | NM_000193 | sonic hedgehog homolog (*Drosophila*) | SHH | 18776995 | |
| FLUOROURACIL | NM_001078174; NM_001078175; NM_001078176; NM_001078177; NM_004955 | solute carrier family 29 (nucleoside transporters), member 1 | SLC29A1 | 18383843, 18992248 | |
| FLUOROURACIL | NM_005631 | smoothened homolog (*Drosophila*) | SMO | 18776995 | |
| FLUOROURACIL | NM_003082 | small nuclear RNA activating complex, polypeptide 1, 43 kDa | SNAPC1 | 15585135 | |
| FLUOROURACIL | NM_003090 | small nuclear ribonucleoprotein polypeptide A' | SNRPA1 | 18927307 | |
| FLUOROURACIL | NM_003109; NM_138473 | Sp1 transcription factor | SP1 | 18927307 | |
| FLUOROURACIL | NM_005417; NM_198291 | v-src sarcoma (Schmidt-Ruppin A-2) viral oncogene homolog (avian) | SRC | 18794807 | |
| FLUOROURACIL | NM_003130; NM_198901 | sorcin | SRI | 18423116 | |
| FLUOROURACIL | NM_006282 | serine/threonine kinase 4 | STK4 | 18927307 | |
| FLUOROURACIL | NM_016169 | suppressor of fused homolog (*Drosophila*) | SUFU | 18776995 | |
| FLUOROURACIL | NM_030756 | transcription factor 7-like 2 (T-cell specific, HMG-box) | TCF7L2 | 18678097 | |
| FLUOROURACIL | NM_005652 | telomeric repeat binding factor 2 | TERF2 | 15585135 | |
| FLUOROURACIL | NM_198253; NM_198255 | telomerase reverse transcriptase | TERT | 18396642 | |
| FLUOROURACIL | NM_003246 | thrombospondin 1 | THBS1 | 18757417 | |
| FLUOROURACIL | NM_018271 | threonine synthase-like 2 (*S. cerevisiae*) | THNSL2 | 16896004 | |
| FLUOROURACIL | NM_004614 | thymidine kinase 2, mitochondrial | TK2 | 19219653 | |
| FLUOROURACIL | NM_003265 | toll-like receptor 3 | TLR3 | 18779317 | |
| FLUOROURACIL | NM_021109 | thymosin beta 4, X-linked | TMSB4X | 16364925 | |
| FLUOROURACIL | — | | TMSL8 | 15067352 | |
| FLUOROURACIL | NM_003842; NM_147187 | tumor necrosis factor receptor superfamily, member 10b | TNFRSF10B | 17922852 | death pathway |
| FLUOROURACIL | NM_003810 | tumor necrosis factor (ligand) superfamily, member 10 | TNFSF10 | 19106633 | |
| FLUOROURACIL | NM_003808; NM_172087; NM_172088 | tumor necrosis factor (ligand) superfamily, member 13 | TNFSF13 | 18423122 | |
| FLUOROURACIL | NM_003286 | topoisomerase (DNA) I | TOP1 | 18509181 | |
| FLUOROURACIL | NM_001067 | topoisomerase (DNA) II alpha 170 kDa | TOP2A | 18465341 | |
| FLUOROURACIL | NM_000546; NM_001126112; NM_001126113; NM_001126114; NM_001126115; NM_001126116; NM_001126117 | tumor protein p53 | TP53 | 15940066, 15999354, 16077963, 16168113, 18498133, 18600534, 18698031, 18779317, 18930000, 19015155, 12082016, 19106633 | death pathway |
| FLUOROURACIL | NM_001126240; NM_001126241; NM_001126242; NM_005427 | tumor protein p73 | TP73 | 18714155 | |
| FLUOROURACIL | NM_000365; NM_001159287 | triosephosphate isomerase 1 | TPI1 | 18309519 | |
| FLUOROURACIL | NM_000367 | thiopurine S-methyltransferase | TPMT | 18927307 | |
| FLUOROURACIL | NM_001093771; NM_003330; NM_182729; NM_182742; NM_182743 | thioredoxin interacting protein | TXNIP | 18930000 | |
| FLUOROURACIL | | thioredoxin reductase 1 | TXNRD1 | 19219653 | |

TABLE 1-continued

| Molecule | RefSeq | Description | Symbol | PMID | Interaction |
|---|---|---|---|---|---|
| FLUOROURACIL | NM_001113755; NM_001113756; NM_001953 | thymidine phosphorylase | TYMP | 15655543, 17454858 | sensitivity |
| FLUOROURACIL | NM_001071 | thymidylate synthetase | TYMS | 15067352, 15213713, 15239142, 15737843, (following) 15788669, (following) 15788669, 18794807, 19020767, 16655543, 18633250, 18505590, 10482907, 18607850, 16168113, 17454858, 18425338, 18448328, 18490900,18593893, 18383874, 18490900,19105824, 18505590, 18600534, 18676755, 18722050, 19082493,18661526, 18794807, 18986760,18507058, 19074750, 19084572, 19219653, 19084572 | resistance |
| FLUOROURACIL | NM_007019; NM_181799; NM_181800; NM_181801; NM_181802; NM_181803 | ubiquitin-conjugating enzyme E2C | UBE2C | 17374387 | |
| FLUOROURACIL | NM_000463 | UDP glucuronosyltransferase 1 family, polypeptide A1 | UGT1A1 | 18797458 | |
| FLUOROURACIL | NM_000373 | uridine monophosphate synthetase | UMPS | 19020767, 19020740, 19082440, 19084572 | |
| FLUOROURACIL | NM_003362; NM_080911 | uracil-DNA glycosylase | UNG | 18714155 | |
| FLUOROURACIL | NM_003364; NM_181597 | uridine phosphorylase 1 | UPP1 | 15067352 | sensitivity |
| FLUOROURACIL | NM_145052 | uracil phosphoribosyltransferase (FUR1) homolog (S. cerevisiae) | UPRT | 18575323 | sensitivity |
| FLUOROURACIL | NM_004182; NM_153477 | ubiquitously-expressed transcript | UXT | 15585135 | |
| FLUOROURACIL | NM_001025366; NM_001025367; NM_001025368; NM_001025369; NM_001025370; NM_001033756; NM_003376 | vascular endothelial growth factor A | VEGFA | 18494554 | |
| FLUOROURACIL | — | XIAP associated factor 1 | WBSCR1 | 15585135 | |
| FLUOROURACIL | NM_017523; NM_199139 | X-ray repair complementing defective repair in Chinese hamster cells 5 (double-strand-break rejoining) | XAF1 | 15843754 | sensitivity |
| FLUOROURACIL | NM_021141 | X-ray repair complementing defective repair in Chinese hamster cells 6 | XRCC5 | 18546291 | |
| FLUOROURACIL | NM_001469 | | XRCC6 | 18546291 | |
| FLUOROURACIL | NM_024493 | zinc finger with KRAB and SCAN domains 3 | ZKSCAN3 | 18519692 | |
| FLUOROURACIL | NM_001005368; NM_006973 | zinc finger protein 32 | ZNF32 | 17327601 | |
| FLUOROURACIL | NM_024762 | zinc finger protein 552 | ZNF552 | 16896004 | |
| FLUOROURACIL | NM_144690 | zinc finger protein 582 | ZNF582 | 17327601 | |
| FLUOROURACIL | NM_005089 | zinc finger (CCCH type), RNA-binding motif and serine/arginine rich 2 | ZRSR2 | 17327601 | |
| CAPECITABINE | NM_001024649; NM_001746 | calnexin | CANX | 18678097 | drug activation |
| CAPECITABINE | NM_001025194; NM_001025195; NM_001266 | carboxylesterase 1 (monocyte/macrophage serine esterase 1) | CES1 | 15687373 | drug activation |
| CAPECITABINE | NM_003869; NM_198061 | carboxylesterase 2 (intestine, liver) | CES2 | 15687373, 18473752 | drug activation |
| CAPECITABINE | NM_024922 | carboxylesterase 3 | CES3 | 15687373 | |
| CAPECITABINE | NM_000110 | dihydropyrimidine dehydrogenase | DPYD | 18846242 | reverse toxicity |
| CAPECITABINE | NM_002229 | jun B proto-oncogene | JUNB | 18678097 | |
| CAPECITABINE | NM_002393 | Mdm4 p53 binding protein homolog (mouse) | MDM4 | 18678097 | |
| CAPECITABINE | NM_001127891; NM_004530 | matrix metallopeptidase 2 (gelatinase A, 72 kDa gelatinase, 72 kDa type IV collagenase) | MMP2 | 18678097 | |
| CAPECITABINE | NM_000321 | retinoblastoma 1 | RB1 | 18678097 | |
| CAPECITABINE | NM_001135255; NM_001135256; NM_005610 | retinoblastoma binding protein 4 | RBBP4 | 18678097 | |

TABLE 1-continued

| Molecule | RefSeq | Description | Symbol | PMID | Interaction |
|---|---|---|---|---|---|
| CAPECITABINE | NM_030756 | transcription factor 7-like 2 (T-cell specific, HMG-box) | TCF7L2 | 18678097 | resistance |
| CAPECITABINE | NM_001071 | thymidylate synthetase | TYMS | — | death pathway |
| GEMCITABINE | NM_004324; NM_138761; NM_138763; NM_138764; NM_138765 | BCL2-associated X protein | BAX | 15770523 | death pathway |
| GEMCITABINE | NM_000633; NM_000657 | B-cell CLL/lymphoma 2 | BCL2 | 15770523 | resistance |
| GEMCITABINE | NM_004346; NM_032991 | caspase 3, apoptosis-related cysteine peptidase | CASP3 | 15770523 | death pathway |
| GEMCITABINE | NM_001785 | cytidine deaminase | CDA | 18728667 | sensitivity |
| GEMCITABINE | NM_000389; NM_078467 | cyclin-dependent kinase inhibitor 1A (p21, Cip1) | CDKN1A | 15770523 | sensitivity |
| GEMCITABINE | — | | CMPK | — | |
| GEMCITABINE | — | cytochrome c oxidase III | COX3 | 17428446 | altered by DFDC |
| GEMCITABINE | NM_001618 | poly (ADP-ribose) polymerase 1 | PARP1 | 15770523 | |
| GEMCITABINE | NM_002613; NM_031268 | 3-phosphoinositide dependent protein kinase-1 | PDPK1 | 16782806 | resistance |
| GEMCITABINE | NM_001145547; NM_032905 | RNA binding motif protein 17 | RBM17 | 16061639 | resistance |
| GEMCITABINE | NM_001033 | ribonucleotide reductase M1 | RRM1 | — | resistance |
| GEMCITABINE | NM_001078174; NM_001078175; NM_001078176; NM_001078177; NM_004955 | solute carrier family 29 (nucleoside transporters), member 1 | SLC29A1 | 18383843, 18490900, 18728667, 18452103, 18992248, 18992248, 18333843 | drug uptake |
| GEMCITABINE | NM_000546; NM_001126112; NM_001126113; NM_001126114; NM_001126115; NM_001126116; NM_001126117 | tumor protein p53 | TP53 | 12082016 | unrelated |
| GEMCITABINE | NM_001113755; NM_001113756; NM_001953 | thymidine phosphorylase | TYMP | 18728667 | |
| GEMCITABINE | NM_001071 | thymidylate synthetase | TYMS | — | resistance |
| CYCLOPHOSPHAMIDE | NM_000927 | ATP-binding cassette, sub-family B (MDR/TAP), member 1 | ABCB1 | 12576456 | resistance |
| CYCLOPHOSPHAMIDE | NM_004996; NM_019862; NM_019898; NM_019899; NM_019900 | ATP-binding cassette, sub-family C (CFTR/MRP), member 1 | ABCC1 | 12576456 | resistance |
| CYCLOPHOSPHAMIDE | NM_004827 | ATP-binding cassette, sub-family G (WHITE), member 2 | ABCG2 | 12576456 | resistance |
| CYCLOPHOSPHAMIDE | NM_001101 | actin, beta | ACTB | 12167460 | |
| CYCLOPHOSPHAMIDE | NM_000689 | aldehyde dehydrogenase 1 family, member A1 | ALDH1A1 | 12513786, 17403535, 17502835, 18496131 | |
| CYCLOPHOSPHAMIDE | NM_000690 | aldehyde dehydrogenase 2 family (mitochondrial) | ALDH2 | 17403535 | |
| CYCLOPHOSPHAMIDE | NM_000691; NM_001135167; NM_001135168 | aldehyde dehydrogenase 3 family, memberA1 | ALDH3A1 | 18496131 | |
| CYCLOPHOSPHAMIDE | NM_001629 | arachidonate 5-lipoxygenase-activating protein | ALOX5AP | 17403535 | |
| CYCLOPHOSPHAMIDE | NM_001144 | autocrine motility factor receptor | AMFR | 16896004 | |
| CYCLOPHOSPHAMIDE | NM_001146 | angiopoietin 1 | ANGPT1 | 17403535 | |
| CYCLOPHOSPHAMIDE | NM_012068 | activating transcription factor 5 | ATF5 | 17403535 | |
| CYCLOPHOSPHAMIDE | NM_004323 | BCL2-associated athanogene | BAG1 | 16322899 | sensitivity |
| CYCLOPHOSPHAMIDE | NM_033028 | Bardet-Biedl syndrome 4 | BBS4 | 16896004 | |
| CYCLOPHOSPHAMIDE | NM_000633; NM_000657 | B-cell CLL/lymphoma 2 | BCL2 | 11723234, 14503796, 15940066, 16322899 | sensitivity |
| CYCLOPHOSPHAMIDE | NM_003766 | beclin 1, autophagy related | BECN1 | 16896004 | |
| CYCLOPHOSPHAMIDE | NM_001197 | BCL2-interacting killer (apoptosis-inducing) | BIK | 17403535 | |
| CYCLOPHOSPHAMIDE | NM_001725 | bactericidal/permeability-increasing protein | BPI | 17403535 | |
| CYCLOPHOSPHAMIDE | NM_001309914; NM_006806 | BTG family, member 3 | BTG3 | 16896004 | |
| CYCLOPHOSPHAMIDE | NM_001007793; NM_004725 | budding uninhibited by benzimidazoles 3 homolog (yeast) | BUB3 | 16322899 | sensitivity |
| CYCLOPHOSPHAMIDE | — | | C13ORF27 | 17403535 | |
| CYCLOPHOSPHAMIDE | NM_001218; NM_206925 | carbonic anhydrase XII | CA12 | 16896004 | |
| CYCLOPHOSPHAMIDE | NM_000067 | carbonic anhydrase II | CA2 | 17403535 | |

TABLE 1-continued

| Molecule | RefSeq | Description | Symbol | PMID | Interaction |
|---|---|---|---|---|---|
| CYCLOPHOSPHAMIDE | NM_001223; NM_033292; NM_033293; NM_033294; NM_033295 | caspase 1, apoptosis-related cysteine peptidase (interleukin 1, beta, convertase) | CASP1 | 17403535 | |
| CYCLOPHOSPHAMIDE | NM_004346; NM_032991 | caspase 3, apoptosis-related cysteine peptidase | CASP3 | 11723234, 14503796, 16675587 | death pathway |
| CYCLOPHOSPHAMIDE | NM_001229; NM_032996 | caspase 9, apoptosis-related cysteine peptidase | CASP9 | 11723234 | death pathway |
| CYCLOPHOSPHAMIDE | NM_005893 | calicin | CCIN | 17475930 | |
| CYCLOPHOSPHAMIDE | NM_005201 | chemokine (C-C motif) receptor 8 | CCR8 | 17403535 | |
| CYCLOPHOSPHAMIDE | NM_004064 | cyclin-dependent kinase inhibitor 1B (p27, Kip1) | CDKN1B | 16322899 | sensitivity |
| CYCLOPHOSPHAMIDE | NM_001865 | cytochrome c oxidase subunit VIIa polypeptide 2 (liver) | COX7A2 | 17403535 | |
| CYCLOPHOSPHAMIDE | NM_003650 | cystatin F (leukocystatin) | CST7 | 17403535 | |
| CYCLOPHOSPHAMIDE | NM_001012329; NM_020248 | catenin, beta interacting protein 1 | CTNNBIP1 | 16322899 | resistance |
| CYCLOPHOSPHAMIDE | NM_001332 | catenin (cadherin-associated protein), delta 2 (neural plakophilin-related arm-repeat protein) | CTNND2 | 16896004 | |
| CYCLOPHOSPHAMIDE | NM_004390; NM_148979 | cathepsin H | CTSH | 17403535 | |
| CYCLOPHOSPHAMIDE | — | | CTSL | 17403535 | |
| CYCLOPHOSPHAMIDE | NM_000104 | cytochrome P450, family 1, subfamily B, polypeptide 1 | CYP1B1 | 12167460 | |
| CYCLOPHOSPHAMIDE | — | | CYP2B1 | 11933215, 16 | |
| CYCLOPHOSPHAMIDE | NM_000767 | cytochrome P450, family 2, subfamily B, polypeptide 6 | CYP2B6 | 10919648, 12498089, 11389073, 12872138, 15248218, 15769884, 18633247, 18212249, 16322899, 17502835, 17502835, 16183265, 12872138, 18496131 | drug activation |
| CYCLOPHOSPHAMIDE | NM_000769 | cytochrome P450, family 2, subfamily C, polypeptide 19 | CYP2C19 | 15248218, 16116487, 17502835, 18496131 | |
| CYCLOPHOSPHAMIDE | NM_000771 | cytochrome P450, family 2, subfamily C, polypeptide 9 | CYP2C9 | 10991840, 18496131 | |
| CYCLOPHOSPHAMIDE | NM_017460 | cytochrome P450, family 3, subfamily A, polypeptide 4 | CYP3A4 | 17502835, 18496131 | |
| CYCLOPHOSPHAMIDE | NM_000777 | cytochrome P450, family 3, subfamily A, polypeptide 5 | CYP3A5 | 17502835, 18496131 | |
| CYCLOPHOSPHAMIDE | NM_006094; NM_024767; NM_182643 | deleted in liver cancer 1 | DLC1 | 17403535 | |
| CYCLOPHOSPHAMIDE | NM_005494; NM_058246 | DnaJ (Hsp40) homolog, subfamily B, member 6 | DNAJB6 | 17475930 | |
| CYCLOPHOSPHAMIDE | NM_014934; NM_198968 | DAZ interacting protein 1 | DZIP1 | 17403535 | |
| CYCLOPHOSPHAMIDE | NM_001949 | E2F transcription factor 3 | E2F3 | 16896004 | |
| CYCLOPHOSPHAMIDE | NM_005228; NM_201282; NM_201283; NM_201284 | epidermal growth factor receptor (erythroblastic leukemia viral (v-erb-b) oncogene homolog, avian) | EGFR | 15981280 | resistance |
| CYCLOPHOSPHAMIDE | NM_001412 | eukaryotic translation initiation factor 1A, X-linked | EIF1AX | 16322899 | resistance |
| CYCLOPHOSPHAMIDE | NM_004095 | eukaryotic translation initiation factor 4E binding protein 1 | EIF4EBP1 | 16322899 | resistance |
| CYCLOPHOSPHAMIDE | NM_001135554; NM_001135555; NM_001431 | erythrocyte membrane protein band 4.1-like 2 | EPB41L2 | 17403535 | |
| CYCLOPHOSPHAMIDE | NM_001005862; NM_004448 | v-erb-b2 erythroblastic leukemia viral oncogene homolog 2, neuro/glioblastoma derived oncogene homolog (avian) | ERBB2 | 15834928, 15940066, 17010609 | resistance |
| CYCLOPHOSPHAMIDE | NM_001042599; NM_005235 | v-erb-a erythroblastic leukemia viral oncogene homolog 4 (avian) | ERBB4 | 16896004 | |
| CYCLOPHOSPHAMIDE | NM_001136154; NM_001136155; NM_004449; NM_182918 | v-ets erythroblastosis virus E26 oncogene homolog (avian) | ERG | 17403535 | |
| CYCLOPHOSPHAMIDE | NM_000125; NM_001122740; NM_001122741; NM_001122742 | estrogen receptor 1 | ESR1 | 16322899 | |
| CYCLOPHOSPHAMIDE | NM_001040275; NM_001040276; NM_001437 | estrogen receptor 2 (ER beta) | ESR2 | 16322899 | |
| CYCLOPHOSPHAMIDE | NM_001993 | coagulation factor III (thromboplastin, tissue factor) | F3 | 17403535 | |
| CYCLOPHOSPHAMIDE | NM_022110 | FK506 binding protein like | FKBPL | 14503796 | |
| CYCLOPHOSPHAMIDE | NM_003088 | fascin homolog 1, actin-bundling protein (Strongylocentrotus purpuratus) | FSCN1 | 17403535 | |

TABLE 1-continued

| Molecule | RefSeq | Description | Symbol | PMID | Interaction |
|---|---|---|---|---|---|
| CYCLOPHOSPHAMIDE | NM_002037; NM_153047; NM_153048 | FYN oncogene related to SRC, FGR, YES | FYN | 17403535 | |
| CYCLOPHOSPHAMIDE | NM_000156; NM_138924 | guanidinoacetate N-methyltransferase | GAMT | 16896004 | |
| CYCLOPHOSPHAMIDE | NM_001143830; NM_005256; NM_177553 | growth arrest-specific 2 | GAS2 | 17475930 | |
| CYCLOPHOSPHAMIDE | NM_001145453; NM_005264; NM_145793 | GDNF family receptor alpha 1 | GFRA1 | 16896004 | |
| CYCLOPHOSPHAMIDE | NM_000824 | glycine receptor, beta | GLRB | 17403535 | |
| CYCLOPHOSPHAMIDE | NM_018841 | guanine nucleotide binding protein (G protein), gamma 12 | GNG12 | 17403535 | |
| CYCLOPHOSPHAMIDE | NM_001039847; NM_001039848; NM_002085 | glutathione peroxidase 4 (phospholipid hydroperoxidase) | GPX4 | 17475930 | |
| CYCLOPHOSPHAMIDE | NM_145740 | glutathione S-transferase alpha 1 | GSTA1 | 12516103, 18496131 | polymorphisms |
| CYCLOPHOSPHAMIDE | NM_000852 | glutathione S-transferase pi 1 | GSTP1 | 18496131 | resistance |
| CYCLOPHOSPHAMIDE | NM_001520 | general transcription factor IIIC, polypeptide 1, alpha 220 kDa | GTF3C1 | 16322899 | |
| CYCLOPHOSPHAMIDE | NM_002140; NM_031262; NM_031263 | heterogeneous nuclear ribonucleoprotein K | HNRNPK | 17475930 | |
| CYCLOPHOSPHAMIDE | NM_002162 | intercellular adhesion molecule 3 | ICAM3 | 17403535 | |
| CYCLOPHOSPHAMIDE | NM_001552 | insulin-like growth factor binding protein 4 | IGFBP4 | 16896004 | |
| CYCLOPHOSPHAMIDE | NM_000575 | interleukin 1, alpha | IL1A | 16636934 | resistance |
| CYCLOPHOSPHAMIDE | NM_001137673; NM_004516; NM_012218; NM_017620; NM_153464 | interleukin enhancer binding factor 3, 90 kDa | ILF3 | 16322899 | |
| CYCLOPHOSPHAMIDE | NM_005544 | insulin receptor substrate 1 | IRS1 | 16322899 | sensitivity |
| CYCLOPHOSPHAMIDE | — | | JMJD2B | 16896004 | |
| CYCLOPHOSPHAMIDE | NM_014867 | kelch repeat and BTB (POZ) domain containing 11 | KBTBD11 | 17403535 | |
| CYCLOPHOSPHAMIDE | NM_020853 | KIAA1467 | KIAA1467 | 16896004 | |
| CYCLOPHOSPHAMIDE | NM_007054 | kinesin family member 3A | KIF3A | 16896004 | |
| CYCLOPHOSPHAMIDE | NM_000240 | lectin, galactoside-binding, soluble, 1 | LGALS1 | 17403535 | |
| CYCLOPHOSPHAMIDE | NM_001315; NM_139012; NM_139013; NM_139014 | monoamine oxidase A | MAOA | 16322899 | |
| CYCLOPHOSPHAMIDE | NM_001123066; NM_001123067; NM_005910; NM_016834; NM_016835; NM_016841 | mitogen-activated protein kinase 14 | MAPK14 | 16322899 | sensitivity |
| CYCLOPHOSPHAMIDE | NM_002356 | microtubule-associated protein tau | MAPT | 16896004 | unrelated |
| CYCLOPHOSPHAMIDE | NM_199072 | myristoylated alanine-rich protein kinase C substrate | MARCKS | 17403535 | |
| CYCLOPHOSPHAMIDE | NM_015335 | MyoD family inhibitor domain containing | MDFIC | 17403535 | |
| CYCLOPHOSPHAMIDE | NM_014791 | mediator complex subunit 13-like | MED13L | 16896004 | |
| CYCLOPHOSPHAMIDE | NM_024042 | maternal embryonic leucine zipper kinase | MELK | 16896004 | |
| CYCLOPHOSPHAMIDE | NM_002412 | meteorin, glial cell differentiation regulator | METRN | 16896004 | |
| CYCLOPHOSPHAMIDE | NM_002417 | O-6-methylguanine-DNA methyltransferase | MGMT | 15741301, 17403535 | resistance |
| CYCLOPHOSPHAMIDE | NM_001031666; NM_001031809; NM_006138 | antigen identified by monoclonal antibody Ki-67 | MKI67 | 15940066 | |
| CYCLOPHOSPHAMIDE | | membrane-spanning 4-domains, subfamily A, member 3 (hematopoietic cell-specific) | MS4A3 | 17403535 | |
| CYCLOPHOSPHAMIDE | NM_002463 | myxovirus (influenza virus) resistance 2 (mouse) | MX2 | 17403535 | |
| CYCLOPHOSPHAMIDE | NM_004536; NM_022892 | NLR family, apoptosis inhibitory protein | NAIP | 16322899 | BIRC1—sensitivity |
| CYCLOPHOSPHAMIDE | — | | NK4 | 17403535 | |
| CYCLOPHOSPHAMIDE | NM_024522 | Na+/K+ transporting ATPase interacting 1 | NKAIN1 | 16896004 | |
| CYCLOPHOSPHAMIDE | NM_002564; NM_176071; NM_176072 | purinergic receptor P2Y, G-protein coupled, 2 | P2RY2 | 17403535 | |
| CYCLOPHOSPHAMIDE | NM_007203; NM_147150 | PALM2-AKAP2 readthrough transcript | PALM2-AKAP2 | 17403535 | |
| CYCLOPHOSPHAMIDE | NM_000926 | progesterone receptor | PGR | 15940066 | |
| CYCLOPHOSPHAMIDE | NM_003311 | pleckstrin homology-like domain, family A, member 2 | PHLDA2 | 17403535 | |
| CYCLOPHOSPHAMIDE | NM_000302 | procollagen-lysine, 2-oxoglutarate 5-dioxygenase 1 | PLOD1 | 16322899 | resistance |
| CYCLOPHOSPHAMIDE | NM_001084 | procollagen-lysine, 2-oxoglutarate 5-dioxygenase 3 | PLOD3 | 16322899 | resistance |

TABLE 1-continued

| Molecule | RefSeq | Description | Symbol | PMID | Interaction |
|---|---|---|---|---|---|
| CYCLOPHOSPHAMIDE | NM_000941 | P450 (cytochrome) oxidoreductase | POR | 10919648 | |
| CYCLOPHOSPHAMIDE | NM_002777 | proteinase 3 | PRTN3 | 17403535 | |
| CYCLOPHOSPHAMIDE | NM_002790 | proteasome (prosome, macropain) subunit, alpha type, 5 | PSMA5 | 17475930 | |
| CYCLOPHOSPHAMIDE | NM_005855 | receptor (G protein-coupled) activity modifying protein 1 | RAMP1 | 16896004, 17403535 | |
| CYCLOPHOSPHAMIDE | NM_001008710; NM_001008711; NM_001008712; NM_006867 | RNA binding protein with multiple splicing | RBPMS | 17403535 | |
| CYCLOPHOSPHAMIDE | NM_002934 | ribonuclease, RNase A family, 2 (liver, eosinophil-derived neurotoxin) | RNASE2 | 17403535 | |
| CYCLOPHOSPHAMIDE | NM_006570 | Ras-related GTP binding A | RRAGA | 17403535 | |
| CYCLOPHOSPHAMIDE | NM_001102669; NM_012250 | related RAS viral (r-ras) oncogene homolog 2 | RRAS2 | 17403535 | |
| CYCLOPHOSPHAMIDE | NM_001034 | ribonucleotide reductase M2 polypeptide | RRM2 | 16896004 | resistance |
| CYCLOPHOSPHAMIDE | NM_016434; NM_032957 | regulator of telomere elongation helicase 1 | RTEL1 | 17475930 | |
| CYCLOPHOSPHAMIDE | NM_005980 | S100 calcium binding protein P | S100P | 17403535 | |
| CYCLOPHOSPHAMIDE | NM_020974 | signal peptide, CUB domain, EGF-like 2 | SCUBE2 | 16896004 | |
| CYCLOPHOSPHAMIDE | NM_003118 | secreted protein, acidic, cysteine-rich (osteonectin) | SPARC | 17403535 | |
| CYCLOPHOSPHAMIDE | NM_003132 | spermidine synthase | SRM | 16322899 | resistance |
| CYCLOPHOSPHAMIDE | NM_021978 | suppression of tumorigenicity 14 (colon carcinoma) | ST14 | 16322899 | resistance |
| CYCLOPHOSPHAMIDE | NM_013233 | serine threonine kinase 39 (STE20/SPS1 homolog, yeast) | STK39 | 16322899 | sensitivity |
| CYCLOPHOSPHAMIDE | NM_018271 | threonine synthase-like 2 (S. cerevisiae) | THNSL2 | 16896004 | |
| CYCLOPHOSPHAMIDE | NM_014220 | transmembrane 4 L six family member 1 | TM4SF1 | 17403535 | |
| CYCLOPHOSPHAMIDE | NM_001067 | topoisomerase (DNA) II alpha 170 kDa | TOP2A | 18465341 | |
| CYCLOPHOSPHAMIDE | NM_000546; NM_001126112; NM_001126113; NM_001126114; NM_001126115; NM_001126116; NM_001126117 | tumor protein p53 | TP53 | 15940066 | death pathway |
| CYCLOPHOSPHAMIDE | NM_024762 | zinc finger protein 552 | ZNF552 | 16896004 | |
| IFOSFAMIDE | NM_000633; NM_000657 | B-cell CLL/lymphoma 2 | BCL2 | 11723234 | |
| IFOSFAMIDE | NM_001229; NM_032996 | caspase 9, apoptosis-related cysteine peptidase | CASP9 | 11723234 | death pathway |
| IFOSFAMIDE | NM_000762 | cytochrome P450, family 2, subfamily A, polypeptide 6 | CYP2A6 | 12136253 | drug activation |
| IFOSFAMIDE | NM_000767 | cytochrome P450, family 2, subfamily B, polypeptide 6 | CYP2B6 | 15875221 | drug activation |
| IFOSFAMIDE | NM_017460 | cytochrome P450, family 3, subfamily A, polypeptide 4 | CYP3A4 | 12136253, 15821045, 15875221 | drug activation |
| IFOSFAMIDE | NM_000777 | cytochrome P450, family 3, subfamily A, polypeptide 5 | CYP3A5 | 15821045, 15875221 | drug activation |
| IFOSFAMIDE | NM_001130823; NM_001379 | DNA (cytosine-5-)-methyltransferase 1 | DNMT1 | | |
| IFOSFAMIDE | NM_000561; NM_146421 | glutathione S-transferase mu 1 | GSTM1 | 12868187 | polymorphism/toxicity |
| IFOSFAMIDE | NM_000852 | glutathione S-transferase pi 1 | GSTP1 | 12868187 | polymorphism/toxicity |
| IFOSFAMIDE | NM_000853 | glutathione S-transferase theta 1 | GSTT1 | 12868187 | polymorphism/toxicity |
| MELPHALAN | NM_004996; NM_019862; NM_019898; NM_019899; NM_019900 | ATP-binding cassette, sub-family C (CFTR/MRP), member 1 | ABCC1 | 11115505 | resistance |
| MELPHALAN | NM_001012270; NM_001012271; NM_001168 | baculoviral IAP repeat-containing 5 | BIRC5 | 16373717 | |
| MELPHALAN | NM_032982; NM_032983 | caspase 2, apoptosis-related cysteine peptidase | CASP2 | 14757846 | death pathway |
| MELPHALAN | NM_004346; NM_032991 | caspase 3, apoptosis-related cysteine peptidase | CASP3 | 16951922 | death pathway |
| MELPHALAN | NM_001785 | cytidine deaminase | CDA | 10830723 | resistance |
| MELPHALAN | NM_000136 | Fanconi anemia, complementation group C | FANCC | 16243825 | |
| MELPHALAN | NM_004629 | Fanconi anemia, complementation group G | FANCG | 16243825 | |
| MELPHALAN | NM_145740 | glutathione S-transferase alpha 1 | GSTA1 | 15779864 | unrelated |
| MELPHALAN | NM_000852 | glutathione S-transferase pi 1 | GSTP1 | 15779864, 27 | unrelated |
| MELPHALAN | NM_000201 | intercellular adhesion molecule 1 | ICAM1 | 16025434 | |
| MELPHALAN | NM_002745; NM_138957 | mitogen-activated protein kinase 1 | MAPK1 | 16025434 | |

TABLE 1-continued

| Molecule | RefSeq | Description | Symbol | PMID | Interaction |
|---|---|---|---|---|---|
| MELPHALAN | NM_001040056; NM_001109891; NM_002746 | mitogen-activated protein kinase 3 | MAPK3 | 16025434 | unrelated |
| MELPHALAN | NM_002412 | O-6-methylguanine-DNA methyltransferase | MGMT | 16039682 | resistance |
| MELPHALAN | NM_002413 | microsomal glutathione S-transferase 2 | MGST2 | 15779864 | resistance |
| MELPHALAN | NM_006788 | ralA binding protein 1 | RALBP1 | — | |
| MELPHALAN | NM_000594 | tumor necrosis factor (TNF superfamily, member 2) | TNF | 16025434 | |
| MELPHALAN | NM_001071 | thymidylate synthetase | TYMS | 10482907 | |
| CARMUSTINE | NM_000927 | ATP-binding cassette, sub-family B (MDR/TAP), member 1 | ABCB1 | 15239124 | resistance |
| CARMUSTINE | NM_004996; NM_019862; NM_019898; NM_019899; NM_019900 | ATP-binding cassette, sub-family C (CFTR/MRP), member 1 | ABCC1 | 12653207 | resistance |
| CARMUSTINE | NM_005159 | actin, alpha, cardiac muscle 1 | ACTC1 | 15980968 | |
| CARMUSTINE | NM_001615 | actin, gamma 2, smooth muscle, enteric | ACTG2 | 15980968 | |
| CARMUSTINE | NM_001102; NM_001130004; NM_001130005 | actinin, alpha 1 | ACTN1 | 15980968 | |
| CARMUSTINE | NM_003815; NM_207191; NM_207194; NM_207195; NM_207196; NM_207197 | ADAM metallopeptidase domain 15 | ADAM15 | 15980968 | |
| CARMUSTINE | NM_005099 | ADAM metallopeptidase with thrombospondin type 1 motif, 4 | ADAMTS4 | 15980968 | |
| CARMUSTINE | NM_001099733; NM_001117 | adenylate cyclase activating polypeptide 1 (pituitary) | ADCYAP1 | 15980968 | |
| CARMUSTINE | NM_000679 | adrenergic, alpha-1B-, receptor | ADRA1B | 15980968 | |
| CARMUSTINE | NM_000029 | angiotensinogen (serpin peptidase inhibitor, clade A, member 8) | AGT | 11034089 | |
| CARMUSTINE | — | | AGTRL1 | 15980968 | |
| CARMUSTINE | NM_001626 | v-akt murine thymoma viral oncogene homolog 2 | AKT2 | 15980968 | |
| CARMUSTINE | NM_000031 | aminolevulinate, delta-, dehydratase | ALAD | 15980968 | |
| CARMUSTINE | NM_001039130; NM_001039131; NM_001141 | arachidonate 15-lipoxygenase, type B | ALOX15B | 15980968 | |
| CARMUSTINE | NM_000479 | anti-Mullerian hormone | AMH | 15980968 | |
| CARMUSTINE | NM_005883 | adenomatosis polyposis coli 2 | APC2 | 15980968 | |
| CARMUSTINE | NM_001169 | aquaporin 8 | AQP8 | 15980968 | |
| CARMUSTINE | — | | ARGBP2 | 15980968 | |
| CARMUSTINE | NM_005731; NM_152862 | actin related protein 2/3 complex, subunit 2, 34 kDa | ARPC2 | 15980968 | |
| CARMUSTINE | NM_001136215; NM_003976; NM_057090; NM_057091; NM_057160 | artemin | ARTN | 15980968 | |
| CARMUSTINE | NM_004192 | acetylserotonin O-methyltransferase-like | ASMTL | 15980968 | |
| CARMUSTINE | NM_152296 | ATPase, Na+/K+ transporting, alpha 3 polypeptide | ATP1A3 | 15980968 | |
| CARMUSTINE | NM_000705 | ATPase, H+/K+ exchanging, beta polypeptide | ATP4B | 15980968 | |
| CARMUSTINE | NM_001001975; NM_001687 | ATP synthase, H+ transporting, mitochondrial F1 complex, delta subunit | ATP5D | 15980968 | |
| CARMUSTINE | NM_001694 | ATPase, H+ transporting, lysosomal 16 kDa, V0 subunit c | ATP6V0C | 15980968 | |
| CARMUSTINE | NM_007245; NM_145714; NM_148414; NM_148415; NM_148416 | ataxin 2-like | ATXN2L | 15980968 | |
| CARMUSTINE | NM_000706 | arginine vasopressin receptor 1A | AVPR1A | 15980968 | |
| CARMUSTINE | NM_004776 | UDP-Gal:betaGlcNAc beta 1,4-galactosyltransferase, polypeptide 5 | B4GALT5 | 15980968 | |
| CARMUSTINE | NM_001144888; NM_006340; NM_017450; NM_017451 | BAI1-associated protein 2 | BAIAP2 | 15980968 | |
| CARMUSTINE | NM_003933 | BAI1-associated protein 3 | BAIAP3 | 15980968 | |
| CARMUSTINE | NM_003921 | B-cell CLL/lymphoma 10 | BCL10 | 15980968 | |
| CARMUSTINE | NM_000633; NM_000657 | B-cell CLL/lymphoma 2 | BCL2 | 16187019 | resistance |
| CARMUSTINE | NM_001191; NM_138578 | BCL2-like 1 | BCL2L1 | 16187019 | |
| CARMUSTINE | NM_003766 | beclin 1, autophagy related | BECN1 | 15980968 | |
| CARMUSTINE | NM_001003398; NM_001714 | bicaudal D homolog 1 (Drosophila) | BICD1 | 15980968 | |

TABLE 1-continued

| Molecule | RefSeq | Description | Symbol | PMID | Interaction |
|---|---|---|---|---|---|
| CARMUSTINE | NM_001715 | B lymphoid tyrosine kinase | BLK | 15980968 | |
| CARMUSTINE | NM_001719 | bone morphogenetic protein 7 | BMP7 | 15980968 | |
| CARMUSTINE | NM_001519; NM_145685 | BRF1 homolog, subunit of RNA polymerase III transcription initiation factor IIIB (S. cerevisiae) | BRF1 | 15980968 | |
| CARMUSTINE | NM_001215 | carbonic anhydrase VI | CA6 | 15980968 | |
| CARMUSTINE | NM_001740; NM_007087; NM_007088 | calbindin 2 | CALB2 | 15980968 | |
| CARMUSTINE | NM_002982 | chemokine (C-C motif) ligand 2 | CCL2 | 15980968 | |
| CARMUSTINE | NM_001039490; NM_004357; NM_139029; NM_139030 | CD151 molecule (Raph blood group) | CD151 | 15980968 | resistance |
| CARMUSTINE | NM_001040059; NM_001251 | CD68 molecule | CD68 | 15980968 | |
| CARMUSTINE | NM_001783; NM_021601 | CD79a molecule, immunoglobulin-associated alpha | CD79A | 15980968 | |
| CARMUSTINE | NM_005191 | CD80 molecule | CD80 | 15980968 | |
| CARMUSTINE | NM_001790; NM_022809 | cell division cycle 25 homolog C (S. pombe) | CDC25C | 15735757 | |
| CARMUSTINE | NM_001260 | cyclin-dependent kinase 8 | CDK8 | 15980968 | |
| CARMUSTINE | NM_000389; NM_078467 | cyclin-dependent kinase inhibitor 1A (p21, Cip1) | CDKN1A | 15735757 | |
| CARMUSTINE | NM_005193 | caudal type homeobox 4 | CDX4 | 15980968 | |
| CARMUSTINE | NM_001815 | carcinoembryonic antigen-related cell adhesion molecule 3 | CEACAM3 | 15980968 | |
| CARMUSTINE | NM_005194 | CCAAT/enhancer binding protein (C/EBP), beta | CEBPB | 15980968 | |
| CARMUSTINE | NM_001114121; NM_001114122; NM_001274 | CHK1 checkpoint homolog (S. pombe) | CHEK1 | 15735757 | |
| CARMUSTINE | NM_000741 | cholinergic receptor, muscarinic 4 | CHRM4 | 15980968 | |
| CARMUSTINE | NM_000749 | cholinergic receptor, nicotinic, beta 3 | CHRNB3 | 15980968 | |
| CARMUSTINE | NM_005199 | cholinergic receptor, nicotinic, gamma | CHRNG | 15980968 | |
| CARMUSTINE | NM_001824 | creatine kinase, muscle | CKM | 15980968 | altered by CNU |
| CARMUSTINE | NM_001835; NM_007098 | clathrin, heavy chain-like 1 | CLTCL1 | 15980968 | |
| CARMUSTINE | NM_003632 | contactin associated protein 1 | CNTNAP1 | 15980968 | |
| CARMUSTINE | NM_001851; NM_078485 | collagen, type IX, alpha 1 | COL9A1 | 15980968 | |
| CARMUSTINE | NM_005205 | cytochrome c oxidase subunit VIa polypeptide 2 | COX6A2 | 15980968 | |
| CARMUSTINE | NM_004378 | cellular retinoic acid binding protein 1 | CRABP1 | 15980968 | |
| CARMUSTINE | NM_000755; NM_004003 | carnitine acetyltransferase | CRAT | 15980968 | |
| CARMUSTINE | NM_001887 | crystallin, beta B1 | CRYBB1 | 15980968 | |
| CARMUSTINE | NM_001900 | cystatin D | CST5 | 15980968 | |
| CARMUSTINE | NM_001142544; NM_001330 | cardiotrophin 1 | CTF1 | 15980968 | |
| CARMUSTINE | NM_003798 | catenin (cadherin-associated protein), alpha-like 1 | CTNNAL1 | 15980968 | |
| CARMUSTINE | NM_000103; NM_031226 | cytochrome P450, family 19, subfamily A, polypeptide 1 | CYP19A1 | 15980968 | |
| CARMUSTINE | NM_004762; NM_017456 | cytohesin 1 | CYTH1 | 15980968 | |
| CARMUSTINE | NM_003587 | DEAH (Asp-Glu-Ala-His) box polypeptide 16 | DHX16 | 15980968 | |
| CARMUSTINE | NM_001374 | deoxyribonuclease I-like 2 | DNASE1L2 | 15980968 | |
| CARMUSTINE | NM_004421 | dishevelled, dsh homolog 1 (Drosophila) | DVL1 | 15980968 | |
| CARMUSTINE | NM_001393 | extracellular matrix protein 2, female organ and adipocyte specific | ECM2 | 15980968 | |
| CARMUSTINE | NM_001404 | eukaryotic translation elongation factor 1 gamma | EEF1G | 15980968 | |
| CARMUSTINE | NM_001414 | eukaryotic translation initiation factor 2B, subunit 1 alpha, 26 kDa | EIF2B1 | 15980968 | |
| CARMUSTINE | NM_002212; NM_181466; NM_181468 | eukaryotic translation initiation factor 6 | EIF6 | 15980968 | |
| CARMUSTINE | NM_000120; NM_001136018 | epoxide hydrolase 1, microsomal (xenobiotic) | EPHX1 | 15980968 | |
| CARMUSTINE | NM_004451 | estrogen-related receptor alpha | ESRRA | 15980968 | |
| CARMUSTINE | NM_004456; NM_152998 | enhancer of zeste homolog 2 (Drosophila) | EZH2 | 15980968 | |
| CARMUSTINE | NM_000138 | fibrillin 1 | FBN1 | 15980968 | resistance ? |
| CARMUSTINE | NM_000801; NM_054014 | FK506 binding protein 1A, 12 kDa | FKBP1A | 15980968 | |

TABLE 1-continued

| Molecule | RefSeq | Description | Symbol | PMID | Interaction |
|---|---|---|---|---|---|
| CARMUSTINE | NM_001018676; NM_001018677; NM_002027 | farnesyltransferase, CAAX box, alpha | FNTA | 15980968 | |
| CARMUSTINE | NM_001454 | forkhead box J1 | FOXJ1 | 15980968 | |
| CARMUSTINE | NM_002032 | ferritin, heavy polypeptide 1 | FTH1 | 15980968 | |
| CARMUSTINE | NM_000146 | ferritin, light polypeptide | FTL | 15980968 | |
| CARMUSTINE | NM_002037; NM_153047; NM_153048 | FYN oncogene related to SRC, FGR, YES | FYN | 15980968 | |
| CARMUSTINE | NM_000807; NM_001114175 | gamma-aminobutyric acid (GABA) A receptor, alpha 2 | GABRA2 | 15980968 | |
| CARMUSTINE | NM_000811 | gamma-aminobutyric acid (GABA) A receptor, alpha 6 | GABRA6 | 15980968 | |
| CARMUSTINE | NM_000156; NM_138924 | guanidinoacetate N-methyltransferase | GAMT | 15980968 | |
| CARMUSTINE | NM_000805 | gastrin | GAST | 15980968 | |
| CARMUSTINE | NM_003643 | glial cells missing homolog 1 (Drosophila) | GCM1 | 15980968 | |
| CARMUSTINE | NM_001493 | GDP dissociation inhibitor 1 | GDI1 | 15980968 | |
| CARMUSTINE | NM_001115156; NM_001494 | GDP dissociation inhibitor 2 | GDI2 | 15980968 | |
| CARMUSTINE | NM_001131019; NM_002055 | glial fibrillary acidic protein | GFAP | 15980968 | |
| CARMUSTINE | NM_004122; NM_198407 | growth hormone secretagogue receptor | GHSR | 15980968 | |
| CARMUSTINE | NM_000406; NM_001012763 | gonadotropin-releasing hormone receptor | GNRHR | 15980968 | |
| CARMUSTINE | NM_004486 | golgi autoantigen, golgin subfamily a, 2 | GOLGA2 | 15980968 | |
| CARMUSTINE | NM_002078 | golgi autoantigen, golgin subfamily a, 4 | GOLGA4 | 15980968 | |
| CARMUSTINE | NM_000407 | glycoprotein Ib (platelet), beta polypeptide | GP1BB | 15980968 | |
| CARMUSTINE | NM_005298 | G protein-coupled receptor 25 | GPR25 | 15980968 | |
| CARMUSTINE | NM_001506 | G protein-coupled receptor 32 | GPR32 | 15980968 | |
| CARMUSTINE | NM_005302 | G protein-coupled receptor 37 (endothelin receptor type B-like) | GPR37 | 15980968 | |
| CARMUSTINE | NM_003608 | G protein-coupled receptor 65 | GPR65 | 15980968 | |
| CARMUSTINE | NM_001030002; NM_005310 | growth factor receptor-bound protein 7 | GRB7 | 15980968 | |
| CARMUSTINE | NM_002087 | granulin | GRN | 15980968 | |
| CARMUSTINE | NM_000637 | glutathione reductase | GSR | — | target |
| CARMUSTINE | NM_145740 | glutathione S-transferase alpha 1 | GSTA1 | 8395980 | unrelated |
| CARMUSTINE | NM_000561; NM_146421 | glutathione S-transferase mu 1 | GSTM1 | 8395980 | unrelated |
| CARMUSTINE | NM_000849 | glutathione S-transferase mu 3 (brain) | GSTM3 | 15247628, 8395980 | resistance |
| CARMUSTINE | NM_000852 | glutathione S-transferase pi 1 | GSTP1 | 16899598, 8395980 | unrelated |
| CARMUSTINE | NM_002096 | general transcription factor IIF, polypeptide 1, 74 kDa | GTF2F1 | 15980968 | |
| CARMUSTINE | NM_002105 | H2A histone family, member X | H2AFX | 15980968 | |
| CARMUSTINE | — | hydroxyacylglutathione hydrolase | HAGH | 15980968 | |
| CARMUSTINE | NM_001040427; NM_005326 | host cell factor C1 (VP16-accessory protein) | HCFC1 | 15980968 | |
| CARMUSTINE | NM_005334 | high-mobility group nucleosomal binding domain 2 | HMGN2 | 15980968 | |
| CARMUSTINE | NM_005517 | HNF1 homeobox A | HNF1A | 15980968 | |
| CARMUSTINE | NM_000545 | homeobox A4 | HOXA4 | 15980968 | |
| CARMUSTINE | NM_002141 | intercellular adhesion molecule 5, telencephalin | ICAM5 | 15980968 | |
| CARMUSTINE | NM_003259 | iduronate 2-sulfatase | IDS | 15980968 | |
| CARMUSTINE | NM_000202; NM_006123 | immediate early response 3 | IER3 | 15980968 | |
| CARMUSTINE | NM_003897 | inhibitor of kappa light polypeptide gene enhancer in B-cells, kinase gamma | IKBKG | 15980968 | |
| CARMUSTINE | NM_001099856; NM_001099857; NM_001145255; NM_003639 | inositol polyphosphate phosphatase-like 1 | INPPL1 | 15980968 | |
| CARMUSTINE | NM_001567 | insulin induced gene 1 | INSIG1 | 15980968 | |
| CARMUSTINE | NM_005542; NM_198336; NM_198337 | insulin-like 3 (Leydig cell) | INSL3 | 15980968 | |
| CARMUSTINE | NM_005543 | insulin receptor substrate 1 | IRS1 | 15980968 | |
| CARMUSTINE | NM_005544 | immunoglobulin superfamily containing leucine-rich repeat | ISLR | 15980968 | |
| CARMUSTINE | NM_005545; NM_201526 | | | | |
| CARMUSTINE | NM_002204; NM_005501 | integrin, alpha 3 (antigen CD49C, alpha 3 subunit of VLA-3 receptor) | ITGA3 | 15980968 | |

TABLE 1-continued

| Molecule | RefSeq | Description | Symbol | PMID | Interaction |
|---|---|---|---|---|---|
| CARMUSTINE | NM_002215 | inter-alpha (globulin) inhibitor H1 | ITH1 | 15980968 | |
| CARMUSTINE | NM_000238; NM_172056; NM_172057 | potassium voltage-gated channel, subfamily H (eag-related), member 2 | KCNH2 | 15980968 | |
| CARMUSTINE | NM_004984 | kinesin family member 5A | KIF5A | 15980968 | |
| CARMUSTINE | NM_000422 | keratin 17 | KRT17 | 15980968 | |
| CARMUSTINE | NM_002277 | keratin 31 | KRT31 | 15980968 | |
| CARMUSTINE | NM_005558 | ladinin 1 | LAD1 | 15980968 | |
| CARMUSTINE | NM_002287; NM_021706 | leukocyte-associated immunoglobulin-like receptor 1 | LAIR1 | 15980968 | |
| CARMUSTINE | NM_000228; NM_001017402; NM_001127641 | laminin, beta 3 | LAMB3 | 15980968 | |
| CARMUSTINE | NM_002316 | LIM homeobox transcription factor 1, beta | LMX1B | 15980968 | |
| CARMUSTINE | NM_005576 | lysyl oxidase-like 1 | LOXL1 | 15980968 | |
| CARMUSTINE | NM_002319 | leucine-rich repeats and calponin homology (CH) domain containing 4 | LRCH4 | 15980968 | |
| CARMUSTINE | NM_006152 | lymphoid-restricted membrane protein | LRMP | 15980968 | |
| CARMUSTINE | NM_001013836; NM_001013837; NM_003550 | MAD1 mitotic arrest deficient-like 1 (yeast) | MAD1L1 | 15980968 | |
| CARMUSTINE | NM_004579 | mitogen-activated protein kinase kinase kinase kinase 2 | MAP4K2 | 15980968 | |
| CARMUSTINE | NM_002753; NM_138980; NM_138981; NM_138982 | mitogen-activated protein kinase 10 | MAPK10 | 15980968 | |
| CARMUSTINE | NM_000429 | methionine adenosyltransferase I, alpha | MAT1A | 15980968 | |
| CARMUSTINE | NM_001012333; NM_001012334; NM_002391 | midkine (neurite growth-promoting factor 2) | MDK | 15980968 | |
| CARMUSTINE | NM_004774 | mediator complex subunit 1 | MED1 | 15980968 | |
| CARMUSTINE | NM_001098270; NM_002409 | mannosyl (beta-1,4-)-glycoprotein beta-1,4-N-acetylglucosaminyltransferase | MGAT3 | 15980968 | |
| CARMUSTINE | NM_002412 | O-6-methylguanine-DNA methyltransferase | MGMT | 15319033, 15833865, 16899598, 16899598 | 16039682, 15814657, 16033832 resistance |
| CARMUSTINE | NM_002445; NM_138715; NM_138716 | macrophage scavenger receptor 1 | MSR1 | 15980968 | |
| CARMUSTINE | NM_002457 | mucin 2, oligomeric mucus/gel-forming | MUC2 | 15980968 | |
| CARMUSTINE | NM_002461 | mevalonate (diphospho) decarboxylase | MVD | 15980968 | |
| CARMUSTINE | NM_004997 | myosin binding protein H | MYBPH | 15980968 | |
| CARMUSTINE | NM_002468 | myeloid differentiation primary response gene (88) | MYD88 | 15980968 | |
| CARMUSTINE | NM_002478 | myogenic differentiation 1 | MYOD1 | 15980968 | |
| CARMUSTINE | NM_002479 | myogenin (myogenic factor 4) | MYOG | 15980968 | |
| CARMUSTINE | NM_002494 | NADH dehydrogenase (ubiquinone) 1, subcomplex unknown, 1, 6 kDa | NDUFC1 | 15980968 | |
| CARMUSTINE | NM_002509 | NK2 homeobox 2 | NKX2-2 | 15980968 | |
| CARMUSTINE | NM_002517 | neuronal PAS domain protein 1 | NPAS1 | 15980968 | |
| CARMUSTINE | NM_005286 | neuropeptides B/W receptor 2 | NPBWR2 | 15980968 | |
| CARMUSTINE | NM_004558 | neurturin | NRTN | 15980968 | |
| CARMUSTINE | NM_002542; NM_016819; NM_016820; NM_016821; NM_016826; NM_016827; NM_016829 | 8-oxoguanine DNA glycosylase | OGG1 | 11181913 | |
| CARMUSTINE | NM_006189 | olfactory marker protein | OMP | 15980968 | |
| CARMUSTINE | NM_001018049; NM_002571 | progestagen-associated endometrial protein | PAEP | 15980968 | |
| CARMUSTINE | NM_003466; NM_013951; NM_013952; NM_013953; NM_013992 | paired box 8 | PAX8 | 15980968 | |
| CARMUSTINE | NM_002586 | pre-B-cell leukemia homeobox 2 | PBX2 | 15980968 | |
| CARMUSTINE | NM_000281 | pterin-4 alpha-carbinolamine dehydratase/dimerization cofactor of hepatocyte nuclear factor 1 alpha | PCBD1 | 15980968 | |
| CARMUSTINE | NM_002588; NM_032402; NM_032403 | protocadherin gamma subfamily C, 3 | PCDHGC3 | 15980968 | |
| CARMUSTINE | NM_002593 | procollagen C-endopeptidase enhancer | PCOLCE | 15980968 | |

TABLE 1-continued

| Molecule | RefSeq | Description | Symbol | PMID | Interaction |
|---|---|---|---|---|---|
| CARMUSTINE | NM_005017 | phosphate cytidylyltransferase 1, choline, alpha | PCYT1A | 15980968 | |
| CARMUSTINE | NM_001018053; NM_006212 | 6-phosphofructo-2-kinase/fructose-2,6-biphosphatase 2 | PFKFB2 | 15980968 | |
| CARMUSTINE | NM_000289 | phosphofructokinase, muscle | PFKM | 15980968 | |
| CARMUSTINE | NM_005022 | profilin 1 | PFN1 | 15980968 | |
| CARMUSTINE | NM_001114172; NM_003629 | phosphoinositide-3-kinase, regulatory subunit 3 (gamma) | PIK3R3 | 15980968 | |
| CARMUSTINE | NR_023383; NR_023383; NR_023383; NR_023383; NR_023383; NR_023383 | postmeiotic segregation increased 2-like 11 pseudogene | PMS2L11 | 15980968 | |
| CARMUSTINE | NM_002695 | polymerase (RNA) II (DNA directed) polypeptide E, 25 kDa | POLR2E | 15980968 | |
| CARMUSTINE | NM_002707; NM_177983 | protein phosphatase 1G (formerly 2C), magnesium-dependent, gamma isoform | PPM1G | 15980968 | |
| CARMUSTINE | NM_003981; NM_199413; NM_199414 | protein regulator of cytokinesis 1 | PRC1 | 15980968 | |
| CARMUSTINE | NM_000948 | prolactin | PRL | 17374387 | |
| CARMUSTINE | NM_002762 | protamine 2 | PRM2 | 15980968 | |
| CARMUSTINE | NM_001145368; NM_001145369; NM_001145370; NM_001145371; NM_001145372; NM_002829 | protein tyrosine phosphatase, non-receptor type 3 | PTPN3 | 15980968 | |
| CARMUSTINE | NM_002864 | pregnancy-zone protein | PZP | 15980968 | |
| CARMUSTINE | NM_005053 | RAD23 homolog A (S. cerevisiae) | RAD23A | 15980968 | |
| CARMUSTINE | NM_002875; NM_133487 | RAD51 homolog (RecA homolog, E. coli) (S. cerevisiae) | RAD51 | 15980968 | |
| CARMUSTINE | — | — | RAD9 | 15980968 | |
| CARMUSTINE | NM_002901 | reticulocalbin 1, EF-hand calcium binding domain | RCN1 | 15980968 | |
| CARMUSTINE | NM_001012720; NM_001012722; NM_002921 | retinal G protein coupled receptor | RGR | 15980968 | |
| CARMUSTINE | NM_002930 | Ras-like without CAAX 2 | RIT2 | 15980968 | |
| CARMUSTINE | NM_002937; NM_194431 | ribonuclease, RNase A family, 4 | RNASE4 | 15980968 | |
| CARMUSTINE | NM_005066 | septin 5 | sept-05 | 15980968 | |
| CARMUSTINE | — | splicing factor proline/glutamine-rich (polypyrimidine tract binding protein associated) | SFPQ | 15980968 | |
| CARMUSTINE | NM_000023; NM_001135697 | sarcoglycan, alpha (50 kDa dystrophin-associated glycoprotein) | SGCA | 15980968 | |
| CARMUSTINE | NM_005412 | serine hydroxymethyltransferase 2 (mitochondrial) | SHMT2 | 15980968 | |
| CARMUSTINE | NM_000451; NM_006883 | short stature homeobox | SHOX | 15980968 | |
| CARMUSTINE | — | — | SIAT1 | 15980968 | |
| CARMUSTINE | NM_003049 | solute carrier family 10 (sodium/bile acid cotransporter family), member 1 | SLC10A1 | 15980968 | |
| CARMUSTINE | NM_006517 | solute carrier family 16, member 2 (monocarboxylic acid transporter 8) | SLC16A2 | 15980968 | |
| CARMUSTINE | NM_003459 | solute carrier family 30 (zinc transporter), member 3 | SLC30A3 | 15980968 | |
| CARMUSTINE | NM_001043 | solute carrier family 6 (neurotransmitter transporter, noradrenalin), member 2 | SLC6A2 | 15980968 | |
| CARMUSTINE | NM_021094; NM_134431 | solute carrier organic anion transporter family, member 1A2 | SLCO1A2 | 15980968 | |
| CARMUSTINE | NM_003076; NM_139071 | SWI/SNF related, matrix associated, actin dependent regulator of chromatin, subfamily d, member 1 | SMARCD1 | 15980968 | |
| CARMUSTINE | NM_003080 | sphingomyelin phosphodiesterase 2, neutral membrane (neutral sphingomyelinase) | SMPD2 | 15980968 | |
| CARMUSTINE | NM_003082 | small nuclear RNA activating complex, polypeptide 1, 43 kDa | SNAPC1 | 15980968 | |

TABLE 1-continued

| Molecule | RefSeq | Description | Symbol | PMID | Interaction |
|---|---|---|---|---|---|
| CARMUSTINE | NM_001039697 | small nuclear RNA activating complex, polypeptide 3, 50 kDa | SNAPC3 | 15980968 | |
| CARMUSTINE | NM_003087 | synuclein, gamma (breast cancer-specific protein 1) | SNCG | 15980968 | |
| CARMUSTINE | NM_003092; NM_198220 | small nuclear ribonucleoprotein polypeptide B" | SNRPB2 | 15980968 | |
| CARMUSTINE | NM_003745 | suppressor of cytokine signaling 1 | SOCS1 | 17374387 | |
| CARMUSTINE | NM_005876 | SPEG complex locus | SPEG | 15980968 | |
| CARMUSTINE | NM_001017418 | small proline-rich protein 2B | SPRR2B | 15980968 | |
| CARMUSTINE | NM_003134 | signal recognition particle 14 kDa (homologous Alu RNA binding protein) | SRP14 | 15980968 | |
| CARMUSTINE | NM_003140 | sex determining region Y | SRY | 15980968 | |
| CARMUSTINE | NM_003034 | ST8 alpha-N-acetyl-neuraminide alpha-2,8-sialyltransferase 1 | ST8SIA1 | 15980968 | |
| CARMUSTINE | NM_003473 | signal transducing adaptor molecule (SH3 domain and ITAM motif) 1 | STAM | 15980968 | |
| CARMUSTINE | NM_000351 | steroid sulfatase (microsomal), isozyme S | STS | 15980968 | |
| CARMUSTINE | NM_052874 | syntaxin 1B | STX1B | 15980968 | |
| CARMUSTINE | NM_001127396; NM_006949 | syntaxin binding protein 2 | STXBP2 | 15980968 | |
| CARMUSTINE | NM_003182; NM_013996; NM_013997; NM_013998 | tachykinin, precursor 1 | TAC1 | 15980968 | |
| CARMUSTINE | NM_003206; NM_198392 | transcription factor 21 | TCF21 | 15980968 | |
| CARMUSTINE | — | | TEGT | 18021753 | |
| CARMUSTINE | NM_198253; NM_198255 | telomerase reverse transcriptase | TERT | 15980968 | |
| CARMUSTINE | NM_001105192; NM_005078; NM_020908 | transducin-like enhancer of split 3 (E(sp1) homolog, Drosophila) | TLE3 | 15980968 | |
| CARMUSTINE | NM_002546 | tumor necrosis factor receptor superfamily, member 11b | TNFRSF11B | 15980968 | |
| CARMUSTINE | NM_000546; NM_001126112; NM_001126113; NM_001126114; NM_001126115; NM_001126116; NM_001126117 | tumor protein p53 | TP53 | 15735757 | resistance |
| CARMUSTINE | NM_005658 | TNF receptor-associated factor 1 | TRAF1 | 15980968 | |
| CARMUSTINE | NM_001025234; NM_001025235; NM_001025236; NM_001025237; NM_001025238; NM_001025239; NM_003271 | tetraspanin 4 | TSPAN4 | 15980968 | |
| CARMUSTINE | NM_178014 | tubulin, beta | TUBB | 15980968 | |
| CARMUSTINE | NM_001070 | tubulin, gamma 1 | TUBG1 | 15980968 | |
| CARMUSTINE | NM_001128174; NM_003360 | UDP glycosyltransferase 8 | UGT8 | 15980968 | |
| CARMUSTINE | NM_002911 | UPF1 regulator of nonsense transcripts homolog (yeast) | UPF1 | 15980968 | |
| CARMUSTINE | NM_003378 | VGF nerve growth factor inducible | VGF | 15980968 | |
| CARMUSTINE | NM_001077269; NM_003387 | WAS/WASL interacting protein family, member 1 | WIPF1 | 15980968 | |
| CARMUSTINE | NM_003405 | tyrosine 3-monooxygenase/tryptophan 5-monooxygenase activation protein, eta polypeptide | YWHAH | 15980968 | |
| CARMUSTINE | NM_003443 | zinc finger and BTB domain containing 17 | ZBTB17 | 15980968 | |
| CARMUSTINE | NM_001010972; NM_003461 | zyxin | ZYX | 15980968 | |
| FOTEMUSTINE | NM_002412 | O-6-methylguanine-DNA methyltransferase | MGMT | 12970393, 16039682, 12970393 | resistance |
| FOTEMUSTINE | NM_001093771; NM_003330; NM_182729; NM_182742; NM_182743 | thioredoxin reductase 1 | TXNRD1 | — | target |
| CARBOPLATIN | NM_000477 | albumin | ALB | 15576332, 15996812 | unrelated |
| CARBOPLATIN | NM_004324; NM_138761; NM_138763; NM_138764; NM_138765 | BCL2-associated X protein | BAX | | death pathway |

TABLE 1-continued

| Molecule | RefSeq | Description | Symbol | PMID | Interaction |
|---|---|---|---|---|---|
| CARBOPLATIN | NM_000633; NM_000657 | B-cell CLL/lymphoma 2 | BCL2 | 15996812, 15996812, 17404015, 15576332 | resistance |
| CARBOPLATIN | NM_001040668; NM_138639 | BCL2-like 12 (proline rich) | BCL2L12 | 15576332 | |
| CARBOPLATIN | NM_001166 | baculoviral IAP repeat-containing 2 | BIRC2 | 10815900 | death pathway |
| CARBOPLATIN | NM_004346; NM_032991 | caspase 3, apoptosis-related cysteine peptidase | CASP3 | 15576332 | death pathway |
| CARBOPLATIN | NM_001229; NM_032996 | caspase 9, apoptosis-related cysteine peptidase | CASP9 | 15996812, 17404015, 15576332 | resistance |
| CARBOPLATIN | NM_001129889; NM_001922 | dopachrome tautomerase (dopachrome delta-isomerase, tyrosine-related protein 2) | DCT | 15897911 | |
| CARBOPLATIN | NM_000043; NM_152871; NM_152872; NM_152873; NM_152874; NM_152875; NM_152876; NM_152877 | Fas (TNF receptor superfamily, member 6) | FAS | 15576332 | death pathway |
| CARBOPLATIN | NM_001618 | poly (ADP-ribose) polymerase 1 | PARP1 | 15996812 | altered by platin |
| CARBOPLATIN | NM_000963 | prostaglandin-endoperoxide synthase 2 (prostaglandin G/H synthase and cyclooxygenase) | PTGS2 | 18089846 | |
| CARBOPLATIN | NM_001145547; NM_032905 | RNA binding motif protein 17 | RBM17 | 16061639 | resistance |
| CISPLATIN | NM_000014 | alpha-2-macroglobulin | A2M | 16773208 | |
| CISPLATIN | NM_000927 | ATP-binding cassette, sub-family B (MDR/TAP), member 1 | ABCB1 | 15650019, 15756446, 15802814, 15990222, 15650019, 15239124 | resistance |
| CISPLATIN | NM_004996; NM_019862; NM_019898; NM_019899; NM_019900 | ATP-binding cassette, sub-family C (CFTR/MRP), member 1 | ABCC1 | 15448748, 15756446, 15802814, 18695918 | resistance |
| CISPLATIN | NM_000392 | ATP-binding cassette, sub-family C (CFTR/MRP), member 2 | ABCC2 | 15688364, 8797578, 15756446, 15985617, 18695918 | resistance |
| CISPLATIN | NM_001023587; NM_005688 | ATP-binding cassette, sub-family C (CFTR/MRP), member 5 | ABCC5 | 15882455 | resistance |
| CISPLATIN | NM_001014431; NM_001014432; NM_005163 | v-akt murine thymoma viral oncogene homolog 1 | AKT1 | 15981204, 18071906 | resistance |
| CISPLATIN | NM_001626 | v-akt murine thymoma viral oncogene homolog 2 | AKT2 | 18071906 | resistance |
| CISPLATIN | NM_005465; NM_181690 | v-akt murine thymoma viral oncogene homolog 3 (protein kinase B, gamma) | AKT3 | 18071906 | resistance |
| CISPLATIN | NM_000477 | albumin | ALB | 16773208 | drug carrier |
| CISPLATIN | NM_001641; NM_080648; NM_080649 | APEX nuclease (multifunctional DNA repair enzyme) 1 | APEX1 | 16373707 | resistance |
| CISPLATIN | NM_001699; NM_021913 | AXL receptor tyrosine kinase | AXL | 16061661 | resistance |
| CISPLATIN | NM_004324; NM_138761; NM_138763; NM_138764; NM_138765 | BCL2-associated X protein | BAX | 14512787, 14601052, 16009487 | death pathway |
| CISPLATIN | NM_000633; NM_000657 | B-cell CLL/lymphoma 2 | BCL2 | 14512787, 15917659, 15981204, 14601052, 16009487, 17404015 | resistance |
| CISPLATIN | NM_001191; NM_138578 | BCL2-like 1 | BCL2L1 | 15917659, 15981204, 14601052 | resistance |
| CISPLATIN | NM_001040668; NM_138639 | BCL2-like 12 (proline rich) | BCL2L12 | 17404015 | sensitivity |
| CISPLATIN | NM_001166 | baculoviral IAP repeat-containing 2 | BIRC2 | 14601052, 14654915, 16142363, 10815900 | resistance |
| CISPLATIN | NM_001165; NM_182962 | baculoviral IAP repeat-containing 3 | BIRC3 | 14654915, 16391810 | resistance |
| CISPLATIN | NM_001012270; NM_001012271; NM_001168 | baculoviral IAP repeat-containing 5 | BIRC5 | 14601052, 15917659, 16382892, 15970709, 11911975, 15981204, 15981204, 16142363, 14654915, 11911975 | resistance |
| CISPLATIN | NM_032982; NM_032983 | caspase 2, apoptosis-related cysteine peptidase | CASP2 | 14757846 | death pathway |
| CISPLATIN | NM_004346; NM_032991 | caspase 3, apoptosis-related cysteine peptidase | CASP3 | 16009487, 15863139, 14512787, 18071906 | death pathway |

TABLE 1-continued

| Molecule | RefSeq | Description | Symbol | PMID | Interaction |
|---|---|---|---|---|---|
| CISPLATIN | NM_001080124; NM_001080125; NM_001228; NM_033355; NM_033356; NM_033358 | caspase 8, apoptosis-related cysteine peptidase | CASP8 | 16009487, 18071906 | death pathway |
| CISPLATIN | NM_001229; NM_032996 | caspase 9, apoptosis-related cysteine peptidase | CASP9 | 16009487, 17404015 | death pathway |
| CISPLATIN | NM_001752 | catalase | CAT | 10754530, 1930895 | altered by platin |
| CISPLATIN | NM_000389; NM_078467 | cyclin-dependent kinase inhibitor 1A (p21, Cip1) | CDKN1A | 11099651, 12807743, 14601052 | resistance |
| CISPLATIN | NM_001127183; NM_001127184; NM_003879 | CASP8 and FADD-like apoptosis regulator | CFLAR | 14601052 | resistance |
| CISPLATIN | NM_020313 | cytokine induced apoptosis inhibitor 1 | CIAPIN1 | 18389626 | |
| CISPLATIN | NM_001831; NM_203339 | clusterin | CLU | 15955107 | resistance |
| CISPLATIN | NM_000614 | ciliary neurotrophic factor | CNTF | 16898872 | |
| CISPLATIN | NM_001079846; NM_004380 | CREB binding protein | CREBBP | 17498666 | |
| CISPLATIN | NM_018947 | cytochrome c, somatic | CYCS | 16009487 | death pathway |
| CISPLATIN | NM_017460 | cytochrome P450, family 3, subfamily A, polypeptide 4 | CYP3A4 | 15650019 | unrelated |
| CISPLATIN | NM_019887; NM_138929 | diablo homolog (Drosophila) | DIABLO | 16391810 | death pathway |
| CISPLATIN | NM_000110 | dihydropyrimidine dehydrogenase | DPYD | 15737843 | resistance |
| CISPLATIN | NM_001956 | endothelin 2 | EDN2 | 16898872 | |
| CISPLATIN | NM_005228; NM_201282; NM_201283; NM_201284 | epidermal growth factor receptor (erythroblastic leukemia viral (v-erb-b) oncogene homolog, avian) | EGFR | 15723263, 15737843, 18337622 | resistance |
| CISPLATIN | NM_001429 | E1A binding protein p300 | EP300 | 17498666 | |
| CISPLATIN | NM_001005862; NM_004448 | v-erb-b2 erythroblastic leukemia viral oncogene homolog 2, neuro/glioblastoma derived oncogene homolog (avian) | ERBB2 | 15737843, 18337622 | resistance |
| CISPLATIN | NM_001983; NM_202001 | excision repair cross-complementing rodent repair deficiency, complementation group 1 (includes overlapping antisense sequence) | ERCC1 | 15737843 | resistance |
| CISPLATIN | NM_001130867 | excision repair cross-complementing rodent repair deficiency, complementation group 2 | ERCC2 | 15882455 | resistance |
| CISPLATIN | NM_001079675; NM_001986 | ets variant 4 | ETV4 | 16061661 | resistance |
| CISPLATIN | NM_003824 | Fas (TNFRSF6)-associated via death domain | FADD | 16009487 | death pathway |
| CISPLATIN | NM_000136 | Fanconi anemia, complementation group C | FANCC | 16243825 | resistance |
| CISPLATIN | NM_004629 | Fanconi anemia, complementation group G | FANCG | 16061661, 16243825 | resistance |
| CISPLATIN | NM_000043; NM_152871; NM_152872; NM_152873; NM_152874; NM_152875; NM_152876; NM_152877 | Fas (TNF receptor superfamily, member 6) | FAS | 16009487, 17305640 | death pathway |
| CISPLATIN | NM_000639 | Fas ligand (TNF superfamily, member 6) | FASLG | 16009487 | death pathway |
| CISPLATIN | NM_002009 | fibroblast growth factor 7 (keratinocyte growth factor) | FGF7 | 18708365 | |
| CISPLATIN | NM_000142; NM_022965 | fibroblast growth factor receptor 3 | FGFR3 | 12066199 | |
| CISPLATIN | NM_005438 | FOS-like antigen 1 | FOSL1 | 15756446, 16061661 | sensitivity |
| CISPLATIN | NM_001924 | growth arrest and DNA-damage-inducible, alpha | GADD45A | 19003803 | |
| CISPLATIN | NM_004864 | growth differentiation factor 15 | GDF15 | 16898872 | |
| CISPLATIN | NM_000561; NM_146421 | glutathione S-transferase mu 1 | GSTM1 | 12851839 | polymorphisms |
| CISPLATIN | NM_000849 | glutathione S-transferase mu 3 (brain) | GSTM3 | 11081456 | polymorphisms |
| CISPLATIN | NM_000852 | glutathione S-transferase pi 1 | GSTP1 | 14678959, 15239142, 15279901, 15737843, 2747627 | resistance |
| CISPLATIN | NM_000853 | glutathione S-transferase theta 1 | GSTT1 | 12851839 | polymorphisms |
| CISPLATIN | NM_000858; NM_001159390; NM_001159391 | guanylate kinase 1 | GUK1 | 16898872 | |
| CISPLATIN | NM_001530; NM_181054 | hypoxia inducible factor 1, alpha subunit (basic helix-loop-helix transcription factor) | HIF1A | 16532342, 17498666 | resistance |
| CISPLATIN | NM_001540 | heat shock 27 kDa protein 1 | HSPB1 | 19088045 | |
| CISPLATIN | NM_002157 | heat shock 10 kDa protein 1 (chaperonin 10) | HSPE1 | 16394183 | resistance |
| CISPLATIN | NM_013247; NM_145074 | HtrA serine peptidase 2 | HTRA2 | 15863139 | death pathway |

TABLE 1-continued

| Molecule | RefSeq | Description | Symbol | PMID | Interaction |
|---|---|---|---|---|---|
| CISPLATIN | NM_003641 | interferon induced transmembrane protein 1 (9-27) | IFITM1 | 16898872 | sensitivity |
| CISPLATIN | NM_000598; NM_001013398 | insulin-like growth factor binding protein 3 | IGFBP3 | 16061661 | sensitivity |
| CISPLATIN | NM_000418; NM_001008699 | interleukin 4 receptor | IL4R | 14678968 | |
| CISPLATIN | NM_000207 | integrin, alpha 9 | ITGA9 | 12066199 | altered by platin |
| CISPLATIN | NM_000213; NM_001005619; NM_001005731 | integrin, beta 4 | ITGB4 | 12066199 | altered by platin |
| CISPLATIN | NM_002228 | jun oncogene | JUN | 16898872 | sensitivity |
| CISPLATIN | NM_002276 | keratin 19 | KRT19 | 16061661 | sensitivity |
| CISPLATIN | NM_002272 | keratin 4 | KRT4 | 16061661 | unrelated |
| CISPLATIN | NM_024552 | LAG1 homolog, ceramide synthase 4 | LASS4 | 15756446 | resistance |
| CISPLATIN | NM_004526 | minichromosome maintenance complex component 2 | MCM2 | 16061661 | sensitivity |
| CISPLATIN | NM_004774 | mediator complex subunit 1 | MED1 | 15650019 | resistance |
| CISPLATIN | NM_002412 | O-6-methylguanine-DNA methyltransferase | MGMT | 15015788, 15809756, 16043385 | 2766459, 7562019, 16043385, 16039682, |
| CISPLATIN | NM_002425 | matrix metallopeptidase 10 (stromelysin 2) | MMP10 | 12066199 | altered by platin |
| CISPLATIN | NM_002428 | matrix metallopeptidase 15 (membrane-inserted) | MMP15 | 12066199 | altered by platin |
| CISPLATIN | NM_005941; NM_022564 | matrix metallopeptidase 16 (membrane-inserted) | MMP16 | 12066199 | altered by platin |
| CISPLATIN | NM_015084 | mitochondrial ribosomal protein S27 | MRPS27 | 15756446 | sensitivity |
| CISPLATIN | NM_005946 | metallothionein 1A | MT1A | 12680227 | resistance |
| CISPLATIN | NM_005953 | metallothionein 2A | MT2A | 12680227, 16394183 | resistance |
| CISPLATIN | NM_005954 | metallothionein 3 | MT3 | 16061661, 16898872 | resistance |
| CISPLATIN | NM_005115; NM_017458 | major vault protein | MVP | 15802814 | resistance |
| CISPLATIN | NM_004536; NM_022892 | NLR family, apoptosis inhibitory protein | NAIP | 11911975, 11911975, 14654915 | |
| CISPLATIN | NM_006534; NM_181659 | nuclear receptor coactivator 3 | NCOA3 | 15650019 | |
| CISPLATIN | NM_004557 | Notch homolog 4 (Drosophila) | NOTCH4 | 16898872 | |
| CISPLATIN | NM_003889; NM_022002; NM_033013 | nuclear receptor subfamily 1, group I, member 2 | NR1I2 | 15650019 | resistance |
| CISPLATIN | NM_002528 | nth endonuclease III-like 1 (E. coli) | NTHL1 | 16898872 | resistance |
| CISPLATIN | NM_001618 | poly (ADP-ribose) polymerase 1 | PARP1 | 16009487, 18 | altered by platin |
| CISPLATIN | NM_002592; NM_182649 | proliferating cell nuclear antigen | PCNA | 11099651 | |
| CISPLATIN | NM_005313 | protein disulfide isomerase family A, member 3 | PDIA3 | 15756446 | |
| CISPLATIN | NM_002624; NM_145897 | prefoldin subunit 5 | PFDN5 | 16898872 | |
| CISPLATIN | NM_000291 | phosphoglycerate kinase 1 | PGK1 | 15756446 | sensitivity |
| CISPLATIN | NM_021127 | phorbol-12-myristate-13-acetate-induced protein 1 | PMAIP1 | 17216584 | |
| CISPLATIN | NM_001081640; NM_006904 | protein kinase, DNA-activated, catalytic polypeptide | PRKDC | 18546291 | |
| CISPLATIN | NM_000311; NM_001080121; NM_001080122; NM_001080123; NM_183079 | prion protein | PRNP | 15386405 | |
| CISPLATIN | NM_000314 | phosphatase and tensin homolog | PTEN | 11707646 | sensitivity |
| CISPLATIN | NM_000963 | prostaglandin-endoperoxide synthase 2 (prostaglandin G/H synthase and cyclooxygenase) | PTGS2 | 15517878, 1895918 | resistance |
| CISPLATIN | NM_005607; NM_153831 | PTK2 protein tyrosine kinase 2 | PTK2 | 16391810 | resistance |
| CISPLATIN | NM_006788 | ralA binding protein 1 | RALBP1 | — | |
| CISPLATIN | NM_000321 | retinoblastoma 1 | RB1 | 14704340 | resistance |
| CISPLATIN | NM_001145138; NM_021975 | v-rel reticuloendotheliosis viral oncogene homolog A (avian) | RELA | 19003803 | resistance |
| CISPLATIN | NM_001042678; NM_001042679; NM_175744 | ras homolog gene family, member C | RHOC | 16898872 | |

TABLE 1-continued

| Molecule | RefSeq | Symbol | Description | PMID | Interaction |
|---|---|---|---|---|---|
| CISPLATIN | NM_015414; NM_033643 | RPL36 | ribosomal protein L36 | 16394183 | resistance |
| CISPLATIN | NM_001009 | RPS5 | ribosomal protein S5 | 16898872 | |
| CISPLATIN | NM_001031680; NM_004350 | RUNX3 | runt-related transcription factor 3 | 15756676 | |
| CISPLATIN | NM_006142 | SFN | stratifin | 15999354 | |
| CISPLATIN | NM_001078174; NM_001078175; NM_001078176; NM_001078177; NM_004955 | SLC29A1 | solute carrier family 29 (nucleoside transporters), member 1 | 18728667 | drug import |
| CISPLATIN | NM_001859 | SLC31A1 | solute carrier family 31 (copper transporters), member 1 | 15985617 | |
| CISPLATIN | NM_003745 | SOCS1 | suppressor of cytokine signaling 1 | 17374387 | unrelated |
| CISPLATIN | NM_021102 | SPINT2 | serine peptidase inhibitor, Kunitz type, 2 | 15756446 | |
| CISPLATIN | NM_198253; NM_198255 | TERT | telomerase reverse transcriptase | 18021753 | |
| CISPLATIN | NM_001063 | TF | transferrin | 16773208 | |
| CISPLATIN | NM_003808; NM_172087; NM_172088 | TNFSF13 | tumor necrosis factor (ligand) superfamily, member 13 | 18423122 | |
| CISPLATIN | NM_000546; NM_001126112; NM_001126113; NM_001126114; NM_001126115; NM_001126116; NM_001126117 | TP53 | tumor protein p53 | 12807743, 15990222, 15990222, 16077963, 17498666, 17498968 | 14562046, 15578696, 12082016, 17555331, 16020667, 15999354, 16211088, 17216584, 17555331 sensitivity |
| CISPLATIN | NM_001126240; NM_001126241; NM_001126242; NM_005427 | TP73 | tumor protein p73 | 17076661 | sensitivity |
| CISPLATIN | NM_000365; NM_001159287 | TPI1 | triosephosphate isomerase 1 | 18309519 | |
| CISPLATIN | NM_014294 | TRAM1 | translocation associated membrane protein 1 | 16061661 | sensitivity |
| CISPLATIN | NM_016292 | TRAP1 | TNF receptor-associated protein 1 | 16061661 | resistance |
| CISPLATIN | NM_006009 | TUBA1A | tubulin, alpha 1a | 16898872 | resistance |
| CISPLATIN | NM_003329 | TXN | thioredoxin | 10754530 | resistance |
| CISPLATIN | NM_001071 | TYMS | thymidylate synthetase | 10482907, 15737843 | resistance |
| CISPLATIN | NM_001025366; NM_001025367; NM_001025368; NM_001025369; NM_001025370; NM_001033756; NM_003376 | VEGFA | vascular endothelial growth factor A | 17498666 | |
| CISPLATIN | NM_001167 | XIAP | X-linked inhibitor of apoptosis | 11911975, 16142363, 15863139, 14654915, 15981204, 14601052, 16391810, 16391810, 15863139, 18071906 | resistance |
| CISPLATIN | NM_000380 | XPA | xeroderma pigmentosum, complementation group A | 15882455 | |
| CISPLATIN | NM_006297 | XRCC1 | X-ray repair complementing defective repair in Chinese hamster cells 1 | 15882455 | |
| CISPLATIN | NM_021141 | XRCC5 | X-ray repair complementing defective repair in Chinese hamster cells 5 (double-strand-break rejoining) | 12384553, 18546291 | |
| CISPLATIN | NM_001469 | XRCC6 | X-ray repair complementing defective repair in Chinese hamster cells 6 | 18546291 | polymorphisms |
| CISPLATIN | NM_004926 | ZFP36L1 | zinc finger protein 36, C3H type-like 1 | 15880358 | altered by platin |
| OXALIPLATIN | NM_001014431; NM_001014432; NM_005163 | AKT1 | v-akt murine thymoma viral oncogene homolog 1 | 18790786, 19147571 | resistance |
| OXALIPLATIN | NM_000633; NM_000657 | BCL2 | B-cell CLL/lymphoma 2 | 16024531 | resistance |
| OXALIPLATIN | NM_001191; NM_138578 | BCL2L1 | BCL2-like 1 | 16024531 | altered by oxaliplatin |
| OXALIPLATIN | NM_001012270; NM_001012271; NM_001168 | BIRC5 | baculoviral IAP repeat-containing 5 | 16004971, 16004971, 16024531, 19147571 | altered by oxaliplatin |
| OXALIPLATIN | NM_001237 | CCNA2 | cyclin A2 | 15204521 | altered by oxaliplatin |
| OXALIPLATIN | NM_031966 | CCNB1 | cyclin B1 | 15204521 | altered by oxaliplatin |
| OXALIPLATIN | NM_053056 | CCND1 | cyclin D1 | 19147571 | altered by oxaliplatin |

TABLE 1-continued

| Molecule | RefSeq | Description | Symbol | PMID | Interaction |
|---|---|---|---|---|---|
| OXALIPLATIN | NM_001238; NM_057182 | cyclin E1 | CCNE1 | 15204521 | altered by oxaliplatin |
| OXALIPLATIN | NM_001785 | cytidine deaminase | CDA | 18728667 | |
| OXALIPLATIN | NM_001130829; NM_001786; NM_033379 | cell division cycle 2, G1 to S and G2 to M | CDC2 | 15204521, 16024531 | altered by oxaliplatin |
| OXALIPLATIN | NM_001798; NM_052827 | cyclin-dependent kinase 2 | CDK2 | 15204521 | altered by oxaliplatin |
| OXALIPLATIN | NM_004064 | cyclin-dependent kinase inhibitor 1B (p27, Kip1) | CDKN1B | 15204521 | |
| OXALIPLATIN | NM_001025248; NM_001025249; NM_001948 | deoxyuridine triphosphatase | DUT | 19015155 | |
| OXALIPLATIN | NM_005228; NM_201282; NM_201283; NM_201284 | epidermal growth factor receptor (erythroblastic leukemia viral (v-erb-b) oncogene homolog, avian) | EGFR | 16098254 | polymorphism |
| OXALIPLATIN | NM_001983; NM_202001 | excision repair cross-complementing rodent repair deficiency, complementation group 1 (includes overlapping antisense sequence) | ERCC1 | 15655543, 17401013, 18448328, 15213713 | resistance |
| OXALIPLATIN | NM_000400; NM_001130867 | excision repair cross-complementing rodent repair deficiency, complementation group 2 | ERCC2 | 15213713, 15655543, 17401013 | |
| OXALIPLATIN | NM_001160030; NM_001160031; NM_002019 | fms-related tyrosine kinase 1 (vascular endothelial growth factor/vascular permeability factor receptor) | FLT1 | 18790786 | |
| OXALIPLATIN | | | FRAP1 | 19147571 | |
| OXALIPLATIN | NM_000852 | glutathione S-transferase pi 1 | GSTP1 | 15213713, 15655543, 17401013 | resistance |
| OXALIPLATIN | NM_005524 | hairy and enhancer of split 1, (Drosophila) | HES1 | 19147571 | |
| OXALIPLATIN | NM_000634 | interleukin 8 receptor, alpha | IL8RA | 16098254 | |
| OXALIPLATIN | NM_002745; NM_138957 | mitogen-activated protein kinase 1 | MAPK1 | 18790786 | |
| OXALIPLATIN | NM_001040056; NM_001109891; NM_002746 | mitogen-activated protein kinase 3 | MAPK3 | 18790786 | |
| OXALIPLATIN | NM_002467 | v-myc myelocytomatosis viral oncogene homolog (avian) | MYC | 15204521 | sensitivity |
| OXALIPLATIN | NM_015331 | nicastrin | NCSTN | 19147571 | |
| OXALIPLATIN | NM_017617 | Notch homolog 1, translocation-associated (Drosophila) | NOTCH1 | 19147571 | |
| OXALIPLATIN | NM_001024628; NM_001024629; NM_003873 | neuropilin 1 | NRP1 | 18790786 | |
| OXALIPLATIN | NM_002632 | placental growth factor | PGF | 18790786 | |
| OXALIPLATIN | NM_000021; NM_007318 | presenilin 1 | PSEN1 | 19147571 | |
| OXALIPLATIN | NM_000321 | retinoblastoma 1 | RB1 | 15204521 | altered by oxaliplatin |
| OXALIPLATIN | NM_005980 | S100 calcium binding protein P | S100P | 18636193 | |
| OXALIPLATIN | NM_003109; NM_138473 | Sp1 transcription factor | SP1 | 19015155 | |
| OXALIPLATIN | NM_005417; NM_198291 | v-src sarcoma (Schmidt-Ruppin A-2) viral oncogene homolog (avian) | SRC | 18790786 | |
| OXALIPLATIN | NM_003286 | topoisomerase (DNA) I | TOP1 | 18509181 | |
| OXALIPLATIN | NM_000546; NM_001126112; NM_001126113; NM_001126114; NM_001126115; NM_001126116; NM_001126117 | tumor protein p53 | TP53 | 19015155 | |
| OXALIPLATIN | NM_001113755; NM_001113756; NM_001953 | thymidine phosphorylase | TYMP | 18728667 | |
| OXALIPLATIN | NM_001071 | thymidylate synthetase | TYMS | 15213713, 18448328, 19074750 | resistance |
| OXALIPLATIN | NM_001025366; NM_001025367; NM_001025368; NM_001025369; NM_001025370; NM_001033756; NM_003376 | vascular endothelial growth factor A | VEGFA | 18790786 | |
| OXALIPLATIN | NM_005429 | vascular endothelial growth factor C | VEGFC | 18790786 | |
| BUSULFAN | NM_145740 | glutathione S-transferase alpha 1 | GSTA1 | 10437668, 10570028, 8886613, 12429583, 15779864 | drug metabolism |

TABLE 1-continued

| Molecule | RefSeq | Description | Symbol | PMID | Interaction |
|---|---|---|---|---|---|
| BUSULFAN | NM_000561; NM_146421 | glutathione S-transferase mu 1 | GSTM1 | 15142875, 8886613 | unrelated |
| BUSULFAN | NM_000852 | glutathione S-transferase pi 1 | GSTP1 | 15779864, 8886613 | unrelated |
| BUSULFAN | NM_002412 | O-6-methylguanine-DNA methyltransferase | MGMT | 16039682 | unrelated |
| BUSULFAN | NM_002413 | microsomal glutathione S-transferase 2 | MGST2 | 15779864 | resistance |
| PROCARBAZINE | NM_002412 | O-6-methylguanine-DNA methyltransferase | MGMT | 16033832 | |
| DACARBAZINE | NM_001641; NM_080648; NM_080649 | APEX nuclease (multifunctional DNA repair enzyme) 1 | APEX1 | 16373707 | resistance |
| DACARBAZINE | NM_001168; NM_001012270; NM_001012271; NM_001168 | baculoviral IAP repeat-containing 5 | BIRC5 | 15577328 | |
| DACARBAZINE | NM_004346; NM_032991 | caspase 3, apoptosis-related cysteine peptidase | CASP3 | 17410615 | death pathway |
| DACARBAZINE | NM_001080124; NM_001080125; NM_001228; NM_033355; NM_033356; NM_033358 | caspase 8, apoptosis-related cysteine peptidase | CASP8 | 17410615 | |
| DACARBAZINE | NM_001775 | CD38 molecule | CD38 | 11583285, 14669796, 16078447 | unrelated |
| DACARBAZINE | NM_001781 | CD69 molecule | CD69 | 14669796, 17973783 | unrelated |
| DACARBAZINE | NM_000499 | cytochrome P450, family 1, subfamily A, polypeptide 1 | CYP1A1 | 11751525 | drug activation |
| DACARBAZINE | NM_000761 | cytochrome P450, family 1, subfamily A, polypeptide 2 | CYP1A2 | 11751525 | drug activation |
| DACARBAZINE | NM_000799 | erythropoietin | EPO | 15743794 | resistance |
| DACARBAZINE | NM_024013 | interferon, alpha 1 | IFNA1 | 11583285, 16078447 | therapy |
| DACARBAZINE | NM_000605 | interferon, alpha 2 | IFNA2 | 14669796, 17973783 | therapy |
| DACARBAZINE | NM_000584 | interleukin 8 | IL8 | 12939465, 15123733, 15026559, 12939465, 15123733, 12939465 | altered by DTIC |
| DACARBAZINE | NM_002198 | interferon regulatory factor 1 | IRF1 | 17973783 | unrelated |
| DACARBAZINE | NM_005921 | mitogen-activated protein kinase kinase kinase 1 | MAP3K1 | 15123733 | |
| DACARBAZINE | NM_002745; NM_138957 | mitogen-activated protein kinase 1 | MAPK1 | 15123733 | |
| DACARBAZINE | NM_001040056; NM_001109891; NM_002746 | mitogen-activated protein kinase 3 | MAPK3 | 15123733 | |
| DACARBAZINE | NM_021960; NM_182763 | myeloid cell leukemia sequence 1 (BCL2-related) | MCL1 | 12787138 | |
| DACARBAZINE | NM_002412 | O-6-methylguanine-DNA methyltransferase | MGMT | 10751609, 12170182, 15870882, 14562026 | resistance |
| DACARBAZINE | NM_002689 | polymerase (DNA directed), alpha 2 (70 kD subunit) | POLA2 | | |
| DACARBAZINE | NM_006516 | solute carrier family 2 (facilitated glucose transporter), member 1 | SLC2A1 | 17520257 | resistance |
| DACARBAZINE | NM_003810 | tumor necrosis factor (ligand) superfamily, member 10 | TNFSF10 | 17410615 | therapy |
| DACARBAZINE | NM_001025366; NM_001025367; NM_001025368; NM_001025369; NM_001025370; NM_001033756; NM_003376 | vascular endothelial growth factor A | VEGFA | 12939465, 15123733, 15026559, 12939465, 15123733, 15026559, 12939465, 15123733, 12939465 | |
| TEMOZOLOMIDE | NM_000029 | angiotensinogen (serpin peptidase inhibitor, clade A, member 8) | AGT | 11034089 | resistance |
| TEMOZOLOMIDE | | | AKT | | resistance |
| TEMOZOLOMIDE | NM_004052 | BCL2/adenovirus E1B 19 kDa interacting protein 3 | BNIP3 | | resistance |
| TEMOZOLOMIDE | NM_001129889; NM_001922 | dopachrome tautomerase (dopachrome delta-isomerase, tyrosine-related protein 2) | DCT | 15897911 | |
| TEMOZOLOMIDE | NM_002006 | fibroblast growth factor 2 (basic) | FGF2 | | resistance |
| TEMOZOLOMIDE | NM_001145336; NM_001145337; NM_001145339; NM_001145340; NM_002392; NM_006878; NM_006879; NM_006881; NM_006882 | Mdm2 p53 binding protein homolog (mouse) | MDM2 | | sensitivity |
| TEMOZOLOMIDE | NM_002412 | O-6-methylguanine-DNA methyltransferase | MGMT | 15319033, 15486188, 15758010, 15814657, 15833865, 16039682, 15865885, 16075413 | resistance |

TABLE 1-continued

| Molecule | RefSeq | Description | Symbol | PMID | Interaction |
|---|---|---|---|---|---|
| TEMOZOLOMIDE | NM_001015052; NM_001015054; NM_002434 | N-methylpurine-DNA glycosylase | MPG | 15299078, 15299078, 16024643 | sensitivity |
| TEMOZOLOMIDE | NM_020529 | nuclear factor of kappa light polypeptide gene enhancer in B-cells inhibitor, alpha | NFKBIA | 17638900 | |
| TEMOZOLOMIDE | NM_001618 | poly (ADP-ribose) polymerase 1 | PARP1 | 15867241 | resistance |
| TEMOZOLOMIDE | NM_021127 | phorbol-12-myristate-13-acetate-induced protein 1 | PMAIP1 | 17216584 | unrelated |
| TEMOZOLOMIDE | NM_002690 | polymerase (DNA directed), beta | POLB | 16024643 | resistance |
| TEMOZOLOMIDE | NM_007195 | polymerase (DNA directed) iota | POLI | 16024643 | unrelated |
| TEMOZOLOMIDE | NM_013274 | polymerase (DNA directed), lambda | POLL | 16024643 | unrelated |
| TEMOZOLOMIDE | NM_000963 | prostaglandin-endoperoxide synthase 2 (prostaglandin G/H synthase and cyclooxygenase) | PTGS2 | 17638900 | |
| TEMOZOLOMIDE | NM_001145138; NM_021975 | v-rel reticuloendotheliosis viral oncogene homolog A (avian) | RELA | 17638900 | |
| TEMOZOLOMIDE | NM_000636; NM_001024465; NM_001024466 | superoxide dismutase 2, mitochondrial | SOD2 | 17638900 | |
| TEMOZOLOMIDE | NM_198253; NM_198255 | telomerase reverse transcriptase | TERT | 18021753 | |
| TEMOZOLOMIDE | NM_000594 | tumor necrosis factor (TNF superfamily, member 2) | TNF | 17638900 | |
| TEMOZOLOMIDE | NM_000546; NM_001126112; NM_001126113; NM_001126114; NM_001126115; NM_001126116; NM_001126117 | tumor protein p53 | TP53 | 17216584 | resistance |
| TEMOZOLOMIDE | NM_001167 | X-linked inhibitor of apoptosis | XIAP | 17638900 | |
| THIOTEPA | NM_004322; NM_032989 | BCL2-associated agonist of cell death | BAD | 10822281 | |
| THIOTEPA | NM_001188 | BCL2-antagonist/killer 1 | BAK1 | 10822281 | |
| THIOTEPA | NM_004324; NM_138761; NM_138763; NM_138764; NM_138765 | BCL2-associated X protein | BAX | 10822281 | |
| THIOTEPA | NM_000633; NM_000657 | B-cell CLL/lymphoma 2 | BCL2 | 10822281 | |
| THIOTEPA | NM_001191; NM_138578 | BCL2-like 1 | BCL2L1 | 10822281 | |
| THIOTEPA | NM_000767 | cytochrome P450, family 2, subfamily B, polypeptide 6 | CYP2B6 | 15769884 | |
| THIOTEPA | NM_145740 | glutathione S-transferase alpha 1 | GSTA1 | 7712478 | polymorphism |
| THIOTEPA | NM_000846 | glutathione S-transferase alpha 2 | GSTA2 | 7712478 | polymorphism |
| THIOTEPA | NM_000561; NM_146421 | glutathione S-transferase mu 1 | GSTM1 | 7712478 | polymorphism |
| THIOTEPA | NM_000852 | glutathione S-transferase pi 1 | GSTP1 | 10334868, 7712478 | |
| THIOTEPA | NM_002412 | O-6-methylguanine-DNA methyltransferase | MGMT | 16039682 | unrelated |
| THIOTEPA | NM_002542; NM_016819; NM_016820; NM_016821; NM_016826; NM_016827; NM_016828; NM_016829 | 8-oxoguanine DNA glycosylase | OGG1 | 11431349, 11 | |
| ECTEINASCIDIN 743 | NM_001237 | cyclin A2 | CCNA2 | — | |
| ECTEINASCIDIN 743 | NM_031966 | cyclin B1 | CCNB1 | — | |
| ECTEINASCIDIN 743 | NM_004701 | cyclin B2 | CCNB2 | — | |
| ECTEINASCIDIN 743 | NM_005225 | E2F transcription factor 1 | E2F1 | — | |
| DOCETAXEL | NM_000927 | ATP-binding cassette, sub-family B (MDR/TAP), member 1 | ABCB1 | 15239124, 15239142 | resistance |
| DOCETAXEL | NM_004996; NM_019862; NM_019898; NM_019899; NM_019900 | ATP-binding cassette, sub-family C (CFTR/MRP), member 1 | ABCC1 | 15239124 | resistance |
| DOCETAXEL | NM_000392 | ATP-binding cassette, sub-family C (CFTR/MRP), member 2 | ABCC2 | 15849751 | resistance |
| DOCETAXEL | NM_000633; NM_000657 | B-cell CLL/lymphoma 2 | BCL2 | | resistance |
| DOCETAXEL | NM_001191; NM_138578 | BCL2-like 1 | BCL2L1 | 16080463 | resistance |
| DOCETAXEL | NM_001012270; NM_001012271; NM_001168 | baculoviral IAP repeat-containing 5 | BIRC5 | 16224667, 19 | resistance |

TABLE 1-continued

| Molecule | RefSeq | Description | Symbol | PMID | Interaction |
|---|---|---|---|---|---|
| DOCETAXEL | NM_001211 | budding uninhibited by benzimidazoles 1 homolog beta (yeast) | BUB1B | 18691855 | death pathway |
| DOCETAXEL | NM_004346; NM_032991 | caspase 3, apoptosis-related cysteine peptidase | CASP3 | 15970518 | |
| DOCETAXEL | NM_031966 | cyclin B1 | CCNB1 | — | |
| DOCETAXEL | NM_001127183; NM_001127184; NM_003879 | CASP8 and FADD-like apoptosis regulator | CFLAR | 16080463 | unrelated |
| DOCETAXEL | NM_000103; NM_031226 | cytochrome P450, family 19, subfamily A, polypeptide 1 | CYP19A1 | 15623590 | drug metabolism |
| DOCETAXEL | NM_000104 | cytochrome P450, family 1, subfamily B, polypeptide 1 | CYP1B1 | 18187806 | drug metabolism |
| DOCETAXEL | NM_017460 | cytochrome P450, family 3, subfamily A, polypeptide 4 | CYP3A4 | 15239142 | unrelated |
| DOCETAXEL | NM_001005862; NM_004448 | v-erb-b2 erythroblastic leukemia viral oncogene homolog 2, neuro/glioblastoma derived oncogene homolog (avian) | ERBB2 | 15567936, 15834928, 17010609 | resistance |
| DOCETAXEL | NM_000852 | glutathione S-transferase pi 1 | GSTP1 | 15239142 | resistance |
| DOCETAXEL | NM_001530; NM_181054 | hypoxia inducible factor 1, alpha subunit (basic helix-loop-helix transcription factor) | HIF1A | 17498666 | altered by docetaxel |
| DOCETAXEL | NM_001130442; NM_005343; NM_176795 | v-Ha-ras Harvey rat sarcoma viral oncogene homolog | HRAS | 15970518 | resistance |
| DOCETAXEL | NM_000600 | interleukin 6 (interferon, beta 2) | IL6 | 15623590 | altered by docetaxel |
| DOCETAXEL | NM_002358 | MAD2 mitotic arrest deficient-like 1 (yeast) | MAD2L1 | 18691855 | |
| DOCETAXEL | NM_002745; NM_138957 | mitogen-activated protein kinase 1 | MAPK1 | 15970518 | resistance |
| DOCETAXEL | NM_001040056; NM_001109891; NM_002746 | mitogen-activated protein kinase 3 | MAPK3 | 15970518 | resistance |
| DOCETAXEL | NM_001145336; NM_001145337; NM_001145339; NM_001145340; NM_002392; NM_006878; NM_006879; NM_006881; NM_006882 | Mdm2 p53 binding protein homolog (mouse) | MDM2 | 16080190 | |
| DOCETAXEL | NR_022009; NR_022009; NR_022009; NR_022009; NR_022009; NR_022009; NR_022009 | Prader-Willi/Angelman region-1 | PAR1 | 16052512 | altered by docetaxel |
| DOCETAXEL | NM_001618 | poly (ADP-ribose) polymerase 1 | PARP1 | 15970518 | |
| DOCETAXEL | NM_000926 | progesterone receptor | PGR | 15623590 | unrelated |
| DOCETAXEL | NM_000941 | P450 (cytochrome) oxidoreductase | POR | 15239142 | unrelated |
| DOCETAXEL | NM_000963 | prostaglandin-endoperoxide synthase 2 (prostaglandin G/H synthase and cyclooxygenase) | PTGS2 | 15623590 | resistance |
| DOCETAXEL | NM_002880 | v-raf-1 murine leukemia viral oncogene homolog 1 | RAF1 | 15970518 | unrelated |
| DOCETAXEL | NM_000321 | retinoblastoma 1 | RB1 | 15297405 | |
| DOCETAXEL | NM_005983; NM_032637 | S-phase kinase-associated protein 2 (p45) | SKP2 | 18644126 | unrelated |
| DOCETAXEL | NM_000594 | tumor necrosis factor (TNF superfamily, member 2) | TNF | 15623590 | |
| DOCETAXEL | NM_003842; NM_147187 | tumor necrosis factor receptor superfamily, member 10b | TNFRSF10B | 17922852 | |
| DOCETAXEL | NM_000546; NM_001126112; NM_001126113; NM_001126114; NM_001126115; NM_001126116; NM_001126117 | tumor protein p53 | TP53 | 15297405, 15970518, 15970518, 16080190, 16080190, 17369602 | |
| DOCETAXEL | NM_178014 | tubulin, beta | TUBB | 15239142, 16080190 | target/resistance |
| DOCETAXEL | NM_030773 | tubulin, beta 1 | TUBB1 | — | target/resistance |
| DOCETAXEL | NM_001071 | thymidylate synthetase | TYMS | 19074750 | |
| DOCETAXEL | NM_001025366; NM_001025367; NM_001025368; NM_001025369; NM_001025370; NM_001033756; NM_003376 | vascular endothelial growth factor A | VEGFA | 17498666 | altered by docetaxel |
| DOCETAXEL | NM_001167 | X-linked inhibitor of apoptosis | XIAP | 19102932 | |

TABLE 1-continued

| Molecule | RefSeq | Description | Symbol | PMID | Interaction |
|---|---|---|---|---|---|
| PACLITAXEL | NM_000927 | ATP-binding cassette, sub-family B (MDR/TAP), member 1 | ABCB1 | 10617675, 15239142, 15650019, 15901749, 15990222, 15252144, 15990222, 15650019, 16322897, 18433974 | resistance |
| PACLITAXEL | NM_004996; NM_019862; NM_019898; NM_019899; NM_019900 | ATP-binding cassette, sub-family C (CFTR/MRP), member 1 | ABCC1 | 15548710 | resistance |
| PACLITAXEL | NM_000392 | ATP-binding cassette, sub-family C (CFTR/MRP), member 2 | ABCC2 | 15645438, 15849751 | resistance |
| PACLITAXEL | NM_001130846; NM_001130847; NM_004208; NM_145812; NM_145813 | apoptosis-inducing factor, mitochondrion-associated, 1 | AIFM1 | 16168113 | death pathway |
| PACLITAXEL | NM_001354; NM_205845 | aldo-keto reductase family 1, member C2 (dihydrodiol dehydrogenase 2; bile acid binding protein; 3-alpha hydroxysteroid dehydrogenase, type III) | AKR1C2 | 16322897 | unrelated |
| PACLITAXEL | NM_001014431; NM_001014432; NM_005163 | v-akt murine thymoma viral oncogene homolog 1 | AKT1 | 16211241, 16782806, 18071906 | resistance |
| PACLITAXEL | NM_001626 | v-akt murine thymoma viral oncogene homolog 2 | AKT2 | 18071906 | resistance |
| PACLITAXEL | NM_005465; NM_181690 | v-akt murine thymoma viral oncogene homolog 3 (protein kinase B, gamma) | AKT3 | 18071906 | resistance |
| PACLITAXEL | NM_001144 | autocrine motility factor receptor | AMFR | 16896004 | |
| PACLITAXEL | NM_001160; NM_013229; NM_181861; NM_181868; NM_181869 | apoptotic peptidase activating factor 1 | APAF1 | 14749477 | death pathway |
| PACLITAXEL | NM_004312 | arrestin 3, retinal (X-arrestin) | ARR3 | 16322897 | |
| PACLITAXEL | NM_018136 | asp (abnormal spindle) homolog, microcephaly associated (Drosophila) | ASPM | 17374387 | |
| PACLITAXEL | NM_003600; NM_198433; NM_198434; NM_198435; NM_198436; NM_198437 | aurora kinase A | AURKA | 17374387 | resistance |
| PACLITAXEL | NM_004322; NM_032989 | BCL2-associated agonist of cell death | BAD | 10822281, 16413505 | death pathway |
| PACLITAXEL | NM_001188 | BCL2-antagonist/killer 1 | BAK1 | 10822281 | |
| PACLITAXEL | NM_004324; NM_138761; NM_138763; NM_138764; NM_138765 | BCL2-associated X protein | BAX | 10822281, 16051289, 16168113 | death pathway |
| PACLITAXEL | NM_033028 | Bardet-Biedl syndrome 4 | BBS4 | 16896004 | |
| PACLITAXEL | NM_000633; NM_000657 | B-cell CLL/lymphoma 2 | BCL2 | 10822281, 12086014, 16168113, 16243823, 16275990, 16322897 | resistance |
| PACLITAXEL | NM_001191; NM_138578 | BCL2-like 1 | BCL2L1 | 10822281, 14749477, 16051289, 16243823, 16275990, 11468182, 16080463 | resistance |
| PACLITAXEL | NM_003766 | beclin 1, autophagy related | BECN1 | 16896004 | |
| PACLITAXEL | NM_001196; NM_197966; NM_197967 | BH3 interacting domain death agonist | BID | 14749477 | unrelated |
| PACLITAXEL | NM_001166 | baculoviral IAP repeat-containing 2 | BIRC2 | 14749477, 16243823 | unrelated |
| PACLITAXEL | NM_001165; NM_182962 | baculoviral IAP repeat-containing 3 | BIRC3 | 14749477, 16243823 | resistance |
| PACLITAXEL | NM_001012270; NM_001012271; NM_001168 | baculoviral IAP repeat-containing 5 | BIRC5 | 14749477, 15970709, 16170024, 16202317, 16211241, 16373717 | resistance |
| PACLITAXEL | NM_001719 | bone morphogenetic protein 7 | BMP7 | 16322897 | |
| PACLITAXEL | NM_001130914; NM_006806 | BTG family, member 3 | BTG3 | 16896004 | |
| PACLITAXEL | NM_001211 | budding uninhibited by benzimidazoles 1 homolog beta (yeast) | BUB1B | 18691855 | resistance |
| PACLITAXEL | — | | C7ORF23 | 15556294 | unrelated |
| PACLITAXEL | NM_001218; NM_206925 | carbonic anhydrase XII | CA12 | 16896004 | |
| PACLITAXEL | NM_001033952; NM_001033953; NM_001741 | calcitonin-related polypeptide alpha | CALCA | 16222118 | |
| PACLITAXEL | NM_004346; NM_032991 | caspase 3, apoptosis-related cysteine peptidase | CASP3 | 10822281, 12086014, 16051289, 16168113, 16170024, 16413505, 18071906 | death pathway |

TABLE 1-continued

| Molecule | RefSeq | Description | Symbol | PMID | Interaction |
|---|---|---|---|---|---|
| PACLITAXEL | NM_001227; NM_033338; NM_033339; NM_033340 | caspase 7, apoptosis-related cysteine peptidase | CASP7 | 14749477, 16168113 | death pathway |
| PACLITAXEL | NM_001080124; NM_001080125; NM_001228; NM_033355; NM_033356; NM_033358 | caspase 8, apoptosis-related cysteine peptidase | CASP8 | 14749477, 16051289, 16168113, 18071906 | death pathway |
| PACLITAXEL | NM_001229; NM_032996 | caspase 9, apoptosis-related cysteine peptidase | CASP9 | 14749477, 16168113, 16170024 | death pathway |
| PACLITAXEL | NM_001753 | caveolin 1, caveolae protein, 22 kDa | CAV1 | 16322897 | altered by paclitaxel |
| PACLITAXEL | NM_031966 | cyclin B1 | CCNB1 | 16356831 | sensitivity/resistance |
| PACLITAXEL | NM_053056 | cyclin D1 | CCND1 | 16243823 | sensitivity/unrelated |
| PACLITAXEL | NM_002389; NM_153826; NM_172351; NM_172352; NM_172353; NM_172354; NM_172355; NM_172356; NM_172357; NM_172358; NM_172359; NM_172360; NM_172361 | CD46 molecule, complement regulatory protein | CD46 | 16322897 | |
| PACLITAXEL | NM_001025079; NM_001777; NM_198793 | CD47 molecule | CD47 | 16322897 | |
| PACLITAXEL | NM_001785 | cytidine deaminase | CDA | 18728667 | |
| PACLITAXEL | NM_000389; NM_078467 | cyclin-dependent kinase inhibitor 1A (p21, Cip1) | CDKN1A | 16168113, 16413505 | sensitivity |
| PACLITAXEL | NM_001127183; NM_001127184; NM_003879 | CASP8 and FADD-like apoptosis regulator | CFLAR | 16080463 | resistance |
| PACLITAXEL | NM_001831; NM_203339 | clusterin | CLU | 16308731, 16 | resistance |
| PACLITAXEL | NM_006565 | CCCTC-binding factor (zinc finger protein) | CTCF | 16322897 | |
| PACLITAXEL | NM_001332 | catenin (cadherin-associated protein), delta 2 (neural plakophilin-related arm-repeat protein) | CTNND2 | 16896004 | |
| PACLITAXEL | NM_001912; NM_145918 | cathepsin L1 | CTSL1 | 16322897 | |
| PACLITAXEL | NM_001008540; NM_003467 | chemokine (C-X-C motif) receptor 4 | CXCR4 | 16322897 | |
| PACLITAXEL | NM_006564 | chemokine (C-X-C motif) receptor 6 | CXCR6 | 16322897 | |
| PACLITAXEL | NM_020311 | chemokine (C-X-C motif) receptor 7 | CXCR7 | 16322897 | |
| PACLITAXEL | NM_018947 | cytochrome c, somatic | CYCS | 14749477, 16051289, 16413505 | death pathway |
| PACLITAXEL | NM_000103; NM_031226 | cytochrome P450, family 19, subfamily A, polypeptide 1 | CYP19A1 | 14691014 | |
| PACLITAXEL | NM_000767 | cytochrome P450, family 2, subfamily B, polypeptide 6 | CYP2B6 | 14977870 | |
| PACLITAXEL | NM_000770 | cytochrome P450, family 2, subfamily C, polypeptide 8 | CYP2C8 | 12464242, 12401345, 16124035, 15239142, 15933212, 15901749 | drug metabolism |
| PACLITAXEL | NM_017460 | cytochrome P450, family 3, subfamily A, polypeptide 4 | CYP3A4 | 12065438, 15650019, 15901749 | drug metabolism |
| PACLITAXEL | NM_019887; NM_138929 | diablo homolog (Drosophila) | DIABLO | 14749477 | sensitivity |
| PACLITAXEL | NM_000110 | dihydropyrimidine dehydrogenase | DPYD | 18506536, 18630517 | |
| PACLITAXEL | NM_000639 | E2F transcription factor 3 | E2F3 | 16896004 | |
| PACLITAXEL | NM_005228; NM_201282; NM_201283; NM_201284 | epidermal growth factor receptor (erythroblastic leukemia viral (v-erb-b) oncogene homolog, avian) | EGFR | 15723263, 16211241, 16413505 | resistance |
| PACLITAXEL | NM_001042599; NM_005235 | v-erb-a erythroblastic leukemia viral oncogene homolog 4 (avian) | ERBB4 | 16896004 | |
| PACLITAXEL | NM_000043; NM_152871; NM_152873; NM_152874; NM_152875; NM_152876; NM_152877 | Fas (TNF receptor superfamily, member 6) | FAS | 16051289 | sensitivity |
| PACLITAXEL | NM_000639 | Fas ligand (TNF superfamily, member 6) | FASLG | 16051289 | sensitivity |
| PACLITAXEL | NM_001135821; NM_001135822; NM_002004 | farnesyl diphosphate synthase (farnesyl pyrophosphate synthetase, dimethylallyltranstransferase, geranyltranstransferase) | FDPS | 16322897 | |
| PACLITAXEL | NM_002032 | ferritin, heavy polypeptide 1 | FTH1 | 16322897 | |
| PACLITAXEL | NM_000146 | ferritin, light polypeptide | FTL | 16322897 | |

TABLE 1-continued

| Molecule | RefSeq | Description | Symbol | PMID | Interaction |
|---|---|---|---|---|---|
| PACLITAXEL | NM_002569 | furin (paired basic amino acid cleaving enzyme) | FURIN | 16322897 | |
| PACLITAXEL | NM_001136007; NM_001136008; NM_001136009; NM_001136010; NM_001136011; NM_001136012; NM_005971; NM_021910 | FXYD domain containing ion transport regulator 3 | FXYD3 | 16322897 | |
| PACLITAXEL | NM_001924 | growth arrest and DNA-damage-inducible, alpha | GADD45A | 16322897 | sensitivity |
| PACLITAXEL | NM_000156; NM_138924 | guanidinoacetate N-methyltransferase | GAMT | 16896004 | |
| PACLITAXEL | NM_145453; NM_005264; NM_145793 | GDNF family receptor alpha 1 | GFRA1 | 12851839 | resistance |
| PACLITAXEL | NM_000561; NM_146421 | glutathione S-transferase mu 1 | GSTM1 | 16322897 | resistance |
| PACLITAXEL | NM_000851 | glutathione S-transferase mu 5 | GSTM5 | 15239142 | resistance |
| PACLITAXEL | NM_000852 | glutathione S-transferase pi 1 | GSTP1 | 12851839 | resistance |
| PACLITAXEL | NM_000853 | glutathione S-transferase theta 1 | GSTT1 | 17498666 | |
| PACLITAXEL | NM_001530; NM_181054 | hypoxia inducible factor 1, alpha subunit (basic helix-loop-helix transcription factor) | HIF1A | | |
| PACLITAXEL | NM_000201 | intercellular adhesion molecule 1 | ICAM1 | 16243823 | altered by paclitaxel |
| PACLITAXEL | NM_006332 | interferon, gamma-inducible protein 30 | IFI30 | 16322897 | |
| PACLITAXEL | NM_000875 | insulin-like growth factor 1 receptor | IGF1R | 15499378 | |
| PACLITAXEL | NM_001552 | insulin-like growth factor binding protein 4 | IGFBP4 | 16896004 | |
| PACLITAXEL | NM_002213 | integrin, beta 5 | ITGB5 | 16322897 | |
| PACLITAXEL | — | — | JMJD2B | 16896004 | |
| PACLITAXEL | NM_002228 | jun oncogene | JUN | 15585644 | altered by paclitaxel |
| PACLITAXEL | NM_020853 | KIAA1467 | KIAA1467 | 16896004 | |
| PACLITAXEL | NM_007054 | kinesin family member 3A | KIF3A | 16896004 | |
| PACLITAXEL | NM_002274; NM_153490 | keratin 13 | KRT13 | 16322897 | |
| PACLITAXEL | NM_002358 | MAD2 mitotic arrest deficient-like 1 (yeast) | MAD2L1 | 18691855 | |
| PACLITAXEL | NM_002745; NM_138957 | mitogen-activated protein kinase 1 | MAPK1 | 16051289, 16211241, 16413505 | death pathway |
| PACLITAXEL | NM_001315; NM_139012; NM_139013; NM_139014 | mitogen-activated protein kinase 14 | MAPK14 | 16051289 | |
| PACLITAXEL | NM_001040056; NM_001109891; NM_002746 | mitogen-activated protein kinase 3 | MAPK3 | 16051289, 16211241, 16413505 | death pathway |
| PACLITAXEL | NM_002750; NM_139046; NM_139047; NM_139049 | mitogen-activated protein kinase 8 | MAPK8 | 16051289 | death pathway |
| PACLITAXEL | NM_001135044; NM_002752; NM_139068; NM_139069; NM_139070 | mitogen-activated protein kinase 9 | MAPK9 | 16051289 | death pathway |
| PACLITAXEL | NM_001123066; NM_001123067; NM_005910; NM_016834; NM_016835; NM_016841 | microtubule-associated protein tau | MAPT | 16896004 | resistance |
| PACLITAXEL | NM_021960; NM_182763 | myeloid cell leukemia sequence 1 (BCL2-related) | MCL1 | 14744777 | resistance |
| PACLITAXEL | NM_001145336; NM_001145337; NM_001145339; NM_001145340; NM_002392; NM_006878; NM_006879; NM_006881; NM_006882 | Mdm2 p53 binding protein homolog (mouse) | MDM2 | 13130078 | resistance |
| PACLITAXEL | NM_004774 | mediator complex subunit 1 | MED1 | 15650019 | |
| PACLITAXEL | NM_015335 | mediator complex subunit 13-like | MED13L | 16896004 | |
| PACLITAXEL | NM_014791 | maternal embryonic leucine zipper kinase | MELK | 16896004 | |
| PACLITAXEL | NM_024042 | meteorin, glial cell differentiation regulator | METRN | 16896004 | |
| PACLITAXEL | NM_004994 | matrix metallopeptidase 9 (gelatinase B, 92 kDa gelatinase, 92 kDa type IV collagenase) | MMP9 | 16243823 | |
| PACLITAXEL | NM_175617 | metallothionein 1E | MT1E | 16322897 | unrelated |
| PACLITAXEL | NM_005953 | metallothionein 2A | MT2A | 16322897 | unrelated |

TABLE 1-continued

| Molecule | RefSeq | Description | Symbol | PMID | Interaction |
|---|---|---|---|---|---|
| PACLITAXEL | NM_002467 | v-myc myelocytomatosis viral oncogene homolog (avian) | MYC | 16243823, 18802399 | death pathway |
| PACLITAXEL | NM_000662 | N-acetyltransferase 1 (arylamine N-acetyltransferase) | NAT1 | 15015580, 17564303 | altered by paclitaxel |
| PACLITAXEL | NM_006534; NM_181659 | nuclear receptor coactivator 3 | NCOA3 | 15650019 | |
| PACLITAXEL | NM_003998 | nuclear factor of kappa light polypeptide gene enhancer in B-cells 1 | NFKB1 | 16243823 | altered by paclitaxel |
| PACLITAXEL | NM_020529 | nuclear factor of kappa light polypeptide gene enhancer in B-cells inhibitor, alpha | NFKBIA | 16243823 | sensitivity |
| PACLITAXEL | NM_024522 | Na+/K+ transporting ATPase interacting 1 | NKAIN1 | 16896004 | |
| PACLITAXEL | NM_003889; NM_022002; NM_033013 | nuclear receptor subfamily 1, group I, member 2 | NR1I2 | 14977870, 15864135, 15650019, 15650019, 12065438, 15864135 | resistance |
| PACLITAXEL | NM_001618 | poly (ADP-ribose) polymerase 1 | PARP1 | 14744477, 15585644, 18071906, 15585644 | altered by paclitaxel |
| PACLITAXEL | NM_002613; NM_031268 | 3-phosphoinositide dependent protein kinase-1 | PDPK1 | 16782806 | resistance |
| PACLITAXEL | NM_000304; NM_153321; NM_153322 | peripheral myelin protein 22 | PMP22 | 16322897 | |
| PACLITAXEL | NM_000941 | P450 (cytochrome) oxidoreductase | POR | 15239142 | unrelated |
| PACLITAXEL | NM_003981; NM_199413; NM_199414 | protein regulator of cytokinesis 1 | PRC1 | 17374387 | |
| PACLITAXEL | NM_000314 | phosphatase and tensin homolog | PTEN | 11707646, 15548710 | resistance/mutation |
| PACLITAXEL | NM_000963 | prostaglandin-endoperoxide synthase 2 (prostaglandin G/H synthase and cyclooxygenase) | PTGS2 | 16127422, 16243823, 16831230 | sensitivity/resistance |
| PACLITAXEL | NM_005855 | receptor (G protein-coupled) activity modifying protein 1 | RAMP1 | 16896004 | |
| PACLITAXEL | NM_000321 | retinoblastoma 1 | RB1 | 15138593 | |
| PACLITAXEL | NM_005611 | retinoblastoma-like 2 (p130) | RBL2 | 15585644 | unrelated |
| PACLITAXEL | NM_001145138; NM_021975 | v-rel reticuloendotheliosis viral oncogene homolog A (avian) | RELA | 15291876, 16243823 | resistance |
| PACLITAXEL | NM_000449; NM_001025603 | regulatory factor X, 5 (influences HLA class II expression) | RFX5 | 16322897 | |
| PACLITAXEL | NM_000984 | ribosomal protein L23a | RPL23A | 16322897 | |
| PACLITAXEL | NM_001003; NM_213725 | ribosomal protein, large, P1 | RPLP1 | 16322897 | |
| PACLITAXEL | NM_001034 | ribonucleotide reductase M2 polypeptide | RRM2 | 16896004 | |
| PACLITAXEL | NM_001015055; NM_001015056; NM_033046 | rhotekin | RTKN | 15480428 | |
| PACLITAXEL | NM_005980 | S100 calcium binding protein P | S100P | 16322897, 18636193 | |
| PACLITAXEL | NM_020974 | signal peptide, CUB domain, EGF-like 2 | SCUBE2 | 16896004 | sensitivity |
| PACLITAXEL | NM_003130; NM_198901 | sorcin | SRI | 18423116 | |
| PACLITAXEL | NM_198253; NM_198255 | telomerase reverse transcriptase | TERT | 18021753 | |
| PACLITAXEL | NM_003225 | trefoil factor 1 | TFF1 | 16322897 | |
| PACLITAXEL | NM_018271 | threonine synthase-like 2 (S. cerevisiae) | THNSL2 | 16896004 | |
| PACLITAXEL | NM_003842; NM_147187 | tumor necrosis factor receptor superfamily, member 10b | TNFRSF10B | 17922852 | altered by paclitaxel |
| PACLITAXEL | NM_001067 | topoisomerase (DNA) II alpha 170 kDa | TOP2A | 16322897 | altered by paclitaxel |
| PACLITAXEL | NM_000546; NM_001126112; NM_001126113; NM_001126114; NM_001126115; NM_001126116; NM_001126117 | tumor protein p53 | TP53 | 15990222, 15990222, 12082016, 16168113, 16413505 | unrelated |
| PACLITAXEL | NM_178014 | tubulin, beta | TUBB | 15239142 | target/resistance |
| PACLITAXEL | NM_030773 | tubulin, beta 1 | TUBB1 | | target ? |
| PACLITAXEL | NM_001113755; NM_001113756; NM_001953 | thymidine phosphorylase | TYMP | 18506536, 18630517 | |

TABLE 1-continued

| Molecule | RefSeq | Description | Symbol | PMID | Interaction |
|---|---|---|---|---|---|
| PACLITAXEL | NM_001071 | thymidylate synthetase | TYMS | 10482907, 16168113, 18630517 | unrelated |
| PACLITAXEL | NM_001025366; NM_001025367; NM_001025368; NM_001025369; NM_001025370; NM_001033756; NM_003376 | vascular endothelial growth factor A | VEGFA | 16243823, 17498666 | resistance |
| PACLITAXEL | NM_001167 | X-linked inhibitor of apoptosis | XIAP | 16243823, 16356831, 18071906 | resistance |
| PACLITAXEL | NM_024762 | zinc finger protein 552 | ZNF552 | 16896004 | resistance |
| VINBLASTINE | NM_000927 | ATP-binding cassette, sub-family B (MDR/TAP), member 1 | ABCB1 | 11355955, 8917702, 15725475, 15466210, 15640379, 15824923, 16221533 | resistance |
| VINBLASTINE | NM_004996; NM_019862; NM_019898; NM_019899; NM_019900 | ATP-binding cassette, sub-family C (CFTR/MRP), member 1 | ABCC1 | 16156793 | resistance |
| VINBLASTINE | NM_000392 | ATP-binding cassette, sub-family C (CFTR/MRP), member 2 | ABCC2 | 15849751, 9525973, 15849751 | resistance |
| VINBLASTINE | NM_032982; NM_032983 | caspase 2, apoptosis-related cysteine peptidase | CASP2 | 14757846 | altered by VB |
| VINBLASTINE | NM_001556 | inhibitor of kappa light polypeptide gene enhancer in B-cells, kinase beta | IKBKB | 17029595 | death pathway |
| VINBLASTINE | NM_002228 | jun oncogene | JUN | 12221076 | resistance |
| VINBLASTINE | NM_002750; NM_139046; NM_139047; NM_139049 | mitogen-activated protein kinase 8 | MAPK8 | 12221076 | death pathway |
| VINBLASTINE | NM_001135044; NM_002752; NM_139068; NM_139069; NM_139070 | mitogen-activated protein kinase 9 | MAPK9 | 12221076 | death pathway |
| VINBLASTINE | NM_002467 | v-myc myelocytomatosis viral oncogene homolog (avian) | MYC | 18802399 | |
| VINBLASTINE | NM_001136022; NM_004554 | nuclear factor of activated T-cells, cytoplasmic, calcineurin-dependent 4 | NFATC4 | 17044076 | |
| VINBLASTINE | NM_020529 | nuclear factor of kappa light polypeptide gene enhancer in B-cells inhibitor, alpha | NFKBIA | 17029595 | |
| VINBLASTINE | NM_006788 | ralA binding protein 1 | RALBP1 | — | resistance |
| VINBLASTINE | NM_003842; NM_147187 | tumor necrosis factor receptor superfamily, member 10b | TNFRSF10B | 17922852 | |
| VINBLASTINE | NM_000546; NM_001126112; NM_001126113; NM_001126114; NM_001126115; NM_001126116; NM_001126117 | tumor protein p53 | TP53 | 12221076 | |
| VINBLASTINE | NM_001069 | tubulin, beta 2A | TUBB2A | — | unrelated |
| VINCRISTINE | NM_000927 | ATP-binding cassette, sub-family B (MDR/TAP), member 1 | ABCB1 | 10617675, 11934808, 15239124, 16038730, 15645438, 16925584 | resistance |
| VINCRISTINE | NM_004996; NM_019862; NM_019898; NM_019899; NM_019900 | ATP-binding cassette, sub-family C (CFTR/MRP), member 1 | ABCC1 | 10900222, 15581632, 15896345, 16042792, 15896345, 10900222, 15044619, 12067707 | resistance |
| VINCRISTINE | NM_000392 | ATP-binding cassette, sub-family C (CFTR/MRP), member 2 | ABCC2 | 15896345 | resistance |
| VINCRISTINE | NM_001014431; NM_001014432; NM_005163 | v-akt murine thymoma viral oncogene homolog 1 | AKT1 | 16740780 | resistance |
| VINCRISTINE | NM_001160; NM_013229; NM_181861; NM_181868; NM_181869 | apoptotic peptidase activating factor 1 | APAF1 | 16001973 | death pathway |
| VINCRISTINE | NM_000039 | apolipoprotein A-I | APOA1 | 16001973 | |
| VINCRISTINE | NM_018136 | asp (abnormal spindle) homolog, microcephaly associated (Drosophila) | ASPM | 17374387 | |
| VINCRISTINE | NM_003600; NM_198433; NM_198434; NM_198435; NM_198436; NM_198437 | aurora kinase A | AURKA | 17374387 | resistance |
| VINCRISTINE | NM_004322; NM_032989 | BCL2-associated agonist of cell death | BAD | 16001973 | death pathway |

TABLE 1-continued

| Molecule | RefSeq | Description | Symbol | PMID | Interaction |
|---|---|---|---|---|---|
| VINCRISTINE | NM_004324; NM_138761; NM_138763; NM_138764; NM_138765 | BCL2-associated X protein | BAX | 16001973 | death pathway |
| VINCRISTINE | NM_000633; NM_000657 | B-cell CLL/lymphoma 2 | BCL2 | 16001973 | resistance |
| VINCRISTINE | NM_001223; NM_033292; NM_033293; NM_033294; NM_033295 | caspase 1, apoptosis-related cysteine peptidase (interleukin 1, beta, convertase) | CASP1 | 16001973 | |
| VINCRISTINE | NM_001230; NM_032974; NM_032977 | caspase 10, apoptosis-related cysteine peptidase | CASP10 | 16001973 | |
| VINCRISTINE | NM_032982; NM_032983 | caspase 2, apoptosis-related cysteine peptidase | CASP2 | 16001973 | death pathway |
| VINCRISTINE | NM_004346; NM_032991 | caspase 3, apoptosis-related cysteine peptidase | CASP3 | 16001973 | death pathway |
| VINCRISTINE | NM_001225; NM_033306 | caspase 4, apoptosis-related cysteine peptidase | CASP4 | 16001973 | |
| VINCRISTINE | NM_001136109; NM_001136110; NM_001136111; NM_001136112; NM_004347 | caspase 5, apoptosis-related cysteine peptidase | CASP5 | 16001973 | |
| VINCRISTINE | NM_001226; NM_032992 | caspase 6, apoptosis-related cysteine peptidase | CASP6 | 16001973 | death pathway |
| VINCRISTINE | NM_001227; NM_033338; NM_033339; NM_033340 | caspase 7, apoptosis-related cysteine peptidase | CASP7 | 16001973 | death pathway |
| VINCRISTINE | NM_001080124; NM_001080125; NM_001228; NM_033355; NM_033356; NM_033358 | caspase 8, apoptosis-related cysteine peptidase | CASP8 | 16001973 | death pathway |
| VINCRISTINE | NM_001229; NM_032996 | caspase 9, apoptosis-related cysteine peptidase | CASP9 | 16001973 | death pathway |
| VINCRISTINE | NM_001752 | catalase | CAT | 11178967 | |
| VINCRISTINE | NM_005194 | CCAAT/enhancer binding protein (C/EBP), beta | CEBPB | 16001973 | |
| VINCRISTINE | NM_001025194; NM_001025195; NM_001266 | carboxylesterase 1 (monocyte/macrophage serine esterase 1) | CES1 | 16001973 | |
| VINCRISTINE | NM_000492 | cystic fibrosis transmembrane conductance regulator (ATP-binding cassette sub-family C, member 7) | CFTR | 16038730 | |
| VINCRISTINE | NM_020313 | cytokine induced apoptosis inhibitor 1 | CIAPIN1 | 18389626 | |
| VINCRISTINE | NM_001916 | cytochrome c-1 | CYC1 | 16001973 | |
| VINCRISTINE | NM_005225 | E2F transcription factor 1 | E2F1 | 16001973 | |
| VINCRISTINE | NM_005228; NM_201282; NM_201283; NM_201284 | epidermal growth factor receptor (erythroblastic leukemia viral (v-erb-b) oncogene homolog, avian) | EGFR | 16001973 | death pathway |
| VINCRISTINE | NM_003824 | Fas (TNFRSF6)-associated via death domain | FADD | 16001973 | |
| VINCRISTINE | NM_012306 | Fas apoptotic inhibitory molecule 2 | FAIM2 | 16001973 | |
| VINCRISTINE | NM_002046 | glyceraldehyde-3-phosphate dehydrogenase | GAPDH | 16001973 | |
| VINCRISTINE | NM_001498 | glutamate-cysteine ligase, catalytic subunit | GCLC | 10900222 | |
| VINCRISTINE | NM_002061 | glutamate-cysteine ligase, modifier subunit | GCLM | 10900222 | |
| VINCRISTINE | NM_000561; NM_146421 | glutathione S-transferase mu 1 | GSTM1 | 15044619, 15713801 | resistance |
| VINCRISTINE | NM_000852 | glutathione S-transferase pi 1 | GSTP1 | 10900222 | |
| VINCRISTINE | NM_016315 | GULP, engulfment adaptor PTB domain containing 1 | GULP1 | 16001973 | |
| VINCRISTINE | NM_001130442; NM_005343; NM_176795 | v-Ha-ras Harvey rat sarcoma viral oncogene homolog | HRAS | 16001973 | resistance |
| VINCRISTINE | NM_000415 | islet amyloid polypeptide | IAPP | 16001973 | |
| VINCRISTINE | NM_000618; NM_001111283; NM_001111284; NM_001111285 | insulin-like growth factor 1 (somatomedin C) | IGF1 | 16740780 | |
| VINCRISTINE | NM_000875 | insulin-like growth factor 1 receptor | IGF1R | 16001973 | resistance |
| VINCRISTINE | NM_000600 | interleukin 6 (interferon, beta 2) | IL6 | 16001973 | unrelated |
| VINCRISTINE | NM_005572; NM_170707; NM_170708 | lamin A/C | LMNA | 16001973 | resistance |
| VINCRISTINE | NM_005573 | lamin B1 | LMNB1 | 16001973 | resistance |
| VINCRISTINE | NM_003010 | mitogen-activated protein kinase kinase 4 | MAP2K4 | 16001973 | altered by vincristine |
| VINCRISTINE | NM_003188; NM_145331; NM_145332; NM_145333 | mitogen-activated protein kinase kinase kinase 7 | MAP3K7 | 16001973 | |
| VINCRISTINE | NM_002745; NM_138957 | mitogen-activated protein kinase 1 | MAPK1 | 16001973 | |

TABLE 1-continued

| Molecule | RefSeq | Description | Symbol | PMID | Interaction |
|---|---|---|---|---|---|
| VINCRISTINE | NM_001145336; NM_001145337; NM_001145339; NM_001145340; NM_002392; NM_006878; NM_006879; NM_006881; NM_006882 | Mdm2 p53 binding protein homolog (mouse) | MDM2 | 16001973 | resistance |
| VINCRISTINE | NM_001130926; NM_001130927; NM_001130928; NM_005587 | myocyte enhancer factor 2A | MEF2A | | |
| VINCRISTINE | NM_002412 | O-6-methylguanine-DNA methyltransferase | MGMT | 16033832 | |
| VINCRISTINE | NM_002467 | v-myc myelocytomatosis viral oncogene homolog (avian) | MYC | 16001973 | |
| VINCRISTINE | NM_003998 | nuclear factor of kappa light polypeptide gene enhancer in B-cells 1 | NFKB1 | 15744361, 16001973 | |
| VINCRISTINE | NM_006025 | 26 serine protease | P11 | 16001973 | |
| VINCRISTINE | — | | PCAF | 16001973 | |
| VINCRISTINE | NM_003981; NM_199413; NM_199414 | protein regulator of cytokinesis 1 | PRC1 | 17374387 | |
| VINCRISTINE | NM_000311; NM_001080121; NM_001080122; NM_001080123; NM_183079 | prion protein | PRNP | 15386405 | |
| VINCRISTINE | NM_000963 | prostaglandin-endoperoxide synthase 2 (prostaglandin G/H synthase and cyclooxygenase) | PTGS2 | 18695918 | |
| VINCRISTINE | NM_004103; NM_173174; NM_173175; NM_173176 | PTK2B protein tyrosine kinase 2 beta | PTK2B | 11478917 | |
| VINCRISTINE | NM_006264; NM_080683; NM_080684; NM_080685 | protein tyrosine phosphatase, non-receptor type 13 (APO-1/CD95 (Fas)-associated phosphatase) | PTPN13 | 16001973 | |
| VINCRISTINE | NM_006788 | ralA binding protein 1 | RALBP1 | — | |
| VINCRISTINE | NM_000965; NM_016152 | retinoic acid receptor, beta | RARB | 17608728 | |
| VINCRISTINE | NM_001145547; NM_032905 | RNA binding motif protein 17 | RBM17 | 16061639 | resistance |
| VINCRISTINE | NM_001145138; NM_021975 | v-rel reticuloendotheliosis viral oncogene homolog A (avian) | RELA | 15744361 | resistance |
| VINCRISTINE | NM_002944 | c-ros oncogene 1, receptor tyrosine kinase | ROS1 | 16001973 | |
| VINCRISTINE | NM_001031680; NM_004350 | runt-related transcription factor 3 | RUNX3 | 15756676 | |
| VINCRISTINE | NM_006516 | solute carrier family 2 (facilitated glucose transporter), member 1 | SLC2A1 | 17520257 | |
| VINCRISTINE | NM_005633 | son of sevenless homolog 1 (Drosophila) | SOS1 | 16001973 | |
| VINCRISTINE | NM_003130; NM_198901 | sorcin | SRI | 18423116 | |
| VINCRISTINE | NM_007315; NM_139266 | signal transducer and activator of transcription 1, 91 kDa | STAT1 | 16001973 | |
| VINCRISTINE | NM_005419 | signal transducer and activator of transcription 2, 113 kDa | STAT2 | 16001973 | |
| VINCRISTINE | NM_003150; NM_139276; NM_213662 | signal transducer and activator of transcription 3 (acute-phase response factor) | STAT3 | 16001973 | |
| VINCRISTINE | NM_000594 | tumor necrosis factor (TNF superfamily, member 2) | TNF | 16001973 | synergistic effects |
| VINCRISTINE | NM_000546; NM_001126112; NM_001126113; NM_001126114; NM_001126115; NM_001126116; NM_001126117 | tumor protein p53 | TP53 | 12082016, 16001973, 17555331 | |
| VINCRISTINE | NM_000365; NM_001159287 | triosephosphate isomerase 1 | TPI1 | 18309519 | |
| VINCRISTINE | NM_001069 | tubulin, beta 2A | TUBB2A | — | target? |
| VINCRISTINE | NM_001071 | thymidylate synthetase | TYMS | 15713801 | |
| VINCRISTINE | NM_000376; NM_001017535 | vitamin D (1,25-dihydroxyvitamin D3) receptor | VDR | 15713801 | |
| VINCRISTINE | NM_001079539; NM_005080 | X-box binding protein 1 | XBP1 | 17353921 | |
| VINFLUNINE | NM_030773 | tubulin, beta 1 | TUBB1 | — | target |
| VINDESINE | NM_030773 | tubulin, beta 1 | TUBB1 | — | target |

TABLE 1-continued

| Molecule | RefSeq | Description | Symbol | PMID | Interaction |
|---|---|---|---|---|---|
| VINORELBINE | NM_006788 | ralA binding protein 1 | RALBP1 | — | resistance |
| VINORELBINE | NM_001145547; NM_032905 | RNA binding motif protein 17 | RBM17 | 16061639 | resistance |
| VINORELBINE | NM_001078174; NM_001078175; NM_001078176; NM_001078177; NM_004955 | solute carrier family 29 (nucleoside transporters), member 1 | SLC29A1 | 18452103 | resistance |
| VINORELBINE | NM_001069 | tubulin, beta 2A | TUBB2A | — | target |
| EPOTHILONES | NM_004324; NM_138761; NM_138763; NM_138764; NM_138765 | BCL2-associated X protein | BAX | 12517783 | death pathway |
| EPOTHILONES | NM_000633; NM_000657 | B-cell CLL/lymphoma 2 | BCL2 | 12517783 | resistance |
| EPOTHILONES | NM_001191; NM_138578 | BCL2-like 1 | BCL2L1 | 12517783 | altered by epothilone |
| EPOTHILONES | NM_001165; NM_182962 | baculoviral IAP repeat-containing 3 | BIRC3 | 12517783 | altered by epothilone |
| EPOTHILONES | NM_021960; NM_182763 | myeloid cell leukemia sequence 1 (BCL2-related) | MCL1 | 12517783 | |
| EPOTHILONES | — | | TUBA1 | — | |
| EPOTHILONES | — | | TUBA2 | — | |
| EPOTHILONES | — | | TUBA3 | — | |
| EPOTHILONES | — | | TUBA6 | — | |
| EPOTHILONES | NM_018943 | tubulin, alpha 8 | TUBA8 | — | |
| EPOTHILONES | NM_030773 | tubulin, beta 1 | TUBB1 | — | target? |
| EPOTHILONES | NM_001069 | tubulin, beta 2A | TUBB2A | — | target? |
| EPOTHILONES | NM_006088 | tubulin, beta 2C | TUBB2C | — | target? |
| EPOTHILONES | NM_006086 | tubulin, beta 3 | TUBB3 | — | target? |
| EPOTHILONES | NM_006087 | tubulin, beta 4 | TUBB4 | — | target? |
| EPOTHILONES | NM_020040 | tubulin, beta polypeptide 4, member Q | TUBB4Q | — | altered by epothilone |
| EPOTHILONES | NM_001167 | X-linked inhibitor of apoptosis | XIAP | 12517783 | |
| DOXORUBICIN | NM_000927 | ATP-binding cassette, sub-family B (MDR/TAP), member 1 | ABCB1 | 11355955, 15765123, 11313874, 17947497, (following) 15725475, 15861398, 15239142, 15501994, 15501994, 16579640, 15501994, 17526808, 15736412, 15861398, 15946544, 15967469, 16223781, 16322897, 16044152, 15765123, 16356834, 16499877, 16544145, 16544145, 18510171, 18560228, 17852453, 16579640, 17085340, 17483874, 8917702, 17526808, 17947497, 17947497, 17526808, 18461970, 8917702 | resistance |
| DOXORUBICIN | — | | ABCB1A | 15695394 | |
| DOXORUBICIN | NM_000443; NM_018849; NM_018850 | ATP-binding cassette, sub-family B (MDR/TAP), member 4 | ABCB4 | 11313874, 12926078, 16579640 | resistance |
| DOXORUBICIN | NM_178559 | ATP-binding cassette, sub-family B (MDR/TAP), member 5 | ABCB5 | 15899824 | resistance |
| DOXORUBICIN | NM_004996; NM_019862; NM_019898; NM_019899; NM_019900 | ATP-binding cassette, sub-family C (CFTR/MRP), member 1 | ABCC1 | 11560771, 12504668, 15473893, 15473893, 12067707, 11560771, 10900222, 12657726, 17940500, 15548710, 15581632, 15880572, 15946544, 16331495, 17352253, 17852453, 18560228, 17940500 | resistance |

TABLE 1-continued

| Molecule | RefSeq | Description | Symbol | PMID | Interaction |
|---|---|---|---|---|---|
| DOXORUBICIN | NM_001144070; NM_003786 | ATP-binding cassette, sub-family C (CFTR/MRP), member 3 | ABCC3 | 15695394, 15884115, 15901850, 18463201 | resistance |
| DOXORUBICIN | NM_004827 | ATP-binding cassette, sub-family G (WHITE), member 2 | ABCG2 | 17273774, 17938326, 18382425 | resistance |
| DOXORUBICIN | NM_023038; NM_033274 | ADAM metallopeptidase domain 19 (meltrin beta) | ADAM19 | 18510171 | |
| DOXORUBICIN | NM_007038 | ADAM metallopeptidase with thrombospondin type 1 motif, 5 | ADAMTS5 | 16404146 | |
| DOXORUBICIN | NM_000687; NM_001161766 | adenosylhomocysteinase | AHCY | 18510171 | |
| DOXORUBICIN | NM_001130846; NM_001130847; NM_004208; NM_145812; NM_145813 | apoptosis-inducing factor, mitochondrion-associated, 1 | AIFM1 | 16168113 | |
| DOXORUBICIN | NM_006066; NM_153326 | aldo-keto reductase family 1, member A1 (aldehyde reductase) | AKR1A1 | 18322072 | drug metabolism |
| DOXORUBICIN | NM_001354; NM_205845 | aldo-keto reductase family 1, member C2 (dihydrodiol dehydrogenase 2; bile acid binding protein; 3-alpha hydroxysteroid dehydrogenase, type III) | AKR1C2 | 18322072 | drug metabolism |
| DOXORUBICIN | NM_003739 | aldo-keto reductase family 1, member C3 (3-alpha hydroxysteroid dehydrogenase, type II) | AKR1C3 | 18635746 | |
| DOXORUBICIN | NM_001014431; NM_001014432; NM_005163 | v-akt murine thymoma viral oncogene homolog 1 | AKT1 | 15494689, 16168102, 17359293, 16059641, 16168102, 16438844, 16740780, 16782806, 17339365, 17359293, 17935137, 17935137, 16168102, 18071906 | resistance |
| DOXORUBICIN | NM_001626 | v-akt murine thymoma viral oncogene homolog 2 | AKT2 | 18071906 | resistance |
| DOXORUBICIN | NM_005465; NM_181690 | v-akt murine thymoma viral oncogene homolog 3 (protein kinase B, gamma) | AKT3 | 18071906 | resistance |
| DOXORUBICIN | NM_000477 | albumin | ALB | 17378599, 17378599, 16211657 | used as drug carrier |
| DOXORUBICIN | NM_001144 | autocrine motility factor receptor | AMFR | 16896004 | |
| DOXORUBICIN | NM_001146 | angiopoietin 1 | ANGPT1 | 15763944 | resistance |
| DOXORUBICIN | NM_007347 | adaptor-related protein complex 4, epsilon 1 subunit | AP4E1 | 16044152 | |
| DOXORUBICIN | NM_001160; NM_013229; NM_181861; NM_181868; NM_181869 | apoptotic peptidase activating factor 1 | APAF1 | 15939500, 16001973, 15939500 | death pathway |
| DOXORUBICIN | NM_001142930; NM_001142931; NM_006595 | apoptosis inhibitor 5 | API5 | 16322897 | |
| DOXORUBICIN | NM_000039 | apolipoprotein A-I | APOA1 | 16001973 | |
| DOXORUBICIN | NM_000484; NM_001136016; NM_001136129; NM_001136130; NM_001136131; NM_201413; NM_201414 | amyloid beta (A4) precursor protein | APP | 17608641 | resistance |
| DOXORUBICIN | NM_004706; NM_198977; NM_199002 | Rho guanine nucleotide exchange factor (GEF) 1 | ARHGEF1 | 16404146 | |
| DOXORUBICIN | NM_014786 | Rho guanine nucleotide exchange factor (GEF) 17 | ARHGEF17 | 16404146 | |
| DOXORUBICIN | NM_006407 | ADP-ribosylation-like factor 6 interacting protein 5 | ARL6IP5 | 16430862 | |
| DOXORUBICIN | NM_001675; NM_182810 | activating transcription factor 4 (tax-responsive enhancer element B67) | ATF4 | 16298333 | |
| DOXORUBICIN | NM_000051; NM_138292 | ataxia telangiectasia mutated | ATM | 15489221 | |
| DOXORUBICIN | NM_003945 | ATPase, H+ transporting, lysosomal 9 kDa, V0 subunit e1 | ATP6V0E1 | 16579640 | |
| DOXORUBICIN | NM_001185 | alpha-2-glycoprotein 1, zinc-binding | AZGP1 | 16404146 | |
| DOXORUBICIN | NM_001497 | UDP-Gal:betaGlcNAc beta 1,4-galactosyltransferase, polypeptide 1 | B4GALT1 | 16404146 | |
| DOXORUBICIN | NM_001011545; NM_001186; NM_206866 | BTB and CNC homology 1, basic leucine zipper transcription factor 1 | BACH1 | 16322897 | |
| DOXORUBICIN | NM_004322; NM_032989 | BCL2-associated agonist of cell death | BAD | 16001973, 16438844, 16705698, 16843435, 17359293 | |

TABLE 1-continued

| Molecule | RefSeq | Description | Symbol | PMID | Interaction |
|---|---|---|---|---|---|
| DOXORUBICIN | NM_004323 | BCL2-associated athanogene | BAG1 | 16322899 | |
| DOXORUBICIN | NM_001188 | BCL2-antagonist/killer 1 | BAK1 | 11313874, 15917298 | |
| DOXORUBICIN | NM_004324; NM_138761; NM_138763; NM_138764; NM_138765 | BCL2-associated X protein | BAX | 14601052, 15456408, 15492826, 15576332, 15939500, 15985719, 16001973, 17404015, 16168113, 16322301, 16705698, 17542780, 17959036, 17959036, 17339365, 17542780, 17922852 | |
| DOXORUBICIN | NM_001127240; NM_001127241; NM_001127242; NM_014417 | BCL2 binding component 3 | BBC3 | 16439685 | |
| DOXORUBICIN | NM_152618 | Bardet-Biedl syndrome 12 | BBS12 | 16044152 | |
| DOXORUBICIN | NM_033028 | Bardet-Biedl syndrome 4 | BBS4 | 16896004 | |
| DOXORUBICIN | NM_000633; NM_000657 | B-cell CLL/lymphoma 2 | BCL2 | 14601052, 15897917, 15571967, 15576332, (following) 15939500, 15985719, 16001973, 17404015, 18560228, 16168113, 16322301, 17541305, 16450387, 16322899, 16705698, 16890185, 17542780, 17959036, 17959036, 17542780, 16890185, 18325115 | |
| DOXORUBICIN | NM_001114735; NM_004049 | BCL2-related protein A1 | BCL2A1 | 16572199 | |
| DOXORUBICIN | NM_001191; NM_138578 | BCL2-like 1 | BCL2L1 | 14601052, 15781649, 11468182, 15911101, 15939500, 15939500, 18560228, 16843435, 17912235, 17922852, 16843435, 17923112 | |
| DOXORUBICIN | NM_006538; NM_138621; NM_207002 | BCL2-like 11 (apoptosis facilitator) | BCL2L11 | 17339365 | |
| DOXORUBICIN | NM_001040668; NM_138639 | BCL2-like 12 (proline rich) | BCL2L12 | 15576332, 17404015 | |
| DOXORUBICIN | NM_003766 | beclin 1, autophagy related | BECN1 | 16718815, 16896004 | |
| DOXORUBICIN | NM_001196; NM_197966; NM_197967 | BH3 interacting domain death agonist | BID | 15812552, 15870702, 16705698, 16868541 | |
| DOXORUBICIN | NM_001197 | BCL2-interacting killer (apoptosis-inducing) | BIK | 16007125, 16705698 | |
| DOXORUBICIN | NM_001166 | baculoviral IAP repeat-containing 2 | BIRC2 | 14601052, 14666661, 15359644, 15571967, 15571967, 14666661, 17521628 | |
| DOXORUBICIN | NM_001165; NM_182962 | baculoviral IAP repeat-containing 3 | BIRC3 | 12926068, 12948851, 15899819, 15911101, 16705698, 17521628 | |
| DOXORUBICIN | NM_001012270; NM_001012271; NM_001168 | baculoviral IAP repeat-containing 5 | BIRC5 | 11911975, 16086872, 16364925, 16108013, 11911975, 17124180, 16108013, 14601052, 16086872, 16086872, 17521628, 16108013, 17124180 | |
| DOXORUBICIN | NM_016252 | baculoviral IAP repeat-containing 6 | BIRC6 | 17521628 | |
| DOXORUBICIN | NM_022161; NM_139317 | baculoviral IAP repeat-containing 7 | BIRC7 | 17521628 | |
| DOXORUBICIN | NM_033341 | baculoviral IAP repeat-containing 8 | BIRC8 | 17521628 | |
| DOXORUBICIN | NM_007294; NM_007295; NM_007296; NM_007297; NM_007298; NM_007299; NM_007300; NM_007302; NM_007303; NM_007304; NM_007305 | breast cancer 1, early onset | BRCA1 | 10344722 | |
| DOXORUBICIN | NM_000059 | breast cancer 2, early onset | BRCA2 | 10344722 | |
| DOXORUBICIN | NM_001731 | B-cell translocation gene 1, anti-proliferative | BTG1 | 16705698 | |

TABLE 1-continued

| Molecule | RefSeq | Description | Symbol | PMID | Interaction |
|---|---|---|---|---|---|
| DOXORUBICIN | NM_006763 | BTG family, member 2 | BTG2 | 16705698 | |
| DOXORUBICIN | NM_001130914; NM_006806 | BTG family, member 3 | BTG3 | 16896004 | |
| DOXORUBICIN | NM_001211 | budding uninhibited by benzimidazoles 1 homolog beta (yeast) | BUB1B | 15870702 | |
| DOXORUBICIN | NM_001007793; NM_004725 | budding uninhibited by benzimidazoles 3 homolog (yeast) | BUB3 | 16322899 | |
| DOXORUBICIN | — | — | C21ORF87 | 16044152 | |
| DOXORUBICIN | — | — | C5ORF13 | 16044152 | |
| DOXORUBICIN | — | — | C7ORF23 | 15556294, 15556294, 18510171 | |
| DOXORUBICIN | NM_001218; NM_206925 | carbonic anhydrase XII | CA12 | 16896004 | |
| DOXORUBICIN | NM_020247 | chaperone, ABC1 activity of bc1 complex homolog (S. pombe) | CABC1 | 16404146 | |
| DOXORUBICIN | NM_004342; NM_033138; NM_033139; NM_033140; NM_033157 | caldesmon 1 | CALD1 | 16044152 | |
| DOXORUBICIN | NM_014289 | calpain 6 | CAPN6 | 16404146 | |
| DOXORUBICIN | NM_001223; NM_033292; NM_033293; NM_033294; NM_033295 | caspase 1, apoptosis-related cysteine peptidase (interleukin 1, beta, convertase) | CASP1 | 16001973 | |
| DOXORUBICIN | NM_001230; NM_032974; NM_032977 | caspase 10, apoptosis-related cysteine peptidase | CASP10 | 16001973 | |
| DOXORUBICIN | NM_032982; NM_032983 | caspase 2, apoptosis-related cysteine peptidase | CASP2 | 14757846, 15917298, 16001973, 17013758 | |
| DOXORUBICIN | NM_004346; NM_032991 | caspase 3, apoptosis-related cysteine peptidase | CASP3 | 15456408, 15557793, 15571967, 15578696, (following) 15812552, 15870702, 15939500, 15981920, 15985719, 15985719, 16962673, 17437844, 15456408, 16364925, 17085670, 17088416, 16909308, 15680309, 15981920, 19106633, 15571967, 15578696, 16823846, 16843435, 15868924, 18508926, 16001973, 15576332, 16705698, 15939500, 16168113, 16364925, 16823846, 16843435, 16868541, 16890185, 16909308, 16962673, 17013758, 17085670, 17088416, 17285121, 17437844, 17542780, 17935137, 17935137, 17542780, 16024631, 18246814, 15897917, 17285121, 16890185, 17651020, 17959036, 17959036, 15557793, 18071906, 15555623, 17653088, 18246814, 18278454, 18508926, 19106633 | |
| DOXORUBICIN | NM_001225; NM_033306 | caspase 4, apoptosis-related cysteine peptidase | CASP4 | 16001973 | |
| DOXORUBICIN | NM_001136109; NM_001136110; NM_001136111; NM_001136112; NM_004347 | caspase 5, apoptosis-related cysteine peptidase | CASP5 | 16001973 | |
| DOXORUBICIN | NM_001226; NM_032992 | caspase 6, apoptosis-related cysteine peptidase | CASP6 | 15870702, 16001973, 17437844, 17922852, 17437844 | |
| DOXORUBICIN | NM_001227; NM_033338; NM_033339; NM_033340 | caspase 7, apoptosis-related cysteine peptidase | CASP7 | 15870702, 16001973, 16705698, 16024631, 16168113, 16298333, 17653088, 19106633 | |

TABLE 1-continued

| Molecule | RefSeq | Description | Symbol | PMID | Interaction |
|---|---|---|---|---|---|
| DOXORUBICIN | NM_001080124; NM_001080125; NM_001228; NM_033355; NM_033356; NM_033358 | caspase 8, apoptosis-related cysteine peptidase | CASP8 | 15812552, 15870702, 15897917, 16024631, 15981920, 16001973, 16168113, 16705698, 16868541, 17013758, 17437844, 18508926, 18868924, 17970047, 18071906, 18508926 | |
| DOXORUBICIN | NM_001229; NM_032996 | caspase 9, apoptosis-related cysteine peptidase | CASP9 | 15812552, 15870702, 15939500, 15981920, (following) 15981920, 18868924, 18508926, 17437844, 16001973, 15576332, 19339500, 16168113, 16311509, 17653088, 15557793, 17935137, 17653088, 15555623, 16364925, 16705698, 17013758, 17285121, 17339365, 17404015, 17437844, 17651020, 17651020, 17285121, 16024631, 16364925, 17935137, 18508926 | |
| DOXORUBICIN | NM_001757 | carbonyl reductase 1 | CBR1 | 18635746 | drug metabolism |
| DOXORUBICIN | NM_002982 | chemokine (C-C motif) ligand 2 | CCL2 | 12908082 | |
| DOXORUBICIN | NM_001237 | cyclin A2 | CCNA2 | 16036217, 16284694, 16537896, 17390037 | |
| DOXORUBICIN | NM_031966 | cyclin B1 | CCNB1 | 15141020, 16537896, 16928833, 17320279, 17893511 | |
| DOXORUBICIN | NM_053056 | cyclin D1 | CCND1 | 16036217 | |
| DOXORUBICIN | NM_001759 | cyclin D2 | CCND2 | 16928833 | |
| DOXORUBICIN | NM_001238; NM_057182 | cyclin E1 | CCNE1 | 16036217 | |
| DOXORUBICIN | NM_000610; NM_001001389; NM_001001390; NM_001001391; NM_001001392 | CD44 molecule (Indian blood group) | CD44 | 16705698 | |
| DOXORUBICIN | NM_001130829; NM_001786; NM_033379 | cell division cycle 2, G1 to S and G2 to M | CDC2 | 15870702, 16036217, 16537896, 17320279, 17320279, 15141020 | |
| DOXORUBICIN | NM_001790; NM_022809 | cell division cycle 25 homolog C (S. pombe) | CDC25C | 17320279, 19074854 | sensitivity |
| DOXORUBICIN | NM_001098533; NM_001160367; NM_052987; NM_052988 | cyclin-dependent kinase 10 | CDK10 | 16404146 | |
| DOXORUBICIN | NM_001798; NM_052827 | cyclin-dependent kinase 2 | CDK2 | 15823547, 16036217 | |
| DOXORUBICIN | NM_000389; NM_078467 | cyclin-dependent kinase inhibitor 1A (p21, Cip1) | CDKN1A | 14601052, 15141020, 15492826, 15601469, (following) 15781256, 15823547, 16168113, 16537896, 15555623, 19074854, 15601469, 15555623, 15781256, 17682292, 17653088, 15781256, 16909308, 17079232, 17653088, 16705698, 16439685, 17682292, 17893511, 17974990, 18269916, 19074854 | |
| DOXORUBICIN | NM_004064 | cyclin-dependent kinase inhibitor 1B (p27, Kip1) | CDKN1B | 16322899, 16705698, 17893511, 16036217, 17935137 | |
| DOXORUBICIN | NM_000077; NM_058195; NM_058197 | cyclin-dependent kinase inhibitor 2A (melanoma, p16, inhibits CDK4) | CDKN2A | 16705698 | |
| DOXORUBICIN | NM_005194 | CCAAT/enhancer binding protein (C/EBP), beta | CEBPB | 16001973 | |

TABLE 1-continued

| Molecule | RefSeq | Description | Symbol | PMID | Interaction |
|---|---|---|---|---|---|
| DOXORUBICIN | NM_001042426; NM_001809 | centromere protein A | CENPA | 15870702 | |
| DOXORUBICIN | NM_001025194; NM_001025195; NM_001266 | carboxylesterase 1 (monocyte/macrophage serine esterase 1) | CES1 | 16001973 | |
| DOXORUBICIN | NM_001127183; NM_001127184; NM_003879 | CASP8 and FADD-like apoptosis regulator | CFLAR | 14601052, 16 | |
| DOXORUBICIN | NM_000492 | cystic fibrosis transmembrane conductance regulator (ATP-binding cassette sub-family C, member 7) | CFTR | 17762173 | |
| DOXORUBICIN | NM_001114121; NM_001114122; NM_001274 | CHK1 checkpoint homolog (S. pombe) | CHEK1 | 15489221, 15870702, 16036217, 17085670, 17088865, 17088865, 17085670, 17320279, 18698031 | |
| DOXORUBICIN | NM_001005735; NM_007194; NM_145862 | CHK2 checkpoint homolog (S. pombe) | CHEK2 | 15489221, 17085670, 17320279 | |
| DOXORUBICIN | NM_001278 | conserved helix-loop-helix ubiquitous kinase | CHUK | 18463201 | |
| DOXORUBICIN | NM_020313 | cytokine induced apoptosis inhibitor 1 | CIAPIN1 | 18389626 | |
| DOXORUBICIN | NM_013324; NM_145071 | cytokine inducible SH2-containing protein | CISH | 16044152 | |
| DOXORUBICIN | NM_021101 | claudin 1 | CLDN1 | 16404146 | |
| DOXORUBICIN | NM_002956; NM_198240 | CAP-GLY domain containing linker protein 1 | CLIP1 | 16404146 | |
| DOXORUBICIN | NM_001294 | cleft lip and palate associated transmembrane protein 1 | CLPTM1 | 16243817 | |
| DOXORUBICIN | NM_001831; NM_203339 | clusterin | CLU | 16322897 | |
| DOXORUBICIN | NM_030582; NM_130444; NM_130445 | collagen, type XVIII, alpha 1 | COL18A1 | 17627616 | |
| DOXORUBICIN | — | cytochrome c oxidase II | COX2 | 16278810 | |
| DOXORUBICIN | NM_001031847; NM_001876 | carnitine palmitoyltransferase 1A (liver) | CPT1A | 16283381 | |
| DOXORUBICIN | NM_001079846; NM_004380 | CREB binding protein | CREBBP | 17498666 | |
| DOXORUBICIN | NM_001142407; NM_001142408; NM_001142417; NM_001142435; NM_003296 | cysteine-rich secretory protein 2 | CRISP2 | 16404146 | |
| DOXORUBICIN | NM_000394 | crystallin, alpha A | CRYAA | 16322897 | |
| DOXORUBICIN | NM_001885 | crystallin, alpha B | CRYAB | 16322897 | |
| DOXORUBICIN | NM_001897 | chondroitin sulfate proteoglycan 4 | CSPG4 | 16404146 | |
| DOXORUBICIN | NM_001901 | connective tissue growth factor | CTGF | 16579640 | |
| DOXORUBICIN | NM_001012329; NM_020248 | catenin, beta interacting protein 1 | CTNNBIP1 | 16322899 | |
| DOXORUBICIN | NM_001332 | catenin (cadherin-associated protein), delta 2 (neural plakophilin-related arm-repeat protein) | CTNND2 | 16896004 | |
| DOXORUBICIN | NM_001908; NM_147780; NM_147781; NM_147782; NM_147783 | cathepsin B | CTSB | 16705698, 17378599 | |
| DOXORUBICIN | NM_001909 | cathepsin D | CTSD | 18566016 | |
| DOXORUBICIN | NM_001911 | cathepsin G | CTSG | 16458935 | |
| DOXORUBICIN | NM_002993 | chemokine (C-X-C motif) ligand 6 (granulocyte chemotactic protein 2) | CXCL6 | 16404146 | |
| DOXORUBICIN | NM_001916 | cytochrome c-1 | CYC1 | 16001973 | |
| DOXORUBICIN | NM_018947 | cytochrome c, somatic | CYCS | 16001973, 16705698, 16331251, 16749863, 16868541 | |
| DOXORUBICIN | NM_000499 | cytochrome P450, family 1, subfamily A, polypeptide 1 | CYP1A1 | 15377855 | |
| DOXORUBICIN | NM_000785 | cytochrome P450, family 27, subfamily B, polypeptide 1 | CYP27B1 | 17716971 | |
| DOXORUBICIN | NM_000767 | cytochrome P450, family 2, subfamily B, polypeptide 6 | CYP2B6 | 16322899 | |
| DOXORUBICIN | NM_001141969; NM_001141970; NM_001350 | death-domain associated protein | DAXX | 12948851 | |
| DOXORUBICIN | NM_004083 | DNA-damage-inducible transcript 3 | DDIT3 | 16404146 | |
| DOXORUBICIN | NM_001134709; NM_003472 | DEK oncogene | DEK | 16298333, 17912235 | |
| DOXORUBICIN | NM_004717 | diacylglycerol kinase, iota | DGKI | 16579640 | |
| DOXORUBICIN | NM_001930; NM_013406; NM_013407 | deoxyhypusine synthase | DHPS | 16404146 | |
| DOXORUBICIN | NM_019887; NM_138929 | diablo homolog (Drosophila) | DIABLO | 16404146 | |
| DOXORUBICIN | NM_014421 | dickkopf homolog 2 (Xenopus laevis) | DKK2 | 12948851, 17521628 | |
| DOXORUBICIN | NM_001539 | DnaJ (Hsp40) homolog, subfamily A, member 1 | DNAJA1 | 16404146 | |
| DOXORUBICIN | | | | 16579640 | |

TABLE 1-continued

| Molecule | RefSeq | Description | Symbol | PMID | Interaction |
|---|---|---|---|---|---|
| DOXORUBICIN | NM_001130823; NM_001379 | DNA (cytosine-5-)-methyltransferase 1 | DNMT1 | 17124180 | |
| DOXORUBICIN | NM_001935 | dipeptidyl-peptidase 4 | DPP4 | 15753397 | |
| DOXORUBICIN | NM_014208 | dentin sialophosphoprotein | DSPP | 16404146 | |
| DOXORUBICIN | NM_012145 | deoxythymidylate kinase (thymidylate kinase) | DTYMK | 18413751 | |
| DOXORUBICIN | NM_005225 | E2F transcription factor 1 | E2F1 | 16001973 | |
| DOXORUBICIN | NM_001949 | E2F transcription factor 3 | E2F3 | 16896004 | |
| DOXORUBICIN | NM_004092 | enoyl Coenzyme A hydratase, short chain, 1, mitochondrial | ECHS1 | 15492826 | |
| DOXORUBICIN | NM_030796 | EGFR-coamplified and overexpressed protein | ECOP | 18510171 | |
| DOXORUBICIN | NM_001955 | endothelin 1 | EDN1 | 17974986 | |
| DOXORUBICIN | NM_001406 | ephrin-B3 | EFNB3 | 16322897 | |
| DOXORUBICIN | NM_001963 | epidermal growth factor (beta-urogastrone) | EGF | 16969495 | |
| DOXORUBICIN | NM_005228; NM_201282; NM_201283; NM_201284 | epidermal growth factor receptor (erythroblastic leukemia viral (v-erb-b) oncogene homolog, avian) | EGFR | 15981280, 16001973, 17938326, 17974986 | |
| DOXORUBICIN | NM_001964 | early growth response 1 | EGR1 | 17330857 | |
| DOXORUBICIN | NM_006709; NM_025256 | euchromatic histone-lysine N-methyltransferase 2 | EHMT2 | 17124180 | |
| DOXORUBICIN | NM_001412 | eukaryotic translation initiation factor 1A, X-linked | EIF1AX | 16322899 | |
| DOXORUBICIN | NM_032025 | eukaryotic translation initiation factor 2A, 65 kDa | EIF2A | 16298333 | |
| DOXORUBICIN | NM_004095 | eukaryotic translation initiation factor 4E binding protein 1 | EIF4EBP1 | 16322899 | |
| DOXORUBICIN | NM_001429 | E1A binding protein p300 | EP300 | 10344722, 17498666, 10344722 | |
| DOXORUBICIN | NM_004431 | EPH receptor A2 | EPHA2 | 16900372 | |
| DOXORUBICIN | NM_001040458; NM_016442 | endoplasmic reticulum aminopeptidase 1 | ERAP1 | 16404146 | |
| DOXORUBICIN | NM_001005862; NM_004448 | v-erb-b2 erythroblastic leukemia viral oncogene homolog 2, neuro/glioblastoma derived oncogene homolog (avian) | ERBB2 | 15486187, 15834928, 16168102, 17010609 | |
| DOXORUBICIN | NM_001005915; NM_001982 | v-erb-b2 erythroblastic leukemia viral oncogene homolog 3 (avian) | ERBB3 | 16168102 | |
| DOXORUBICIN | NM_001042599; NM_005235 | v-erb-a erythroblastic leukemia viral oncogene homolog 4 (avian) | ERBB4 | 16896004 | |
| DOXORUBICIN | NM_000125; NM_001122740; NM_001122741; NM_001122742 | estrogen receptor 1 | ESR1 | 16322899 | |
| DOXORUBICIN | NM_001040275; NM_001040276; NM_001437 | estrogen receptor 2 (ER beta) | ESR2 | 16322899, 16900372 | |
| DOXORUBICIN | NM_001987 | ets variant 6 | ETV6 | 15217836 | |
| DOXORUBICIN | NM_001993 | coagulation factor III (thromboplastin, tissue factor) | F3 | 18246814, 18278454, 18325115 | |
| DOXORUBICIN | NM_000131; NM_019616 | coagulation factor VII (serum prothrombin conversion accelerator) | F7 | 18325115 | |
| DOXORUBICIN | NM_003824 | Fas (TNFRSF6)-associated via death domain | FADD | 16001973, 16705698, 17970047 | |
| DOXORUBICIN | NM_012306 | Fas apoptotic inhibitory molecule 2 | FAIM2 | 16001973 | |
| DOXORUBICIN | NM_000043; NM_152871; NM_152872; NM_152873; NM_152874; NM_152875; NM_152876; NM_152877 | Fas (TNF receptor superfamily, member 6) | FAS | 15763944, 15576332, 17088865, 16705698, 15981920, 17088865, 17404015, 17970047 | |
| DOXORUBICIN | NM_000639 | Fas ligand (TNF superfamily, member 6) | FASLG | 15763944, 15763944, 17088865, 15981920, 17088865 | |
| DOXORUBICIN | NM_000569; NM_001127592; NM_001127593; NM_001127595; NM_001127596 | Fc fragment of IgG, low affinity IIIa, receptor (CD16a) | FCGR3A | 17852453 | |
| DOXORUBICIN | NM_004462 | farnesyl-diphosphate farnesyltransferase 1 | FDFT1 | 16322897 | |
| DOXORUBICIN | NM_001039492; NM_001450; NM_201555; NM_201557 | four and a half LIM domains 2 | FHL2 | 17682292 | |

TABLE 1-continued

| Molecule | RefSeq | Description | Symbol | PMID | Interaction |
|---|---|---|---|---|---|
| DOXORUBICIN | NM_001145775; NM_001145776; NM_001145777; NM_004117 | FK506 binding protein 5 | FKBP5 | 15571967 | |
| DOXORUBICIN | NM_012181 | FK506 binding protein 8, 38 kDa | FKBP8 | 16404146 | |
| DOXORUBICIN | NM_002026; NM_054034; NM_212474; NM_212475; NM_212476; NM_212478; NM_212482 | fibronectin 1 | FN1 | 17703109 | |
| DOXORUBICIN | NM_000802; NM_016724; NM_016725; NM_016729; NM_016730; NM_016731 | folate receptor 1 (adult) | FOLR1 | 15634643, 16404146 | |
| DOXORUBICIN | NM_005252 | v-fos FBJ murine osteosarcoma viral oncogene homolog | FOS | 16900372 | |
| DOXORUBICIN | NM_001454 | forkhead box J1 | FOXJ1 | 16044152 | |
| DOXORUBICIN | NM_002015 | forkhead box O1 | FOXO1 | 17935137 | |
| DOXORUBICIN | NM_001455; NM_201559 | forkhead box O3 | FOXO3 | 17935137 | |
| DOXORUBICIN | NM_000510; NM_001018080 | follicle stimulating hormone, beta polypeptide | FSHB | 17028438 | |
| DOXORUBICIN | NM_000146 | ferritin, light polypeptide | FTL | 12644586 | |
| DOXORUBICIN | NM_177478 | ferritin mitochondrial | FTMT | 12644586 | |
| DOXORUBICIN | NM_002033 | fucosyltransferase 4 (alpha (1,3) fucosyltransferase, myeloid-specific) | FUT4 | 17852453 | |
| DOXORUBICIN | NM_000402; NM_001042351 | glucose-6-phosphate dehydrogenase | G6PD | 16404146 | |
| DOXORUBICIN | NM_006705 | growth arrest and DNA-damage-inducible, gamma | GADD45G | 16404146 | |
| DOXORUBICIN | NM_000156; NM_138924 | guanidinoacetate N-methyltransferase | GAMT | 16896004 | |
| DOXORUBICIN | NM_002046 | glyceraldehyde-3-phosphate dehydrogenase | GAPDH | 16001973 | |
| DOXORUBICIN | NM_002049 | GATA binding protein 1 (globin transcription factor 1) | GATA1 | 14623254, 17097070 | |
| DOXORUBICIN | NM_001498 | glutamate-cysteine ligase, catalytic subunit | GCLC | 10900222, 11560771 | |
| DOXORUBICIN | NM_002061 | glutamate-cysteine ligase, modifier subunit | GCLM | 10900222 | |
| DOXORUBICIN | NM_004864 | growth differentiation factor 15 | GDF15 | 16705698 | |
| DOXORUBICIN | NM_001135031; NM_004188 | growth factor independent 1B transcription repressor | GFI1B | 16322897 | |
| DOXORUBICIN | NM_001145453; NM_005264; NM_145793 | GDNF family receptor alpha 1 | GFRA1 | 16896004 | |
| DOXORUBICIN | NM_006708 | glyoxalase I | GLO1 | 16085563 | |
| DOXORUBICIN | NM_000406; NM_001012763 | gonadotropin-releasing hormone receptor | GNRHR | 17943530 | |
| DOXORUBICIN | NM_000174 | glycoprotein IX (platelet) | GP9 | 16404146 | |
| DOXORUBICIN | NM_000581; NM_201397 | glutathione peroxidase 1 | GPX1 | 15473893 | |
| DOXORUBICIN | NM_002093 | glycogen synthase kinase 3 beta | GSK3B | 17339365 | |
| DOXORUBICIN | NM_145740 | glutathione S-transferase alpha 1 | GSTA1 | 16890185 | |
| DOXORUBICIN | NM_001512 | glutathione S-transferase alpha 4 | GSTA4 | 18225754 | |
| DOXORUBICIN | NM_000852 | glutathione S-transferase pi 1 | GSTP1 | 10900222, 14623254, 15448748, resistance 15946544, 16356834, 16579640, 15533597, 14623254, 18225754 | |
| DOXORUBICIN | NM_001520 | general transcription factor IIIC, polypeptide 1, alpha 220 kDa | GTF3C1 | 16322899 | |
| DOXORUBICIN | NM_016315 | GULP, engulfment adaptor PTB domain containing 1 | GULP1 | 16001973 | |
| DOXORUBICIN | NM_002105 | H2A histone family, member X | H2AFX | 15489221, 16432175 | |
| DOXORUBICIN | NM_000184 | hemoglobin, gamma G | HBG2 | 17097070 | |
| DOXORUBICIN | NM_001525 | hypocretin (orexin) receptor 1 | HCRTR1 | 16404146 | |
| DOXORUBICIN | NM_004964 | histone deacetylase 1 | HDAC1 | 17124180 | |
| DOXORUBICIN | NM_000410; NM_139003; NM_139004; NM_139006; NM_139007; NM_139008; NM_139009; NM_139010; NM_139011 | hemochromatosis | HFE | 16823846 | |
| DOXORUBICIN | NM_000601; NM_001010931; NM_001010932; NM_001010933; NM_001010934 | hepatocyte growth factor (hepapoietin A; scatter factor) | HGF | 15688034, 16 | |

TABLE 1-continued

| Molecule | RefSeq | Description | Symbol | PMID | Interaction |
|---|---|---|---|---|---|
| DOXORUBICIN | NM_001530; NM_181054 | hypoxia inducible factor 1, alpha subunit (basic helix-loop-helix transcription factor) | HIF1A | 16532342, 17498666, 17912235 | |
| DOXORUBICIN | NM_003526 | histone cluster 1, H2bc | HIST1H2BC | 16322897 | |
| DOXORUBICIN | NM_002123 | major histocompatibility complex, class II, DQ beta 1 | HLA-DQB1 | 16322897, 16404146 | |
| DOXORUBICIN | NM_021983 | major histocompatibility complex, class II, DR beta 4 | HLA-DRB4 | 16322897 | |
| DOXORUBICIN | NM_015980 | HMP19 protein | HMP19 | 16044152 | |
| DOXORUBICIN | NM_005968; NM_031203 | heterogeneous nuclear ribonucleoprotein M | HNRNPM | 16928833 | |
| DOXORUBICIN | NM_001130442; NM_005343; NM_176795 | v-Ha-ras Harvey rat sarcoma viral oncogene homolog | HRAS | 16001973 | |
| DOXORUBICIN | NM_005114 | heparan sulfate (glucosamine) 3-O-sulfotransferase 1 | HS3ST1 | 16044152 | |
| DOXORUBICIN | NM_001017963; NM_005348 | heat shock protein 90 kDa alpha (cytosolic), class A member 1 | HSP90AA1 | 17680992 | |
| DOXORUBICIN | NM_002154 | heat shock 70 kDa protein 4 | HSPA4 | 16311509 | |
| DOXORUBICIN | NM_005347 | heat shock 70 kDa protein 5 (glucose-regulated protein, 78 kDa) | HSPA5 | 16298333, 17680992 | |
| DOXORUBICIN | NM_006597; NM_153201 | heat shock 70 kDa protein 8 | HSPA8 | 16579640, 16579640, 17680992 | |
| DOXORUBICIN | NM_004134 | heat shock 70 kDa protein 9 (mortalin) | HSPA9 | 17680992 | |
| DOXORUBICIN | NM_001540 | heat shock 27 kDa protein 1 | HSPB1 | 17680992 | |
| DOXORUBICIN | NM_002156; NM_199440 | heat shock 60 kDa protein 1 (chaperonin) | HSPD1 | 17680992 | |
| DOXORUBICIN | NM_002775 | HtrA serine peptidase 1 | HTRA1 | 16243817 | |
| DOXORUBICIN | NM_031407 | HECT, UBA and WWE domain containing 1 | HUWE1 | 16404146 | |
| DOXORUBICIN | NM_000415 | islet amyloid polypeptide | IAPP | 16001973 | |
| DOXORUBICIN | NM_024013 | interferon, alpha 1 | IFNA1 | 17959036 | |
| DOXORUBICIN | NM_000618; NM_001111283; NM_001111284; NM_001111285 | insulin-like growth factor 1 (somatomedin C) | IGF1 | 16740780 | |
| DOXORUBICIN | NM_000875 | insulin-like growth factor 1 receptor | IGF1R | 16001973 | |
| DOXORUBICIN | NM_001552 | insulin-like growth factor binding protein 4 | IGFBP4 | 16896004 | |
| DOXORUBICIN | NM_001556 | inhibitor of kappa light polypeptide gene enhancer in B-cells, kinase beta | IKBKB | 15899819, 18463201 | |
| DOXORUBICIN | NM_001099856; NM_001099857; NM_001145255; NM_003639 | inhibitor of kappa light polypeptide gene enhancer in B-cells, kinase gamma | IKBKG | 17890907 | |
| DOXORUBICIN | NM_000600 | interleukin 6 (interferon, beta 2) | IL6 | 16001973 | |
| DOXORUBICIN | NM_000584 | interleukin 8 | IL8 | 12908082, 15899819, 18510171 | |
| DOXORUBICIN | NM_001137673; NM_004516; NM_012218; NM_017620; NM_153464 | interleukin enhancer binding factor 3, 90 kDa | ILF3 | 16322899 | |
| DOXORUBICIN | NM_005544 | insulin receptor substrate 1 | IRS1 | 16322899 | |
| DOXORUBICIN | NM_002226; NM_145159 | jagged 2 | JAG2 | 16404146 | |
| DOXORUBICIN | — | | JMJD2B | 16896004 | |
| DOXORUBICIN | NM_002228 | jun oncogene | JUN | 15585644, 15880572, 18645001 | |
| DOXORUBICIN | NM_000238; NM_172056; NM_172057 | potassium voltage-gated channel, subfamily H (eag-related), member 2 | KCNH2 | 16086867 | |
| DOXORUBICIN | NM_002242 | potassium inwardly-rectifying channel, subfamily J, member 13 | KCNJ13 | 16404146 | |
| DOXORUBICIN | NM_018658; NM_170741; NM_170742 | potassium inwardly-rectifying channel, subfamily J, member 16 | KCNJ16 | 16404146 | |
| DOXORUBICIN | NM_002035 | 3-ketodihydrosphingosine reductase | KDSR | 16322897 | |
| DOXORUBICIN | NM_003685 | KH-type splicing regulatory protein | KHSRP | 16404146 | |
| DOXORUBICIN | NM_020853 | KIAA1467 | KIAA1467 | 16896004 | |
| DOXORUBICIN | NM_007054 | kinesin family member 3A | KIF3A | 16896004 | |
| DOXORUBICIN | NM_016270 | Kruppel-like factor 2 (lung) | KLF2 | 18510171 | |

TABLE 1-continued

| Molecule | RefSeq | Description | Symbol | PMID | Interaction |
|---|---|---|---|---|---|
| DOXORUBICIN | NM_000224; NM_199187 | keratin 18 | KRT18 | 16928833 | |
| DOXORUBICIN | NM_002306 | lectin, galactoside-binding, soluble, 3 | LGALS3 | 16322897 | |
| DOXORUBICIN | NM_001098268; NM_002312; NM_206937 | ligase IV, DNA, ATP-dependent | LIG4 | 18508926 | |
| DOXORUBICIN | NM_001113546; NM_001113547; NM_016357 | LIM domain and actin binding 1 | LIMA1 | 16044152 | |
| DOXORUBICIN | NM_005572; NM_170707; NM_170708 | lamin A/C | LMNA | 16001973 | |
| DOXORUBICIN | NM_005573 | lamin B1 | LMNB1 | 16001973 | |
| DOXORUBICIN | NM_002349 | lymphocyte antigen 75 | LY75 | 16404146 | |
| DOXORUBICIN | NM_002358 | MAD2 mitotic arrest deficient-like 1 (yeast) | MAD2L1 | 15870702 | |
| DOXORUBICIN | NM_002755 | mitogen-activated protein kinase kinase 1 | MAP2K1 | 17974986 | |
| DOXORUBICIN | NM_030662 | mitogen-activated protein kinase kinase 2 | MAP2K2 | 17974986 | |
| DOXORUBICIN | NM_002756; NM_145109 | mitogen-activated protein kinase kinase 3 | MAP2K3 | 15870702 | |
| DOXORUBICIN | NM_003010 | mitogen-activated protein kinase kinase 4 | MAP2K4 | 15870702, 16001973 | |
| DOXORUBICIN | NM_002758 | mitogen-activated protein kinase kinase 6 | MAP2K6 | 15870702 | |
| DOXORUBICIN | NM_003188; NM_145331; NM_145332; NM_145333 | mitogen-activated protein kinase kinase kinase 7 | MAP3K7 | 16001973 | |
| DOXORUBICIN | NM_005204 | mitogen-activated protein kinase kinase kinase 8 | MAP3K8 | 16322897 | |
| DOXORUBICIN | NM_002745; NM_138957 | mitogen-activated protein kinase 1 | MAPK1 | 15557793, 16001973, 17526808, 17974986, 15557793, 18468633, 18468633, 18468633, 15557793 | |
| DOXORUBICIN | NM_001315; NM_139012; NM_139013; NM_139014 | mitogen-activated protein kinase 14 | MAPK14 | 15494689, 16843435, 15557793, 15870702, 16322899, 16843435 | |
| DOXORUBICIN | NM_001040056; NM_001109891; NM_002746 | mitogen-activated protein kinase 3 | MAPK3 | 15557793, 16059641, 16928833, 17526808, 17974986, 18468633, 15557793, 18468633, 15557793 | |
| DOXORUBICIN | NM_002750; NM_139046; NM_139047; NM_139049 | mitogen-activated protein kinase 8 | MAPK8 | 15494689, 15870702, 15880572, 15917298, 15917298, 16890185, 16868541, 16890185 | |
| DOXORUBICIN | NM_001135044; NM_002752; NM_139068; NM_139069; NM_139070 | mitogen-activated protein kinase 9 | MAPK9 | 15494689, 15557793, 15557793, 15585644, 15585644 | |
| DOXORUBICIN | NM_001123606; NM_001123067; NM_005910; NM_016834; NM_016835; NM_016841 | microtubule-associated protein tau | MAPT | 16896004 | |
| DOXORUBICIN | NM_021960; NM_182763 | myeloid cell leukemia sequence 1 (BCL2-related) | MCL1 | 17935137 | |
| DOXORUBICIN | NM_005918 | malate dehydrogenase 2, NAD (mitochondrial) | MDH2 | 16322897 | |
| DOXORUBICIN | NM_001012333; NM_001012334; NM_002391 | midkine (neurite growth-promoting factor 2) | MDK | 16322897 | |
| DOXORUBICIN | NM_001145336; NM_001145337; NM_001145339; NM_001145340; NM_002392; NM_006878; NM_006879; NM_006881; NM_006882 | Mdm2 p53 binding protein homolog (mouse) | MDM2 | 16001973, 17935137, 17959036, 17959036, 19074854, 17653088 | |
| DOXORUBICIN | NM_015335 | mediator complex subunit 13-like | MED13L | 16896004 | |
| DOXORUBICIN | NM_001130926; NM_001130927; NM_001130928; NM_005587 | myocyte enhancer factor 2A | MEF2A | 16001973 | |
| DOXORUBICIN | NM_014791 | maternal embryonic leucine zipper kinase | MELK | 16896004 | |
| DOXORUBICIN | NM_006838 | methionyl aminopeptidase 2 | METAP2 | 16404146 | |
| DOXORUBICIN | NM_024042 | meteorin, glial cell differentiation regulator | METRN | 16896004 | |
| DOXORUBICIN | NM_001114614; NM_005928 | milk fat globule-EGF factor 8 protein | MFGE8 | 16404146 | |
| DOXORUBICIN | NM_002412 | O-6-methylguanine-DNA methyltransferase | MGMT | 16356834 | |
| DOXORUBICIN | NM_005933 | myeloid/lymphoid or mixed-lineage leukemia (trithorax homolog, Drosophila) | MLL | 16322897 | |
| DOXORUBICIN | NM_004529 | myeloid/lymphoid or mixed-lineage leukemia (trithorax homolog, Drosophila); translocated to, 3 | MLLT3 | 16404146 | |

TABLE 1-continued

| Molecule | RefSeq | Description | Symbol | PMID | Interaction |
|---|---|---|---|---|---|
| DOXORUBICIN | NM_000902; NM_007287; NM_007288; NM_007289 | membrane metallo-endopeptidase | MME | 16997790 | |
| DOXORUBICIN | NM_002421 | matrix metallopeptidase 1 (interstitial collagenase) | MMP1 | 11313874 | |
| DOXORUBICIN | NM_001127891; NM_004530 | matrix metallopeptidase 2 (gelatinase A, 72 kDa gelatinase, 72 kDa type IV collagenase) | MMP2 | 16458935 | |
| DOXORUBICIN | NM_018135 | mitochondrial ribosomal protein S18A | MRPS18A | 16404146 | |
| DOXORUBICIN | NM_000179 | mutS homolog 6 (E. coli) | MSH6 | 16404146 | |
| DOXORUBICIN | NM_005950 | metallothionein 1G | MT1G | 16579640 | |
| DOXORUBICIN | NR_001447; NR_001447; NR_001447; NR_001447; NR_001447; NR_001447 | metallothionein 1L (gene/pseudogene) | MT1L | 16579640 | |
| DOXORUBICIN | NM_005953 | metallothionein 2A | MT2A | 16579640 | |
| DOXORUBICIN | NM_000254 | 5-methyltetrahydrofolate-homocysteine methyltransferase | MTR | 16322897 | |
| DOXORUBICIN | NM_014751 | metastasis suppressor 1 | MTSS1 | 16243817 | |
| DOXORUBICIN | NM_005115; NM_017458 | major vault protein | MVP | 17575109 | |
| DOXORUBICIN | NM_002467 | v-myc myelocytomatosis viral oncogene homolog (avian) | MYC | 15911101, 16001973, 11585056, 18606404, 11802399 | |
| DOXORUBICIN | NM_004536; NM_022892 | NLR family, apoptosis inhibitory protein | NAIP | 11911975, 15911101, 16322899, 17521628 | |
| DOXORUBICIN | NM_002485 | nibrin | NBN | 15489221 | |
| DOXORUBICIN | NM_004146 | NADH dehydrogenase (ubiquinone) 1 beta subcomplex, 7, 18 kDa | NDUFB7 | 16404146 | |
| DOXORUBICIN | NM_003998 | nuclear factor of kappa light polypeptide gene enhancer in B-cells 1 | NFKB1 | 15555623, 15571967, 15870702, 15905586, 16001973, 16322301, 17912235, 18463201 | |
| DOXORUBICIN | NM_001077493; NM_001077494; NM_002502 | nuclear factor of kappa light polypeptide gene enhancer in B-cells 2 (p49/p100) | NFKB2 | 17890907 | |
| DOXORUBICIN | NM_020529 | nuclear factor of kappa light polypeptide gene enhancer in B-cells inhibitor, alpha | NFKBIA | 15571967, 15870702, 15899819, 17542780, 17935137, 17935137, 15899819, 17542780, 18463201 | |
| DOXORUBICIN | NM_002508 | nidogen 1 | NID1 | 17703109 | |
| DOXORUBICIN | NM_024522 | Na+/K+ transporting ATPase interacting 1 | NKAIN1 | 16896004 | |
| DOXORUBICIN | NM_002511 | neuromedin B receptor | NMBR | 16404146 | |
| DOXORUBICIN | NM_004741 | nucleolar and coiled-body phosphoprotein 1 | NOLC1 | 17129415 | |
| DOXORUBICIN | NM_000625 | nitric oxide synthase 2, inducible | NOS2 | 15695394, 15695394, 18463201, 18463201 | |
| DOXORUBICIN | NM_002135; NM_173157 | nuclear receptor subfamily 4, group A, member 1 | NR4A1 | 16322897 | |
| DOXORUBICIN | NM_013936 | olfactory receptor, family 12, subfamily D, member 2 | OR12D2 | 16404146 | |
| DOXORUBICIN | NM_012369 | olfactory receptor, family 2, subfamily F, member 1 | OR2F1 | 16404146 | |
| DOXORUBICIN | NM_000916 | oxytocin receptor | OXTR | 11313874 | |
| DOXORUBICIN | NM_006025 | 26 serine protease | P11 | 16001973 | |
| DOXORUBICIN | NM_012226; NM_016318; NM_170682; NM_170683; NM_174872; NM_174873 | purinergic receptor P2X, ligand-gated ion channel, 2 | P2RX2 | 16404146 | |
| DOXORUBICIN | NM_004154; NM_176796; NM_176797; NM_176798 | pyrimidinergic receptor P2Y, G-protein coupled, 6 | P2RY6 | 16044152 | |

TABLE 1-continued

| Molecule | RefSeq | Description | Symbol | PMID | Interaction |
|---|---|---|---|---|---|
| DOXORUBICIN | NM_001618 | poly (ADP-ribose) polymerase 1 | PARP1 | 15456408, 15557793, 15585644, 15753397, (following) 15870702, 15981920, 16311509, 16311509, 17651020, 16890185, 15557793, 18071906, 15585644, 16843435, 16962673, 15555623, 17285121, 17935137, 17959036, 16843435, 16890185, 16962673, 17285121, 17339365, 17418594, 17651020, 17935137, 17959036 | |
| DOXORUBICIN | NM_002583 | | PAWR | 12948851 | |
| DOXORUBICIN | NM_000280; NM_001127612; NM_001604 | PRKC, apoptosis, WT1, regulator | PAX6 | 16404146 | |
| DOXORUBICIN | — | paired box 6 | PCAF | 16001973 | |
| DOXORUBICIN | NM_002592; NM_182649 | proliferating cell nuclear antigen | PCNA | 16322897, 16537896 | |
| DOXORUBICIN | NM_004708 | programmed cell death 5 | PDCD5 | 16579640 | |
| DOXORUBICIN | NM_002613; NM_031268 | 3-phosphoinositide dependent protein kinase-1 | PDPK1 | 16782806 | |
| DOXORUBICIN | NM_002653 | paired-like homeodomain 1 | PITX1 | 16404146 | |
| DOXORUBICIN | NM_001145031; NM_002658 | plasminogen activator, urokinase | PLAU | 12908082, 15557793, 16356834 | |
| DOXORUBICIN | NM_000302 | procollagen-lysine 1,2-oxoglutarate 5-dioxygenase 1 | PLOD1 | 16322899 | |
| DOXORUBICIN | NM_001084 | procollagen-lysine, 2-oxoglutarate 5-dioxygenase 3 | PLOD3 | 16322899 | |
| DOXORUBICIN | NM_021127 | phorbol-12-myristate-13-acetate-induced protein 1 | PMAIP1 | 17653088 | |
| DOXORUBICIN | NM_021173 | polymerase (DNA-directed), delta 4 | POLD4 | 16404146 | |
| DOXORUBICIN | NM_013382 | protein-O-mannosyltransferase 2 | POMT2 | 16404146 | |
| DOXORUBICIN | NM_000941 | P450 (cytochrome) oxidoreductase | POR | 15942634, 16322897 | |
| DOXORUBICIN | NM_006238; NM_177435 | peroxisome proliferator-activated receptor delta | PPARD | 16404146 | |
| DOXORUBICIN | NM_005155; NM_138717 | palmitoyl-protein thioesterase 2 | PPT2 | 16404146 | |
| DOXORUBICIN | NM_002730; NM_207518 | protein kinase, cAMP-dependent, catalytic, alpha | PRKACA | 16404146 | |
| DOXORUBICIN | NM_002737 | protein kinase C, alpha | PRKCA | 16087181, 16579994 | |
| DOXORUBICIN | NM_006254; NM_212539 | protein kinase C, delta | PRKCD | 15917298 | |
| DOXORUBICIN | NM_001081640; NM_006904 | protein kinase, DNA-activated, catalytic polypeptide | PRKDC | 18508926 | |
| DOXORUBICIN | NM_000948 | prolactin | PRL | 18681966 | |
| DOXORUBICIN | NM_000311; NM_001080121; NM_001080122; NM_001080123; NM_183079 | prion protein | PRNP | 15386405 | |
| DOXORUBICIN | NM_000312 | protein C (inactivator of coagulation factors Va and VIIIa) | PROC | 17172434 | |
| DOXORUBICIN | NM_006404 | protein C receptor, endothelial (EPCR) | PROCR | 17172434 | |
| DOXORUBICIN | NM_001143937; NM_002786; NM_148976 | proteasome (prosome, macropain) subunit, alpha type, 1 | PSMA1 | 17346995 | |
| DOXORUBICIN | NM_002787 | proteasome (prosome, macropain) subunit, alpha type, 2 | PSMA2 | 17346995 | |
| DOXORUBICIN | NM_002788; NM_152132 | proteasome (prosome, macropain) subunit, alpha type, 3 | PSMA3 | 17346995 | |
| DOXORUBICIN | NM_001102667; NM_001102668; NM_002789 | proteasome (prosome, macropain) subunit, alpha type, 4 | PSMA4 | 17346995 | |
| DOXORUBICIN | NM_002790 | proteasome (prosome, macropain) subunit, alpha type, 5 | PSMA5 | 17346995 | |
| DOXORUBICIN | NM_002791 | proteasome (prosome, macropain) subunit, alpha type, 6 | PSMA6 | 17346995 | |
| DOXORUBICIN | NM_002792 | proteasome (prosome, macropain) subunit, alpha type, 7 | PSMA7 | 17346995 | |
| DOXORUBICIN | NM_002794 | proteasome (prosome, macropain) subunit, beta type, 2 | PSMB2 | 17346995 | |
| DOXORUBICIN | NM_002795 | proteasome (prosome, macropain) subunit, beta type, 3 | PSMB3 | 17346995 | |
| DOXORUBICIN | NM_002799 | proteasome (prosome, macropain) subunit, beta type, 7 | PSMB7 | 17346995 | |
| DOXORUBICIN | NM_000314 | phosphatase and tensin homolog | PTEN | 11707646, 15548710, 16438844, 17330857, 17359293, 17935137, 17935137, 16438844, 17359293 | |

TABLE 1-continued

| Molecule | RefSeq | Description | Symbol | PMID | Interaction |
|---|---|---|---|---|---|
| DOXORUBICIN | NM_000963 | prostaglandin-endoperoxide synthase 2 (prostaglandin G/H synthase and cyclooxygenase) | PTGS2 | 15501994, 16127422, 18498876 | |
| DOXORUBICIN | NM_005607; NM_153831 | PTK2 protein tyrosine kinase 2 | PTK2 | 15870702, 16168102 | |
| DOXORUBICIN | NM_004103; NM_173174; NM_173175; NM_173176 | PTK2B protein tyrosine kinase 2 beta | PTK2B | 16168102 | |
| DOXORUBICIN | NM_006264; NM_080683; NM_080684; NM_080685 | protein tyrosine phosphatase, non-receptor type 13 (APO-1/CD95 (Fas)-associated phosphatase) | PTPN13 | 16001973 | |
| DOXORUBICIN | NM_001161440; NM_002842 | protein tyrosine phosphatase, receptor type, H | PTPRH | 16044152 | |
| DOXORUBICIN | NM_002875; NM_133487 | RAD51 homolog (RecA homolog, E. coli) (S. cerevisiae) | RAD51 | 10344722, 17351394 | |
| DOXORUBICIN | NM_006788 | ralA binding protein 1 | RALBP1 | 15386349, 15950949, 16087181, 16579994, 17273774 | resistance |
| DOXORUBICIN | NM_005855 | receptor (G protein-coupled) activity modifying protein 1 | RAMP1 | 16896004 | |
| DOXORUBICIN | NM_000965; NM_016152 | retinoic acid receptor, beta | RARB | 17608728 | |
| DOXORUBICIN | NM_000321 | retinoblastoma 1 | RB1 | 15141020, 16537896 | |
| DOXORUBICIN | NM_002895; NM_183404 | retinoblastoma-like 1 (p107) | RBL1 | 16537896 | |
| DOXORUBICIN | NM_005611 | retinoblastoma-like 2 (p130) | RBL2 | 15585644, 16537896 | |
| DOXORUBICIN | NM_001145547; NM_032905 | RNA binding motif protein 17 | RBM17 | 16061639 | resistance |
| DOXORUBICIN | NM_001008710; NM_001008711; NM_001008712; NM_006867 | RNA binding protein with multiple splicing | RBPMS | 16404146 | |
| DOXORUBICIN | NM_002908 | v-rel reticuloendotheliosis viral oncogene homolog (avian) | REL | 15870702, 16404146, 17890907 | |
| DOXORUBICIN | NM_001145138; NM_021975 | v-rel reticuloendotheliosis viral oncogene homolog A (avian) | RELA | 15555623, 15571967, 15823547, 15899819, (following) 15905586, 15911101, 16322301, 17097285, 17097285, 15870702, 17542780, 17890907, 18269916, 18463201, 18463201, 17542780 | |
| DOXORUBICIN | NM_006509 | v-rel reticuloendotheliosis viral oncogene homolog B | RELB | 17890907 | |
| DOXORUBICIN | NM_002927; NM_144766 | regulator of G-protein signalling 13 | RGS13 | 16404146 | |
| DOXORUBICIN | NM_016321 | Rh family, C glycoprotein | RHCG | 16404146 | |
| DOXORUBICIN | NM_002944 | c-ros oncogene 1, receptor tyrosine kinase | ROS1 | 16001973 | |
| DOXORUBICIN | NM_001034 | ribonucleotide reductase M2 polypeptide | RRM2 | 16896004 | |
| DOXORUBICIN | NM_001001890; NM_001122607; NM_001754 | runt-related transcription factor 1 | RUNX1 | 15217836 | |
| DOXORUBICIN | NM_001031680; NM_004350 | runt-related transcription factor 3 | RUNX3 | 15756676 | |
| DOXORUBICIN | NM_002970 | spermidine/spermine N1-acetyltransferase 1 | SAT1 | 16322897 | |
| DOXORUBICIN | NM_001039 | sodium channel, nonvoltage-gated 1, gamma | SCNN1G | 15564131 | |
| DOXORUBICIN | NM_020974 | signal peptide, CUB domain, EGF-like 2 | SCUBE2 | 16896004 | |
| DOXORUBICIN | NM_004892 | SEC22 vesicle trafficking protein homolog B (S. cerevisiae) | SEC22B | 16404146 | |
| DOXORUBICIN | NM_000602 | serpin peptidase inhibitor, clade E (nexin, plasminogen activator inhibitor type 1), member 1 | SERPINE1 | 15870702, 16705698 | |
| DOXORUBICIN | NM_001235 | serpin peptidase inhibitor, clade H (heat shock protein 47), member 1, (collagen binding protein 1) | SERPINH1 | 17680992 | |
| DOXORUBICIN | NM_005983; NM_032637 | S-phase kinase-associated protein 2 (p45) | SKP2 | 17893511 | |
| DOXORUBICIN | NM_033125 | solute carrier family 22 (organic cation/carnitine transporter), member 16 | SLC22A16 | 15963465 | |
| DOXORUBICIN | NM_003060 | solute carrier family 22 (organic cation/carnitine transporter), member 5 | SLC22A5 | 16283381 | |
| DOXORUBICIN | NM_001078174; NM_001078175; NM_001078176; NM_001078177; NM_004955 | solute carrier family 29 (nucleoside transporters), member 1 | SLC29A1 | 18452103 | |

TABLE 1-continued

| Molecule | RefSeq | Description | Symbol | PMID | Interaction |
|---|---|---|---|---|---|
| DOXORUBICIN | NM_018976 | solute carrier family 38, member 2 | SLC38A2 | 16044152 | |
| DOXORUBICIN | NM_000453 | solute carrier family 5 (sodium iodide symporter), member 5 | SLC5A5 | 15671536 | |
| DOXORUBICIN | NM_003047 | solute carrier family 9 (sodium/hydrogen exchanger), member 1 | SLC9A1 | 15729714 | |
| DOXORUBICIN | NM_003062 | slit homolog 3 (Drosophila) | SLIT3 | 16404146 | |
| DOXORUBICIN | NM_001003652; NM_001135937; NM_005901 | SMAD family member 2 | SMAD2 | 18606404 | |
| DOXORUBICIN | NM_001145102; NM_001145103; NM_001145104; NM_005902 | SMAD family member 3 | SMAD3 | 18606404 | |
| DOXORUBICIN | NM_005359 | SMAD family member 4 | SMAD4 | 18606404 | |
| DOXORUBICIN | NM_005904 | SMAD family member 7 | SMAD7 | 18606404 | |
| DOXORUBICIN | NM_006306 | structural maintenance of chromosomes 1A | SMC1A | 15489221 | |
| DOXORUBICIN | NM_000454 | superoxide dismutase 1, soluble | SOD1 | 16579640 | |
| DOXORUBICIN | NM_000636; NM_001024465; NM_001024466 | superoxide dismutase 2, mitochondrial | SOD2 | 14660625, 10969820, 18384434 | |
| DOXORUBICIN | NM_005633 | son of sevenless homolog 1 (Drosophila) | SOS1 | 16001973 | |
| DOXORUBICIN | NM_003109; NM_138473 | Sp1 transcription factor | SP1 | 17108358, 17124180 | |
| DOXORUBICIN | NM_003118 | secreted protein, acidic, cysteine-rich (osteonectin) | SPARC | 15870702 | |
| DOXORUBICIN | NM_020126 | sphingosine kinase 2 | SPHK2 | 17974990 | |
| DOXORUBICIN | NM_003130; NM_198901 | sorcin | SRI | 18423116 | |
| DOXORUBICIN | NM_003132 | spermidine synthase | SRM | 16322899 | |
| DOXORUBICIN | NM_017857 | slingshot homolog 3 (Drosophila) | SSH3 | 16404146 | |
| DOXORUBICIN | NM_021978 | suppression of tumorigenicity 14 (colon carcinoma) | ST14 | 16322899 | |
| DOXORUBICIN | NM_007315; NM_139266 | signal transducer and activator of transcription 1, 91 kDa | STAT1 | 16001973, 1072862 | |
| DOXORUBICIN | NM_005419 | signal transducer and activator of transcription 2, 113 kDa | STAT2 | 16001973 | |
| DOXORUBICIN | NM_003150; NM_139276; NM_213662 | signal transducer and activator of transcription 3 (acute-phase response factor) | STAT3 | 16001973, 1920763 | |
| DOXORUBICIN | NM_013233 | serine threonine kinase 39 (STE20/SPS1 homolog, yeast) | STK39 | 16322899 | |
| DOXORUBICIN | NM_001145454; NM_005563; NM_203399; NM_203401 | stathmin 1 | STMN1 | 16458935 | |
| DOXORUBICIN | NM_004177 | syntaxin 3 | STX3 | 16322897 | |
| DOXORUBICIN | NM_001001522; NM_003186 | transgelin | TAGLN | 15870702 | |
| DOXORUBICIN | NM_001136139; NM_003200 | transcription factor 3 (E2A immunoglobulin enhancer binding factors E12/E47) | TCF3 | 16886622 | |
| DOXORUBICIN | NM_198253; NM_198255 | telomerase reverse transcriptase | TERT | 16077987, 18396642, 18560228 | |
| DOXORUBICIN | NM_003225 | trefoil factor 1 | TFF1 | 16579640 | |
| DOXORUBICIN | NM_000660 | transforming growth factor, beta 1 | TGFB1 | 17418594, 18606404 | |
| DOXORUBICIN | NM_004613; NM_198951 | transglutaminase 2 (C polypeptide, protein-glutamine-gamma-glutamyltransferase) | TGM2 | 15870702, 17073438 | |
| DOXORUBICIN | NM_000361 | thrombomodulin | THBD | 17172434 | |
| DOXORUBICIN | NM_003246 | thrombospondin 1 | THBS1 | 16962673 | |
| DOXORUBICIN | NM_018271 | threonine synthase-like 2 (S. cerevisiae) | THNSL2 | 16896004 | |
| DOXORUBICIN | NM_022037; NM_022173 | TIA1 cytotoxic granule-associated RNA binding protein | TIA1 | 16404146 | |
| DOXORUBICIN | NM_021025 | T-cell leukemia homeobox 3 | TLX3 | 16404146 | |
| DOXORUBICIN | NM_021109 | thymosin beta 4, X-linked | TMSB4X | 16364925 | |
| DOXORUBICIN | NM_000594 | tumor necrosis factor (TNF superfamily, member 2) | TNF | 12908082, 15823547, 15899819, 16001973, 17651020 | |
| DOXORUBICIN | NM_003844 | tumor necrosis factor receptor superfamily, member 10a | TNFRSF10A | 16098063, 17437844, 16364925, 17437844, 17437844, 15897917 | |

TABLE 1-continued

| Molecule | RefSeq | Description | Symbol | PMID | Interaction |
|---|---|---|---|---|---|
| DOXORUBICIN | NM_003842; NM_147187 | tumor necrosis factor receptor superfamily, member 10b | TNFRSF10B | 16364925, 17922852, 15897917, 17922852, 16098063, 17922852, 16705698 | |
| DOXORUBICIN | NM_001065 | tumor necrosis factor receptor superfamily, member 1A | TNFRSF1A | 17651020 | |
| DOXORUBICIN | NM_001066 | tumor necrosis factor receptor superfamily, member 1B | TNFRSF1B | 17651020 | |
| DOXORUBICIN | NM_001039664; NM_003790; NM_148965; NM_148966; NM_148967; NM_148970 | tumor necrosis factor receptor superfamily, member 25 | TNFRSF25 | 16705698 | |
| DOXORUBICIN | NM_003810 | tumor necrosis factor (ligand) superfamily, member 10 | TNFSF10 | 16364925, 19106633 | |
| DOXORUBICIN | NM_014765 | translocase of outer mitochondrial membrane 20 homolog (yeast) | TOMM20 | 16322897 | |
| DOXORUBICIN | NM_001067 | topoisomerase (DNA) II alpha 170 kDa | TOP2A | 11470519, 15239142, 15486187, 15753397, 15765123, 16969495, 17351394 | |
| DOXORUBICIN | NM_001068 | topoisomerase (DNA) II beta 180 kDa | TOP2B | 16239602, 16957942 | |
| DOXORUBICIN | NM_000546; NM_001126112; NM_001126113; NM_001126114; NM_001126115; NM_001126116; NM_001126117 | tumor protein p53 | TP53 | 15141020, 17124180, 15489221, 15578696, (following) 15671536, 19106633, 15763944, 15781256, 15823547, 15823547, 15601469, 16211088, 15939500, 16001973, 16404146, 15939500, 17959036, 16168113, 16432175, 16537896, 15781256, 17959036, 17339365, 17912235, 16108013, 10969820, 12082016, 15555623, 15601469, 17285121, 19074854, 17088865, 15763944, 15671536, 16826403, 17079232, 17085670, 17088865, 17124180, 17285121, 17369602, 15578696, 17555331, 17608641, 17653088, 17682292, 17893511, 17912235, 17959036, 18269916, 18510171, 18698031, 19074854, 19106633 | |
| DOXORUBICIN | NM_001126240; NM_001126241; NM_001126242; NM_005427 | tumor protein p73 | TP73 | 17716971 | |
| DOXORUBICIN | NM_000365; NM_001159287 | triosephosphate isomerase 1 | TPI1 | 18309519 | |
| DOXORUBICIN | NM_016292 | TNF receptor-associated protein 1 | TRAP1 | 17680992 | |
| DOXORUBICIN | NM_001656; NM_033227; NM_033228 | tripartite motif-containing 23 | TRIM23 | 16404146 | |
| DOXORUBICIN | NM_005762 | tripartite motif-containing 28 | TRIM28 | 17079232 | |
| DOXORUBICIN | NM_001003827; NM_021616; NM_130389; NM_130390 | tripartite motif-containing 34 | TRIM34 | 16404146 | |
| DOXORUBICIN | — | | TRP53 | 16013437 | |
| DOXORUBICIN | NM_000370 | tocopherol (alpha) transfer protein | TTPA | 16404146 | |
| DOXORUBICIN | NM_006000 | tubulin, alpha 4a | TUBA4A | 16322897 | |
| DOXORUBICIN | NM_178014 | tubulin, beta | TUBB | 16579640 | |
| DOXORUBICIN | NM_006087 | tubulin, beta 4 | TUBB4 | 16322897 | |
| DOXORUBICIN | NM_001071 | thymidylate synthetase | TYMS | 10482907, 16168113 | |
| DOXORUBICIN | NM_003358 | UDP-glucose ceramide glucosyltransferase | UGCG | 16404146, 18245173 | |
| DOXORUBICIN | NM_021139 | UDP glucuronosyltransferase 2 family, polypeptide B4 | UGT2B4 | 16404146 | |
| DOXORUBICIN | NM_003364; NM_181597 | uridine phosphorylase 1 | UPP1 | 18510171 | |

TABLE 1-continued

| Molecule | RefSeq | Description | Symbol | PMID | Interaction |
|---|---|---|---|---|---|
| DOXORUBICIN | NM_006004 | ubiquinol-cytochrome c reductase hinge protein | UQCRH | 18510171 | |
| DOXORUBICIN | NM_000376; NM_001017535 | vitamin D (1,25-dihydroxyvitamin D3) receptor | VDR | 17716971 | |
| DOXORUBICIN | NM_001025366; NM_001025367; NM_001025368; NM_001025369; NM_001025370; NM_001033756; NM_003376 | vascular endothelial growth factor A | VEGFA | 16900372, 17431384, 17498666, 17627616, 17627616, 17498666, 17912235, 18494554 | |
| DOXORUBICIN | NM_001167 | X-linked inhibitor of apoptosis | XIAP | 1911975, 1911975, 16211302, 12948851, 14601052, 15897917, 15359644, 1911101, 17521628, 18071906 | |
| DOXORUBICIN | NM_006887 | zinc finger protein 36, C3H type-like 2 | ZFP36L2 | 16322897 | |
| DOXORUBICIN | NM_022470; NM_152240 | zinc finger, matrin type 3 | ZMAT3 | 16439685 | |
| DOXORUBICIN | NM_003453; NM_197968 | zinc finger, MYM-type 2 | ZMYM2 | 16579640 | |
| DOXORUBICIN | NM_006963 | zinc finger protein 22 (KOX 15) | ZNF22 | 16404146 | |
| DOXORUBICIN | NM_024762 | zinc finger protein 552 | ZNF552 | 16896004 | |
| EPIRUBICIN | NM_000927 | ATP-binding cassette, sub-family B (MDR/TAP), member 1 | ABCB1 | 12576456 | resistance |
| EPIRUBICIN | NM_004996; NM_019862; NM_019898; NM_019899; NM_019900 | ATP-binding cassette, sub-family C (CFTR/MRP), member 1 | ABCC1 | 12576456, 12657726 | resistance |
| EPIRUBICIN | NM_004827 | ATP-binding cassette, sub-family G (WHITE), member 2 | ABCG2 | 12576456 | resistance |
| EPIRUBICIN | NM_000633; NM_000657 | B-cell CLL/lymphoma 2 | BCL2 | 14503796 | |
| EPIRUBICIN | NM_001012270; NM_001012271; NM_001168 | baculoviral IAP repeat-containing 5 | BIRC5 | 16188142 | resistance |
| EPIRUBICIN | NM_004346; NM_032991 | caspase 3, apoptosis-related cysteine peptidase | CASP3 | 14503796, 15996160 | death pathway |
| EPIRUBICIN | NM_001270 | chromodomain helicase DNA binding protein 1 | CHD1 | — | |
| EPIRUBICIN | NM_005228; NM_201282; NM_201283; NM_201284 | epidermal growth factor receptor (erythroblastic leukemia viral (v-erb-b) oncogene homolog, avian) | EGFR | 18768436 | |
| EPIRUBICIN | NM_001005862; NM_004448 | v-erb-b2 erythroblastic leukemia viral oncogene homolog 2, neuro/glioblastoma derived oncogene homolog (avian) | ERBB2 | 18768436 | |
| EPIRUBICIN | NM_001005915; NM_001982 | v-erb-b2 erythroblastic leukemia viral oncogene homolog 3 (avian) | ERBB3 | 18768436 | |
| EPIRUBICIN | NM_022110 | FK506 binding protein like | FKBPL | 14503796 | |
| EPIRUBICIN | NM_005980 | S100 calcium binding protein P | S100P | 18636193 | |
| EPIRUBICIN | NM_000636; NM_001024465; NM_001024466 | superoxide dismutase 2, mitochondrial | SOD2 | 9569045 | |
| EPIRUBICIN | NM_001067 | topoisomerase (DNA) II alpha 170 kDa | TOP2A | 18465341 | target |
| MITOXANTRONE | NM_000927 | ATP-binding cassette, sub-family B (MDR/TAP), member 1 | ABCB1 | 15239124 | resistance |
| MITOXANTRONE | NM_004827 | ATP-binding cassette, sub-family G (WHITE), member 2 | ABCG2 | 15239124, 15640379, 15695404, 15703302, 15875186, 17032904, 16636798, 17032904 | resistance |
| MITOXANTRONE | NM_130847 | angiomotin like 1 | AMOTL1 | 16044152 | |
| MITOXANTRONE | NM_001166 | baculoviral IAP repeat-containing 2 | BIRC2 | 15359644 | |
| MITOXANTRONE | NM_001165; NM_182962 | baculoviral IAP repeat-containing 3 | BIRC3 | 12948851 | |
| MITOXANTRONE | — | | C4ORF28 | 16044152 | |
| MITOXANTRONE | NM_007359 | cancer susceptibility candidate 3 | CASC3 | 16044152 | |
| MITOXANTRONE | NM_032982; NM_032983 | caspase 2, apoptosis-related cysteine peptidase | CASP2 | 14757846 | |
| MITOXANTRONE | NM_004346; NM_032991 | caspase 3, apoptosis-related cysteine peptidase | CASP3 | 12948851 | |
| MITOXANTRONE | NM_001226; NM_032992 | caspase 6, apoptosis-related cysteine peptidase | CASP6 | 12948851 | |
| MITOXANTRONE | NM_001227; NM_033338; NM_033339; NM_033340 | caspase 7, apoptosis-related cysteine peptidase | CASP7 | 12948851 | |
| MITOXANTRONE | NM_001080124; NM_001080125; NM_001228; NM_033355; NM_033356; NM_033358 | caspase 8, apoptosis-related cysteine peptidase | CASP8 | 12948851 | |

TABLE 1-continued

| Molecule | RefSeq | Description | Symbol | PMID | Interaction |
|---|---|---|---|---|---|
| MITOXANTRONE | NM_001229; NM_032996 | caspase 9, apoptosis-related cysteine peptidase | CASP9 | 12948851 | |
| MITOXANTRONE | NM_030809 | cysteine-serine-rich nuclear protein 2 | CSRNP2 | 16044152 | |
| MITOXANTRONE | NM_001141969; NM_001141970; NM_001350 | death-domain associated protein | DAXX | 12948851 | |
| MITOXANTRONE | NM_019887; NM_138929 | diablo homolog (Drosophila) | DIABLO | 12948851 | |
| MITOXANTRONE | NM_001144774; NM_001144775; NM_001144776; NM_001144777; NM_021952 | ELAV (embryonic lethal, abnormal vision, Drosophila)-like 4 (Hu antigen D) | ELAVL4 | 16044152 | |
| MITOXANTRONE | NM_021814 | ELOVL family member 5, elongation of long chain fatty acids (FEN1/Elo2, SUR4/Elo3-like, yeast) | ELOVL5 | 16044152 | |
| MITOXANTRONE | NM_001135554; NM_001135555; NM_001431 | erythrocyte membrane protein band 4.1-like 2 | EPB41L2 | 16044152 | |
| MITOXANTRONE | NM_000875 | insulin-like growth factor 1 receptor | IGF1R | 15499378 | |
| MITOXANTRONE | NM_024337 | iroquois homeobox 1 | IRX1 | 16044152 | |
| MITOXANTRONE | NM_000426; NM_001079823 | laminin, alpha 2 | LAMA2 | 16044152 | |
| MITOXANTRONE | NM_001143944; NM_181336 | LEM domain containing 2 | LEMD2 | 16044152 | |
| MITOXANTRONE | NM_001161572; NM_001161573; NM_001161574; NM_012323; NM_152878 | v-maf musculoaponeurotic fibrosarcoma oncogene homolog F (avian) | MAFF | 16044152 | |
| MITOXANTRONE | NM_001145336; NM_001145337; NM_001145339; NM_001145340; NM_002392; NM_006878; NM_006879; NM_006881; NM_006882 | Mdm2 p53 binding protein homolog (mouse) | MDM2 | 17575151 | variant allelic/resistance |
| MITOXANTRONE | NM_002583 | PRKC, apoptosis, WT1, regulator | PAWR | 12948851 | altered by mitox |
| MITOXANTRONE | NM_000965; NM_016152 | retinoic acid receptor, beta | RARB | 17608728 | resistance |
| MITOXANTRONE | NM_002890; NM_022650 | RAS p21 protein activator (GTPase activating protein) 1 | RASA1 | 16044152 | |
| MITOXANTRONE | NM_001145547; NM_032905 | RNA binding motif protein 17 | RBM17 | 16061639 | |
| MITOXANTRONE | NM_021244 | Ras-related GTP binding D | RRAGD | 16044152 | |
| MITOXANTRONE | NM_003014 | secreted frizzled-related protein 4 | SFRP4 | 16044152 | |
| MITOXANTRONE | NM_032379; NM_032943; NM_206927; NM_206928; NM_206929; NM_206930 | synaptotagmin-like 2 | SYTL2 | 16044152 | |
| MITOXANTRONE | NM_145274 | transmembrane protein 99 | TMEM99 | 16044152 | |
| MITOXANTRONE | NM_001067 | topoisomerase (DNA) II alpha 170 kDa | TOP2A | — | target |
| MITOXANTRONE | NM_001167 | X-linked inhibitor of apoptosis | XIAP | 12948851, 15359644 | |
| BLEOMYCIN | NM_001166 | baculoviral IAP repeat-containing 2 | BIRC2 | 10815900 | resistance |
| BLEOMYCIN | NM_000386 | bleomycin hydrolase | BLMH | 12082022 | unrelated |
| BLEOMYCIN | NM_001752 | catalase | CAT | 10751631 | unrelated |
| BLEOMYCIN | NM_000234 | ligase I, DNA, ATP-dependent | LIG1 | — | resistance |
| BLEOMYCIN | NM_002311; NM_013975 | ligase III, DNA, ATP-dependent | LIG3 | — | |
| BLEOMYCIN | NM_000963 | prostaglandin-endoperoxide synthase 2 (prostaglandin G/H synthase and cyclooxygenase) | PTGS2 | 18695918 | |
| BLEOMYCIN | NM_003745 | suppressor of cytokine signaling 1 | SOCS1 | 17374387 | resistance |
| BLEOMYCIN | NM_006297 | X-ray repair complementing defective repair in Chinese hamster cells 1 | XRCC1 | 12082022 | resistance |
| BLEOMYCIN | NM_021141 | X-ray repair complementing defective repair in Chinese hamster cells 5 (double-strand-break rejoining) | XRCC5 | 12384553 | |
| MITOMYCIN | NM_000691; NM_001135167; NM_001135168 | aldehyde dehydrogenase 3 family, memberA1 | ALDH3A1 | 15905174 | resistance |
| MITOMYCIN | NM_000484; NM_001136016; NM_001136129; NM_001136130; NM_001136131; NM_201413; NM_201414 | amyloid beta (A4) precursor protein | APP | 12760830 | |
| MITOMYCIN | NM_001675; NM_182810 | activating transcription factor 4 (tax-responsive enhancer element B67) | ATF4 | 12760830 | |
| MITOMYCIN | NM_000633; NM_000657 | B-cell CLL/lymphoma 2 | BCL2 | 15793875 | |
| MITOMYCIN | NM_001202; NM_130850; NM_130851 | bone morphogenetic protein 4 | BMP4 | 12760830 | |

TABLE 1-continued

| Molecule | RefSeq | Description | Symbol | PMID | Interaction |
|---|---|---|---|---|---|
| MITOMYCIN | NM_031966 | cyclin B1 | CCNB1 | 12760830 | |
| MITOMYCIN | NM_000611; NM_001127223; NM_001127225; NM_001127226; NM_001127227; NM_203329; NM_203330; NM_203331 | CD59 molecule, complement regulatory protein | CD59 | 17045307 | |
| MITOMYCIN | NM_001785 | cytidine deaminase | CDA | 18728667 | sensitivity |
| MITOMYCIN | NM_001964 | early growth response 1 | EGR1 | 12760830 | resistance |
| MITOMYCIN | NM_004431 | EPH receptor A2 | EPHA2 | 12760830 | |
| MITOMYCIN | — | — | GRP58 | 12760830 | |
| MITOMYCIN | NM_000852 | glutathione S-transferase pi 1 | GSTP1 | 15239142 | sensitivity |
| MITOMYCIN | NM_002117 | major histocompatibility complex, class I, C | HLA-C | 12760830 | |
| MITOMYCIN | NM_000234 | ligase I, DNA, ATP-dependent | LIG1 | 12760830 | |
| MITOMYCIN | NM_012325 | microtubule-associated protein, RP/EB family, member 1 | MAPRE1 | 12760830 | |
| MITOMYCIN | NM_002412 | O-6-methylguanine-DNA methyltransferase | MGMT | 16039682 | sensitivity |
| MITOMYCIN | NM_004995 | matrix metallopeptidase 14 (membrane-inserted) | MMP14 | 12760830 | |
| MITOMYCIN | NM_002505; NM_021705 | nuclear transcription factor Y, alpha | NFYA | 12760830 | |
| MITOMYCIN | NM_000903; NM_001025433; NM_001025434 | NAD(P)H dehydrogenase, quinone 1 | NQO1 | 15239142 | drug activation |
| MITOMYCIN | NM_000941 | P450 (cytochrome) oxidoreductase | POR | 15239142 | drug activation |
| MITOMYCIN | NM_000311; NM_001080121; NM_001080122; NM_001080123; NM_183079 | prion protein | PRNP | 12760830 | |
| MITOMYCIN | NM_000963 | prostaglandin-endoperoxide synthase 2 (prostaglandin G/H synthase and cyclooxygenase) | PTGS2 | 15793875 | |
| MITOMYCIN | NM_000321 | retinoblastoma 1 | RB1 | 15617745 | |
| MITOMYCIN | NM_002893 | retinoblastoma binding protein 7 | RBBP7 | 12760830 | |
| MITOMYCIN | NM_002916; NM_181573 | replication factor C (activator 1) 4, 37 kDa | RFC4 | 12760830 | |
| MITOMYCIN | NM_001006 | ribosomal protein S3A | RPS3A | 12760830 | |
| MITOMYCIN | NM_001031680; NM_004350 | runt-related transcription factor 3 | RUNX3 | 15756676 | |
| MITOMYCIN | NM_006713 | SUB1 homolog (*S. cerevisiae*) | SUB1 | 12760830 | |
| MITOMYCIN | NM_198253; NM_198255 | telomerase reverse transcriptase | TERT | — | resistance |
| MITOMYCIN | NM_000546; NM_001126112; NM_001126113; NM_001126114; NM_001126115; NM_001126116; NM_001126117 | tumor protein p53 | TP53 | 12082016 | sensitivity |
| MITOMYCIN | NM_001113755; NM_001113756; NM_001953 | thymidine phosphorylase | TYMP | 18728667 | |
| HYDROXYUREA | NM_004324; NM_138761; NM_138763; NM_138764; NM_138765 | BCL2-associated X protein | BAX | 16005713 | death pathway |
| HYDROXYUREA | — | — | C13ORF34 | 17374387 | death pathway |
| HYDROXYUREA | NM_004346; NM_032991 | caspase 3, apoptosis-related cysteine peptidase | CASP3 | 16005713 | |
| HYDROXYUREA | NM_001237 | cyclin A2 | CCNA2 | 11468187 | |
| HYDROXYUREA | NM_031966 | cyclin B1 | CCNB1 | 11468187 | |
| HYDROXYUREA | NM_053056 | cyclin D1 | CCND1 | 11468187 | |
| HYDROXYUREA | NM_001759 | cyclin D2 | CCND2 | 11468187 | |
| HYDROXYUREA | NM_001136017; NM_001136125; NM_001136126; NM_001760 | cyclin D3 | CCND3 | 11468187 | |
| HYDROXYUREA | NM_001238; NM_057182 | cyclin E1 | CCNE1 | 11468187 | altered by HU |
| HYDROXYUREA | NM_004060; NM_199246 | cyclin G1 | CCNG1 | 16005713 | altered by HU |
| HYDROXYUREA | NM_001790; NM_022809 | cell division cycle 25 homolog C (*S. pombe*) | CDC25C | 19074854 | altered by HU |
| HYDROXYUREA | NM_018101 | cell division cycle associated 8 | CDCA8 | 17374387 | |
| HYDROXYUREA | NM_000389; NM_078467 | cyclin-dependent kinase inhibitor 1A (p21, Cip1) | CDKN1A | 16005713 | resistance |
| HYDROXYUREA | NM_001827 | CDC28 protein kinase regulatory subunit 2 | CKS2 | 17374387 | |
| HYDROXYUREA | NM_000114; NM_207032; NM_207033; NM_207034 | endothelin 3 | EDN3 | 15020278 | altered by HU |

TABLE 1-continued

| Molecule | RefSeq | Description | Symbol | PMID | Interaction |
|---|---|---|---|---|---|
| HYDROXYUREA | NM_000043; NM_152871; NM_152872; NM_152873; NM_152874; NM_152875; NM_152876; NM_152877 | Fas (TNF receptor superfamily, member 6) | FAS | 16005713 | altered by HU |
| HYDROXYUREA | NM_002266 | karyopherin alpha 2 (RAG cohort 1, importin alpha 1) | KPNA2 | 17374387 | |
| HYDROXYUREA | NM_003981; NM_199413; NM_199414 | protein regulator of cytokinesis 1 | PRC1 | 17374387 | |
| HYDROXYUREA | NM_001005290; NM_001032290; NM_001032291; NM_032636 | proline/serine-rich coiled-coil 1 | PSRC1 | 17374387 | |
| HYDROXYUREA | NM_001033 | ribonucleotide reductase M1 | RRM1 | — | unrelated |
| HYDROXYUREA | NM_001034 | ribonucleotide reductase M2 polypeptide | RRM2 | — | resistance |
| HYDROXYUREA | NM_000546; NM_001126112; NM_001126113; NM_001126114; NM_001126115; NM_001126116; NM_001126117 | tumor protein p53 | TP53 | 16005713 | death pathway |
| HYDROXYUREA | NM_007019; NM_181799; NM_181800; NM_181801; NM_181802; NM_181803 | ubiquitin-conjugating enzyme E2C | UBE2C | 17374387 | |
| CAMPTOTHECIN | NM_000927 | ATP-binding cassette, sub-family B (MDR/TAP), member 1 | ABCB1 | 10692111 | resistance |
| CAMPTOTHECIN | NM_198576 | agrin | AGRN | 17374387 | |
| CAMPTOTHECIN | NM_000477 | albumin | ALB | 10803926, 17378599 | used as a drug carrier |
| CAMPTOTHECIN | NM_001153 | annexin A4 | ANXA4 | 17374387 | |
| CAMPTOTHECIN | NM_004324; NM_138761; NM_138763; NM_138764; NM_138765 | BCL2-associated X protein | BAX | 15665116, 17555331 | |
| CAMPTOTHECIN | NM_000633; NM_000657 | B-cell CLL/lymphoma 2 | BCL2 | 10692111 | |
| CAMPTOTHECIN | NM_001012270; NM_001012271; NM_001168 | baculoviral IAP repeat-containing 5 | BIRC5 | 16061681 | |
| CAMPTOTHECIN | NM_007294; NM_007295; NM_007296; NM_007297; NM_007298; NM_007299; NM_007300; NM_007302; NM_007303; NM_007304; NM_007305 | breast cancer 1, early onset | BRCA1 | 10344722 | |
| CAMPTOTHECIN | NM_000059 | breast cancer 2, early onset | BRCA2 | 10344722 | |
| CAMPTOTHECIN | NM_001130849; NM_011130850; NM_016289 | calcium binding protein 39 | CAB39 | 17374387 | |
| CAMPTOTHECIN | NM_032982; NM_032983 | caspase 2, apoptosis-related cysteine peptidase | CASP2 | 14757846 | |
| CAMPTOTHECIN | NM_004346; NM_032991 | caspase 3, apoptosis-related cysteine peptidase | CASP3 | 16273314, 16962673, 16962673 | |
| CAMPTOTHECIN | NM_031966 | cyclin B1 | CCNB1 | 16061681 | |
| CAMPTOTHECIN | NM_001798; NM_052827 | cyclin-dependent kinase 2 | CDK2 | 15141020 | |
| CAMPTOTHECIN | NM_000389; NM_078467 | cyclin-dependent kinase inhibitor 1A (p21, Cip1) | CDKN1A | 11741290, 9673414, 17555331 | |
| CAMPTOTHECIN | NM_001024912; NM_001712 | carcinoembryonic antigen-related cell adhesion molecule 1 (biliary glycoprotein) | CEACAM1 | 17374387 | |
| CAMPTOTHECIN | NM_005760 | CCAAT/enhancer binding protein (C/EBP), zeta | CEBPZ | 17374387 | |
| CAMPTOTHECIN | NM_001908; NM_147780; NM_147781; NM_147782; NM_147783 | cathepsin B | CTSB | 17378599 | |
| CAMPTOTHECIN | NM_001007277; NM_004879 | etoposide induced 2.4 mRNA | EI24 | 17374387 | |
| CAMPTOTHECIN | NM_001429 | E1A binding protein p300 | EP300 | 10344722 | |
| CAMPTOTHECIN | NM_014805 | EPM2A (laforin) interacting protein 1 | EPM2AIP1 | 17374387 | |
| CAMPTOTHECIN | NM_004110; NM_024417 | ferredoxin reductase | FDXR | 17374387 | |
| CAMPTOTHECIN | NM_000852 | glutathione S-transferase pi 1 | GSTP1 | 15500952, 15500952, 14732228 | |
| CAMPTOTHECIN | NM_001077442; NM_001077443; NM_004500; NM_031314 | heterogeneous nuclear ribonucleoprotein C (C1/C2) | HNRNPC | 16960656 | |
| CAMPTOTHECIN | NM_000576 | interleukin 1, beta | IL1B | 16356833 | |
| CAMPTOTHECIN | NM_000584 | interleukin 8 | IL8 | 16356833 | |
| CAMPTOTHECIN | NM_002228 | jun oncogene | JUN | 15585644 | |
| CAMPTOTHECIN | NM_002756; NM_145109 | mitogen-activated protein kinase kinase 3 | MAP2K3 | 17374387 | |

TABLE 1-continued

| Molecule | RefSeq | Description | Symbol | PMID | Interaction |
|---|---|---|---|---|---|
| CAMPTOTHECIN | NM_005923 | mitogen-activated protein kinase kinase kinase 5 | MAP3K5 | 17374387 | |
| CAMPTOTHECIN | NM_001135044; NM_002752; NM_139068; NM_139069; NM_139070 | mitogen-activated protein kinase 9 | MAPK9 | 15585644 | |
| CAMPTOTHECIN | NM_001145336; NM_001145337; NM_001145339; NM_001145340; NM_002392; NM_006878; NM_006879; NM_006881; NM_006882 | Mdm2 p53 binding protein homolog (mouse) | MDM2 | 17555331 | |
| CAMPTOTHECIN | NM_001004720; NM_001004722; NM_003581 | NCK adaptor protein 2 | NCK2 | 17374387 | |
| CAMPTOTHECIN | NM_001618 | poly (ADP-ribose) polymerase 1 | PARP1 | 11741290, 15585644, 16962673, 15585644, 16962673 | |
| CAMPTOTHECIN | NM_004073 | polo-like kinase 3 (Drosophila) | PLK3 | 17374387 | |
| CAMPTOTHECIN | NM_032192; NM_181505 | protein phosphatase 1, regulatory (inhibitor) subunit 1B | PPP1R1B | 16061638 | |
| CAMPTOTHECIN | NM_003981; NM_199413; NM_199414 | protein regulator of cytokinesis 1 | PRC1 | 17374387 | |
| CAMPTOTHECIN | NM_002875; NM_133487 | RAD51 homolog (RecA homolog, E. coli) (S. cerevisiae) | RAD51 | 10344722 | |
| CAMPTOTHECIN | NM_000321 | retinoblastoma 1 | RB1 | 14704340, 15585644 | |
| CAMPTOTHECIN | NM_002895; NM_183404 | retinoblastoma-like 1 (p107) | RBL1 | 15585644 | |
| CAMPTOTHECIN | NM_005611 | retinoblastoma-like 2 (p130) | RBL2 | 15585644 | |
| CAMPTOTHECIN | NM_001006946; NM_002997 | syndecan 1 | SDC1 | 17374387 | |
| CAMPTOTHECIN | NM_000593 | transporter 1, ATP-binding cassette, sub-family B (MDR/TAP) | TAP1 | 17374387 | |
| CAMPTOTHECIN | NM_014604 | Tax1 (human T-cell leukemia virus type I) binding protein 3 | TAX1BP3 | 17374387 | |
| CAMPTOTHECIN | NM_003246 | thrombospondin 1 | THBS1 | 16962673 | |
| CAMPTOTHECIN | NM_003811 | tumor necrosis factor (ligand) superfamily, member 9 | TNFSF9 | 17374387 | |
| CAMPTOTHECIN | NM_003286 | topoisomerase (DNA) I | TOP1 | | |
| CAMPTOTHECIN | NM_000546; NM_001126112; NM_001126113; NM_001126114; NM_001126115; NM_001126116; NM_001126117 | tumor protein p53 | TP53 | 10692111, 11741290, 17555331, 9673414, 15585644, 17555331, 12082016 | |
| CAMPTOTHECIN | NM_004881; NM_147184 | tumor protein p53 inducible protein 3 | TP53I3 | 17374387 | |
| CAMPTOTHECIN | NR_015381; NR_015381; NR_015381; NR_015381; NR_015381; NR_015381; NR_015381 | TP53 target 1 (non-protein coding) | TP53TG1 | 17374387 | |
| CAMPTOTHECIN | NM_001025366; NM_001025367; NM_001025368; NM_001025369; NM_001025370; NM_001033756; NM_003376 | vascular endothelial growth factor A | VEGFA | 16356833 | |
| CAMPTOTHECIN | NM_001167 | X-linked inhibitor of apoptosis | XLAP | 16061681, 16211302 | |
| TOPOTECAN | NM_004827 | ATP-binding cassette, sub-family G (WHITE), member 2 | ABCG2 | 15695404, 15875186, 17032904, 17032904 | resistance |
| TOPOTECAN | NM_001668; NM_178426; NM_178427 | aryl hydrocarbon receptor nuclear translocator | ARNT | 15930297 | |
| TOPOTECAN | NM_002105 | H2A histone family, member X | H2AFX | 16432175 | |
| TOPOTECAN | NM_001530; NM_181054 | hypoxia inducible factor 1, alpha subunit (basic helix-loop-helix transcription factor) | HIF1A | 15930297 | target |
| TOPOTECAN | NM_003286 | topoisomerase (DNA) I | TOP1 | | target |
| TOPOTECAN | NM_052963 | topoisomerase (DNA) I, mitochondrial | TOP1MT | | target |
| TOPOTECAN | NM_001025366; NM_001025367; NM_001025368; NM_001025369; NM_001025370; NM_001033756; NM_003376 | vascular endothelial growth factor A | VEGFA | 15930297 | target |
| IRINOTECAN | NM_000927 | ATP-binding cassette, sub-family B (MDR/TAP), member 1 | ABCB1 | 12960109, 15655543, 15801936, 16815871 | resistance |
| IRINOTECAN | NM_004996; NM_019862; NM_019898; NM_019899; NM_019900 | ATP-binding cassette, sub-family C (CFTR/MRP), member 1 | ABCC1 | 15897249, 16815871, 18927307 | resistance |

TABLE 1-continued

| Molecule | RefSeq | Description | Symbol | PMID | Interaction |
|---|---|---|---|---|---|
| IRINOTECAN | NM_000392 | ATP-binding cassette, sub-family C (CFTR/MRP), member 2 | ABCC2 | 16815871, 18981587 | resistance |
| IRINOTECAN | NM_001105515; NM_005845 | ATP-binding cassette, sub-family C (CFTR/MRP), member 4 | ABCC4 | 15827327 | resistance |
| IRINOTECAN | NM_004827 | ATP-binding cassette, sub-family G (WHITE), member 2 | ABCG2 | 15239142, 15695404, 15655543, 15801936 | resistance |
| IRINOTECAN | NM_032859 | abhydrolase domain containing 13 | ABHD13 | 18927307 | |
| IRINOTECAN | NM_198834; NM_198836; NM_198837; NM_198838; NM_198839 | acetyl-Coenzyme A carboxylase alpha | ACACA | 18927307 | |
| IRINOTECAN | NM_023038; NM_033274 | ADAM metallopeptidase domain 19 (meltrin beta) | ADAM19 | 18927307 | |
| IRINOTECAN | NM_001121; NM_016824; NM_019903 | adducin 3 (gamma) | ADD3 | 15956246 | |
| IRINOTECAN | NM_018269 | acireductone dioxygenase 1 | ADI1 | 18927307 | |
| IRINOTECAN | NM_000029 | angiotensinogen (serpin peptidase inhibitor, clade A, member 8) | AGT | 18927307 | |
| IRINOTECAN | NM_007202 | A kinase (PRKA) anchor protein 10 | AKAP10 | 15956246 | |
| IRINOTECAN | NM_000032; NM_001037967; NM_001037968 | aminolevulinate, delta-, synthase 2 | ALAS2 | 15956246 | |
| IRINOTECAN | NM_000477 | albumin | ALB | 18927307 | |
| IRINOTECAN | NM_000689 | aldehyde dehydrogenase 1 family, member A1 | ALDH1A1 | 15956246 | |
| IRINOTECAN | NM_001143668; NM_181847 | adhesion molecule with Ig-like domain 2 | AMIGO2 | 18927307 | |
| IRINOTECAN | NM_012098 | angiopoietin-like 2 | ANGPTL2 | 17327601 | |
| IRINOTECAN | NM_032217; NM_198889 | ankyrin repeat domain 17 | ANKRD17 | 18927307 | |
| IRINOTECAN | NM_015199 | ankyrin repeat domain 28 | ANKRD28 | 18927307 | |
| IRINOTECAN | NM_001003954; NM_004306 | annexin A13 | ANXA13 | 18927307 | |
| IRINOTECAN | NM_001155; NM_004033 | annexin A6 | ANXA6 | 15956246 | |
| IRINOTECAN | NM_001030006; NM_001282 | adaptor-related protein complex 2, beta 1 subunit | AP2B1 | 18927307 | |
| IRINOTECAN | NM_000038; NM_001127510; NM_001127511 | adenomatous polyposis coli | APC | 15956246 | |
| IRINOTECAN | NM_001654 | v-raf murine sarcoma 3611 viral oncogene homolog | ARAF | 15956246 | |
| IRINOTECAN | NM_001657 | amphiregulin | AREG | 15723263 | |
| IRINOTECAN | NM_001024226; NM_001024227; NM_001024228; NM_001658 | ADP-ribosylation factor 1 | ARF1 | 18927307 | |
| IRINOTECAN | NM_001030055; NM_001173 | Rho GTPase activating protein 5 | ARHGAP5 | 15956246 | |
| IRINOTECAN | NM_015313 | Rho guanine nucleotide exchange factor (GEF) 12 | ARHGEF12 | 18927307 | |
| IRINOTECAN | NM_152641 | AT rich interactive domain 2 (ARID, RFX-like) | ARID2 | 18927307 | |
| IRINOTECAN | NM_002892; NM_023000; NM_023001 | AT rich interactive domain 4A (RBP1-like) | ARID4A | 15956246 | |
| IRINOTECAN | — | — | ARL6IP2 | 18927307 | |
| IRINOTECAN | NM_014154; NM_015396; NM_213654 | — | ARL7 | 18927307 | |
| IRINOTECAN | NM_000046; NM_198709 | armadillo repeat containing 8 | ARMC8 | 18927307 | |
| IRINOTECAN | NM_001030287; NM_001040619; NM_001674; NM_004024 | arylsulfatase B | ARSB | 18927307 | |
| IRINOTECAN | NM_001131028; NM_031482 | activating transcription factor 3 | ATF3 | 15956246 | |
| IRINOTECAN | NM_001697 | ATG10 autophagy related 10 homolog (S. cerevisiae) | ATG10 | 15956246 | |
| IRINOTECAN | NM_001003803; NM_001003805; NM_015684 | ATP synthase, H+ transporting, mitochondrial F1 complex, O subunit | ATP5O | 17327601 | |
| IRINOTECAN | NM_001141972; NM_080650 | ATP synthase, H+ transporting, mitochondrial F0 complex, subunit s (factor B) | ATP5S | 18927307 | |
| IRINOTECAN | NM_000489; NM_138270 | ATP binding domain 4 | ATPBD4 | 18927307 | |
| IRINOTECAN | NM_004217 | alpha thalassemia/mental retardation syndrome X-linked (RAD54 homolog, S. cerevisiae) | ATRX | 18927307 | |
| IRINOTECAN | NM_012342 | aurora kinase B | AURKB | 15956246 | |
| IRINOTECAN | | BMP and activin membrane-bound inhibitor homolog (Xenopus laevis) | BAMBI | 18927307 | |

TABLE 1-continued

| Molecule | RefSeq | Description | Symbol | PMID | Interaction |
|---|---|---|---|---|---|
| IRINOTECAN | NM_000633; NM_000657 | B-cell CLL/lymphoma 2 | BCL2 | 18949393 | |
| IRINOTECAN | NM_001024808; NM_020993 | B-cell CLL/lymphoma 7A | BCL7A | 15956246 | |
| IRINOTECAN | NM_004326 | B-cell CLL/lymphoma 9 | BCL9 | 15956246 | |
| IRINOTECAN | NM_004327; NM_021574 | breakpoint cluster region | BCR | 18927307 | |
| IRINOTECAN | NM_001012270; NM_001012271; NM_001168 | baculoviral IAP repeat-containing 5 | BIRC5 | 15956246, 16373703 | |
| IRINOTECAN | — | — | BMI_06115 | 18927307 | |
| IRINOTECAN | NM_181809 | bone morphogenetic protein 8a | BMP8A | 15956246 | |
| IRINOTECAN | NM_033030; NM_197970 | bol, boule-like (*Drosophila*) | BOLL | 17327601 | |
| IRINOTECAN | NM_014962; NM_181443 | BTB (POZ) domain containing 3 | BTBD3 | 18927307 | |
| IRINOTECAN | NM_004336 | budding uninhibited by benzimidazoles 1 homolog (yeast) | BUB1 | 15956246 | |
| IRINOTECAN | — | — | C11ORF80 | 18927307 | |
| IRINOTECAN | — | — | C14ORF118 | 18927307 | |
| IRINOTECAN | — | — | C15ORF5 | 18927307 | |
| IRINOTECAN | — | — | C16ORF87 | 18927307 | |
| IRINOTECAN | — | — | C1ORF43 | 18927307 | |
| IRINOTECAN | — | — | C5ORF28 | 18927307 | |
| IRINOTECAN | — | — | C7ORF44 | 18927307 | |
| IRINOTECAN | — | — | C9ORF100 | 18927307 | |
| IRINOTECAN | — | — | C9ORF126 | 18927307 | |
| IRINOTECAN | — | — | C9ORF25 | 18927307 | |
| IRINOTECAN | NM_012295 | calcineurin binding protein 1 | CABIN1 | 18927307 | |
| IRINOTECAN | NM_001003406; NM_021096 | calcium channel, voltage-dependent, T type, alpha 1I subunit | CACNA1I | 18927307 | |
| IRINOTECAN | NM_001225; NM_033306 | caspase 4, apoptosis-related cysteine peptidase | CASP4 | 15956246 | |
| IRINOTECAN | NM_019083 | coiled-coil domain containing 76 | CCDC76 | 18927307 | |
| IRINOTECAN | NM_001237 | cyclin A2 | CCNA2 | 15956246 | |
| IRINOTECAN | NM_004701 | cyclin B2 | CCNB2 | 15956246 | |
| IRINOTECAN | NM_001761 | cyclin F | CCNF | 15956246 | |
| IRINOTECAN | NM_004354 | cyclin G2 | CCNG2 | 18927307 | |
| IRINOTECAN | NM_001295 | chemokine (C-C motif) receptor 1 | CCR1 | 15956246 | |
| IRINOTECAN | NM_004367; NM_031409 | chemokine (C-C motif) receptor 6 | CCR6 | 15956246 | |
| IRINOTECAN | NM_001009186; NM_001762 | chaperonin containing TCP1, subunit 6A (zeta 1) | CCT6A | 18927307 | |
| IRINOTECAN | NM_001025079; NM_001777; NM_198793 | CD47 molecule | CD47 | 15956246 | |
| IRINOTECAN | NM_001252 | CD70 molecule | CD70 | 15956246 | |
| IRINOTECAN | NM_005191 | CD80 molecule | CD80 | 15956246 | |
| IRINOTECAN | NM_001130829; NM_001786; NM_033379 | cell division cycle 2, G1 to S and G2 to M | CDC2 | 15956246 | |
| IRINOTECAN | NM_004358; NM_021872; NM_021873 | cell division cycle 25 homolog B (*S. pombe*) | CDC25B | 15956246 | |
| IRINOTECAN | NM_003718; NM_031267 | cell division cycle 2-like 5 (cholinesterase-related cell division controller) | CDC2L5 | 15956246 | |
| IRINOTECAN | NM_003607; NM_014826 | CDC42 binding protein kinase alpha (DMPK-like) | CDC42BPA | 18927307 | |
| IRINOTECAN | NM_001794 | cadherin 4, type 1, R-cadherin (retinal) | CDH4 | 18927307 | |
| IRINOTECAN | NM_003936 | cyclin-dependent kinase 5, regulatory subunit 2 (p39) | CDK5R2 | 15956246 | |
| IRINOTECAN | NM_001145306; NM_001259 | cyclin-dependent kinase 6 | CDK6 | 18927307 | |
| IRINOTECAN | NM_000389; NM_078467 | cyclin-dependent kinase inhibitor 1A (p21, Cip1) | CDKN1A | 15132777 | |
| IRINOTECAN | NM_001130851; NM_005192 | cyclin-dependent kinase inhibitor 3 | CDKN3 | 15956246 | |
| IRINOTECAN | NM_016952 | Cdon homolog (mouse) | CDON | 18927307 | |
| IRINOTECAN | NM_001813 | centromere protein E, 312 kDa | CENPE | 15956246, 18927307 | |
| IRINOTECAN | NM_016343 | centromere protein F, 350/400ka (mitosin) | CENPF | 15956246 | |
| IRINOTECAN | — | — | CENTG2 | 18927307 | |
| IRINOTECAN | NM_032142 | centrosomal protein 192 kDa | CEP192 | 18927307 | |

TABLE 1-continued

| Molecule | RefSeq | Description | Symbol | PMID | Interaction |
|---|---|---|---|---|---|
| IRINOTECAN | NM_025114 | centrosomal protein 290 kDa | CEP290 | 18927307 | |
| IRINOTECAN | NM_001025194; NM_001025195; NM_001266 | carboxylesterase 1 (monocyte/macrophage serine esterase 1) | CES1 | 15100172, 15239142 | |
| IRINOTECAN | NM_003869; NM_198061 | carboxylesterase 2 (intestine, liver) | CES2 | 10728672, 12171891, 11716702, 12171903, (following) 12171891, 15592324, 16203781, 11716702, 15475733, 14581373, 15100172, 15592324, 15655543, 16033949, 16203781 | |
| IRINOTECAN | NM_024922 | carboxylesterase 3 | CES3 | 15100172 | |
| IRINOTECAN | NM_001270 | chromodomain helicase DNA binding protein 1 | CHD1 | 15956246 | |
| IRINOTECAN | NM_001130675; NM_004362 | calmegin | CLGN | 18927307 | |
| IRINOTECAN | NM_004859 | clathrin, heavy chain (Hc) | CLTC | 18927307 | |
| IRINOTECAN | NM_017649; NM_199076; NM_199077 | cyclin M2 | CNNM2 | 18927307 | |
| IRINOTECAN | NM_001130103; NM_005203; NM_080798; NM_080799; NM_080800; NM_080801; NM_080802; NM_080803; NM_080804; NM_080805; NM_080806; NM_080807; NM_080808; NM_080809; NM_080810; NM_080811; NM_080812; NM_080813; NM_080814; NM_080815 | collagen, type XIII, alpha 1 | COL13A1 | 18927307 | |
| IRINOTECAN | NM_000092 | collagen, type IV, alpha 4 | COL4A4 | 18927307 | |
| IRINOTECAN | NM_001848 | collagen, type VI, alpha 1 | COL6A1 | 15956246 | |
| IRINOTECAN | NM_203495; NM_203497 | COMM domain containing 6 | COMMD6 | 15956246 | |
| IRINOTECAN | NM_001098398; NM_004371 | coatomer protein complex, subunit alpha | COPA | 18927307 | |
| IRINOTECAN | NM_001873 | carboxypeptidase E | CPE | 18927307 | |
| IRINOTECAN | NM_001079846; NM_004380 | CREB binding protein | CREBBP | 15956246, 18927307 | |
| IRINOTECAN | NM_016441 | cysteine rich transmembrane BMP regulator 1 (chordin-like) | CRIM1 | 18927307 | |
| IRINOTECAN | NM_020991; NM_022644; NM_022645 | chorionic somatomammotropin hormone 2 | CSH2 | 18927307 | |
| IRINOTECAN | NM_001083914; NM_001329; NM_022802 | C-terminal binding protein 2 | CTBP2 | 18927307 | |
| IRINOTECAN | NM_001902; NM_153742 | cystathionase (cystathionine gamma-lyase) | CTH | 18927307 | |
| IRINOTECAN | NM_003589 | cullin 4A | CUL4A | 18927307 | |
| IRINOTECAN | NM_000609; NM_001033886; NM_199168 | chemokine (C-X-C motif) ligand 12 (stromal cell-derived factor 1) | CXCL12 | 18927307 | |
| IRINOTECAN | NM_000761 | cytochrome P450, family 1, subfamily A, polypeptide 2 | CYP1A2 | 11901092 | unrelated |
| IRINOTECAN | NM_000762 | cytochrome P450, family 2, subfamily A, polypeptide 6 | CYP2A6 | 11901092 | |
| IRINOTECAN | NM_000767 | cytochrome P450, family 2, subfamily B, polypeptide 6 | CYP2B6 | 11901092 | |
| IRINOTECAN | NM_000769 | cytochrome P450, family 2, subfamily C, polypeptide 19 | CYP2C19 | 11901092 | |
| IRINOTECAN | NM_000770 | cytochrome P450, family 2, subfamily C, polypeptide 8 | CYP2C8 | 11901092 | unrelated |
| IRINOTECAN | NM_000771 | cytochrome P450, family 2, subfamily C, polypeptide 9 | CYP2C9 | 11901092 | unrelated |
| IRINOTECAN | NM_000106; NM_001025161 | cytochrome P450, family 2, subfamily D, polypeptide 6 | CYP2D6 | 11901092 | |
| IRINOTECAN | NM_000773 | cytochrome P450, family 2, subfamily E, polypeptide 1 | CYP2E1 | 11901092 | |
| IRINOTECAN | NM_017460 | cytochrome P450, family 3, subfamily A, polypeptide 4 | CYP3A4 | 11901092, 15100172, 15239142, 15523087, 15655543 | drug metabolism |
| IRINOTECAN | NM_000777 | cytochrome P450, family 3, subfamily A, polypeptide 5 | CYP3A5 | 15897249 | drug metabolism |
| IRINOTECAN | NM_001142936; NM_139179 | diacylglycerol lipase, beta | DAGLB | 18927307 | |
| IRINOTECAN | NM_014881 | DNA cross-link repair 1A (PSO2 homolog, S. cerevisiae) | DCLRE1A | 15956246 | |
| IRINOTECAN | NM_006400 | dynactin 2 (p50) | DCTN2 | 18927307 | |

| Molecule | RefSeq | Description | Symbol | PMID | Interaction |
|---|---|---|---|---|---|
| IRINOTECAN | NM_000107 | damage-specific DNA binding protein 2, 48 kDa | DDB2 | 15956246 | |
| IRINOTECAN | NM_030637 | DDHD domain containing 1 | DDHD1 | 18927307 | |
| IRINOTECAN | NM_001039711; NM_001039712; NM_032998 | death effector domain containing | DEDD | 18927307 | |
| IRINOTECAN | NM_004084 | defensin, alpha 1 | DEFA1 | 15956246 | |
| IRINOTECAN | NM_001144823; NM_005848 | DENN/MADD domain containing 4A | DENND4A | 15956246 | |
| IRINOTECAN | NM_003677 | density-regulated protein | DENR | 18927307 | |
| IRINOTECAN | NM_001145208; NM_018369 | DEP domain containing 1B | DEPDC1B | 18927307 | |
| IRINOTECAN | NM_022720 | DiGeorge syndrome critical region gene 8 | DGCR8 | 18927307 | |
| IRINOTECAN | NM_176815 | dihydrofolate reductase-like 1 | DHFRL1 | 18927307 | |
| IRINOTECAN | NM_001146114; NM_001146115; NM_015151; NM_206889; NM_206890; NM_206891 | DIP2 disco-interacting protein 2 homolog A (*Drosophila*) | DIP2A | 18927307 | |
| IRINOTECAN | NM_006094; NM_024767; NM_182643 | deleted in liver cancer 1 | DLC1 | 18927307 | |
| IRINOTECAN | NM_001098424; NM_004087 | discs, large homolog 1 (*Drosophila*) | DLG1 | 18927307 | |
| IRINOTECAN | NM_001934; NM_138281 | distal-less homeobox 4 | DLX4 | 18927307 | |
| IRINOTECAN | NM_004943 | dystrophia myotonica, WD repeat containing | DMWD | 15956246 | |
| IRINOTECAN | — | | DNMT2 | 15956246 | |
| IRINOTECAN | NM_001039589; NM_001384 | DPH2 homolog (*S. cerevisiae*) | DPH2 | 18927307 | |
| IRINOTECAN | NM_000110 | dihydropyrimidine dehydrogenase | DPYD | 15956246 | |
| IRINOTECAN | NM_000798 | dopamine receptor D5 | DRD5 | 15956246 | |
| IRINOTECAN | NM_004147 | developmentally regulated GTP binding protein 1 | DRG1 | 17327601 | |
| IRINOTECAN | NM_001144769; NM_001144770; NM_001144771; NM_001723; NM_015548; NM_020388; NM_183380 | dystonin | DST | 15897249 | |
| | | | | 18927307 | |
| IRINOTECAN | NM_004418 | dual specificity phosphatase 2 | DUSP2 | 15956246 | |
| IRINOTECAN | NM_001396; NM_101395; NM_130436; NM_130437; NM_130438 | dual-specificity tyrosine-(Y)-phosphorylation regulated kinase 1A | DYRK1A | 15956246 | |
| IRINOTECAN | NM_003583; NM_006482 | dual-specificity tyrosine-(Y)-phosphorylation regulated kinase 2 | DYRK2 | 15956246 | |
| IRINOTECAN | — | | EBI2 | 15956246 | |
| IRINOTECAN | NM_005228; NM_201282; NM_201283; NM_201284 | epidermal growth factor receptor (erythroblastic leukemia viral (v-erb-b) oncogene homolog, avian) | EGFR | 15723263 | |
| IRINOTECAN | NM_001964 | early growth response 1 | EGR1 | 15956246 | |
| IRINOTECAN | NM_001013703 | eukaryotic translation initiation factor 2 alpha kinase 4 | EIF2AK4 | 18927307 | |
| IRINOTECAN | NM_012155 | echinoderm microtubule associated protein like 2 | EML2 | 17327601 | |
| IRINOTECAN | NM_001428 | enolase 1, (alpha) | ENO1 | 18927307 | |
| IRINOTECAN | NM_001429 | E1A binding protein p300 | EP300 | 18927307 | |
| IRINOTECAN | NM_031308 | epiplakin 1 | EPPK1 | 15956246 | |
| IRINOTECAN | NM_001042599; NM_005235 | v-erb-a erythroblastic leukemia viral oncogene homolog 4 (avian) | ERBB4 | 18927307 | |
| | | | | 15956246 | |
| IRINOTECAN | NM_015064; NM_178037; NM_178038; NM_178039; NM_178040 | ELKS/RAB6-interacting/CAST family member 1 | ERC1 | 18927307 | |
| IRINOTECAN | NM_001432 | epiregulin | EREG | 18927307 | |
| IRINOTECAN | NM_005239 | v-ets erythroblastosis virus E26 oncogene homolog 2 (avian) | ETS2 | 15956246 | |
| IRINOTECAN | NM_001987 | ets variant 6 | ETV6 | 15956246 | |
| IRINOTECAN | NM_001037126; NM_021807 | exocyst complex component 4 | EXOC4 | 18927307 | |
| IRINOTECAN | NM_000132; NM_019863 | coagulation factor VIII, procoagulant component | F8 | 17327601 | |
| IRINOTECAN | NM_001040442; NM_001130958; NM_001445 | fatty acid binding protein 6, ileal | FABP6 | 18927307 | |
| IRINOTECAN | — | | FAM152A | 18927307 | |
| IRINOTECAN | NM_001040020; NM_014888 | family with sequence similarity 3, member C | FAM3C | 18927307 | |
| IRINOTECAN | — | | FAM44A | 18927307 | |

TABLE 1-continued

| Molecule | RefSeq | Description | Symbol | PMID | Interaction |
|---|---|---|---|---|---|
| IRINOTECAN | NM_004629 | Fanconi anemia, complementation group G | FANCG | 15956246 | |
| IRINOTECAN | NM_005687 | phenylalanyl-tRNA synthetase, beta subunit | FARSB | 18927307 | |
| IRINOTECAN | NM_000639 | Fas ligand (TNF superfamily, member 6) | FASLG | 15897249 | |
| IRINOTECAN | NM_015962 | FCF1 small subunit (SSU) processome component homolog (S. cerevisiae) | FCF1 | 18927307 | |
| IRINOTECAN | NM_002006 | fibroblast growth factor 2 (basic) | FGF2 | 15956246 | |
| IRINOTECAN | NM_002010 | fibroblast growth factor 9 (glia-activating factor) | FGF9 | 18927307 | |
| IRINOTECAN | NM_002026; NM_054034; NM_212474; NM_212475; NM_212476; NM_212478; NM_212482 | fibronectin 1 | FN1 | 15956246, 18927307 | |
| IRINOTECAN | NM_005252 | v-fos FBJ murine osteosarcoma viral oncogene homolog | FOS | 15956246 | |
| IRINOTECAN | NM_001114171; NM_006732 | FBJ murine osteosarcoma viral oncogene homolog B | FOSB | 15956246 | |
| IRINOTECAN | NM_032892 | FERM domain containing 5 | FRMD5 | 18927307 | |
| IRINOTECAN | NM_001080432 | fat mass and obesity associated | FTO | 18927307 | |
| IRINOTECAN | NM_001465; NM_199335 | FYN binding protein (FYB-120/130) | FYB | 18927307 | |
| IRINOTECAN | — | — | G1P3 | 18927307 | |
| IRINOTECAN | NM_001002295; NM_002051 | GATA binding protein 3 | GATA3 | 15956246 | |
| IRINOTECAN | NM_004864 | growth differentiation factor 15 | GDF15 | 15956246 | |
| IRINOTECAN | NM_001032364; NM_001032365; NM_005265; NM_013430 | gamma-glutamyltransferase 1 | GGT1 | 18927307 | |
| IRINOTECAN | NM_000165 | gap junction protein, alpha 1, 43 kDa | GJA1 | 18927307 | |
| IRINOTECAN | NM_000167; NM_001128127; NM_203391 | glycerol kinase | GK | 18927307 | |
| IRINOTECAN | NM_006541 | glutaredoxin 3 | GLRX3 | 18927307 | |
| IRINOTECAN | NM_006572 | guanine nucleotide binding protein (G protein), alpha 13 | GNA13 | 18927307 | |
| IRINOTECAN | NM_181077 | golgi autoantigen, golgin subfamily a, 8A | GOLGA8A | 17327601 | |
| IRINOTECAN | NM_015590; NM_182679 | G patch domain containing 4 | GPATCH4 | 18927307 | |
| IRINOTECAN | NM_002084 | glutathione peroxidase 3 (plasma) | GPX3 | 15956246 | |
| IRINOTECAN | NM_002105 | H2A histone family, member X | H2AFX | 15956246 | |
| IRINOTECAN | NM_001945 | heparin-binding EGF-like growth factor | HBEGF | 15723263 | |
| IRINOTECAN | NM_000559 | hemoglobin, gamma A | HBG1 | 18927307 | |
| IRINOTECAN | NM_005334 | host cell factor C1 (VP16-accessory protein) | HCFC1 | 18927307 | |
| IRINOTECAN | NM_173497; NM_182765 | HECT domain containing 2 | HECTD2 | 18927307 | |
| IRINOTECAN | NM_018063 | helicase, lymphoid-specific | HELLS | 18927307 | |
| IRINOTECAN | NM_005524 | hairy and enhancer of split 1, (Drosophila) | HES1 | 19147571 | |
| IRINOTECAN | NM_003512 | histone cluster 1, H2ac | HIST1H2AC | 15956246 | |
| IRINOTECAN | NM_003542 | histone cluster 1, H4c | HIST1H4C | 18927307 | |
| IRINOTECAN | NM_005514 | major histocompatibility complex, class I, B | HLA-B | 18927307 | |
| IRINOTECAN | NM_002124 | major histocompatibility complex, class II, DR beta 1 | HLA-DRB1 | 18927307 | |
| IRINOTECAN | NM_021983 | major histocompatibility complex, class II, DR beta 4 | HLA-DRB4 | 18927307 | |
| IRINOTECAN | NM_001142556; NM_001142557; NM_012484; NM_012485 | hyaluronan-mediated motility receptor (RHAMM) | HMMR | 15956246 | |
| IRINOTECAN | NM_001002032; NM_001002033; NM_016185 | hematological and neurological expressed 1 | HN1 | 18927307 | |
| IRINOTECAN | — | — | HNRPA1 | 18927307 | |
| IRINOTECAN | — | — | HNRPD | 18927307 | |
| IRINOTECAN | NM_031372 | heterogeneous nuclear ribonucleoprotein D-like | HNRPDL | 18927307 | |
| IRINOTECAN | NM_000412 | histidine-rich glycoprotein | HRG | 15956246 | |

TABLE 1-continued

| Molecule | RefSeq | Description | Symbol | PMID | Interaction |
|---|---|---|---|---|---|
| IRINOTECAN | NM_006041 | heparan sulfate (glucosamine) 3-O-sulfotransferase 3B1 | HS3ST3B1 | 18927307 | |
| IRINOTECAN | NM_014278 | heat shock 70 kDa protein 4-like | HSPA4L | 15956246 | |
| IRINOTECAN | — | — | HYPK | 18927307 | |
| IRINOTECAN | NM_002166 | inhibitor of DNA binding 2, dominant negative helix-loop-helix protein | ID2 | 15956246 | |
| IRINOTECAN | NM_003641 | interferon induced transmembrane protein 1 (9-27) | IFITM1 | 18927307 | |
| IRINOTECAN | NM_000618; NM_001111283; NM_001111284; NM_001111285 | insulin-like growth factor 1 (somatomedin C) | IGF1 | 15956246 | |
| IRINOTECAN | — | immunoglobulin heavy constant gamma 1 (G1m marker) | IGHG1 | 18927307 | |
| IRINOTECAN | NM_000576 | interleukin 1, beta | IL1B | 15956246 | |
| IRINOTECAN | NM_000584 | interleukin 8 | IL8 | 15723263 | |
| IRINOTECAN | NM_032549 | IMP2 inner mitochondrial membrane peptidase-like (S. cerevisiae) | IMMP2L | 18927307 | |
| IRINOTECAN | NM_001100169; NM_001100170; NM_006839 | inner membrane protein, mitochondrial (mitofilin) | IMMT | 18927307 | |
| IRINOTECAN | NM_019071; NM_198267 | inhibitor of growth family, member 3 | ING3 | 18927307 | |
| IRINOTECAN | NM_005542; NM_198336; NM_198337 | insulin induced gene 1 | INSIG1 | 18927307 | |
| IRINOTECAN | NM_002203 | integrin, alpha 2 (CD49B, alpha 2 subunit of VLA-2 receptor) | ITGA2 | 18927307 | |
| IRINOTECAN | NM_001144999; NM_001145000; NM_002210 | integrin, alpha V (vitronectin receptor, alpha polypeptide, antigen CD51) | ITGAV | 15956246 | |
| IRINOTECAN | NM_000887 | integrin, alpha X (complement component 3 receptor 4 subunit) | ITGAX | 15956246 | |
| IRINOTECAN | NM_014288 | integrin beta 3 binding protein (beta3-endonexin) | ITGB3BP | 15956246 | |
| IRINOTECAN | NM_002228 | jun oncogene | JUN | 15956246 | |
| IRINOTECAN | NM_006559 | KH domain containing, RNA binding, signal transduction associated 1 | KHDRBS1 | 18927307 | |
| IRINOTECAN | NM_001162893; NM_001162894; NM_001162895; NM_014656 | KIAA0040 | KIAA0040 | 18927307 | |
| IRINOTECAN | NM_015443 | KIAA1267 | KIAA1267 | 18927307 | |
| IRINOTECAN | — | | KIAA1333 | 18927307 | |
| IRINOTECAN | — | KIAA1731 | KIAA1731 | 18927307 | |
| IRINOTECAN | NM_033395 | kinesin family member 14 | KIF14 | 18927307 | |
| IRINOTECAN | NM_014875 | Kruppel-like factor 4 (gut) | KLF4 | 18927307 | |
| IRINOTECAN | NM_004235 | Kruppel-like factor 9 | KLF9 | 15956246 | |
| IRINOTECAN | NM_001206 | kelch-like 24 (Drosophila) | KLHL24 | 18927307 | |
| IRINOTECAN | NM_017644 | KRIT1, ankyrin repeat containing | KRIT1 | 18927307 | |
| IRINOTECAN | NM_001013406; NM_004912; NM_194454; NM_194455; NM_194456 | keratin 5 | KRT5 | 15956246 | |
| IRINOTECAN | NM_000424 | limb bud and heart development homolog (mouse) | LBH | 18927307 | |
| IRINOTECAN | NM_030915 | lectin, galactoside-binding, soluble, 8 | LGALS8 | 17327601 | |
| IRINOTECAN | NM_006499; NM_201543; NM_201544; NM_201545 | | | | |
| IRINOTECAN | — | LIM | LIM | 18927307 | |
| IRINOTECAN | NM_032603 | lysyl oxidase-like 3 | LOXL3 | 18927307 | |
| IRINOTECAN | NM_024830 | lysophosphatidylcholine acyltransferase 1 | LPCAT1 | 18927307 | |
| IRINOTECAN | NM_032773 | leucine-rich repeats and calponin homology (CH) domain containing 3 | LRCH3 | 18927307 | |
| IRINOTECAN | NM_002343 | lactotransferrin | LTF | 15956246 | |
| IRINOTECAN | NM_032860 | LITV1 homolog (S. cerevisiae) | LITV1 | 18927307 | |
| IRINOTECAN | NM_002358 | MAD2 mitotic arrest deficient-like 1 (yeast) | MAD2L1 | 15956246 | |

TABLE 1-continued

| Molecule | RefSeq | Description | Symbol | PMID | Interaction |
|---|---|---|---|---|---|
| IRINOTECAN | NM_002371; NM_022438; NM_022439; NM_022440 | mal, T-cell differentiation protein | MAL | 15956246 | |
| IRINOTECAN | NM_002819; NR_002819; NR_002819; NR_002819; NR_002819; NR_002819 | metastasis associated lung adenocarcinoma transcript 1 (non-protein coding) | MALAT1 | 18927307 | |
| IRINOTECAN | NM_005434 | mal, T-cell differentiation protein-like | MALL | 15956246 | |
| IRINOTECAN | NM_005923 | mitogen-activated protein kinase kinase kinase 5 | MAP3K5 | 15956246 | |
| IRINOTECAN | NM_003618 | mitogen-activated protein kinase kinase kinase 3 | MAP4K3 | 18927307 | |
| IRINOTECAN | NM_005885 | membrane-associated ring finger (C3HC4) 6 | MARCH6 | 18927307 | |
| IRINOTECAN | NM_002380; NM_030583 | matrilin 2 | MATN2 | 18927307 | |
| IRINOTECAN | NM_018834; NM_199189 | matrin 3 | MATR3 | 18927307 | |
| IRINOTECAN | NM_021038; NM_207292; NM_207293; NM_207294; NM_207295; NM_207296; NM_207297 | muscleblind-like (*Drosophila*) | MBNL1 | 18927307 | |
| IRINOTECAN | NM_001025081; NM_001025090; NM_001025092; NM_001025100; NM_001025101; NM_002385 | myelin basic protein | MBP | 18927307 | |
| IRINOTECAN | NM_022132 | methylcrotonoyl-Coenzyme A carboxylase 2 (beta) | MCCC2 | 18927307 | |
| IRINOTECAN | NM_001112732; NM_024979 | MCF.2 cell line derived transforming sequence-like | MCF2L | 15956246 | |
| IRINOTECAN | NM_005914; NM_182746 | minichromosome maintenance complex component 4 | MCM4 | 15956246 | |
| IRINOTECAN | NM_001145336; NM_001145337; NM_001145339; NM_001145340; NM_002392; NM_006878; NM_006879; NM_006881; NM_006882 | Mdm2 p53 binding protein homolog (mouse) | MDM2 | 15956246 | |
| IRINOTECAN | NM_014611 | MDN1, midasin homolog (yeast) | MDN1 | 18927307 | |
| IRINOTECAN | NM_005121 | mediator complex subunit 13 | MED13 | 18927307 | |
| IRINOTECAN | NM_001145785 | myocyte enhancer factor 2B | MEF2B | 15956246 | |
| IRINOTECAN | NM_002412 | O-6-methylguanine-DNA methyltransferase | MGMT | 15239142 | |
| IRINOTECAN | NM_012064 | major intrinsic protein of lens fiber | MIP | 18927307 | |
| IRINOTECAN | NR_027350; XR_079513; XR_079513; XR_079539; XR_079539; XR_079554; XR_079554 | microRNA host gene 1 (non-protein coding) | MIRHG1 | 18927307 | |
| IRINOTECAN | NM_173576 | mohawk homeobox | MKX | 18927307 | |
| IRINOTECAN | NM_000249 | mutL homolog 1, colon cancer, nonpolyposis type 2 (*E. coli*) | MLH1 | 18949393 | |
| IRINOTECAN | NM_004994 | matrix metallopeptidase 9 (gelatinase B, 92 kDa gelatinase, 92 kDa type IV collagenase) | MMP9 | 15956246 | |
| IRINOTECAN | NM_000250 | myeloperoxidase | MPO | 15956246 | |
| IRINOTECAN | NM_173496 | membrane protein, palmitoylated 7 (MAGUK p55 subfamily member 7) | MPP7 | 18927307 | |
| IRINOTECAN | NM_016640 | mitochondrial ribosomal protein S30 | MRPS30 | 18927307 | |
| IRINOTECAN | NM_000251 | mutS homolog 2, colon cancer, nonpolyposis type 1 (*E. coli*) | MSH2 | 15956246, 18949393 | |
| IRINOTECAN | NM_015440 | methylenetetrahydrofolate dehydrogenase (NADP+ dependent) 1-like | MTHFD1L | 18927307 | |
| IRINOTECAN | NM_006441 | 5,10-methenyltetrahydrofolate synthetase (5-formyltetrahydrofolate cyclo-ligase) | MTHFS | 15956246 | |
| IRINOTECAN | NM_002463 | myxovirus (influenza virus) resistance 2 (mouse) | MX2 | 15956246 | |
| IRINOTECAN | NM_005964 | myosin, heavy chain 10, non-muscle | MYH10 | 18927307 | |
| IRINOTECAN | NM_001085487 | Myb-like, SWIRM and MPN domains 1 | MYSM1 | 18927307 | |
| IRINOTECAN | NM_153029 | NEDD4 binding protein 1 | N4BP1 | 18927307 | |
| IRINOTECAN | NM_017940 | neuroblastoma breakpoint family, member 1 | NBPF1 | 18927307 | |
| IRINOTECAN | NM_006153 | NCK adaptor protein 1 | NCK1 | 15956246 | |

TABLE 1-continued

| Molecule | RefSeq | Description | Symbol | PMID | Interaction |
|---|---|---|---|---|---|
| IRINOTECAN | NM_003743; NM_147223; NM_147233 | nuclear receptor coactivator 1 | NCOA1 | 15956246 | |
| IRINOTECAN | NM_006311 | nuclear receptor co-repressor 1 | NCOR1 | 18927307 | |
| IRINOTECAN | NM_015331 | nicastrin | NCSTN | 19147571 | |
| IRINOTECAN | NM_002497 | NIMA (never in mitosis gene a)-related kinase 2 | NEK2 | 15956246 | |
| IRINOTECAN | NM_006018 | niacin receptor 2 | NIACR2 | 15956246 | |
| IRINOTECAN | NM_002508 | nidogen 1 | NID1 | 15956246 | |
| IRINOTECAN | NM_000903; NM_001025433; NM_001025434 | NAD(P)H dehydrogenase, quinone 1 | NQO1 | 18927307 | |
| IRINOTECAN | NM_006178 | N-ethylmaleimide-sensitive factor | NSF | 18927307 | |
| IRINOTECAN | NM_005124 | nucleoporin 153 kDa | NUP153 | 18927307 | |
| IRINOTECAN | NM_001129897; NM_016359; NM_018454 | nucleolar and spindle associated protein 1 | NUSAP1 | 18927307 | |
| IRINOTECAN | NM_002547 | oligophrenin 1 | OPHN1 | 18927307 | |
| IRINOTECAN | NM_003999 | oncostatin M receptor | OSMR | 15956246 | |
| IRINOTECAN | NM_018440 | phosphoprotein associated with glycosphingolipid microdomains 1 | PAG1 | 18927307 | |
| IRINOTECAN | NM_000919; NM_138766; NM_138821; NM_138822 | peptidylglycine alpha-amidating monooxygenase | PAM | 18927307 | |
| IRINOTECAN | NM_175854 | PAN3 poly(A) specific ribonuclease subunit homolog (S. cerevisiae) | PAN3 | 18927307 | |
| IRINOTECAN | NM_016734 | paired box 5 | PAX5 | 18927307 | |
| IRINOTECAN | NM_001135254; NM_002584; NM_013945 | paired box 7 | PAX7 | 18927307 | |
| IRINOTECAN | — | | PCAF | 18927307 | |
| IRINOTECAN | NM_032151 | pterin-4 alpha-carbinolamine dehydratase/dimerization cofactor of hepatocyte nuclear factor 1 alpha (TCF1) 2 | PCBD2 | 18927307 | |
| IRINOTECAN | NM_002588; NM_032402; NM_032403 | protocadherin gamma subfamily C, 3 | PCDHGC3 | 15956246 | |
| IRINOTECAN | NM_001037339; NM_001037340; NM_001037341; NM_002600 | phosphodiesterase 4B, cAMP-specific (phosphodiesterase E4 dunce homolog, Drosophila) | PDE4B | 15956246 | |
| IRINOTECAN | NM_173582 | phosphoglucomutase 2-like 1 | PGM2L1 | 18927307 | |
| IRINOTECAN | NM_007350 | pleckstrin homology-like domain, family A, member 1 | PHLDA1 | 18927307 | |
| IRINOTECAN | NR_003700; NR_003700; NR_003700; NR_003700 | phosphatidylinositol 4-kinase, catalytic, alpha pseudogene 2 | PI4KAP2 | 15956246 | |
| IRINOTECAN | NM_178517 | phosphatidylinositol glycan anchor biosynthesis, class W | PIGW | 18927307 | |
| IRINOTECAN | NM_000930; NM_033011 | plasminogen activator, tissue | PLAT | 18927307 | |
| IRINOTECAN | NM_001134478; NM_153268 | phosphatidylinositol-specific phospholipase C, X domain containing 2 | PLCXD2 | 18927307 | |
| IRINOTECAN | NM_001143821; NM_019012 | pleckstrin homology domain containing, family A member 5 | PLEKHA5 | 18927307 | |
| IRINOTECAN | NM_024927 | pleckstrin homology domain containing, family H (with MyTH4 domain) member 3 | PLEKHH3 | 15956246 | |
| IRINOTECAN | NM_005030 | polo-like kinase 1 (Drosophila) | PLK1 | 15956246 | |
| IRINOTECAN | NM_006622 | polo-like kinase 2 (Drosophila) | PLK2 | 15956246 | |
| IRINOTECAN | NM_004073 | polo-like kinase 3 (Drosophila) | PLK3 | 15956246 | |
| IRINOTECAN | NM_021127 | phorbol-12-myristate-13-acetate-induced protein 1 | PMAIP1 | 15956246 | |
| IRINOTECAN | NM_006813 | proline-rich nuclear receptor coactivator 1 | PNRC1 | 18927307 | |
| IRINOTECAN | NM_015100; NM_145796; NM_207171 | pogo transposable element with ZNF domain | POGZ | 18927307 | |
| IRINOTECAN | NM_016218 | polymerase (DNA directed) kappa | POLK | 18927307 | |
| IRINOTECAN | NM_000941 | P450 (cytochrome) oxidoreductase | POR | 15239142 | |
| IRINOTECAN | NM_003620 | protein phosphatase 1D magnesium-dependent, delta isoform | PPM1D | 18927307 | |
| IRINOTECAN | NM_000944; NM_001130691; NM_001130692 | protein phosphatase 3 (formerly 2B), catalytic subunit, alpha isoform | PPP3CA | 18927307 | |

TABLE 1-continued

| Molecule | RefSeq | Description | Symbol | PMID | Interaction |
|---|---|---|---|---|---|
| IRINOTECAN | NM_001142353; NM_001143354; NM_021132 | protein phosphatase 3 (formerly 2B), catalytic subunit, beta isoform | PPP3CB | 15956246 | |
| IRINOTECAN | NM_006251; NM_206907 | protein kinase, AMP-activated, alpha 1 catalytic subunit | PRKAA1 | 18927307 | |
| IRINOTECAN | NM_002737 | protein kinase C, alpha | PRKCA | 15723263 | |
| IRINOTECAN | NM_002738; NM_212535 | protein kinase C, beta | PRKCB | 15723263 | |
| IRINOTECAN | NM_006254; NM_212539 | protein kinase C, delta | PRKCD | 15723263 | |
| IRINOTECAN | NM_002740 | protein kinase C, iota | PRKCI | 15723263 | |
| IRINOTECAN | NM_001145848; NM_001145849; NM_001145850; NM_001145851; NM_001145852; NM_006017 | prominin 1 | PROM1 | 15956246 | |
| IRINOTECAN | NM_002784 | pregnancy specific beta-1-glycoprotein 9 | PSG9 | 17327601 | |
| IRINOTECAN | NM_004878 | prostaglandin E synthase | PTGES | 15956246 | |
| IRINOTECAN | NM_005607; NM_153831 | PTK2 protein tyrosine kinase 2 | PTK2 | 18927307 | |
| IRINOTECAN | NM_003463 | protein tyrosine phosphatase type IVA, member 1 | PTP4A1 | 18927307 | |
| IRINOTECAN | NM_006264; NM_080683; NM_080684; NM_080685 | protein tyrosine phosphatase, non-receptor type 13 (APO-1/CD95 (Fas)-associated phosphatase) | PTPN13 | 15956246 | |
| IRINOTECAN | NM_012411; NM_015967 | protein tyrosine phosphatase, non-receptor type 22 (lymphoid) | PTPN22 | 15956246 | |
| IRINOTECAN | NM_001040712; NM_002839; NM_130391; NM_130392; NM_130393 | protein tyrosine phosphatase, receptor type, D | PTPRD | 15956246 | |
| IRINOTECAN | NM_002841 | protein tyrosine phosphatase, receptor type, G | PTPRG | 18927307 | |
| IRINOTECAN | NM_002846 | protein tyrosine phosphatase, receptor type, N | PTPRN | 15956246 | |
| IRINOTECAN | NM_005052 | ras-related C3 botulinum toxin substrate 3 (rho family, small GTP binding protein Rac3) | RAC3 | 15956246 | |
| IRINOTECAN | NM_002874 | RAD23 homolog B (S. cerevisiae) | RAD23B | 15956246 | |
| IRINOTECAN | NM_002877; NM_133509; NM_133510 | RAD51-like 1 (S. cerevisiae) | RAD51L1 | 18927307 | |
| IRINOTECAN | NM_002890; NM_022650 | RAS p21 protein activator (GTPase activating protein) 1 | RASA1 | 18927307 | |
| IRINOTECAN | NM_000321 | retinoblastoma 1 | RB1 | 15132777 | |
| IRINOTECAN | NM_005057 | retinoblastoma binding protein 5 | RBBP5 | 15956246 | |
| IRINOTECAN | NM_002895; NM_183404 | retinoblastoma-like 1 (p107) | RBL1 | 18927307 | |
| IRINOTECAN | NM_001143941; NM_001143942; NM_153020 | RNA binding motif protein 24 | RBM24 | 18927307 | |
| IRINOTECAN | | | RBPSUH | 18927307 | |
| IRINOTECAN | NM_021111 | reversion-inducing-cysteine-rich protein with kazal motifs | RECK | 18927307 | |
| IRINOTECAN | NM_001145138; NM_021975 | v-rel reticuloendotheliosis viral oncogene homolog A (avian) | RELA | 15161687, 16685529 | |
| IRINOTECAN | NM_001128617; NM_031922 | RALBP1 associated Eps domain containing 1 | REPS1 | 18927307 | |
| IRINOTECAN | NM_002915; NM_181558 | replication factor C (activator 1) 3, 38 kDa | RFC3 | 15956246 | |
| IRINOTECAN | NM_002922 | regulator of G-protein signaling 1 | RGS1 | 15956246 | |
| IRINOTECAN | NM_015668 | regulator of G-protein signaling 22 | RGS22 | 18927307 | |
| IRINOTECAN | NM_021205 | ras homolog gene family, member U | RHOU | 18927307 | |
| IRINOTECAN | | | RNF12 | 18927307 | |
| IRINOTECAN | NM_000968 | ribosomal protein L4 | RPL4 | 18927307 | |
| IRINOTECAN | NM_001001890; NM_001122607; NM_001754 | runt-related transcription factor 1 | RUNX1 | 15956246 | |
| IRINOTECAN | NM_017654 | sterile alpha motif domain containing 9 | SAMD9 | 18927307 | |
| IRINOTECAN | NM_015474 | SAM domain and HD domain 1 | SAMHD1 | 18927307 | |
| IRINOTECAN | | | SCD4 | 18927307 | |
| IRINOTECAN | NM_002999 | syndecan 4 | SDC4 | 15956246 | |
| IRINOTECAN | NM_001077206; NM_001077207; NM_001077208; NM_014933; NM_016211 | SEC31 homolog A (S. cerevisiae) | SEC31A | 18927307 | |

TABLE 1-continued

| Molecule | RefSeq | Description | Symbol | PMID | Interaction |
|---|---|---|---|---|---|
| IRINOTECAN | NM_006379 | sema domain, immunoglobulin domain (Ig), short basic domain, secreted, (semaphorin) 3C | SEMA3C | 18927307 | |
| IRINOTECAN | NM_001100409; NM_015571 | SUMO1/sentrin specific peptidase 6 | SENP6 | 18927307 | |
| IRINOTECAN | NM_001136528; NM_001136529; NM_001136530; NM_006216 | serpin peptidase inhibitor, clade E (nexin, plasminogen activator inhibitor type 1), member 2 | SERPINE2 | 17327601 | |
| IRINOTECAN | NM_031459 | sestrin 2 | SESN2 | 15956246 | |
| IRINOTECAN | NM_015048 | SET domain containing 1B | SETD1B | 18927307 | |
| IRINOTECAN | NM_001080517 | SET domain containing 5 | SETD5 | 18927307 | |
| IRINOTECAN | NM_006142 | stratifin | SFN | 16373703 | |
| IRINOTECAN | NM_001145444; NM_001145445; NM_020706 | splicing factor, arginine/serine-rich 15 | SFRS15 | 18927307 | |
| IRINOTECAN | | | SGK | 15956246, 18927307 | |
| IRINOTECAN | NM_152524 | shugoshin-like 2 (S. pombe) | SGOL2 | 18927307 | |
| IRINOTECAN | NM_004696 | solute carrier family 16, member 4 (monocarboxylic acid transporter 5) | SLC16A4 | 15956246 | |
| IRINOTECAN | NM_194255 | solute carrier family 19 (folate transporter), member 1 | SLC19A1 | 18927307 | |
| IRINOTECAN | NM_030631 | solute carrier family 25 (mitochondrial oxodicarboxylate carrier), member 21 | SLC25A21 | 18927307 | |
| IRINOTECAN | NM_021194 | solute carrier family 30 (zinc transporter), member 1 | SLC30A1 | 18927307 | |
| IRINOTECAN | NM_001130012; NM_004785 | solute carrier family 9 (sodium/hydrogen exchanger), member 3 regulator 2 | SLC9A3R2 | 15956246 | |
| IRINOTECAN | NM_001145102; NM_001145103; NM_001145104; NM_005902 | SMAD family member 3 | SMAD3 | 18927307 | |
| IRINOTECAN | NM_015295 | structural maintenance of chromosomes flexible hinge domain containing 1 | SMCHD1 | 18927307 | |
| IRINOTECAN | NM_001122964; NM_020463 | SMEK homolog 2, suppressor of mek1 (Dictyostelium) | SMEK2 | 18927307 | |
| IRINOTECAN | NM_018225 | smu-1 suppressor of mec-8 and unc-52 homolog (C. elegans) | SMU1 | 18927307 | |
| IRINOTECAN | NM_020429; NM_181349 | SMAD specific E3 ubiquitin protein ligase 1 | SMURF1 | 18927307 | |
| IRINOTECAN | | | SNAG1 | 15956246 | |
| IRINOTECAN | NM_003090 | small nuclear ribonucleoprotein polypeptide A' | SNRPA1 | 18927307 | |
| IRINOTECAN | NM_003109; NM_138473 | Sp1 transcription factor | SP1 | 18927307 | |
| IRINOTECAN | NM_003121 | Spi-B transcription factor (Spi-1/PU.1 related) | SPIB | 15956246 | |
| IRINOTECAN | NM_007271 | serine/threonine kinase 38 | STK38 | 15956246 | |
| IRINOTECAN | NM_006282 | serine/threonine kinase 4 | STK4 | 15956246, 18927307 | |
| IRINOTECAN | NM_001017389; NM_001017390 | sulfotransferase family, cytosolic, 1A, phenol-preferring, member 4 | SULT1A4 | 15956246 | |
| IRINOTECAN | NM_032184 | synapse defective 1, Rho GTPase, homolog 2 (C. elegans) | SYDE2 | 18927307 | |
| IRINOTECAN | NM_001135805; NM_001135806; NM_005639 | synaptotagmin I | SYT1 | 18927307 | |
| IRINOTECAN | NM_003184 | TAF2 RNA polymerase II, TATA box binding protein (TBP)-associated factor, 150 kDa | TAF2 | 15956246 | |
| IRINOTECAN | NM_003192 | tubulin folding cofactor C | TBCC | 15956246 | |
| IRINOTECAN | NM_003205; NM_207036; NM_207037; NM_207038; NM_207040 | transcription factor 12 | TCF12 | 18927307 | |
| IRINOTECAN | NM_030756 | transcription factor 7-like 2 (T-cell specific, HMG-box) | TCF7L2 | 18927307 | |
| IRINOTECAN | NM_005653 | transcription factor CP2 | TFCP2 | 18927307 | |
| IRINOTECAN | NM_001032281; NM_006287 | tissue factor pathway inhibitor (lipoprotein-associated coagulation inhibitor) | TFPI | 18927307 | |
| IRINOTECAN | NM_001128148; NM_003234 | transferrin receptor (p90, CD71) | TFRC | 18927307 | |
| IRINOTECAN | NM_001099691; NM_003236 | transforming growth factor, alpha | TGFA | 15723263 | |
| IRINOTECAN | NM_000358 | transforming growth factor, beta-induced, 68 kDa | TGFBI | 18927307 | |
| IRINOTECAN | NM_053055 | thioesterase superfamily member 4 | THEM4 | 18927307 | |
| IRINOTECAN | NM_024838 | threonine synthase-like 1 (S. cerevisiae) | THNSL1 | 18927307 | |

TABLE 1-continued

| Molecule | RefSeq | Description | Symbol | PMID | Interaction |
|---|---|---|---|---|---|
| IRINOTECAN | NM_005119 | thyroid hormone receptor associated protein 3 | THRAP3 | 18927307 | |
| IRINOTECAN | NM_006288 | Thy-1 cell surface antigen | THY1 | 15956246 | |
| IRINOTECAN | NM_052932 | transmembrane protein 123 | TMEM123 | 18927307 | |
| IRINOTECAN | NM_015012 | transmembrane protein 41B | TMEM41B | 15956246 | |
| IRINOTECAN | NM_021109 | thymosin beta 4, X-linked | TMSB4X | 16364925 | |
| IRINOTECAN | NM_007115 | tumor necrosis factor, alpha-induced protein 6 | TNFAIP6 | 15956246 | |
| IRINOTECAN | NM_005749 | transducer of ERBB2, 1 | TOB1 | 15956246 | |
| IRINOTECAN | NM_016272 | transducer of ERBB2, 2 | TOB2 | 15956246 | |
| IRINOTECAN | NM_003286 | topoisomerase (DNA) I | TOP1 | 11914913, 15655543, 18509181 | |
| IRINOTECAN | NM_052963 | topoisomerase (DNA) I, mitochondrial | TOP1MT | | |
| IRINOTECAN | NM_001067 | topoisomerase (DNA) II alpha 170 kDa | TOP2A | 15239142, 15956246 | |
| IRINOTECAN | NM_005802 | topoisomerase I binding, arginine/serine-rich | TOPORS | 15956246 | |
| IRINOTECAN | NM_000546; NM_001126112; NM_001126113; NM_001126114; NM_001126115; NM_001126116; NM_001126117 | tumor protein p53 | TP53 | 16373703 | |
| IRINOTECAN | NM_001135733; NM_033285 | tumor protein p53 inducible nuclear protein 1 | TP53INP1 | 18927307 | |
| IRINOTECAN | NM_000367 | thiopurine S-methyltransferase | TPMT | 18927307 | |
| IRINOTECAN | NM_007030 | tubulin polymerization promoting protein | TPPP | 18927307 | |
| IRINOTECAN | NM_012112 | TPX2, microtubule-associated, homolog (Xenopus laevis) | TPX2 | 15956246 | |
| IRINOTECAN | NM_003789 | TNFRSF1A-associated via death domain | TRADD | 15956246 | |
| IRINOTECAN | NM_005658 | TNF receptor-associated factor 1 | TRAF1 | 15956246 | |
| IRINOTECAN | NM_025195 | tribbles homolog 1 (Drosophila) | TRIB1 | 18927307 | |
| IRINOTECAN | NM_021643 | tribbles homolog 2 (Drosophila) | TRIB2 | 18927307 | |
| IRINOTECAN | NM_033017; NM_033091 | tripartite motif-containing 4 | TRIM4 | 18927307 | |
| IRINOTECAN | NM_015163; NM_052978 | tripartite motif-containing 9 | TRIM9 | 18927307 | |
| IRINOTECAN | NM_003318 | TTK protein kinase | TTK | 15956246 | |
| IRINOTECAN | NM_001113755; NM_011113756; NM_001953 | thymidine phosphorylase | TYMP | 17454858 | |
| IRINOTECAN | NM_001071 | thymidylate synthetase | TYMS | 10482907, 17454858 | |
| IRINOTECAN | NM_007019; NM_181799; NM_181800; NM_181801; NM_181802; NM_181803 | ubiquitin-conjugating enzyme E2C | UBE2C | 15956246 | |
| IRINOTECAN | NM_006357; NM_182678 | ubiquitin-conjugating enzyme E2E 3 (UBC4/5 homolog, yeast) | UBE2E3 | 18927307 | |
| IRINOTECAN | NM_058167; NM_194315; NM_194457; NM_194458 | ubiquitin-conjugating enzyme E2, J2 (UBC6 homolog, yeast) | UBE2J2 | 18927307 | |
| IRINOTECAN | NM_015984 | ubiquitin carboxyl-terminal hydrolase L5 | UCHL5 | 15956246 | |
| IRINOTECAN | NM_020121 | UDP-glucose ceramide glucosyltransferase-like 2 | UGCGL2 | 18927307 | |
| IRINOTECAN | NM_000463 | UDP glucuronosyltransferase 1 family, polypeptide A1 | UGT1A1 | 12960109, 15517893, 15523087, 15833930, 17898154, 15716465, 15655543, 15858133, 17898154, 18478930, 18300238, 18797458 | |
| IRINOTECAN | NM_019075 | UDP glucuronosyltransferase 1 family, polypeptide A10 | UGT1A10 | 15517893, 17898154,15716465 | |
| IRINOTECAN | NM_001072; NM_205862 | UDP glucuronosyltransferase 1 family, polypeptide A6 | UGT1A6 | 15716465 | |
| IRINOTECAN | NM_019077 | UDP glucuronosyltransferase 1 family, polypeptide A7 | UGT1A7 | 15833930, 15716465, 17898154 | |
| IRINOTECAN | NM_019076 | UDP glucuronosyltransferase 1 family, polypeptide A8 | UGT1A8 | 15833930, 18 | |
| IRINOTECAN | NM_021027 | UDP glucuronosyltransferase 1 family, polypeptide A9 | UGT1A9 | 15833930, 18 | |
| IRINOTECAN | NM_025217 | UL16 binding protein 2 | ULBP2 | 18927307 | |
| IRINOTECAN | NM_017886 | unc-51-like kinase 4 (C. elegans) | ULK4 | 18927307 | |
| IRINOTECAN | NM_015306 | ubiquitin specific peptidase 24 | USP24 | 18927307 | |
| IRINOTECAN | — | | VDP | 18927307 | |

TABLE 1-continued

| Molecule | RefSeq | Description | Symbol | PMID | Interaction |
|---|---|---|---|---|---|
| IRINOTECAN | NM_013245 | vacuolar protein sorting 4 homolog A (*S. cerevisiae*) | VPS4A | 18927307 | |
| IRINOTECAN | NM_145206 | vesicle transport through interaction with t-SNAREs homolog 1A (yeast) | VTI1A | 18927307 | |
| IRINOTECAN | NM_015045 | wings apart-like homolog (*Drosophila*) | WAPAL | 18927307 | |
| IRINOTECAN | NM_003941 | Wiskott-Aldrich syndrome-like | WASL | 18927307 | |
| IRINOTECAN | NM_015726 | WD repeat domain 42A | WDR42A | 18927307 | |
| IRINOTECAN | NM_016087; NM_057168 | wingless-type MMTV integration site family, member 16 | WNT16 | 18927307 | |
| IRINOTECAN | NM_015626; NM_134265 | WD repeat and SOCS box-containing 1 | WSB1 | 18927307 | |
| IRINOTECAN | NM_001100161; NM_001100162; NM_015024 | exportin 7 | XPO7 | 18927307 | |
| IRINOTECAN | NM_003401; NM_022406; NM_022550 | X-ray repair complementing defective repair in Chinese hamster cells 4 | XRCC4 | 15956246 | |
| IRINOTECAN | NM_021141 | X-ray repair complementing defective repair in Chinese hamster cells 5 (double-strand-break rejoining) | XRCC5 | 18927307 | |
| IRINOTECAN | NM_005748 | YY1 associated factor 2 | YAF2 | 18927307 | |
| IRINOTECAN | NM_005433 | v-yes-1 Yamaguchi sarcoma viral oncogene homolog 1 | YES1 | 15956246 | |
| IRINOTECAN | NM_015642 | zinc finger and BTB domain containing 20 | ZBTB20 | 18927307 | |
| IRINOTECAN | NM_020119; NM_024625 | zinc finger CCCH-type, antiviral 1 | ZC3HAV1 | 18927307 | |
| IRINOTECAN | NM_173798 | zinc finger, CCHC domain containing 12 | ZCCHC12 | 18927307 | |
| IRINOTECAN | NM_178566 | zinc finger, DHHC-type containing 21 | ZDHHC21 | 18927307 | |
| IRINOTECAN | NM_001143823; NM_003409 | zinc finger protein 161 homolog (mouse) | ZFP161 | 18927307 | |
| IRINOTECAN | NM_006887 | zinc finger protein 36, C3H type-like 2 | ZFP36L2 | 15956246 | |
| IRINOTECAN | NM_003410 | zinc finger protein, X-linked | ZFX | 15956246 | |
| IRINOTECAN | NM_001032293; NM_001098507; NM_003457 | zinc finger protein 207 | ZNF207 | 18927307 | |
| IRINOTECAN | NM_001005368; NM_006973 | zinc finger protein 32 | ZNF32 | 17327601 | |
| IRINOTECAN | NM_001135215; NM_001135216; NM_030899; NM_145909 | zinc finger protein 323 | ZNF323 | 18927307 | |
| IRINOTECAN | NM_022752 | zinc finger protein 574 | ZNF574 | 18927307 | |
| IRINOTECAN | NM_144690 | zinc finger protein 582 | ZNF582 | 17327601 | |
| IRINOTECAN | NM_024706 | zinc finger protein 668 | ZNF668 | 18927307 | |
| IRINOTECAN | NM_032268 | zinc and ring finger 1 | ZNRF1 | 17327601 | |
| IRINOTECAN | NM_005089 | zinc finger (CCCH type), RNA-binding motif and serine/arginine rich 2 | ZRSR2 | 17327601 | |
| ETOPOSIDE | NM_000927 | ATP-binding cassette, sub-family B (MDR/TAP), member 1 | ABCB1 | 12969965, 15239124 | resistance |
| ETOPOSIDE | NM_004996; NM_019862; NM_019898; NM_019899; NM_019900 | ATP-binding cassette, sub-family C (CFTR/MRP), member 1 | ABCC1 | 10900222, 12067707, 15460906, 15617835, 15999103, 16156793, 10900222, 16156793 | resistance |
| ETOPOSIDE | NM_000392 | ATP-binding cassette, sub-family C (CFTR/MRP), member 2 | ABCC2 | 15751272, 15849751, 15849751 | resistance |
| ETOPOSIDE | NM_001144070; NM_003786 | ATP-binding cassette, sub-family C (CFTR/MRP), member 3 | ABCC3 | 15884115 | resistance |
| ETOPOSIDE | NM_198576 | agrin | AGRN | 17374387 | |
| ETOPOSIDE | NM_001014431; NM_001014432; NM_005163 | v-akt murine thymoma viral oncogene homolog 1 | AKT1 | 17935137 | |
| ETOPOSIDE | NM_000691; NM_001135167; NM_001135168 | aldehyde dehydrogenase 3 family, memberA1 | ALDH3A1 | 15905174 | |
| ETOPOSIDE | NM_001153 | annexin A4 | ANXA4 | 17374387 | |
| ETOPOSIDE | NM_001657 | amphiregulin | AREG | 15228094 | |
| ETOPOSIDE | NM_001675; NM_182810 | activating transcription factor 4 (tax-responsive enhancer element B67) | ATF4 | 16298333 | |
| ETOPOSIDE | NM_001188 | BCL2-antagonist/killer 1 | BAK1 | 15215046 | |

TABLE 1-continued

| Molecule | RefSeq | Description | Symbol | PMID | Interaction |
|---|---|---|---|---|---|
| ETOPOSIDE | NM_000633; NM_000657 | B-cell CLL/lymphoma 2 | BCL2 | 15917659 | |
| ETOPOSIDE | NM_001191; NM_138578 | BCL2-like 1 | BCL2L1 | 11468182, 15215046, 15917659 | |
| ETOPOSIDE | NM_004050 | BCL2-like 2 | BCL2L2 | 14973057 | |
| ETOPOSIDE | NM_001197 | BCL2-interacting killer (apoptosis-inducing) | BIK | 16007125 | |
| ETOPOSIDE | NM_001166; NM_182962 | baculoviral IAP repeat-containing 2 | BIRC2 | 10815900, 15050749, 14970392 | |
| ETOPOSIDE | NM_001165; NM_182962 | baculoviral IAP repeat-containing 3 | BIRC3 | 14666661, 15050749 | |
| ETOPOSIDE | NM_001012270; NM_001012271; NM_001168 | baculoviral IAP repeat-containing 5 | BIRC5 | 15917659, 16382892, 16322251, 16364925 | |
| ETOPOSIDE | NM_007294; NM_007295; NM_007296; NM_007297; NM_007298; NM_007299; NM_007300; NM_007302; NM_007303; NM_007304; NM_007305 | breast cancer 1, early onset | BRCA1 | 16417649 | |
| ETOPOSIDE | NM_001729 | betacellulin | BTC | 15228094 | |
| ETOPOSIDE | NM_001130849; NM_001130850; NM_016289 | calcium binding protein 39 | CAB39 | 17374387 | |
| ETOPOSIDE | NM_001033952; NM_001033953; NM_001741 | calcitonin-related polypeptide alpha | CALCA | 16222118 | |
| ETOPOSIDE | NM_032982; NM_032983 | caspase 2, apoptosis-related cysteine peptidase | CASP2 | 14757846 | |
| ETOPOSIDE | NM_004346; NM_032991 | caspase 3, apoptosis-related cysteine peptidase | CASP3 | 15215046, 16364925, 16844113, 16951922, 17935137, 18056177, 16844113, 16364925, 18056177, 16364925, 16844113, 16951922 | |
| ETOPOSIDE | NM_001227; NM_033338; NM_033339; NM_033340 | caspase 7, apoptosis-related cysteine peptidase | CASP7 | 16298333, 18056177 | |
| ETOPOSIDE | NM_001229; NM_032996 | caspase 9, apoptosis-related cysteine peptidase | CASP9 | 15215046, 16364925, 17935137, 18056177 | |
| ETOPOSIDE | NM_001237 | cyclin A2 | CCNA2 | 17390037 | |
| ETOPOSIDE | NM_004354 | cyclin G2 | CCNG2 | 18754885 | |
| ETOPOSIDE | NM_000610; NM_001001389; NM_001001390; NM_001001391; NM_001001392 | CD44 molecule (Indian blood group) | CD44 | 15215046 | |
| ETOPOSIDE | NM_001798; NM_052827 | cyclin-dependent kinase 2 | CDK2 | 16417649 | |
| ETOPOSIDE | NM_000389; NM_078467 | cyclin-dependent kinase inhibitor 1A (p21, Cip1) | CDKN1A | 14601052 | |
| ETOPOSIDE | NM_004064 | cyclin-dependent kinase inhibitor 1B (p27, Kip1) | CDKN1B | 17935137 | |
| ETOPOSIDE | NM_001024912; NM_001712 | carcinoembryonic antigen-related cell adhesion molecule 1 (biliary glycoprotein) | CEACAM1 | 17374387 | |
| ETOPOSIDE | NM_005760 | CCAAT/enhancer binding protein (C/EBP), zeta | CEBPZ | 17374387 | |
| ETOPOSIDE | NM_001127183; NM_001127184; NM_003879 | CASP8 and FADD-like apoptosis regulator | CFLAR | 14601052 | |
| ETOPOSIDE | NM_001114121; NM_001114122; NM_001274 | CHK1 checkpoint homolog (S. pombe) | CHEK1 | 18698031 | |
| ETOPOSIDE | NM_020313 | cytokine induced apoptosis inhibitor 1 | CIAPIN1 | 18389626 | |
| ETOPOSIDE | NM_000785 | cytochrome P450, family 27, subfamily B, polypeptide 1 | CYP27B1 | 17716971 | |
| ETOPOSIDE | NM_000762 | cytochrome P450, family 2, subfamily A, polypeptide 6 | CYP2A6 | 8114683 | unrelated |
| ETOPOSIDE | NM_000767 | cytochrome P450, family 2, subfamily B, polypeptide 6 | CYP2B6 | 8114683 | unrelated |
| ETOPOSIDE | NM_000770 | cytochrome P450, family 2, subfamily C, polypeptide 8 | CYP2C8 | 8114683 | unrelated |
| ETOPOSIDE | NM_000771 | cytochrome P450, family 2, subfamily C, polypeptide 9 | CYP2C9 | 8114683 | unrelated |
| ETOPOSIDE | NM_017460 | cytochrome P450, family 3, subfamily A, polypeptide 4 | CYP3A4 | 12969965, 17279585, 8114683 | drug metabolism |
| ETOPOSIDE | NM_000777 | cytochrome P450, family 3, subfamily A, polypeptide 5 | CYP3A5 | 12969965, 8114683 | drug metabolism |
| ETOPOSIDE | NM_004083 | DNA-damage-inducible transcript 3 | DDIT3 | 16298333 | |
| ETOPOSIDE | NM_001963 | epidermal growth factor (beta-urogastrone) | EGF | 15228094, 16969495 | |
| ETOPOSIDE | NM_005228; NM_201282; NM_201283; NM_201284 | epidermal growth factor receptor (erythroblastic leukemia viral (v-erb-b) oncogene homolog, avian) | EGFR | 15228094 | |

TABLE 1-continued

| Molecule | RefSeq | Description | Symbol | PMID | Interaction |
|---|---|---|---|---|---|
| ETOPOSIDE | NM_001007277; NM_004879 | etoposide induced 2.4 mRNA | EI24 | 17374387 | |
| ETOPOSIDE | NM_014805 | EPM2A (laforin) interacting protein 1 | EPM2AIP1 | 17374387 | |
| ETOPOSIDE | NM_001005862; NM_004448 | v-erb-b2 erythroblastic leukemia viral oncogene homolog 2, neuro/glioblastoma derived oncogene homolog (avian) | ERBB2 | 15228094 | |
| ETOPOSIDE | NM_001005915; NM_001982 | v-erb-b2 erythroblastic leukemia viral oncogene homolog 3 (avian) | ERBB3 | 15228094 | |
| ETOPOSIDE | NM_001042599; NM_005235 | v-erb-a erythroblastic leukemia viral oncogene homolog 4 (avian) | ERBB4 | 15228094 | |
| ETOPOSIDE | NM_001432 | epiregulin | EREG | 15228094 | |
| ETOPOSIDE | NM_001987 | ets variant 6 | ETV6 | 15217836 | |
| ETOPOSIDE | NM_004110; NM_024417 | ferredoxin reductase | FDXR | 17374387 | |
| ETOPOSIDE | NM_002015 | forkhead box O1 | FOXO1 | 17935137 | |
| ETOPOSIDE | NM_001455; NM_201559 | forkhead box O3 | FOXO3 | 17935137 | |
| ETOPOSIDE | NM_001924 | growth arrest and DNA-damage-inducible, alpha | GADD45A | 19003803 | |
| ETOPOSIDE | NM_001498 | glutamate-cysteine ligase, catalytic subunit | GCLC | 10900222 | |
| ETOPOSIDE | NM_002061 | glutamate-cysteine ligase, modifier subunit | GCLM | 10900222 | |
| ETOPOSIDE | NM_000561; NM_146421 | glutathione S-transferase mu 1 | GSTM1 | 15713801 | |
| ETOPOSIDE | NM_000852 | glutathione S-transferase pi 1 | GSTP1 | 10900222, 15999103, 16298333 | 10900222, 12969965, 15999103, 10900222 |
| ETOPOSIDE | NM_001945 | heparin-binding EGF-like growth factor | HBEGF | 15228094 | |
| ETOPOSIDE | NM_005347 | heat shock 70 kDa protein 5 (glucose-regulated protein, 78 kDa) | HSPA5 | 16298333 | |
| ETOPOSIDE | NM_000875 | insulin-like growth factor 1 receptor | IGF1R | 15499378 | |
| ETOPOSIDE | NM_002756; NM_145109 | mitogen-activated protein kinase kinase 3 | MAP2K3 | 17374387 | |
| ETOPOSIDE | NM_145185 | mitogen-activated protein kinase kinase 7 | MAP2K7 | — | |
| ETOPOSIDE | NM_005923 | mitogen-activated protein kinase kinase kinase 5 | MAP3K5 | 17374387 | |
| ETOPOSIDE | NM_021960; NM_182763 | myeloid cell leukemia sequence 1 (BCL2-related) | MCL1 | 17935137 | |
| ETOPOSIDE | NM_001145336; NM_001145337; NM_001145339; NM_001145340; NM_002392; NM_006878; NM_006879; NM_006881; NM_006882 | Mdm2 p53 binding protein homolog (mouse) | MDM2 | 17575151, 17935137 | resistance |
| ETOPOSIDE | NM_001004720; NM_001004722; NM_003581 | NCK adaptor protein 2 | NCK2 | 17935137 | |
| ETOPOSIDE | NM_020529 | nuclear factor of kappa light polypeptide gene enhancer in B-cells inhibitor, alpha | NFKBIA | 17935137 | |
| ETOPOSIDE | NM_003889; NM_022002; NM_033013 | nuclear receptor subfamily 1, group I, member 2 | NR1I2 | 17279585 | |
| ETOPOSIDE | NM_001618 | poly (ADP-ribose) polymerase 1 | PARP1 | 17935137, 17935137, 16844113 | |
| ETOPOSIDE | NM_004073 | polo-like kinase 3 | PLK3 | 17374387 | |
| ETOPOSIDE | NM_003981; NM_199413; NM_199414 | protein regulator of cytokinesis 1 | PRC1 | 17374387 | |
| ETOPOSIDE | NM_000311; NM_001080121; NM_001080122; NM_183079 | prion protein | PRNP | 15386405 | |
| ETOPOSIDE | NM_000314 | phosphatase and tensin homolog | PTEN | 17935137 | |
| ETOPOSIDE | NM_134424 | RAD52 homolog (S. cerevisiae) | RAD52 | 16417649 | |
| ETOPOSIDE | NM_001142548; NM_003579 | RAD54-like (S. cerevisiae) | RAD54L | 16417649 | |
| ETOPOSIDE | NM_001145547; NM_032905 | RNA binding motif protein 17 | RBM17 | 16061639 | |
| ETOPOSIDE | NM_001001890; NM_001122607; NM_001754 | runt-related transcription factor 1 | RUNX1 | 15217836 | |
| ETOPOSIDE | NM_001031680; NM_004350 | runt-related transcription factor 3 | RUNX3 | 15756676 | |
| ETOPOSIDE | NM_005980 | S100 calcium binding protein P | S100P | 18636193 | |
| ETOPOSIDE | NM_001006946; NM_002997 | syndecan 1 | SDC1 | 17374387 | |
| ETOPOSIDE | NM_000593 | transporter 1, ATP-binding cassette, sub-family B (MDR/TAP) | TAP1 | 17374387 | resistance |

TABLE 1-continued

| Molecule | RefSeq | Description | Symbol | PMID | Interaction |
|---|---|---|---|---|---|
| ETOPOSIDE | NM_014604 | Tax1 (human T-cell leukemia virus type I) binding protein 3 | TAX1BP3 | 17374387 | |
| ETOPOSIDE | NM_001099691; NM_003236 | transforming growth factor, alpha | TGFA | 15228094 | |
| ETOPOSIDE | NM_021109 | thymosin beta 4, X-linked | TMSB4X | 16364925 | |
| ETOPOSIDE | NM_003844 | tumor necrosis factor receptor superfamily, member 10a | TNFRSF10A | 16364925 | |
| ETOPOSIDE | NM_003842; NM_147187 | tumor necrosis factor receptor superfamily, member 10b | TNFRSF10B | 15964798, 16364925 | |
| ETOPOSIDE | NM_003810 | tumor necrosis factor (ligand) superfamily, member 10 | TNFSF10 | 16364925 | |
| ETOPOSIDE | NM_003811 | tumor necrosis factor (ligand) superfamily, member 9 | TNFSF9 | 17374387 | |
| ETOPOSIDE | NM_001067 | topoisomerase (DNA) II alpha 170 kDa | TOP2A | 11470519, 11531262, 11676865, 12569090, 16969495, 17575151 | |
| ETOPOSIDE | NM_001068 | topoisomerase (DNA) II beta 180 kDa | TOP2B | 15322234, 16239602 | |
| ETOPOSIDE | NM_000546; NM_001126112; NM_001126113; NM_001126114; NM_001126115; NM_001126116; NM_001126117 | tumor protein p53 | TP53 | 12082016, 15964798, 18698031 | |
| ETOPOSIDE | NM_004881; NM_147184 | tumor protein p53 inducible protein 3 | TP53I3 | 17374387 | |
| ETOPOSIDE | NR_015381; NR_015381; NR_015381; NR_015381; NR_015381; NR_015381; NR_015381 | TP53 target 1 (non-protein coding) | TP53TG1 | 17374387 | |
| ETOPOSIDE | NM_001126240; NM_001126241; NM_001126242; NM_005427 | tumor protein p73 | TP73 | 17716971 | |
| ETOPOSIDE | NM_001071 | thymidylate synthetase | TYMS | 15713801 | |
| ETOPOSIDE | NM_007019; NM_181799; NM_181800; NM_181801; NM_181802; NM_181803 | ubiquitin-conjugating enzyme E2C | UBE2C | 17374387 | |
| ETOPOSIDE | NM_000463 | UDP glucuronosyltransferase 1 family, polypeptide A1 | UGT1A1 | 12969965, 17151191 | |
| ETOPOSIDE | NM_019093 | UDP glucuronosyltransferase 1 family, polypeptide A3 | UGT1A3 | 17151191 | |
| ETOPOSIDE | NM_019076 | UDP glucuronosyltransferase 1 family, polypeptide A8 | UGT1A8 | 17151191 | |
| ETOPOSIDE | NM_000376; NM_001017535 | vitamin D (1,25-dihydroxyvitamin D3) receptor | VDR | 12969965, 15713801, 17716971 | |
| ETOPOSIDE | NM_001025366; NM_001025367; NM_001025368; NM_001025369; NM_001025370; NM_001033756; NM_003376 | vascular endothelial growth factor A | VEGFA | 18494554 | |
| ETOPOSIDE | NM_000553 | Werner syndrome, RecQ helicase-like | WRN | 10725663 | |
| ETOPOSIDE | NM_017523; NM_199139 | XIAP associated factor 1 | XAF1 | 15843754 | |
| ETOPOSIDE | NM_001167 | X-linked inhibitor of apoptosis | XIAP | 14666661 | |
| ETOPOSIDE | NM_005431 | X-ray repair complementing defective repair in Chinese hamster cells 2 | XRCC2 | 16417649 | |
| ETOPOSIDE | NM_001100118; NM_001100119; NM_005432 | X-ray repair complementing defective repair in Chinese hamster cells 3 | XRCC3 | 16417649 | |
| ETOPOSIDE | NM_003401; NM_022406; NM_022550 | X-ray repair complementing defective repair in Chinese hamster cells 4 | XRCC4 | 16417649 | |
| ETOPOSIDE | NM_021141 | X-ray repair complementing defective repair in Chinese hamster cells 5 (double-strand-break rejoining) | XRCC5 | 12384553 | |
| BEXAROTENE | NM_001121; NM_016824; NM_019903 | adducin 3 (gamma) | ADD3 | 17178900 | |
| BEXAROTENE | NM_000024 | adrenergic, beta-2-, receptor, surface | ADRB2 | 17178900 | |
| BEXAROTENE | NM_001353 | aldo-keto reductase family 1, member C1 (dihydrodiol dehydrogenase 1; 20-alpha (3-alpha)-hydroxysteroid dehydrogenase) | AKR1C1 | 17178900 | |
| BEXAROTENE | NM_003739 | aldo-keto reductase family 1, member C3 (3-alpha hydroxysteroid dehydrogenase, type II) | AKR1C3 | 17178900 | |
| BEXAROTENE | NM_016201 | angiomotin like 2 | AMOTL2 | 17178900 | |

TABLE 1-continued

| Molecule | RefSeq | Description | Symbol | PMID | Interaction |
|---|---|---|---|---|---|
| BEXAROTENE | NM_006407 | ADP-ribosylation-like factor 6 interacting protein 5 | ARL6IP5 | 17178900 | |
| BEXAROTENE | NM_001673; NM_133436; NM_183356 | asparagine synthetase | ASNS | 17178900 | |
| BEXAROTENE | NM_004330 | BCL2/adenovirus E1B 19 kDa interacting protein 2 | BNIP2 | 17178900 | |
| BEXAROTENE | — | — | C10ORF10 | 17178900 | |
| BEXAROTENE | — | — | C10ORF116 | 17178900 | |
| BEXAROTENE | NM_001806 | CCAAT/enhancer binding protein (C/EBP), gamma | CEBPG | 17178900 | |
| BEXAROTENE | NM_001902; NM_153742 | cytochrome c oxidase II | COX2 | 17178900 | |
| BEXAROTENE | NM_004390; NM_148979 | cystathionase (cystathionine gamma-lyase) | CTH | 17178900 | |
| BEXAROTENE | NM_018947 | cathepsin H | CTSH | 17178900 | |
| BEXAROTENE | NM_000783; NM_057157 | cytochrome c, somatic | CYCS | 17178900 | |
| BEXAROTENE | NM_001554 | cytochrome P450, family 26, subfamily A, polypeptide 1 | CYP26A1 | 17178900 | |
| BEXAROTENE | NM_019058 | cysteine-rich, angiogenic inducer, 61 | CYR61 | 17178900 | |
| BEXAROTENE | NM_004753 | DNA-damage-inducible transcript 4 | DDIT4 | 17178900 | |
| BEXAROTENE | NM_012242 | dehydrogenase/reductase (SDR family) member 3 | DHRS3 | 17178900 | |
| BEXAROTENE | NM_004417 | dickkopf homolog 1 (Xenopus laevis) | DKK1 | 17178900 | |
| BEXAROTENE | NM_004419 | dual specificity phosphatase 1 | DUSP1 | 17178900 | |
| BEXAROTENE | NM_004430 | dual specificity phosphatase 5 | DUSP5 | 17178900 | |
| BEXAROTENE | NM_005801 | early growth response 3 | EGR3 | 17178900 | |
| BEXAROTENE | NM_004431 | eukaryotic translation initiation factor 1 | EIF1 | 17178900 | |
| BEXAROTENE | NM_002047 | EPH receptor A2 | EPHA2 | 17178900 | |
| BEXAROTENE | NM_001001994; NM_001001995; NM_001001996; NM_005278 | glycyl-tRNA synthetase | GARS | 17178900 | |
| BEXAROTENE | NM_001010989; NM_001010990; NM_014685 | glycoprotein M6B | GPM6B | 17178900 | |
| BEXAROTENE | NM_002165; NM_181353 | homocysteine-inducible, endoplasmic reticulum stress-inducible, ubiquitin-like domain member 1 | HERPUD1 | 17178900 | |
| BEXAROTENE | NM_004907 | inhibitor of DNA binding 1, dominant negative helix-loop-helix protein | ID1 | 17178900 | |
| BEXAROTENE | NM_002178 | immediate early response 2 | IER2 | 17178900 | |
| BEXAROTENE | NM_000585; NM_172174 | insulin-like growth factor binding protein 6 | IGFBP6 | 17178900 | |
| BEXAROTENE | NM_000888 | interleukin 15 | IL15 | 17178900 | |
| BEXAROTENE | NM_004867 | integrin, beta 6 | ITGB6 | 17178900 | |
| BEXAROTENE | NM_001099952; NM_002222 | integral membrane protein 2A | ITM2A | 17178900 | |
| BEXAROTENE | NM_001032282; NM_005655 | inositol 1,4,5-triphosphate receptor, type 1 | ITPR1 | 17178900 | |
| BEXAROTENE | NM_002275 | Kruppel-like factor 10 | KLF10 | 17178900 | |
| BEXAROTENE | NM_000422 | keratin 15 | KRT15 | 17178900 | |
| BEXAROTENE | NM_002318 | keratin 17 | KRT17 | 17178900 | |
| BEXAROTENE | NM_001031804; NM_005360 | lysyl oxidase-like 2 | LOXL2 | 17178900 | |
| BEXAROTENE | NM_001161572; NM_001161573; NM_001161574; NM_012323; NM_152878 | v-maf musculoaponeurotic fibrosarcoma oncogene homolog (avian) | MAF | 17178900 | |
| BEXAROTENE | NM_006818 | v-maf musculoaponeurotic fibrosarcoma oncogene homolog F (avian) | MAFF | 17178900 | |
| BEXAROTENE | NM_002421 | myeloid/lymphoid or mixed-lineage leukemia (trithorax homolog, Drosophila); translocated to, 11 | MLLT11 | 17178900 | |
| BEXAROTENE | NM_006636 | matrix metallopeptidase 1 (interstitial collagenase) | MMP1 | 17178900 | |
| BEXAROTENE | NM_002539 | methylenetetrahydrofolate dehydrogenase (NADP+ dependent) 2, methenyltetrahydrofolate cyclohydrolase | MTHFD2 | 17178900 | |
| BEXAROTENE | NM_022817 | ornithine decarboxylase 1 | ODC1 | 17178900 | |
| BEXAROTENE | NM_000930; NM_033011 | period homolog 2 (Drosophila) | PER2 | 17178900 | |
| BEXAROTENE | NM_001005376; NM_001005377; NM_002659 | plasminogen activator, urokinase receptor | PLAUR | 17178900 | |
| BEXAROTENE | NM_000935; NM_182943 | procollagen-lysine, 2-oxoglutarate 5-dioxygenase 2 | PLOD2 | 17178900 | |

TABLE 1-continued

| Molecule | RefSeq | Description | Symbol | PMID | Interaction |
|---|---|---|---|---|---|
| BEXAROTENE | NM_020143 | partner of NOB1 homolog (*S. cerevisiae*) | PNO1 | 17178900 | |
| BEXAROTENE | NM_006813 | proline-rich nuclear receptor coactivator 1 | PNRC1 | 17178900 | |
| BEXAROTENE | NM_000965; NM_016152 | retinoic acid receptor, beta | RARB | 17178900 | |
| BEXAROTENE | NM_000321 | retinoblastoma 1 | RB1 | 16273314 | |
| BEXAROTENE | NM_021976 | retinoid X receptor, beta | RXRB | — | |
| BEXAROTENE | NM_002965 | S100 calcium binding protein A9 | S100A9 | 17178900 | |
| BEXAROTENE | NM_005063 | stearoyl-CoA desaturase (delta-9-desaturase) | SCD | 17178900 | |
| BEXAROTENE | NM_003016 | splicing factor, arginine/serine-rich 2 | SFRS2 | 17178900 | |
| BEXAROTENE | NM_005067 | seven in absentia homolog 2 (*Drosophila*) | SIAH2 | 17178900 | |
| BEXAROTENE | NM_003045 | solute carrier family 7 (cationic amino acid transporter, y+ system), member 1 | SLC7A1 | 17178900 | |
| BEXAROTENE | NM_003486 | solute carrier family 7 (cationic amino acid transporter, y+ system), member 5 | SLC7A5 | 17178900 | |
| BEXAROTENE | NM_001001419; NM_001001420; NM_005903 | SMAD family member 5 | SMAD5 | 17178900 | |
| BEXAROTENE | NM_003118 | secreted protein, acidic, cysteine-rich (osteonectin) | SPARC | 17178900 | |
| BEXAROTENE | NM_004613; NM_198951 | transglutaminase 2 (C polypeptide, protein-glutamine-gamma-glutamyltransferase) | TGM2 | 17178900 | |
| BEXAROTENE | NM_014220 | transmembrane 4 L six family member 1 | TM4SF1 | 17178900 | |
| BEXAROTENE | NM_001015881; NM_004089; NM_198057 | TSC22 domain family, member 3 | TSC22D3 | 17178900 | |
| BEXAROTENE | NM_003115 | UDP-N-acetylglucosamine pyrophosphorylase 1 | UAP1 | 17178900 | |
| BEXAROTENE | NM_003761 | vesicle-associated membrane protein 8 (endobrevin) | VAMP8 | 17178900 | |
| BEXAROTENE | NM_001079539; NM_005080 | X-box binding protein 1 | XBP1 | 17178900 | |
| CETUXIMAB | NM_001963 | epidermal growth factor (beta-urogastrone) | EGF | — | |
| CETUXIMAB | NM_005228; NM_201282; NM_201283; NM_201284 | epidermal growth factor receptor (erythroblastic leukemia viral (v-erb-b) oncogene homolog, avian) | EGFR | — | target |
| CETUXIMAB | NM_001432 | epiregulin | EREG | — | |
| TRASTUZUMAB | NM_001963 | epidermal growth factor (beta-urogastrone) | EGF | — | |
| TRASTUZUMAB | NM_005228; NM_201282; NM_201283; NM_201284 | epidermal growth factor receptor (erythroblastic leukemia viral (v-erb-b) oncogene homolog, avian) | EGFR | — | resistance |
| TRASTUZUMAB | NM_001005862; NM_004448 | v-erb-b2 erythroblastic leukemia viral oncogene homolog 2, neuro/glioblastoma derived oncogene homolog (avian) | ERBB2 | — | target |
| TRASTUZUMAB | NM_001432 | epiregulin | EREG | — | |
| RITUXIMAB | NM_021950; NM_152866 | membrane-spanning 4-domains, subfamily A, member 1 | MS4A1 | — | target |
| TOSITUMOMAB | NM_021950; NM_152866 | membrane-spanning 4-domains, subfamily A, member 1 | MS4A1 | — | target |
| ALEMTUZUMAB | NM_001803 | CD52 molecule | CD52 | — | target |
| BEVACIZUMAB | NM_001025366; NM_001025367; NM_001025368; NM_001025369; NM_001025370; NM_001033756; NM_003376 | vascular endothelial growth factor A | VEGFA | — | target |
| EDRECOLOMAB | — | | TACSTD1 | — | target |
| GEMTUZUMAB | NM_001082618; NM_001772 | CD33 molecule | CD33 | — | target |
| AXITINIB | NM_001160030; NM_001160031; NM_002019 | fms-related tyrosine kinase 1 (vascular endothelial growth factor/vascular permeability factor receptor) | FLT1 | — | target |
| AXITINIB | NM_002020; NM_182925 | fms-related tyrosine kinase 4 | FLT4 | — | target |
| AXITINIB | NM_002253 | kinase insert domain receptor (a type III receptor tyrosine kinase) | KDR | — | target |
| AXITINIB | NM_000222; NM_001093772 | v-kit Hardy-Zuckerman 4 feline sarcoma viral oncogene homolog | KIT | — | target |
| AXITINIB | NM_006206 | platelet-derived growth factor receptor, alpha polypeptide | PDGFRA | — | target |

TABLE 1-continued

| Molecule | RefSeq | Description | Symbol | PMID | Interaction |
|---|---|---|---|---|---|
| AXITINIB | NM_002609 | platelet-derived growth factor receptor, beta polypeptide | PDGFRB | 17114238 | target |
| BOSUTINIB | — | — | ABL | — | |
| BOSUTINIB | NM_005157; NM_007313 | c-abl oncogene 1, receptor tyrosine kinase | ABL1 | 16489032 | target |
| BOSUTINIB | NM_004327; NM_021574 | breakpoint cluster region | BCR | 16489032 | |
| BOSUTINIB | NM_053056 | cyclin D1 | CCND1 | 16489032 | |
| BOSUTINIB | NM_004360 | cadherin 1, type 1, E-cadherin (epithelial) | CDH1 | 16489032 | |
| BOSUTINIB | NM_001098209; NM_001098210; NM_001904 | catenin (cadherin-associated protein), beta 1, 88 kDa | CTNNB1 | 16489032 | |
| BOSUTINIB | NM_005417; NM_198291 | v-src sarcoma (Schmidt-Ruppin A-2) viral oncogene homolog (avian) | SRC | 16489032 | target |
| BOSUTINIB | NM_001083962; NM_003199 | transcription factor 4 | TCF4 | 16489032 | |
| CEDIRANIB | NM_001160030; NM_001160031; NM_002019 | fms-related tyrosine kinase 1 (vascular endothelial growth factor/vascular permeability factor receptor) | FLT1 | | target |
| CEDIRANIB | NM_002020; NM_182925 | fms-related tyrosine kinase 4 | FLT4 | | target |
| DASATINIB | NM_005157; NM_007313 | c-abl oncogene 1, receptor tyrosine kinase | ABL1 | | target |
| DASATINIB | NM_001100108; NM_001136000; NM_001136001; NM_005158; NM_007314 | v-abl Abelson murine leukemia viral oncogene homolog 2 (arg, Abelson-related gene) | ABL2 | | target ? |
| DASATINIB | NM_004327; NM_021574 | breakpoint cluster region | BCR | | |
| DASATINIB | NM_004431 | EPH receptor A2 | EPHA2 | | target |
| DASATINIB | NM_002037; NM_153047; NM_153048 | FYN oncogene related to SRC, FGR, YES | FYN | | |
| DASATINIB | NM_000222; NM_001093772 | v-kit Hardy-Zuckerman 4 feline sarcoma viral oncogene homolog | KIT | | target |
| DASATINIB | NM_001042771; NM_005356 | lymphocyte-specific protein tyrosine kinase | LCK | | target |
| DASATINIB | NM_002609 | platelet-derived growth factor receptor, beta polypeptide | PDGFRB | | target |
| DASATINIB | NM_005417; NM_198291 | v-src sarcoma (Schmidt-Ruppin A-2) viral oncogene homolog (avian) | SRC | | target |
| DASATINIB | NM_012448 | signal transducer and activator of transcription 5B | STAT5B | | |
| DASATINIB | NM_005433 | v-yes-1 Yamaguchi sarcoma viral oncogene homolog 1 | YES1 | | |
| ERLOTINIB | NM_001963 | epidermal growth factor (beta-urogastrone) | EGF | | |
| ERLOTINIB | NM_005228; NM_201282; NM_201283; NM_201284 | epidermal growth factor receptor (erythroblastic leukemia viral (v-erb-b) oncogene homolog, avian) | EGFR | 12907618 | target |
| ERLOTINIB | NM_001432 | epiregulin | EREG | | |
| GEFITINIB | NM_004827 | ATP-binding cassette, sub-family G (WHITE), member 2 | ABCG2 | 17938326 | resistance |
| GEFITINIB | NM_000674; NM_001048230 | adenosine A1 receptor | ADORA1 | 16685379 | |
| GEFITINIB | NM_001014431; NM_001014432; NM_005163 | v-akt murine thymoma viral oncogene homolog 1 | AKT1 | 17805209 | |
| GEFITINIB | NM_001657 | amphiregulin | AREG | 15496427, 16230376, 15723263 | sensitivity/resistence |
| GEFITINIB | NM_020714 | apoptosis, caspase activation inhibitor | AVEN | 15496427 | |
| GEFITINIB | NM_006568 | cell growth regulator with ring finger domain 1 | CGRRF1 | 16685379 | |
| GEFITINIB | NM_001130105; NM_005713; NM_031361 | collagen, type IV, alpha 3 (Goodpasture antigen) binding protein | COL4A3BP | 15496427 | |
| GEFITINIB | NM_014325 | coronin, actin binding protein, 1C | CORO1C | 15496427 | unrelated |
| GEFITINIB | NM_000761 | cytochrome P450, family 1, subfamily A, polypeptide 2 | CYP1A2 | 15788367 | unrelated |
| GEFITINIB | NM_000769 | cytochrome P450, family 2, subfamily C, polypeptide 19 | CYP2C19 | 15788367 | |
| GEFITINIB | NM_000771 | cytochrome P450, family 2, subfamily C, polypeptide 9 | CYP2C9 | 15788367 | unrelated |
| GEFITINIB | NM_000106; NM_001025161 | cytochrome P450, family 2, subfamily D, polypeptide 6 | CYP2D6 | 15788367 | drug metabolism |
| GEFITINIB | NM_000774 | cytochrome P450, family 2, subfamily F, polypeptide 1 | CYP2F1 | 16685379 | |
| GEFITINIB | NM_017460 | cytochrome P450, family 3, subfamily A, polypeptide 4 | CYP3A4 | 15788367 | drug metabolism |

TABLE 1-continued

| Molecule | RefSeq | Description | Symbol | PMID | Interaction |
|---|---|---|---|---|---|
| GEFITINIB | NM_000777 | cytochrome P450, family 3, subfamily A, polypeptide 5 | CYP3A5 | 15788367 | drug metabolism |
| GEFITINIB | NM_004090 | dual specificity phosphatase 3 | DUSP3 | 15496427 | |
| GEFITINIB | NM_001395 | dual specificity phosphatase 9 | DUSP9 | 16685379 | |
| GEFITINIB | NM_005225 | E2F transcription factor 1 | E2F1 | 18347146 | |
| GEFITINIB | NM_001963 | epidermal growth factor (beta-urogastrone) | EGF | 17805209, 17898861 | |
| GEFITINIB | NM_005228; NM_201282; NM_201283; NM_201284 | epidermal growth factor receptor (erythroblastic leukemia viral (v-erb-b) oncogene homolog, avian) | EGFR | 15723263, 15976333, 16361624, 17290066, 17898861, 17938326 | target |
| GEFITINIB | NM_000121 | erythropoietin receptor | EPOR | 16685379 | |
| GEFITINIB | NM_001159969; NM_001981 | epidermal growth factor receptor pathway substrate 15 | EPS15 | 16685379 | |
| GEFITINIB | NM_001005862; NM_004448 | v-erb-b2 erythroblastic leukemia viral oncogene homolog 2, neuro/glioblastoma derived oncogene homolog (avian) | ERBB2 | 17898861 | sensitivity |
| GEFITINIB | NM_001432 | epiregulin | EREG | — | |
| GEFITINIB | NM_000125; NM_001122740; NM_001122741; NM_001122742 | estrogen receptor 1 | ESR1 | 16261397 | |
| GEFITINIB | NM_020996 | fibroblast growth factor 6 | FGF6 | 16685379 | |
| GEFITINIB | NM_001924 | growth arrest and DNA-damage-inducible, alpha | GADD45A | 16685379 | |
| GEFITINIB | NM_006705 | growth arrest and DNA-damage-inducible, gamma | GADD45G | 16685379 | |
| GEFITINIB | NM_002047 | glycyl-tRNA synthetase | GARS | 16685379 | |
| GEFITINIB | NM_001498 | glutamate-cysteine ligase, catalytic subunit | GCLC | 15496427 | |
| GEFITINIB | NM_005273 | guanine nucleotide binding protein (G protein), beta polypeptide 2 | GNB2 | 16685379 | |
| GEFITINIB | NM_000180 | guanylate cyclase 2D, membrane (retina-specific) | GUCY2D | 16685379 | |
| GEFITINIB | NM_001945 | heparin-binding EGF-like growth factor | HBEGF | 15723263 | altered by gefitinib |
| GEFITINIB | NM_002038; NM_022872; NM_022873 | interferon, alpha-inducible protein 6 | IFI6 | 16685379 | |
| GEFITINIB | NM_000598; NM_001013398 | insulin-like growth factor binding protein 3 | IGFBP3 | — | |
| GEFITINIB | NM_000584 | interleukin 8 | IL8 | 15723263 | altered by gefitinib |
| GEFITINIB | NM_001003679; NM_001003680; NM_002303 | leptin receptor | LEPR | 16685379 | |
| GEFITINIB | NM_002745; NM_138957 | mitogen-activated protein kinase 1 | MAPK1 | 17805209, 17898861 | |
| GEFITINIB | NM_001040056; NM_001109891; NM_002746 | mitogen-activated protein kinase 3 | MAPK3 | 17805209, 17898861 | |
| GEFITINIB | NM_000249 | mutL homolog 1, colon cancer, nonpolyposis type 2 (E. coli) | MLH1 | 16685379 | |
| GEFITINIB | NM_003998 | nuclear factor of kappa light polypeptide gene enhancer in B-cells 1 | NFKB1 | 16685379 | |
| GEFITINIB | NM_002523 | neuronal pentraxin II | NPTX2 | 16685379 | |
| GEFITINIB | NM_006177 | neural retina leucine zipper | NRL | 16685379 | |
| GEFITINIB | NM_003999 | oncostatin M receptor | OSMR | 15496427 | |
| GEFITINIB | NM_003311 | pleckstrin homology-like domain, family A, member 2 | PHLDA2 | 15496427 | |
| GEFITINIB | NM_000314 | phosphatase and tensin homolog | PTEN | — | |
| GEFITINIB | NM_001004128; NM_002826 | quiescin Q6 sulfhydryl oxidase 1 | QSOX1 | 16685379 | altered by gefitinib |
| GEFITINIB | NM_016090 | RNA binding motif protein 7 | RBM7 | 15496427 | |
| GEFITINIB | NM_002945 | replication protein A1, 70 kDa | RPA1 | 16685379 | |
| GEFITINIB | NM_006142 | stratifin | SFN | 16685379 | |
| GEFITINIB | NM_003036 | v-ski sarcoma viral oncogene homolog (avian) | SKI | 16685379 | |
| GEFITINIB | NM_001099691; NM_003236 | transforming growth factor, alpha | TGFA | 15723263, 16230376 | |
| GEFITINIB | NM_001066 | tumor necrosis factor receptor superfamily, member 1B | TNFRSF1B | 16685379 | |
| GEFITINIB | NM_001071 | thymidylate synthetase | TYMS | 18347146 | resistance |

TABLE 1-continued

| Molecule | RefSeq | Description | Symbol | PMID | Interaction |
|---|---|---|---|---|---|
| IMATINIB | NM_000927 | ATP-binding cassette, sub-family B (MDR/TAP), member 1 | ABCB1 | 15970668 | resistance |
| IMATINIB | NM_004827 | ATP-binding cassette, sub-family G (WHITE), member 2 | ABCG2 | 15970668 | resistance |
| IMATINIB | NM_005157; NM_007313 | c-abl oncogene 1, receptor tyrosine kinase | ABL1 | 15329907 | target |
| IMATINIB | NM_001014431; NM_001014432; NM_005163 | v-akt murine thymoma viral oncogene homolog 1 | AKT1 | 16740780 | activity altered by imatinib |
| IMATINIB | NM_001191; NM_138578 | BCL2-like 1 | BCL2L1 | 16960866 | resistance |
| IMATINIB | NM_004327; NM_021574 | breakpoint cluster region | BCR | 15329907 | |
| IMATINIB | NM_001012270; NM_001012271; NM_001168 | baculoviral IAP repeat-containing 5 | BIRC5 | 16254145, 16254145, 16166298 | resistance |
| IMATINIB | NM_001136017; NM_001136125; NM_001136126; NM_001760 | cyclin D3 | CCND3 | 15100154 | |
| IMATINIB | NM_001781 | CD69 molecule | CD69 | 15100154 | target |
| IMATINIB | NM_005211 | colony stimulating factor 1 receptor | CSF1R | — | target |
| IMATINIB | NM_001954; NM_013993; NM_013994 | discoidin domain receptor tyrosine kinase 1 | DDR1 | 14562121 | |
| IMATINIB | NM_000142; NM_022965 | fibroblast growth factor receptor 3 | FGFR3 | 16740780 | activity altered by imatinib |
| IMATINIB | — | | FRAP1 | 16740780 | resistance |
| IMATINIB | NM_002133 | heme oxygenase (decycling) 1 | HMOX1 | 17420286 | |
| IMATINIB | NM_000618; NM_001111283; NM_001111284; NM_001111285 | insulin-like growth factor 1 (somatomedin C) | IGF1 | 16740780 | |
| IMATINIB | NM_000417 | interleukin 2 receptor, alpha | IL2RA | 15100154 | |
| IMATINIB | NM_000222; NM_001093772 | v-kit Hardy-Zuckerman 4 feline sarcoma viral oncogene homolog | KIT | 17420286 | target V560G D816V |
| IMATINIB | NM_001042771; NM_005356 | lymphocyte-specific protein tyrosine kinase | LCK | 15100154 | target |
| IMATINIB | NM_002745; NM_138957 | mitogen-activated protein kinase 1 | MAPK1 | 15100154 | activity altered by imatinib |
| IMATINIB | NM_001040056; NM_001109891; NM_002746 | mitogen-activated protein kinase 3 | MAPK3 | 15100154 | activity altered by imatinib |
| IMATINIB | NM_003998 | nuclear factor of kappa light polypeptide gene enhancer in B-cells 1 | NFKB1 | 15100154 | activity altered by imatinib |
| IMATINIB | NM_001007792; NM_001012331; NM_002529 | neurotrophic tyrosine kinase, receptor, type 1 | NTRK1 | — | |
| IMATINIB | NM_006206 | platelet-derived growth factor receptor, alpha polypeptide | PDGFRA | 17614352 | target |
| IMATINIB | NM_002609 | platelet-derived growth factor receptor, beta polypeptide | PDGFRB | — | target |
| IMATINIB | NM_000321 | retinoblastoma 1 | RB1 | 15100154 | |
| IMATINIB | NM_001145138; NM_021975 | v-rel reticuloendotheliosis viral oncogene homolog A (avian) | RELA | 15100154 | activity altered by imatinib |
| IMATINIB | NM_020630; NM_020975 | ret proto-oncogene | RET | 15709206 | altered by imatinib |
| IMATINIB | NM_001025366; NM_001025367; NM_001025368; NM_001025369; NM_001025370; NM_001033756; NM_003376 | vascular endothelial growth factor A | VEGFA | 16740780 | |
| IMATINIB | NM_000378; NM_024424; NM_024425; NM_024426 | Wilms tumor 1 | WT1 | 15329907 | resistance |
| LAPATINIB | NM_001014431; NM_001014432; NM_005163 | v-akt murine thymoma viral oncogene homolog 1 | AKT1 | 15665275, 16091755 | altered by lapatinib |
| LAPATINIB | NM_001012270; NM_001012271; NM_001168 | baculoviral IAP repeat-containing 5 | BIRC5 | 16091755 | altered by lapatinib |
| LAPATINIB | NM_053056 | cyclin D1 | CCND1 | 15665275 | altered by lapatinib |

TABLE 1-continued

| Molecule | RefSeq | Description | Symbol | PMID | Interaction |
|---|---|---|---|---|---|
| LAPATINIB | NM_001238; NM_057182 | cyclin E1 | CCNE1 | 15665275 | altered by lapatinib |
| LAPATINIB | NM_001798; NM_052827 | cyclin-dependent kinase 2 | CDK2 | 15665275 | altered by lapatinib |
| LAPATINIB | NM_004064 | cyclin-dependent kinase inhibitor 1B (p27, Kip1) | CDKN1B | 15665275 | altered by lapatinib |
| LAPATINIB | NM_001963 | epidermal growth factor (beta-urogastrone) | EGF | | target |
| LAPATINIB | NM_005228; NM_201282; NM_201283; NM_201284 | epidermal growth factor receptor (erythroblastic leukemia viral (v-erb-b) oncogene homolog, avian) | EGFR | 15665275 | target |
| LAPATINIB | NM_001005862; NM_004448 | v-erb-b2 erythroblastic leukemia viral oncogene homolog 2, neuro/glioblastoma derived oncogene homolog (avian) | ERBB2 | 15665275, 16091755 | target |
| LAPATINIB | NM_001432 | epiregulin | EREG | | |
| LAPATINIB | NM_000125; NM_001122740; NM_001122741; NM_001122742 | estrogen receptor 1 | ESR1 | 15665275 | |
| LAPATINIB | NM_002745; NM_138957 | mitogen-activated protein kinase 1 | MAPK1 | 16091755 | altered by lapatinib |
| LAPATINIB | NM_001040056; NM_001109891; NM_002746 | mitogen-activated protein kinase 3 | MAPK3 | 16091755 | altered by lapatinib |
| LAPATINIB | NM_021960; NM_182763 | myeloid cell leukemia sequence 1 (BCL2-related) | MCL1 | | resistance |
| LAPATINIB | — | | PI3KCA | | resistance |
| LAPATINIB | NM_000314 | phosphatase and tensin homolog | PTEN | | sensitivity |
| LESTAURTINIB | NM_004119 | fms-related tyrosine kinase 3 | FLT3 | | target |
| NILOTINIB | NM_005157; NM_007313 | c-abl oncogene 1, receptor tyrosine kinase | ABL1 | | target |
| NILOTINIB | NM_004327; NM_021574 | breakpoint cluster region | BCR | | |
| NILOTINIB | NM_000222; NM_001093772 | v-kit Hardy-Zuckerman 4 feline sarcoma viral oncogene homolog | KIT | | target |
| NILOTINIB | NM_006206 | platelet-derived growth factor receptor, alpha polypeptide | PDGFRA | | target |
| NILOTINIB | NM_002609 | platelet-derived growth factor receptor, beta polypeptide | PDGFRB | | target |
| SEMAXANIB | NM_002253 | kinase insert domain receptor (a type III receptor tyrosine kinase) | KDR | | target |
| SORAFENIB | NM_001188 | BCL2-antagonist/killer 1 | BAK1 | 16007148 | death pathway |
| SORAFENIB | NM_004324; NM_138761; NM_138763; NM_138764; NM_138765 | BCL2-associated X protein | BAX | 16007148 | death pathway |
| SORAFENIB | NM_000633; NM_000657 | B-cell CLL/lymphoma 2 | BCL2 | 16007148 | altered by soraf |
| SORAFENIB | NM_001191; NM_138578 | BCL2-like 1 | BCL2L1 | 16007148 | altered by soraf |
| SORAFENIB | NM_006538; NM_138621; NM_207002 | BCL2-like 11 (apoptosis facilitator) | BCL2L11 | 16007148 | death pathway |
| SORAFENIB | NM_001196; NM_197966; NM_197967 | BH3 interacting domain death agonist | BID | 16007148 | death pathway |
| SORAFENIB | NM_004333 | v-raf murine sarcoma viral oncogene homolog B1 | BRAF | | target |
| SORAFENIB | NM_004346; NM_032991 | caspase 3, apoptosis-related cysteine peptidase | CASP3 | 16007148 | death pathway |
| SORAFENIB | NM_001080124; NM_001080125; NM_001228; NM_033355; NM_033356; NM_033358 | caspase 8, apoptosis-related cysteine peptidase | CASP8 | 16007148 | death pathway |
| SORAFENIB | NM_018947 | cytochrome c, somatic | CYCS | 16007148 | death pathway |
| SORAFENIB | NM_001433 | endoplasmic reticulum to nucleus signaling 1 | ERN1 | | resistance |
| SORAFENIB | NM_004119 | fms-related tyrosine kinase 3 | FLT3 | | target |
| SORAFENIB | NM_002020; NM_182925 | fms-related tyrosine kinase 4 | FLT4 | | target |

TABLE 1-continued

| Molecule | RefSeq | Description | Symbol | PMID | Interaction |
|---|---|---|---|---|---|
| SORAFENIB | NM_002253 | kinase insert domain receptor (a type III receptor tyrosine kinase) | KDR | — | target |
| SORAFENIB | NM_000222; NM_001093772 | v-kit Hardy-Zuckerman 4 feline sarcoma viral oncogene homolog | KIT | — | target |
| SORAFENIB | NM_002745; NM_138957 | mitogen-activated protein kinase 1 | MAPK1 | — | resistance |
| SORAFENIB | NM_001040056; NM_001109891; NM_002746 | mitogen-activated protein kinase 3 | MAPK3 | — | resistance |
| SORAFENIB | NM_021960; NM_182763 | myeloid cell leukemia sequence 1 (BCL2-related) | MCL1 | 16007148 | altered by soraf |
| SORAFENIB | NM_002609 | platelet-derived growth factor receptor, beta polypeptide | PDGFRB | — | target |
| SORAFENIB | NM_002880 | v-raf-1 murine leukemia viral oncogene homolog 1 | RAF1 | — | target |
| SORAFENIB | NM_001167 | X-linked inhibitor of apoptosis | XIAP | 16007148 | altered by soraf |
| SUNITINIB | NM_004333 | v-raf murine sarcoma viral oncogene homolog B1 | BRAF | — | target |
| SUNITINIB | NM_005211 | colony stimulating factor 1 receptor | CSF1R | — | target |
| SUNITINIB | NM_001160030; NM_001160031; NM_002019 | fms-related tyrosine kinase 1 (vascular endothelial growth factor/vascular permeability factor receptor) | FLT1 | — | target |
| SUNITINIB | NM_004119 | fms-related tyrosine kinase 3 | FLT3 | — | target |
| SUNITINIB | NM_004120; NM_182925 | fms-related tyrosine kinase 4 | FLT4 | — | target |
| SUNITINIB | NM_002253 | kinase insert domain receptor (a type III receptor tyrosine kinase) | KDR | — | target |
| SUNITINIB | NM_000222; NM_001093772 | v-kit Hardy-Zuckerman 4 feline sarcoma viral oncogene homolog | KIT | — | target |
| SUNITINIB | NM_006206 | platelet-derived growth factor receptor, alpha polypeptide | PDGFRA | — | target |
| SUNITINIB | NM_002609 | platelet-derived growth factor receptor, beta polypeptide | PDGFRB | — | target |
| SUNITINIB | NM_002880 | v-raf-1 murine leukemia viral oncogene homolog 1 | RAF1 | — | target |
| SUNITINIB | NM_020630; NM_020975 | ret proto-oncogene | RET | — | target |
| VANDETANIB | NM_001963 | epidermal growth factor (beta-urogastrone) | EGF | — | target |
| VANDETANIB | NM_005228; NM_201282; NM_201283; NM_201284 | epidermal growth factor receptor (erythroblastic leukemia viral (v-erb-b) oncogene homolog, avian) | EGFR | — | target |
| VANDETANIB | NM_001432 | epiregulin | EREG | — | target |
| VANDETANIB | NM_002253 | kinase insert domain receptor (a type III receptor tyrosine kinase) | KDR | — | target |
| TEMSIROLIMUS | NM_053056 | cyclin D1 | CCND1 | 16954435 | resistance? |
| TEMSIROLIMUS | NM_004095 | eukaryotic translation initiation factor 4E binding protein 1 | EIF4EBP1 | 16033649 | altered by temsirolimus |
| TEMSIROLIMUS | NM_000125; NM_001122740; NM_001122741; NM_001122742 | estrogen receptor 1 | ESR1 | 16954435 | altered by temsirolimus |
| TEMSIROLIMUS | — | — | FRAP1 | 16033649 | target |
| TEMSIROLIMUS | NM_000321 | retinoblastoma 1 | RB1 | 16954435 | altered by temsirolimus |
| TEMSIROLIMUS | NM_003161 | ribosomal protein S6 kinase, 70 kDa, polypeptide 1 | RPS6KB1 | 16954435, 16954435, 16033649 | altered by temsirolimus |
| EVEROLIMUS | NM_001014431; NM_001014432; NM_005163 | v-akt murine thymoma viral oncogene homolog 1 | AKT1 | 16033851 | altered by everolimus |
| EVEROLIMUS | NM_000633; NM_000657 | B-cell CLL/lymphoma 2 | BCL2 | — | resistance |
| EVEROLIMUS | NM_053056 | cyclin D1 | CCND1 | 16033851 | altered by everolimus |
| EVEROLIMUS | NM_001759 | cyclin D2 | CCND2 | 16033851 | altered by everolimus |

TABLE 1-continued

| Molecule | RefSeq | Description | Symbol | PMID | Interaction |
|---|---|---|---|---|---|
| EVEROLIMUS | NM_001136017; NM_001136125; NM_001136126; NM_001760 | cyclin D3 | CCND3 | 16033851 | altered by everolimus |
| EVEROLIMUS | NM_001130678; NM_001130679; NM_001968 | eukaryotic translation initiation factor 4E | EIF4E | 16033851 | altered by everolimus |
| EVEROLIMUS | NM_004095 | eukaryotic translation initiation factor 4E binding protein 1 | EIF4EBP1 | 16033851 | altered by everolimus |
| EVEROLIMUS | NM_004953; NM_182917; NM_198241; NM_198242; NM_198244 | eukaryotic translation initiation factor 4 gamma, 1 | EIF4G1 | 16033851 | altered by everolimus |
| EVEROLIMUS | — | — | FRAP1 | 16033851 | target |
| EVEROLIMUS | NM_000321 | retinoblastoma 1 | RB1 | 16033851 | |
| EVEROLIMUS | NM_001010 | ribosomal protein S6 | RPS6 | 16033851 | |
| EVEROLIMUS | NM_003161 | ribosomal protein S6 kinase, 70 kDa, polypeptide 1 | RPS6KB1 | 16033851 | altered by everolimus |
| FLAVOPIRIDOL | NM_004323 | BCL2-associated athanogene | BAG1 | 15972445 | altered by flavopiridol |
| FLAVOPIRIDOL | NM_004324; NM_138761; NM_138763; NM_138764; NM_138765 | BCL2-associated X protein | BAX | 12517783, 15634644, 15770523 | unrelated |
| FLAVOPIRIDOL | NM_000633; NM_000657 | B-cell CLL/lymphoma 2 | BCL2 | 12170773, 12517783, 15770523, 15972445 | unrelated |
| FLAVOPIRIDOL | NM_001191; NM_138578 | BCL2-like 1 | BCL2L1 | 12517783, 15634644 | altered by flavopiridol |
| FLAVOPIRIDOL | NM_001196; NM_197966; NM_197967 | BH3 interacting domain death agonist | BID | 12170773, 15634644 | unrelated |
| FLAVOPIRIDOL | NM_001165; NM_182962 | baculoviral IAP repeat-containing 3 | BIRC3 | 12517783 | altered by flavopiridol |
| FLAVOPIRIDOL | NM_001012270; NM_001012271; NM_001168 | baculoviral IAP repeat-containing 5 | BIRC5 | 12517783, 16012789 | altered by flavopiridol |
| FLAVOPIRIDOL | NM_004346; NM_032991 | caspase 3, apoptosis-related cysteine peptidase | CASP3 | 12170773, 12517783, 15634644, 15770523, 16012789 | death pathway |
| FLAVOPIRIDOL | NM_001080124; NM_001080125; NM_001228; NM_033355; NM_033356; NM_003358 | caspase 8, apoptosis-related cysteine peptidase | CASP8 | 15634644, 16012789 | unrelated |
| FLAVOPIRIDOL | NM_001229; NM_032996 | caspase 9, apoptosis-related cysteine peptidase | CASP9 | 12170773, 15634644 | death pathway |
| FLAVOPIRIDOL | NM_031966 | cyclin B1 | CCNB1 | 12517783 | sensitivity |
| FLAVOPIRIDOL | NM_053056 | cyclin D1 | CCND1 | 12517783, 15634644 | sensitivity |
| FLAVOPIRIDOL | NM_001130829; NM_001786; NM_033379 | cell division cycle 2, G1 to S and G2 to M | CDC2 | 12517783 | target |
| FLAVOPIRIDOL | NM_001798; NM_052827 | cyclin-dependent kinase 2 | CDK2 | 12517783 | target |
| FLAVOPIRIDOL | NM_000075 | cyclin-dependent kinase 4 | CDK4 | 12517783 | target |
| FLAVOPIRIDOL | NM_004935 | cyclin-dependent kinase 5 | CDK5 | 12517783 | |
| FLAVOPIRIDOL | NM_001145306; NM_001259 | cyclin-dependent kinase 6 | CDK6 | | |
| FLAVOPIRIDOL | NM_001799 | cyclin-dependent kinase 7 | CDK7 | | |
| FLAVOPIRIDOL | NM_001260 | cyclin-dependent kinase 8 | CDK8 | | |
| FLAVOPIRIDOL | NM_001261 | cyclin-dependent kinase 9 | CDK9 | | |
| FLAVOPIRIDOL | NM_000389; NM_078467 | cyclin-dependent kinase inhibitor 1A (p21, Cip1) | CDKN1A | 15180955, 15770523 | target |
| FLAVOPIRIDOL | NM_004064 | cyclin-dependent kinase inhibitor 1B (p27, Kip1) | CDKN1B | 15180955 | altered by flavopiridol |
| FLAVOPIRIDOL | NM_018947 | cytochrome c, somatic | CYCS | 12170773, 12170773, 12517783, 15634644 | death pathway |
| FLAVOPIRIDOL | NM_019887; NM_138929 | diablo homolog (Drosophila) | DIABLO | 12517783, 15634644 | death pathway |
| FLAVOPIRIDOL | NM_001963 | epidermal growth factor (beta-urogastrone) | EGF | — | |
| FLAVOPIRIDOL | NM_005228; NM_201282; NM_201283; NM_201284 | epidermal growth factor receptor (erythroblastic leukemia viral (v-erb-b) oncogene homolog, avian) | EGFR | — | |
| FLAVOPIRIDOL | NM_001432 | epiregulin | EREG | — | |

TABLE 1-continued

| Molecule | RefSeq | Description | Symbol | PMID | Interaction |
|---|---|---|---|---|---|
| FLAVOPIRIDOL | NM_002105 | H2A histone family, member X | H2AFX | 15078984 | death pathway |
| FLAVOPIRIDOL | NM_013247; NM_145074 | HtrA serine peptidase 2 | HTRA2 | 12517783 | |
| FLAVOPIRIDOL | NM_001315; NM_139012; NM_139013; NM_139014 | mitogen-activated protein kinase 14 | MAPK14 | 15634644 | |
| FLAVOPIRIDOL | NM_002750; NM_139046; NM_139047; NM_139049 | mitogen-activated protein kinase 8 | MAPK8 | 15634644 | |
| FLAVOPIRIDOL | NM_021960; NM_182763 | myeloid cell leukemia sequence 1 (BCL2-related) | MCL1 | 12517783, 15634644, 15972445, 12517783 | altered by flavopiridol |
| FLAVOPIRIDOL | NM_001618 | poly (ADP-ribose) polymerase 1 | PARP1 | 12170773, 15634644, 15770523, 15972445, 12517783, 12170773, 16012789 | |
| FLAVOPIRIDOL | NM_005609 | phosphorylase, glycogen, muscle | PYGM | | |
| FLAVOPIRIDOL | NM_000321 | retinoblastoma 1 | RB1 | 15078984, 15180955, 15297405 | |
| FLAVOPIRIDOL | NM_000546; NM_001126112; NM_001126113; NM_001126114; NM_001126115; NM_001126116; NM_001126117 | tumor protein p53 | TP53 | 15180955, 15297405 | unrelated |
| FLAVOPIRIDOL | NM_001167 | X-linked inhibitor of apoptosis | XIAP | 12517783, 15972445, 12517783, 15972445, 15385934, 12517783 | altered by flavopiridol |
| ROSCOVITINE | NM_004324; NM_138761; NM_138763; NM_138764; NM_138765 | BCL2-associated X protein | BAX | 16230394, 16275999 | death pathway |
| ROSCOVITINE | NM_001012270; NM_001012271; NM_001168 | baculoviral IAP repeat-containing 5 | BIRC5 | 16230394 | altered by roscovitine |
| ROSCOVITINE | NM_004346; NM_032991 | caspase 3, apoptosis-related cysteine peptidase | CASP3 | 16140939 | death pathway |
| ROSCOVITINE | NM_001229; NM_032996 | caspase 9, apoptosis-related cysteine peptidase | CASP9 | 16140939 | death pathway |
| ROSCOVITINE | NM_001130829; NM_001786; NM_033379 | cell division cycle 2, G1 to S and G2 to M | CDC2 | 15231455, 15 | target |
| ROSCOVITINE | NM_001798; NM_052827 | cyclin-dependent kinase 2 | CDK2 | | target |
| ROSCOVITINE | NM_000075 | cyclin-dependent kinase 4 | CDK4 | 15741232 | |
| ROSCOVITINE | NM_004935 | cyclin-dependent kinase 5 | CDK5 | 15741232 | target |
| ROSCOVITINE | NM_001145306; NM_001259 | cyclin-dependent kinase 6 | CDK6 | 15741232 | |
| ROSCOVITINE | NM_000389; NM_078467 | cyclin-dependent kinase inhibitor 1A (p21, Cip1) | CDKN1A | 16275999 | altered by roscovitine |
| ROSCOVITINE | NM_018947 | cytochrome c, somatic | CYCS | 16140939, 16275999 | death pathway |
| ROSCOVITINE | NM_019887; NM_138929 | diablo homolog (Drosophila) | DIABLO | 16275999 | |
| ROSCOVITINE | NM_021960; NM_182763 | myeloid cell leukemia sequence 1 (BCL2-related) | MCL1 | 16275999 | altered by roscovitine |
| ROSCOVITINE | — | — | PDCD8 | 16275999 | death pathway |
| ROSCOVITINE | NM_000321 | retinoblastoma 1 | RB1 | 14653808, 15231455, 15741232 | altered by roscovitine |
| ROSCOVITINE | NM_003109; NM_138473 | Sp1 transcription factor | SP1 | 14653808 | altered by roscovitine |
| ROSCOVITINE | NM_000546; NM_001126112; NM_001126113; NM_001126114; NM_001126115; NM_001126116; NM_001126117 | tumor protein p53 | TP53 | 16003486, 16 | altered by roscovitine sensitivity |
| ROSCOVITINE | NM_001167 | X-linked inhibitor of apoptosis | XIAP | 16140939, 16230394, 16275999 | altered by roscovitine |
| AFLIBERCEPT | NM_001025366; NM_001025367; NM_001025368; NM_001025369; NM_001025370; NM_001033756; NM_003376 | vascular endothelial growth factor A | VEGFA | — | target |
| DENILEUKIN DIFTITOX | NM_000417 | interleukin 2 receptor, alpha | IL2RA | — | target |

TABLE 1-continued

| Molecule | RefSeq | Description | Symbol | PMID | Interaction |
|---|---|---|---|---|---|
| DENILEUKIN DIFTITOX | NM_000878 | interleukin 2 receptor, beta | IL2RB | — | target |
| DENILEUKIN DIFTITOX | NM_000206 | interleukin 2 receptor, gamma (severe combined immunodeficiency) | IL2RG | — | target |
| ARSENIC TRIOXIDE | NM_000927 | ATP-binding cassette, sub-family B (MDR/TAP), member 1 | ABCB1 | 15979894, 15979894, 14642128 | resistance |
| ARSENIC TRIOXIDE | NM_004827 | ATP-binding cassette, sub-family G (WHITE), member 2 | ABCG2 | 17547211 | resistance |
| ARSENIC TRIOXIDE | NM_005157; NM_007313 | c-abl oncogene 1, receptor tyrosine kinase | ABL1 | 14633726 | |
| ARSENIC TRIOXIDE | NM_006111 | acetyl-Coenzyme A acyltransferase 2 | ACAA2 | 15761015 | |
| ARSENIC TRIOXIDE | NM_001116 | adenylate cyclase 9 | ADCY9 | 15761015 | |
| ARSENIC TRIOXIDE | NM_001134647; NM_198595 | actin filament associated protein 1 | AFAP1 | 17547211 | |
| ARSENIC TRIOXIDE | NM_005100; NM_144497 | A kinase (PRKA) anchor protein 12 | AKAP12 | 17547211 | |
| ARSENIC TRIOXIDE | NM_001628 | aldo-keto reductase family 1, member B1 (aldose reductase) | AKR1B1 | 17547211 | |
| ARSENIC TRIOXIDE | NM_001014431; NM_001014432; NM_005163 | v-akt murine thymoma viral oncogene homolog 1 | AKT1 | 16882451, 17077332 | |
| ARSENIC TRIOXIDE | NM_000688; NM_199166 | aminolevulinate, delta-, synthase 1 | ALAS1 | 15725085 | |
| ARSENIC TRIOXIDE | NM_005589 | aldehyde dehydrogenase 6 family, member A1 | ALDH6A1 | 17547211 | |
| ARSENIC TRIOXIDE | NM_005165 | aldolase C, fructose-bisphosphate | ALDOC | 15725085 | |
| ARSENIC TRIOXIDE | NM_018466 | asparagine-linked glycosylation 13 homolog (S. cerevisiae) | ALG13 | 15761015 | |
| ARSENIC TRIOXIDE | NM_001629 | arachidonate 5-lipoxygenase-activating protein | ALOX5AP | 15761015, 15 | |
| ARSENIC TRIOXIDE | NM_001149; NM_020987 | ankyrin 3, node of Ranvier (ankyrin G) | ANK3 | 15761015 | |
| ARSENIC TRIOXIDE | NM_001083625; NM_015208 | ankyrin repeat domain 12 | ANKRD12 | 15761015 | |
| ARSENIC TRIOXIDE | NM_001150 | alanyl (membrane) aminopeptidase | ANPEP | 15949261 | |
| ARSENIC TRIOXIDE | NM_001002857; NM_001002858; NM_001136015; NM_004039 | annexin A2 | ANXA2 | 17547211 | |
| ARSENIC TRIOXIDE | NM_001284 | adaptor-related protein complex 3, sigma 1 subunit | AP3S1 | 15761015 | |
| ARSENIC TRIOXIDE | NM_020980 | aquaporin 9 | AQP9 | 15336539, 16968895 | |
| ARSENIC TRIOXIDE | NM_015161 | ADP-ribosylation factor-like 6 interacting protein 1 | ARL6IP1 | 14703492 | |
| ARSENIC TRIOXIDE | NM_006407 | ADP-ribosylation-like factor 6 interacting protein 5 | ARL6IP5 | 16430862, 16468075 | |
| ARSENIC TRIOXIDE | — | — | ARL7 | 15725085 | |

TABLE 1-continued

| Molecule | RefSeq | Description | Symbol | PMID | Interaction |
|---|---|---|---|---|---|
| ARSENIC TRIOXIDE | NM_025139 | armadillo repeat containing 9 | ARMC9 | 15761015 | |
| ARSENIC TRIOXIDE | NM_001673; NM_133436; NM_183356 | asparagine synthetase | ASNS | 17547211 | |
| ARSENIC TRIOXIDE | NM_000050; NM_054012 | argininosuccinate synthetase 1 | ASS1 | 15761015, 15 | |
| ARSENIC TRIOXIDE | NM_001001787; NM_001677 | ATPase, Na+/K+ transporting, beta 1 polypeptide | ATP1B1 | 15761015 | |
| ARSENIC TRIOXIDE | NM_001001323; NM_001682 | ATPase, Ca++ transporting, plasma membrane 1 | ATP2B1 | 12852829, 18 | |
| ARSENIC TRIOXIDE | NM_001001485; NM_001001486; NM_001001487; NM_014382 | ATPase, Ca++ transporting, type 2C, member 1 | ATP2C1 | — | |
| ARSENIC TRIOXIDE | NM_001001937; NM_004046 | ATP synthase, H+ transporting, mitochondrial F1 complex, alpha subunit 1, cardiac muscle | ATP5A1 | 15949261 | |
| ARSENIC TRIOXIDE | — | ATP synthase subunit 6 | ATP6 | 14703492, 15949261 | |
| ARSENIC TRIOXIDE | NM_001105529; NM_006095 | ATPase, aminophospholipid transporter (APLT), class I, type 8A, member 1 | ATP8A1 | 15761015 | |
| ARSENIC TRIOXIDE | NM_001184 | ataxia telangiectasia and Rad3 related | ATR | 16891316 | |
| ARSENIC TRIOXIDE | NM_001185 | alpha-2-glycoprotein 1, zinc-binding | AZGP1 | 17547211 | |
| ARSENIC TRIOXIDE | NM_021813 | BTB and CNC homology 1, basic leucine zipper transcription factor 2 | BACH2 | 15725085 | |
| ARSENIC TRIOXIDE | NM_012342 | BMP and activin membrane-bound inhibitor homolog (Xenopus laevis) | BAMBI | 15725085 | |
| ARSENIC TRIOXIDE | NM_004324; NM_138761; NM_138764; NM_138765 | BCL2-associated X protein | BAX | 11135700, 11775218, 15622746, 15665116, 16010437, 16867262, 16020671, 16867262, 16882451, 16972261 | |
| ARSENIC TRIOXIDE | NM_000633; NM_000657 | B-cell CLL/lymphoma 2 | BCL2 | 11775218, 12490120, 16105982, 11780464, (following) 16818652, 11589617, 11135700, 11775218, 12845720, 15979894, 16029599, 16007134, 16904648, 11775218, 16010437, 16867262, 16818652, 16867262, 16904648, 15622746, 11775218, 16966277 12130515 | |
| ARSENIC TRIOXIDE | NM_001114735; NM_004049 | BCL2-related protein A1 | BCL2A1 | 11468182, 15622746, 16105982, 15665116 | |
| ARSENIC TRIOXIDE | NM_001191; NM_138578 | BCL2-like 1 | BCL2L1 | 15761015 | |
| ARSENIC TRIOXIDE | NM_017429 | beta-carotene 15,15'-monooxygenase 1 | BCMO1 | 14633726 | |
| ARSENIC TRIOXIDE | NM_004327; NM_021574 | breakpoint cluster region | BCR | 16882451 | |
| ARSENIC TRIOXIDE | NM_003766 | beclin 1, autophagy related | BECN1 | 15761015 | |
| ARSENIC TRIOXIDE | — | — | BHLHB2 | | |

TABLE 1-continued

| Molecule | RefSeq | Description | Symbol | PMID | Interaction |
|---|---|---|---|---|---|
| ARSENIC TRIOXIDE | NM_001196; NM_197966; NM_197967 | BH3 interacting domain death agonist | BID | 15665116, 16972261 | |
| ARSENIC TRIOXIDE | NM_001012270; NM_001012271; NM_001168 | baculoviral IAP repeat-containing 5 | BIRC5 | 15587394, 16328441 | |
| ARSENIC TRIOXIDE | NM_000713 | biliverdin reductase B (flavin reductase (NADPH)) | BLVRB | 15725085 | |
| ARSENIC TRIOXIDE | NM_003666 | basic leucine zipper nuclear factor 1 | BLZF1 | 15761015 | |
| ARSENIC TRIOXIDE | NM_004052 | BCL2/adenovirus E1B 19 kDa interacting protein 3 | BNIP3 | 15592527 | |
| ARSENIC TRIOXIDE | NM_004331 | BCL2/adenovirus E1B 19 kDa interacting protein 3-like | BNIP3L | 15592527 | |
| ARSENIC TRIOXIDE | NM_001725 | bactericidal/permeability-increasing protein | BPI | 15761015 | |
| ARSENIC TRIOXIDE | — | | BRDG1 | 15761015 | |
| ARSENIC TRIOXIDE | NM_017797 | BTB (POZ) domain containing 2 | BTBD2 | 15725085 | |
| ARSENIC TRIOXIDE | NM_014962; NM_181443 | BTB (POZ) domain containing 3 | BTBD3 | 15725085 | |
| ARSENIC TRIOXIDE | — | | C14ORF105 | 15761015 | |
| ARSENIC TRIOXIDE | — | | C16ORF58 | 15761015 | |
| ARSENIC TRIOXIDE | — | | C5ORF13 | 15725085 | |
| ARSENIC TRIOXIDE | — | | C6ORF48 | 17547211 | |
| ARSENIC TRIOXIDE | — | | C8ORF4 | 15761015 | |
| ARSENIC TRIOXIDE | NM_001005505; NM_006030 | calcium channel, voltage-dependent, alpha 2/delta subunit 2 | CACNA2D2 | 15761015 | |
| ARSENIC TRIOXIDE | NM_021251; NM_023083; NM_023085; NM_023089 | calpain 10 | CAPN10 | 15761015 | |
| ARSENIC TRIOXIDE | NM_004930 | capping protein (actin filament) muscle Z-line, beta | CAPZB | 12852829 | |
| ARSENIC TRIOXIDE | NM_001014437; NM_001014438; NM_001751; NM_139273 | cysteinyl-tRNA synthetase | CARS | 12852829 | |
| ARSENIC TRIOXIDE | NM_001230; NM_032974; NM_032977 | caspase 10, apoptosis-related cysteine peptidase | CASP10 | 12388546 | |
| ARSENIC TRIOXIDE | NM_004346; NM_032991 | caspase 3, apoptosis-related cysteine peptidase | CASP3 | 14668793, 15979894, 15979894, 15665116, 16951922, 16867262, 16951922 | |
| ARSENIC TRIOXIDE | NM_001080124; NM_001080125; NM_001228; NM_033355; NM_033356; NM_033358 | caspase 8, apoptosis-related cysteine peptidase | CASP8 | 16010437, 16972261 | |
| ARSENIC TRIOXIDE | NM_001229; NM_032996 | caspase 9, apoptosis-related cysteine peptidase | CASP9 | 16010437, 17 | |
| ARSENIC TRIOXIDE | NM_001753 | caveolin 1, caveolae protein, 22 kDa | CAV1 | 15725085 | |
| ARSENIC TRIOXIDE | NM_001233; NM_198212 | caveolin 2 | CAV2 | 15725085, 15761015 | |

TABLE 1-continued

| Molecule | RefSeq | Description | Symbol | PMID | Interaction |
|---|---|---|---|---|---|
| ARSENIC TRIOXIDE | NM_001093729; NM_024781 | coiled-coil domain containing 102B | CCDC102B | 15761015 | |
| ARSENIC TRIOXIDE | NM_144718 | coiled-coil domain containing 52 | CCDC52 | 15761015 | |
| ARSENIC TRIOXIDE | NM_004167; NM_032964; NM_032965 | chemokine (C-C motif) ligand 15 | CCL15 | 15761015 | |
| ARSENIC TRIOXIDE | NM_002982 | chemokine (C-C motif) ligand 2 | CCL2 | 15761015 | |
| ARSENIC TRIOXIDE | NM_005064; NM_145898 | chemokine (C-C motif) ligand 23 | CCL23 | 15761015 | |
| ARSENIC TRIOXIDE | NM_001111045; NM_001111046; NM_001111047; NM_003914 | cyclin A1 | CCNA1 | 15761015 | |
| ARSENIC TRIOXIDE | NM_031966 | cyclin B1 | CCNB1 | 12783709 | |
| ARSENIC TRIOXIDE | NM_004701 | cyclin B2 | CCNB2 | 17547211 | |
| ARSENIC TRIOXIDE | NM_053056 | cyclin D1 | CCND1 | — | |
| ARSENIC TRIOXIDE | NM_001766 | CD1d molecule | CD1D | 15761015 | |
| ARSENIC TRIOXIDE | NM_000610; NM_001001389; NM_001001390; NM_001001391; NM_001001392 | CD44 molecule (Indian blood group) | CD44 | 15553829 | |
| ARSENIC TRIOXIDE | NM_001803 | CD52 molecule | CD52 | 15761015 | |
| ARSENIC TRIOXIDE | NM_001252 | CD70 molecule | CD70 | 15761015 | |
| ARSENIC TRIOXIDE | NM_006889; NM_175862 | CD86 molecule | CD86 | 15761015 | |
| ARSENIC TRIOXIDE | NM_003607; NM_014826 | CDC42 binding protein kinase alpha (DMPK-like) | CDC42BPA | 15761015 | |
| ARSENIC TRIOXIDE | NM_024529 | cell division cycle 73, Paf1/RNA polymerase II complex component, homolog (S. cerevisiae) | CDC73 | 15761015 | |
| ARSENIC TRIOXIDE | NM_000389; NM_078467 | cyclin-dependent kinase inhibitor 1A (p21, Cip1) | CDKN1A | 12749819, 15961274 | |
| ARSENIC TRIOXIDE | NM_000077; NM_058195; NM_058197 | cyclin-dependent kinase inhibitor 2A (melanoma, p16, inhibits CDK4) | CDKN2A | 15191659, 16008847, 15191659 | 16008847, |
| ARSENIC TRIOXIDE | NM_004936; NM_078487 | cyclin-dependent kinase inhibitor 2B (p15, inhibits CDK4) | CDKN2B | 11877046, 12679007, 12679007 | |
| ARSENIC TRIOXIDE | NM_001130851; NM_005192 | cyclin-dependent kinase inhibitor 3 | CDKN3 | 17547211 | |
| ARSENIC TRIOXIDE | NM_001805 | CCAAT/enhancer binding protein (C/EBP), epsilon | CEBPE | 12130515 | |
| ARSENIC TRIOXIDE | NM_014679 | centrosomal protein 57 kDa | CEP57 | 14703492 | |
| ARSENIC TRIOXIDE | NM_001710 | complement factor B | CFB | 17547211 | |
| ARSENIC TRIOXIDE | NM_001127183; NM_001127184; NM_003879 | CASP8 and FADD-like apoptosis regulator | CFLAR | 16105982, 16105982, 16174796 | |
| ARSENIC TRIOXIDE | NM_001114121; NM_001114122; NM_001274 | CHK1 checkpoint homolog (S. pombe) | CHEK1 | 16891316 | |

TABLE 1-continued

| Molecule | RefSeq | Description | Symbol | PMID | Interaction |
|---|---|---|---|---|---|
| ARSENIC TRIOXIDE | NM_001005735; NM_007194; NM_145862 | CHK2 checkpoint homolog (S. pombe) | CHEK2 | 16891316 | |
| ARSENIC TRIOXIDE | NM_001819 | chromogranin B (secretogranin 1) | CHGB | 15761015 | |
| ARSENIC TRIOXIDE | NM_001276 | chitinase 3-like 1 (cartilage glycoprotein-39) | CHI3L1 | 15761015 | |
| ARSENIC TRIOXIDE | NM_021615 | carbohydrate (N-acetylglucosamine 6-O) sulfotransferase 6 | CHST6 | 15761015, 15 | |
| ARSENIC TRIOXIDE | NM_014430 | cell death-inducing DFFA-like effector b | CIDEB | 17547211 | |
| ARSENIC TRIOXIDE | NM_006079 | Cbp/p300-interacting transactivator, with Glu/Asp-rich carboxy-terminal domain, 2 | CITED2 | 15725085 | |
| ARSENIC TRIOXIDE | NM_006825 | cytoskeleton-associated protein 4 | CKAP4 | 12852829 | |
| ARSENIC TRIOXIDE | NM_001828 | Charcot-Leyden crystal protein | CLC | 15761015, 15 | |
| ARSENIC TRIOXIDE | NM_022570; NM_197947; NM_197948; NM_197949; NM_197950; NM_197954 | C-type lectin domain family 7, member A | CLEC7A | 15725085 | |
| ARSENIC TRIOXIDE | NM_001130675; NM_004362 | calmegin | CLGN | 17547211 | |
| ARSENIC TRIOXIDE | NM_178868 | CKLF-like MARVEL transmembrane domain containing 8 | CMTM8 | 15761015 | |
| ARSENIC TRIOXIDE | NM_014515 | CCR4-NOT transcription complex, subunit 2 | CNOT2 | 15761015 | |
| ARSENIC TRIOXIDE | NM_014900 | COBL-like 1 | COBLL1 | 15761015 | |
| ARSENIC TRIOXIDE | NM_006438 | collectin sub-family member 10 (C-type lectin) | COLEC10 | 15761015 | |
| ARSENIC TRIOXIDE | NM_006837 | COP9 constitutive photomorphogenic homolog subunit 5 (Arabidopsis) | COPS5 | 17077332 | |
| ARSENIC TRIOXIDE | NM_001011666; NM_004904; NM_182898; NM_182899 | cAMP responsive element binding protein 5 | CREB5 | 15761015 | |
| ARSENIC TRIOXIDE | NM_000756 | corticotropin releasing hormone | CRH | 15761015 | |
| ARSENIC TRIOXIDE | NM_016441 | cysteine rich transmembrane BMP regulator 1 (chordin-like) | CRIM1 | 15761015, 16 | |
| ARSENIC TRIOXIDE | NM_000395 | colony stimulating factor 2 receptor, beta, low-affinity (granulocyte-macrophage) | CSF2RB | 15070760 | |
| ARSENIC TRIOXIDE | NM_001317; NM_022640; NM_022641 | chorionic somatomammotropin hormone 1 (placental lactogen) | CSH1 | 15761015 | |
| ARSENIC TRIOXIDE | NM_001077204; NM_024790 | centrosome and spindle pole associated protein 1 | CSPP1 | 15761015 | |
| ARSENIC TRIOXIDE | NM_001127656; NM_003476 | cysteine and glycine-rich protein 3 (cardiac LIM protein) | CSRP3 | 15725085 | |
| ARSENIC TRIOXIDE | NM_000099 | cystatin C | CST3 | 15725085 | |
| ARSENIC TRIOXIDE | NM_001903 | catenin (cadherin-associated protein), alpha 1, 102 kDa | CTNNA1 | 15761015 | |
| ARSENIC TRIOXIDE | NM_004390; NM_148979 | cathepsin H | CTSH | 15761015 | |

| Molecule | RefSeq | Description | Symbol | PMID | Interaction |
|---|---|---|---|---|---|
| ARSENIC TRIOXIDE | NM_002996 | chemokine (C-X3-C motif) ligand 1 | CX3CL1 | 17547211 | |
| ARSENIC TRIOXIDE | NM_000398; NM_001129819; NM_007326 | cytochrome b5 reductase 3 | CYB5R3 | 15725085 | |
| ARSENIC TRIOXIDE | NM_000101 | cytochrome b-245, alpha polypeptide | CYBA | 15070760 | |
| ARSENIC TRIOXIDE | NM_001127383; NM_024843 | cytochrome b reductase 1 | CYBRD1 | 15761015 | |
| ARSENIC TRIOXIDE | NM_018947 | cytochrome c, somatic | CYCS | 16972261 | |
| ARSENIC TRIOXIDE | NM_001042355; NM_001042412; NM_015247 | cylindromatosis (turban tumor syndrome) | CYLD | 15761015 | |
| ARSENIC TRIOXIDE | NM_000499 | cytochrome P450, family 1, subfamily A, polypeptide 1 | CYP1A1 | 11678611, 12490585 | |
| ARSENIC TRIOXIDE | NM_016593 | cytochrome P450, family 39, subfamily A, polypeptide 1 | CYP39A1 | 15761015 | |
| ARSENIC TRIOXIDE | NM_022820; NM_057095; NM_057096 | cytochrome P450, family 3, subfamily A, polypeptide 43 | CYP3A43 | 15761015 | |
| ARSENIC TRIOXIDE | NM_018659 | cytokine-like 1 | CYTL1 | 15761015, 15761015, 15070760 | |
| ARSENIC TRIOXIDE | NM_001141969; NM_001141970; NM_001350 | death-domain associated protein | DAXX | 17081986 | |
| ARSENIC TRIOXIDE | NM_001005375; NM_020420 | deleted in azoospermia 4 | DAZ4 | 15761015 | |
| ARSENIC TRIOXIDE | NM_014618 | deleted in bladder cancer 1 | DBC1 | 15761015 | |
| ARSENIC TRIOXIDE | NM_012242 | dickkopf homolog 1 (*Xenopus laevis*) | DKK1 | 11678611, 12749819 | |
| ARSENIC TRIOXIDE | NM_004083 | DNA-damage-inducible transcript 3 | DDIT3 | 17547211 | |
| ARSENIC TRIOXIDE | NM_004084 | defensin, alpha 1 | DEFA1 | 15761015 | |
| ARSENIC TRIOXIDE | NM_001925 | defensin, alpha 4, corticostatin | DEFA4 | 15761015 | |
| ARSENIC TRIOXIDE | NM_007034 | DnaJ (Hsp40) homolog, subfamily B, member 4 | DNAJB4 | 15761015, 15 | |
| ARSENIC TRIOXIDE | NM_015190 | DnaJ (Hsp40) homolog, subfamily C, member 9 | DNAJC9 | 15761015, 15 | |
| ARSENIC TRIOXIDE | NM_001130823; NM_001379 | DNA (cytosine-5-)-methyltransferase 1 | DNMT1 | 12679007 | |
| ARSENIC TRIOXIDE | NM_022552; NM_153759; NM_175629; NM_175630 | DNA (cytosine-5-)-methyltransferase 3 alpha | DNMT3A | 12679007 | |
| ARSENIC TRIOXIDE | NM_006892; NM_175848; NM_175849; NM_175850 | DNA (cytosine-5-)-methyltransferase 3 beta | DNMT3B | 12679007 | |
| ARSENIC TRIOXIDE | NM_001394; NM_057158 | dual specificity phosphatase 4 | DUSP4 | 15725085 | |
| ARSENIC TRIOXIDE | NM_001376 | dynein, cytoplasmic 1, heavy chain 1 | DYNC1H1 | 15725085 | |
| ARSENIC TRIOXIDE | NM_004714; NM_006483; NM_006484 | dual-specificity tyrosine-(Y)-phosphorylation regulated kinase 1B | DYRK1B | 15070760 | |

TABLE 1-continued

| Molecule | RefSeq | Description | Symbol | PMID | Interaction |
|---|---|---|---|---|---|
| ARSENIC TRIOXIDE | — | — | EBI2 | 15761015 | |
| ARSENIC TRIOXIDE | NM_005228; NM_201282; NM_201283; NM_201284 | epidermal growth factor receptor (erythroblastic leukemia viral (v-erb-b) oncogene homolog, avian) | EGFR | 15961274 | |
| ARSENIC TRIOXIDE | NM_001964 | early growth response 1 | EGR1 | 12749819 | |
| ARSENIC TRIOXIDE | — | — | ELA2A | 15761015 | |
| ARSENIC TRIOXIDE | — | — | ENDOGL1 | 15761015 | |
| ARSENIC TRIOXIDE | NM_001429 | E1A binding protein p300 | EP300 | 15031205 | |
| ARSENIC TRIOXIDE | NM_001135554; NM_001135555; NM_001431 | erythrocyte membrane protein band 4.1-like 2 | EPB41L2 | 15761015 | |
| ARSENIC TRIOXIDE | NM_000120; NM_001136018 | epoxide hydrolase 1, microsomal (xenobiotic) | EPHX1 | 17547211 | |
| ARSENIC TRIOXIDE | NM_000502 | eosinophil peroxidase | EPX | 15761015, 15 | |
| ARSENIC TRIOXIDE | NM_015576 | ELKS/RAB6-interacting/CAST family member 2 | ERC2 | 15761015 | |
| ARSENIC TRIOXIDE | NM_016570 | ERGIC and golgi 2 | ERGIC2 | — | |
| ARSENIC TRIOXIDE | NM_000125; NM_001122740; NM_001122741; NM_001122742 | estrogen receptor 1 | ESR1 | 12014631 | |
| ARSENIC TRIOXIDE | NM_001040275; NM_001040276; NM_001437 | estrogen receptor 2 (ER beta) | ESR2 | 12014631 | |
| ARSENIC TRIOXIDE | NM_016337 | Enah/Vasp-like | EVL | 15725085 | |
| ARSENIC TRIOXIDE | NM_001993 | coagulation factor III (thromboplastin, tissue factor) | F3 | 15761015, 16206674 | |
| ARSENIC TRIOXIDE | NM_147189 | family with sequence similarity 110, member B | FAM110B | 15761015 | |
| ARSENIC TRIOXIDE | NM_017709 | family with sequence similarity 46, member C | FAM46C | 15725085 | |
| ARSENIC TRIOXIDE | NM_000136 | Fanconi anemia, complementation group C | FANCC | 15070760 | |
| ARSENIC TRIOXIDE | NM_000043; NM_152871; NM_152872; NM_152873; NM_152874; NM_152875; NM_152876; NM_152877 | Fas (TNF receptor superfamily, member 6) | FAS | 15979894, 12478894, 15979894, 15382040, 11135700, 12452020, 16029599, 12126518 | |
| ARSENIC TRIOXIDE | NM_000639 | Fas ligand (TNF superfamily, member 6) | FASLG | 12452020, 12 | |
| ARSENIC TRIOXIDE | NM_006329 | fibulin 5 | FBLN5 | 15761015 | |
| ARSENIC TRIOXIDE | NM_012304 | F-box and leucine-rich repeat protein 7 | FBXL7 | 15725085 | |
| ARSENIC TRIOXIDE | NM_015850; NM_023105; NM_023106; NM_023107; NM_023108; NM_023110; NM_023111 | fibroblast growth factor receptor 1 | FGFR1 | 15761015, 17027752 | |

TABLE 1-continued

| Molecule | RefSeq | Description | Symbol | PMID | Interaction |
|---|---|---|---|---|---|
| ARSENIC TRIOXIDE | NM_000141; NM_001144913; NM_001144914; NM_001144915; NM_001144916; NM_001144917; NM_001144918; NM_001144919; NM_022970 | fibroblast growth factor receptor 2 | FGFR2 | 15761015 | |
| ARSENIC TRIOXIDE | NM_001042729; NM_001042747; NM_005248 | Gardner-Rasheed feline sarcoma viral (v-fgr) oncogene homolog | FGR | 15761015 | |
| ARSENIC TRIOXIDE | NM_001024948; NM_017737 | formin binding protein 1-like | FNBP1L | 15761015 | |
| ARSENIC TRIOXIDE | NM_005252 | v-fos FBJ murine osteosarcoma viral oncogene homolog | FOS | 11678611, 11678611, 14682389, 12749819, 14682389 | |
| ARSENIC TRIOXIDE | NM_001102371; NM_024955 | FAD-dependent oxidoreductase domain containing 2 | FOXRED2 | 15761015 | |
| ARSENIC TRIOXIDE | NM_002031 | fyn-related kinase | FRK | 15761015 | |
| ARSENIC TRIOXIDE | NM_003088 | fascin homolog 1, actin-bundling protein (Strongylocentrotus purpuratus) | FSCN1 | 15761015, 15 | |
| ARSENIC TRIOXIDE | NM_002032 | ferritin, heavy polypeptide 1 | FTH1 | 15725085, 15 | |
| ARSENIC TRIOXIDE | NM_001465; NM_199335 | FYN binding protein (FYB-120/130) | FYB | 15761015 | |
| ARSENIC TRIOXIDE | NM_005458 | gamma-aminobutyric acid (GABA) B receptor, 2 | GABBR2 | 15761015 | |
| ARSENIC TRIOXIDE | NM_144618 | GA binding protein transcription factor, beta subunit 2 | GABPB2 | 12852829 | |
| ARSENIC TRIOXIDE | NM_001924 | growth arrest and DNA-damage-inducible, alpha | GADD45A | 11678611, 15761015, 11678611 | |
| ARSENIC TRIOXIDE | NM_000157; NM_001005741; NM_001005742; NM_001005749; NM_001005750 | glucosidase, beta; acid (includes glucosylceramidase) | GBA | 15761015 | |
| ARSENIC TRIOXIDE | NM_002061 | glutamate-cysteine ligase, modifier subunit | GCLM | 15725085 | |
| ARSENIC TRIOXIDE | NM_024711 | GTPase, IMAP family member 6 | GIMAP6 | 15761015 | |
| ARSENIC TRIOXIDE | NM_001135213; NM_001135214; NM_014776; NM_057169; NM_057170; NM_139201 | G protein-coupled receptor kinase interacting ArfGAP 2 | GIT2 | 15761015 | |
| ARSENIC TRIOXIDE | NM_000165 | gap junction protein, alpha 1, 43 kDa | GJA1 | 15761015, 15 | |
| ARSENIC TRIOXIDE | NM_000169 | galactosidase, alpha | GLA | 17547211 | |
| ARSENIC TRIOXIDE | NM_001142339; NM_002071; NM_182978 | guanine nucleotide binding protein (G protein), alpha activating activity polypeptide, olfactory type | GNAL | 15761015 | |
| ARSENIC TRIOXIDE | NM_001039966; NM_001098201; NM_001505 | G protein-coupled estrogen receptor 1 | GPER | 17547211 | |
| ARSENIC TRIOXIDE | NM_005277; NM_201591; NM_201592 | glycoprotein M6A | GPM6A | 15761015 | |
| ARSENIC TRIOXIDE | NM_004778 | G protein-coupled receptor 44 | GPR44 | 15761015 | |
| ARSENIC TRIOXIDE | NM_018654 | G protein-coupled receptor, family C, group 5, member D | GPRC5D | 15725085 | |
| ARSENIC TRIOXIDE | NM_000581; NM_201397 | glutathione peroxidase 1 | GPX1 | 16867262 | |

TABLE 1-continued

| Molecule | RefSeq | Description | Symbol | PMID | Interaction |
|---|---|---|---|---|---|
| ARSENIC TRIOXIDE | NM_001146320; NM_023927 | GRAM domain containing 3 | GRAMD3 | 15070760 | |
| ARSENIC TRIOXIDE | NM_001004056; NM_001004057; NM_182982 | G protein-coupled receptor kinase 4 | GRK4 | 15761015 | |
| ARSENIC TRIOXIDE | NM_145740 | glutathione S-transferase alpha 1 | GSTA1 | 11678611 | |
| ARSENIC TRIOXIDE | NM_000852 | glutathione S-transferase pi 1 | GSTP1 | 15231573, 15665116 | |
| ARSENIC TRIOXIDE | NM_001513; NM_145870; NM_145871 | glutathione transferase zeta 1 | GSTZ1 | 15761015 | |
| ARSENIC TRIOXIDE | NM_002105 | H2A histone family, member X | H2AFX | 16891316 | |
| ARSENIC TRIOXIDE | NR_024052; NR_024052; NR_024052; NR_024052; NR_024052; NR_024052; NR_024053; NR_024053; NR_024053; NR_024053; NR_024053; NR_024053 | HLA complex group 18 | HCG18 | 15761015 | |
| ARSENIC TRIOXIDE | NM_001525 | hypocretin (orexin) receptor 1 | HCRTR1 | 15761015 | |
| ARSENIC TRIOXIDE | NM_000601; NM_001010931; NM_001010932; NM_001010933; NM_001010934 | hepatocyte growth factor (hepapoietin A; scatter factor) | HGF | 15761015 | |
| ARSENIC TRIOXIDE | NM_001530; NM_181054 | hypoxia inducible factor 1, alpha subunit (basic helix-loop-helix transcription factor) | HIF1A | 12482858, 16330433 | |
| ARSENIC TRIOXIDE | — | | HIG2 | 15725085 | |
| ARSENIC TRIOXIDE | NM_003521 | histone cluster 1, H2bm | HIST1H2BM | 15761015 | |
| ARSENIC TRIOXIDE | NM_003542 | histone cluster 1, H4c | HIST1H4C | 17547211 | |
| ARSENIC TRIOXIDE | NM_003493 | histone cluster 3, H3 | HIST3H3 | 12388546 | |
| ARSENIC TRIOXIDE | NM_000188; NM_033496; NM_033497; NM_033498; NM_033500 | hexokinase 1 | HK1 | 15761015 | |
| ARSENIC TRIOXIDE | NM_005514 | major histocompatibility complex, class I, B | HLA-B | 15761015, 16 | |
| ARSENIC TRIOXIDE | NM_002117 | major histocompatibility complex, class I, C | HLA-C | 15761015, 16 | |
| ARSENIC TRIOXIDE | NM_019111 | major histocompatibility complex, class II, DR alpha | HLA-DRA | 15725085 | |
| ARSENIC TRIOXIDE | NM_001098478; NM_001098479; NM_018950 | major histocompatibility complex, class I, F | HLA-F | 15725085 | |
| ARSENIC TRIOXIDE | NM_002127 | major histocompatibility complex, class I, G | HLA-G | 15761015, 16 | |
| ARSENIC TRIOXIDE | NM_002131; NM_145899; NM_145901; NM_145902; NM_145903; NM_145905 | high mobility group AT-hook 1 | HMGA1 | 17547211 | |
| ARSENIC TRIOXIDE | NM_001130688; NM_001130689; NM_002129 | high-mobility group box 2 | HMGB2 | 14703492 | |

TABLE 1-continued

| Molecule | RefSeq | Description | Symbol | PMID | Interaction |
|---|---|---|---|---|---|
| ARSENIC TRIOXIDE | NM_005517 | high-mobility group nucleosomal binding domain 2 | HMGN2 | 17547211 | |
| ARSENIC TRIOXIDE | NM_002133 | heme oxygenase (decycling) 1 | HMOX1 | 16487037, 17547211, 15725085 | |
| ARSENIC TRIOXIDE | NM_002153 | hydroxysteroid (17-beta) dehydrogenase 2 | HSD17B2 | 17547211 | |
| ARSENIC TRIOXIDE | NM_005526 | heat shock transcription factor 1 | HSF1 | 15978632 | |
| ARSENIC TRIOXIDE | — | — | HSP27 | 15665116 | |
| ARSENIC TRIOXIDE | NM_005345 | heat shock 70 kDa protein 1A | HSPA1A | 12749819 | |
| ARSENIC TRIOXIDE | NM_002154 | heat shock 70 kDa protein 4 | HSPA4 | 11678611, 11678611, 14682389, 15665116, 14682389 | |
| ARSENIC TRIOXIDE | NM_005347 | heat shock 70 kDa protein 5 (glucose-regulated protein, 78 kDa) | HSPA5 | 11678611 | |
| ARSENIC TRIOXIDE | NM_002155 | heat shock 70 kDa protein 6 (HSP70B') | HSPA6 | 15978632 | |
| ARSENIC TRIOXIDE | NM_001540 | heat shock 27 kDa protein 1 | HSPB1 | 15761015, 15 | |
| ARSENIC TRIOXIDE | NM_001098520; NM_001098521; NM_001098522; NM_001098523; NM_006410 | HIV-1 Tat interactive protein 2, 30 kDa | HTATIP2 | 15761015 | |
| ARSENIC TRIOXIDE | NM_002162 | intercellular adhesion molecule 3 | ICAM3 | 15761015 | |
| ARSENIC TRIOXIDE | NM_002165; NM_181353 | inhibitor of DNA binding 1, dominant negative helix-loop-helix protein | ID1 | 15761015 | |
| ARSENIC TRIOXIDE | NM_002166 | inhibitor of DNA binding 2, dominant negative helix-loop-helix protein | ID2 | 15761015 | |
| ARSENIC TRIOXIDE | NM_000202; NM_006123 | iduronate 2-sulfatase | IDS | 15761015 | |
| ARSENIC TRIOXIDE | NM_004907 | immediate early response 2 | IER2 | 12749819 | |
| ARSENIC TRIOXIDE | NM_005531 | interferon, gamma-inducible protein 16 | IFI16 | 15761015 | |
| ARSENIC TRIOXIDE | NM_022168 | interferon induced with helicase C domain 1 | IFIH1 | 15761015 | |
| ARSENIC TRIOXIDE | NM_000605 | interferon, alpha 2 | IFNA2 | 12560223, 17077332 | |
| ARSENIC TRIOXIDE | NM_000619 | interferon, gamma | IFNG | 14668793, 16914093 | |
| ARSENIC TRIOXIDE | NM_001007245; NM_001550 | interferon-related developmental regulator 1 | IFRD1 | 17547211 | |
| ARSENIC TRIOXIDE | NM_000597 | insulin-like growth factor binding protein 2, 36 kDa | IGFBP2 | 15761015, 15 | |
| ARSENIC TRIOXIDE | NM_001553 | insulin-like growth factor binding protein 7 | IGFBP7 | 15725085 | |
| ARSENIC TRIOXIDE | NM_001556 | inhibitor of kappa light polypeptide gene enhancer in B-cells, kinase beta | IKBKB | — | |
| ARSENIC TRIOXIDE | NM_001559 | interleukin 12 receptor, beta 2 | IL12RB2 | 15761015 | |

TABLE 1-continued

| Molecule | RefSeq | Description | Symbol | PMID | Interaction |
|---|---|---|---|---|---|
| ARSENIC TRIOXIDE | NM_006850; NM_181339 | interleukin 24 | IL24 | 15580305 | |
| ARSENIC TRIOXIDE | NM_000600 | interleukin 6 (interferon, beta 2) | IL6 | 12560223 | |
| ARSENIC TRIOXIDE | NM_001557 | interleukin 8 receptor, beta | IL8RB | 15761015 | |
| ARSENIC TRIOXIDE | NM_005540 | inositol polyphosphate-5-phosphatase, 75 kDa | INPP5B | 15761015 | |
| ARSENIC TRIOXIDE | NM_002196 | insulinoma-associated 1 | INSM1 | 15761015 | |
| ARSENIC TRIOXIDE | NM_001031715; NM_022784 | IQ motif containing H | IQCH | 15761015 | |
| ARSENIC TRIOXIDE | NM_002198 | interferon regulatory factor 1 | IRF1 | 14668793, 16914093 | |
| ARSENIC TRIOXIDE | NM_000419 | integrin, alpha 2b (platelet glycoprotein IIb of IIb/IIIa complex, antigen CD41) | ITGA2B | 15761015 | |
| ARSENIC TRIOXIDE | NM_000632; NM_001145808 | integrin, alpha M (complement component 3 receptor 3 subunit) | ITGAM | 16430862, 16468075 | |
| ARSENIC TRIOXIDE | NM_002211; NM_033666; NM_033667; NM_033668; NM_033669; NM_133376 | integrin, beta 1 (fibronectin receptor, beta polypeptide, antigen CD29 includes MDF2, MSK12) | ITGB1 | 12852829 | |
| ARSENIC TRIOXIDE | NM_014288 | integrin beta 3 binding protein (beta3-endonexin) | ITGB3BP | 17547211 | |
| ARSENIC TRIOXIDE | NM_000889 | integrin, beta 7 | ITGB7 | 15761015 | |
| ARSENIC TRIOXIDE | NM_004867 | integral membrane protein 2A | ITM2A | 15725085 | |
| ARSENIC TRIOXIDE | NM_002228 | jun oncogene | JUN | 12749819 | |
| ARSENIC TRIOXIDE | NM_005354 | jun D proto-oncogene | JUND | 15761015, 17077332 | |
| ARSENIC TRIOXIDE | NM_000238; NM_172056; NM_172057 | potassium voltage-gated channel, subfamily H (eag-related), member 2 | KCNH2 | 15070760, 15213294 | |
| ARSENIC TRIOXIDE | NM_138444 | potassium channel tetramerisation domain containing 12 | KCTD12 | 15761015 | |
| ARSENIC TRIOXIDE | NR_022006; NR_022006; NR_022006; NR_022006; NR_022006; NR_022006; NR_022006 | KIAA0087 | KIAA0087 | 15761015 | |
| ARSENIC TRIOXIDE | NM_020947 | KIAA1609 | KIAA1609 | 15761015 | |
| ARSENIC TRIOXIDE | NM_017596 | kinesin family member 21B | KIF21B | 15761015 | |
| ARSENIC TRIOXIDE | NM_000899; NM_003994 | KIT ligand | KITLG | 15761015 | |
| ARSENIC TRIOXIDE | NM_003597 | Kruppel-like factor 11 | KLF11 | 15761015 | |
| ARSENIC TRIOXIDE | NM_001730 | Kruppel-like factor 5 (intestinal) | KLF5 | 15761015 | |
| ARSENIC TRIOXIDE | NM_005554 | keratin 6A | KRT6A | 15949261 | |
| ARSENIC TRIOXIDE | NM_001032998; NM_003937 | kynureninase (L-kynurenine hydrolase) | KYNU | 15761015 | |

TABLE 1-continued

| Molecule | RefSeq | Description | Symbol | PMID | Interaction |
|---|---|---|---|---|---|
| ARSENIC TRIOXIDE | NM_002293 | laminin, gamma 1 (formerly LAMB2) | LAMC1 | 12852829 | |
| ARSENIC TRIOXIDE | NM_001014987; NM_001014988; NM_001014989; NM_014387 | linker for activation of T cells | LAT | 15761015 | |
| ARSENIC TRIOXIDE | NM_002308; NM_009587 | lectin, galactoside-binding, soluble, 9 | LGALS9 | 15761015 | |
| ARSENIC TRIOXIDE | NM_001008530; NM_005606 | legumain | LGMN | 15725085 | |
| ARSENIC TRIOXIDE | NM_005780 | lipoma HMGIC fusion partner | LHFP | 15761015, 15 | |
| ARSENIC TRIOXIDE | NM_014368; NM_199160 | LIM homeobox 6 | LHX6 | 15761015 | |
| ARSENIC TRIOXIDE | NM_001013253; NM_001013254; NM_001013255; NM_002339 | lymphocyte-specific protein 1 | LSP1 | 15761015 | |
| ARSENIC TRIOXIDE | NM_145867 | leukotriene C4 synthase | LTC4S | 15761015 | |
| ARSENIC TRIOXIDE | NM_001161572; NM_001161573; NM_001161574; NM_012323; NM_152878 | v-maf musculoaponeurotic fibrosarcoma oncogene homolog F (avian) | MAFF | 16487037 | |
| ARSENIC TRIOXIDE | NM_002359; NM_032711 | v-maf musculoaponeurotic fibrosarcoma oncogene homolog G (avian) | MAFG | 16487037 | |
| ARSENIC TRIOXIDE | NM_002360 | v-maf musculoaponeurotic fibrosarcoma oncogene homolog K (avian) | MAFK | 16487037 | |
| ARSENIC TRIOXIDE | NM_005907 | mannosidase, alpha, class 1A, member 1 | MAN1A1 | 15761015 | |
| ARSENIC TRIOXIDE | NM_000240 | monoamine oxidase A | MAOA | 15761015 | |
| ARSENIC TRIOXIDE | NM_002756; NM_145109 | mitogen-activated protein kinase kinase 3 | MAP2K3 | 16818652 | |
| ARSENIC TRIOXIDE | NM_003010 | mitogen-activated protein kinase kinase 4 | MAP2K4 | 15978632 | |
| ARSENIC TRIOXIDE | NM_002758 | mitogen-activated protein kinase kinase 6 | MAP2K6 | 16818652 | |
| ARSENIC TRIOXIDE | NM_003980 | microtubule-associated protein 7 | MAP7 | 15761015 | |
| ARSENIC TRIOXIDE | NM_002745; NM_138957 | mitogen-activated protein kinase 1 | MAPK1 | 15580305, 15961274, 16328441, 16328441, 15961274, 16818652, 17 | |
| ARSENIC TRIOXIDE | NM_001315; NM_139012; NM_139013; NM_139014 | mitogen-activated protein kinase 14 | MAPK14 | 16818652, 17050201 | |
| ARSENIC TRIOXIDE | NM_001040056; NM_001109891; NM_002746 | mitogen-activated protein kinase 3 | MAPK3 | 15580305, 15961274, 16328441, 16328441, 15961274, 17050201 | |
| ARSENIC TRIOXIDE | NM_002749; NM_139032; NM_139033; NM_139034 | mitogen-activated protein kinase 7 | MAPK7 | 15580305 | |
| ARSENIC TRIOXIDE | NM_002750; NM_139046; NM_139047; NM_139049 | mitogen-activated protein kinase 8 | MAPK8 | 15580305, 15961274, 16646077, 16818652 | |
| ARSENIC TRIOXIDE | NM_001135044; NM_002752; NM_139068; NM_139069; NM_139070 | mitogen-activated protein kinase 9 | MAPK9 | 15580305, 16818652 | |
| ARSENIC TRIOXIDE | NM_001005415; NM_001005416; NM_016496 | membrane-associated ring finger (C3HC4) 2 | MARCH2 | 15761015 | |
| ARSENIC TRIOXIDE | — | — | MASK | 17547211 | |

TABLE 1-continued

| Molecule | RefSeq | Description | Symbol | PMID | Interaction |
|---|---|---|---|---|---|
| ARSENIC TRIOXIDE | NM_001112732; NM_024979 | MCF.2 cell line derived transforming sequence-like | MCF2L | 12852829 | |
| ARSENIC TRIOXIDE | NM_004526 | minichromosome maintenance complex component 2 | MCM2 | 17547211 | |
| ARSENIC TRIOXIDE | NM_002395 | malic enzyme 1, NADP(+)-dependent, cytosolic | ME1 | 15725085 | |
| ARSENIC TRIOXIDE | NM_032390 | MKI67 (FHA domain) interacting nucleolar phosphoprotein | MKI67IP | 14703492 | |
| ARSENIC TRIOXIDE | NM_002421 | matrix metallopeptidase 1 (interstitial collagenase) | MMP1 | 15761015 | |
| ARSENIC TRIOXIDE | NM_001127891; NM_004530 | matrix metallopeptidase 2 (gelatinase A, 72 kDa gelatinase, 72 kDa type IV collagenase) | MMP2 | 15553829, 16624393, 16624393 | |
| ARSENIC TRIOXIDE | NM_001032278; NM_024302 | matrix metallopeptidase 28 | MMP28 | 15761015 | |
| ARSENIC TRIOXIDE | NM_004994 | matrix metallopeptidase 9 (gelatinase B, 92 kDa gelatinase, 92 kDa type IV collagenase) | MMP9 | 15949266, 16624393 | |
| ARSENIC TRIOXIDE | NM_005373 | myeloproliferative leukemia virus oncogene | MPL | 15761015 | |
| ARSENIC TRIOXIDE | NM_000250 | myeloperoxidase | MPO | 12130515 | |
| ARSENIC TRIOXIDE | NM_016065 | mitochondrial ribosomal protein S16 | MRPS16 | 14703492 | |
| ARSENIC TRIOXIDE | NM_005098 | musculin (activated B-cell factor-1) | MSC | 15761015 | |
| ARSENIC TRIOXIDE | NM_012228 | methionine sulfoxide reductase B2 | MSRB2 | 15725085 | |
| ARSENIC TRIOXIDE | NM_175617 | metallothionein 1E | MT1E | 15725085 | |
| ARSENIC TRIOXIDE | NM_005950 | metallothionein 1G | MT1G | 15725085 | |
| ARSENIC TRIOXIDE | NM_005951 | metallothionein 1H | MT1H | 15725085 | |
| ARSENIC TRIOXIDE | NR_001447; NR_001447; NR_001447; NR_001447; NR_001447; NR_001447 | metallothionein 1L (gene/pseudogene) | MT1L | 15725085 | |
| ARSENIC TRIOXIDE | — | metallothionein 1 pseudogene 2 | MT1P2 | 15725085 | |
| ARSENIC TRIOXIDE | NM_005952 | metallothionein 1X | MT1X | 15725085 | |
| ARSENIC TRIOXIDE | NM_005953 | metallothionein 2A | MT2A | 15725085 | |
| ARSENIC TRIOXIDE | NM_004689 | metastasis associated 1 | MTA1 | 15725085 | |
| ARSENIC TRIOXIDE | NM_001008528; NM_001008529; NM_198530 | matrix-remodelling associated 7 | MXRA7 | 17547211 | |
| ARSENIC TRIOXIDE | NM_001080416; NM_001144755 | v-myb myeloblastosis viral oncogene homolog (avian)-like 1 | MYBL1 | 15725085 | |
| ARSENIC TRIOXIDE | NM_002467 | v-myc myelocytomatosis viral oncogene homolog (avian) | MYC | 11678611, 11678611, 15725085, 14682389, 14682389, 12478894 | |
| ARSENIC TRIOXIDE | NM_005378 | v-myc myelocytomatosis viral related oncogene, neuroblastoma derived (avian) | MYCN | 11714746, 12903512, 12903497, 11775218, 11775218, 12903512, 11714746, 15622746, 15761015, 12478894 | |

TABLE 1-continued

| Molecule | RefSeq | Description | Symbol | PMID | Interaction |
|---|---|---|---|---|---|
| ARSENIC TRIOXIDE | NM_001130158; NM_001161819; NM_012223 | myosin IB | MYO1B | 15761015, 15 | |
| ARSENIC TRIOXIDE | NM_012330 | MYST histone acetyltransferase (monocytic leukemia) 4 | MYST4 | 15761015 | |
| ARSENIC TRIOXIDE | NM_153029 | NEDD4 binding protein 1 | N4BP1 | 15761015 | |
| ARSENIC TRIOXIDE | NM_001079691; NM_052818 | NEDD4 binding protein 2-like 1 | N4BP2L1 | 15761015 | |
| ARSENIC TRIOXIDE | NM_005967 | NGFI-A binding protein 2 (EGR1 binding protein 2) | NAB2 | 15761015 | |
| ARSENIC TRIOXIDE | NM_014903 | neuron navigator 3 | NAV3 | 15761015 | |
| ARSENIC TRIOXIDE | NM_000265 | neutrophil cytosolic factor 1 | NCF1 | 15070760, 15761015, 15070760 | |
| ARSENIC TRIOXIDE | NM_000433; NM_001127651 | neutrophil cytosolic factor 2 | NCF2 | 15070760 | |
| ARSENIC TRIOXIDE | — | NADH dehydrogenase, subunit 4 (complex I) | ND4 | 14703492 | |
| ARSENIC TRIOXIDE | NM_006656 | sialidase 3 (membrane sialidase) | NEU3 | 15070760 | |
| ARSENIC TRIOXIDE | NM_003204 | nuclear factor (erythroid-derived 2)-like 1 | NFE2L1 | 16487037 | |
| ARSENIC TRIOXIDE | NM_020529 | nuclear factor of kappa light polypeptide gene enhancer in B-cells inhibitor, alpha | NFKBIA | 12560223 | |
| ARSENIC TRIOXIDE | NM_004556 | nuclear factor of kappa light polypeptide gene enhancer in B-cells inhibitor, epsilon | NFKBIE | 12560223 | |
| ARSENIC TRIOXIDE | NM_000269; NM_198175 | non-metastatic cells 1, protein (NM23A) expressed in | NME1 | 12452020, 12478894 | |
| ARSENIC TRIOXIDE | NM_002517 | neuronal PAS domain protein 1 | NPAS1 | 15761015 | |
| ARSENIC TRIOXIDE | NM_002523 | neuronal pentraxin II | NPTX2 | 17081986 | |
| ARSENIC TRIOXIDE | NM_000176; NM_001018074; NM_001018075; NM_001018076;NM_001018077; NM_001020825; NM_001024094 | nuclear receptor subfamily 3, group C, member 1 (glucocorticoid receptor) | NR3C1 | 17547211 | |
| ARSENIC TRIOXIDE | NM_005013 | nucleobindin 2 | NUCB2 | 17547211 | |
| ARSENIC TRIOXIDE | NM_024815 | nudix (nucleoside diphosphate linked moiety X)-type motif 18 | NUDT18 | 15761015 | |
| ARSENIC TRIOXIDE | NM_020401 | nucleoporin 107 kDa | NUP107 | 17547211 | |
| ARSENIC TRIOXIDE | NM_015311 | obscurin-like 1 | OBSL1 | 15761015 | |
| ARSENIC TRIOXIDE | NM_002552; NM_181741; NM_181742 | origin recognition complex, subunit 4-like (yeast) | ORC4L | 15761015 | |
| ARSENIC TRIOXIDE | NM_001017956; NM_001017957; NM_001017958; NM_006812 | osteosarcoma amplified 9, endoplasmic reticulum associated protein | OS9 | 17547211 | |
| ARSENIC TRIOXIDE | NM_000917; NM_001017962; NM_001142595; NM_001142596 | prolyl 4-hydroxylase, alpha polypeptide I | P4HA1 | 15725085 | |
| ARSENIC TRIOXIDE | NM_000437 | platelet-activating factor acetylhydrolase 2, 40 kDa | PAFAH2 | 15761015 | |

TABLE 1-continued

| Molecule | RefSeq | Description | Symbol | PMID | Interaction |
|---|---|---|---|---|---|
| ARSENIC TRIOXIDE | NM_152911; NM_207127; NM_207128 | polyamine oxidase (exo-N4-amino) | PAOX | 15761015 | |
| ARSENIC TRIOXIDE | NM_024897; NM_198406 | progestin and adipoQ receptor family member VI | PAQR6 | 15725085 | |
| ARSENIC TRIOXIDE | NM_001618 | poly (ADP-ribose) polymerase 1 | PARP1 | 16328441, 16328441, 16646077 | |
| ARSENIC TRIOXIDE | NM_002583 | PRKC, apoptosis, WT1, regulator | PAWR | 16966277 | |
| ARSENIC TRIOXIDE | NM_002592; NM_182649 | proliferating cell nuclear antigen | PCNA | 12783709, 16029599 | |
| ARSENIC TRIOXIDE | NM_006200 | proprotein convertase subtilisin/kexin type 5 | PCSK5 | 15761015 | |
| ARSENIC TRIOXIDE | NM_014456; NM_145341 | programmed cell death 4 (neoplastic transformation inhibitor) | PDCD4 | 17259349 | |
| ARSENIC TRIOXIDE | NM_001111307; NM_001111308; NM_001111309; NM_006202 | phosphodiesterase 4A, cAMP-specific (phosphodiesterase E2 dunce homolog, Drosophila) | PDE4A | 15070760 | |
| ARSENIC TRIOXIDE | NM_001037339; NM_001037340; NM_001037341; NM_002600 | phosphodiesterase 4B, cAMP-specific (phosphodiesterase E4 dunce homolog, Drosophila) | PDE4B | 15761015 | |
| ARSENIC TRIOXIDE | NM_001002810; NM_001002811; NM_001002812; NM_014644; NM_022359 | phosphodiesterase 4D interacting protein | PDE4DIP | 15761015 | |
| ARSENIC TRIOXIDE | NM_005451; NM_203352; NM_213636 | PDZ and LIM domain 7 (enigma) | PDLIM7 | 15761015 | |
| ARSENIC TRIOXIDE | NM_002613; NM_031268 | 3-phosphoinositide dependent protein kinase-1 | PDPK1 | 14633726 | |
| ARSENIC TRIOXIDE | NM_178140 | PDZ domain containing 2 | PDZD2 | 15761015 | |
| ARSENIC TRIOXIDE | NM_000442 | platelet/endothelial cell adhesion molecule | PECAM1 | 15761015 | |
| ARSENIC TRIOXIDE | NM_003630 | peroxisomal biogenesis factor 3 | PEX3 | 17547211 | |
| ARSENIC TRIOXIDE | NM_002630 | progastricsin (pepsinogen C) | PGC | 17547211 | |
| ARSENIC TRIOXIDE | NM_002632 | placental growth factor | PGF | 15761015 | |
| ARSENIC TRIOXIDE | NM_003311 | pleckstrin homology-like domain, family A, member 2 | PHLDA2 | 15761015 | |
| ARSENIC TRIOXIDE | NM_032634; NM_152850 | phosphatidylinositol glycan anchor biosynthesis, class O | PIGO | 15761015 | |
| ARSENIC TRIOXIDE | — | — | PIK4CA | 12852829 | |
| ARSENIC TRIOXIDE | NM_001018109; NM_003662 | pirin (iron-binding nuclear protein) | PIR | 15761015 | |
| ARSENIC TRIOXIDE | NM_004571 | PBX/knotted 1 homeobox 1 | PKNOX1 | 15761015 | |
| ARSENIC TRIOXIDE | NM_001005376; NM_001005377; NM_002659 | plasminogen activator, urokinase receptor | PLAUR | 15761015 | |
| ARSENIC TRIOXIDE | NM_016274 | pleckstrin homology domain containing, family O member 1 | PLEKHO1 | 15761015 | |
| ARSENIC TRIOXIDE | NM_005761 | plexin C1 | PLXNC1 | 15761015 | |

TABLE 1-continued

| Molecule | RefSeq | Description | Symbol | PMID | Interaction |
|---|---|---|---|---|---|
| ARSENIC TRIOXIDE | NM_002675; NM_033238; NM_033239; NM_033240; NM_033244; NM_033246; NM_033247;NM_033249; NM_033250 | promyelocytic leukemia | PML | 15748426, 15748426, 16891316, 16330433, 17081986 | |
| ARSENIC TRIOXIDE | — | | PPGB | 15725085 | |
| ARSENIC TRIOXIDE | NM_006347 | peptidylprolyl isomerase H (cyclophilin H) | PPIH | 17547211 | |
| ARSENIC TRIOXIDE | NM_002709; NM_206876 | protein phosphatase 1, catalytic subunit, beta isoform | PPP1CB | 12852829 | |
| ARSENIC TRIOXIDE | NM_006093 | proteoglycan 3 | PRG3 | 15761015 | |
| ARSENIC TRIOXIDE | NM_002738; NM_212535 | protein kinase C, beta | PRKCB | 15725085 | |
| ARSENIC TRIOXIDE | NM_016644 | proline rich 16 | PRR16 | 15761015 | |
| ARSENIC TRIOXIDE | NM_002769 | protease, serine, 1 (trypsin 1) | PRSS1 | 15761015 | |
| ARSENIC TRIOXIDE | NM_002798 | proteasome (prosome, macropain) subunit, beta type, 6 | PSMB6 | 12852829 | |
| ARSENIC TRIOXIDE | NM_004159; NM_148919 | proteasome (prosome, macropain) subunit, beta type, 8 (large multifunctional peptidase 7) | PSMB8 | 15725085 | |
| ARSENIC TRIOXIDE | NM_000959; NM_001039585 | prostaglandin F receptor (FP) | PTGFR | 15761015 | |
| ARSENIC TRIOXIDE | NM_016077 | peptidyl-tRNA hydrolase 2 | PTRH2 | 14703492 | |
| ARSENIC TRIOXIDE | NM_004219 | pituitary tumor-transforming 1 | PTTG1 | 17547211 | |
| ARSENIC TRIOXIDE | NM_001015508; NM_013357 | purine-rich element binding protein G | PURG | 15761015 | |
| ARSENIC TRIOXIDE | NM_012293 | peroxidasin homolog (Drosophila) | PXDN | 15761015 | |
| ARSENIC TRIOXIDE | NM_004163 | RAB27B, member RAS oncogene family | RAB27B | 15761015 | |
| ARSENIC TRIOXIDE | NM_001126103; NM_001126104; NM_013277 | Rac GTPase activating protein 1 | RACGAP1 | 17547211 | |
| ARSENIC TRIOXIDE | NM_001100397; NM_007023 | Rap guanine nucleotide exchange factor (GEF) 4 | RAPGEF4 | 15761015 | |
| ARSENIC TRIOXIDE | NM_000964; NM_001024809; NM_001145301; NM_001145302 | retinoic acid receptor, alpha | RARA | 15748426, 16891316, 16330433 | |
| ARSENIC TRIOXIDE | NM_007211 | Ras association (RalGDS/AF-6) domain family (N-terminal) member 8 | RASSF8 | 15761015 | |
| ARSENIC TRIOXIDE | NM_002139 | RNA binding motif protein, X-linked | RBMX | 12852829 | |
| ARSENIC TRIOXIDE | NM_001145138; NM_021975 | v-rel reticuloendotheliosis viral oncogene homolog A (avian) | RELA | 16105982, 16174796, 16174796 | |
| ARSENIC TRIOXIDE | NM_001042681; NM_001042682; NM_012102 | arginine-glutamic acid dipeptide (RE) repeats | RERE | 15761015 | |
| ARSENIC TRIOXIDE | NM_002914; NM_181471 | replication factor C (activator 1) 2, 40 kDa | RFC2 | 17547211 | |
| ARSENIC TRIOXIDE | NM_002923 | regulator of G-protein signaling 2, 24 kDa | RGS2 | 12852829 | |

TABLE 1-continued

| Molecule | RefSeq | Description | Symbol | PMID | Interaction |
|---|---|---|---|---|---|
| ARSENIC TRIOXIDE | NM_006397 | ribonuclease H2, subunit A | RNASEH2A | 17547211 | |
| ARSENIC TRIOXIDE | NM_014746 | ring finger protein 144A | RNF144A | 15761015 | |
| ARSENIC TRIOXIDE | NM_001134337; NM_001134338; NM_007219 | ring finger protein 24 | RNF24 | 15761015 | |
| ARSENIC TRIOXIDE | NM_005977; NM_183043; NM_183044 | ring finger protein (C3H2C3 type) 6 | RNF6 | 15725085 | |
| ARSENIC TRIOXIDE | NM_002941; NM_133631 | roundabout, axon guidance receptor, homolog 1 (Drosophila) | ROBO1 | 15725085 | |
| ARSENIC TRIOXIDE | NM_000985; NM_001035006 | ribosomal protein L17 | RPL17 | 12852829 | |
| ARSENIC TRIOXIDE | NM_000980 | ribosomal protein L18a | RPL18A | 15725085 | |
| ARSENIC TRIOXIDE | NM_000978 | ribosomal protein L23 | RPL23 | 14703492 | |
| ARSENIC TRIOXIDE | NM_000971 | ribosomal protein L7 | RPL7 | 12852829 | |
| ARSENIC TRIOXIDE | NM_001019; NM_001030009 | ribosomal protein S15a | RPS15A | 14703492 | |
| ARSENIC TRIOXIDE | NM_003161 | ribosomal protein S6 kinase, 70 kDa, polypeptide 1 | RPS6KB1 | 14633726 | |
| ARSENIC TRIOXIDE | NM_001042576; NM_004587 | ribosome binding protein 1 homolog 180 kDa (dog) | RRBP1 | 15761015 | |
| ARSENIC TRIOXIDE | NM_015659 | ribosomal L1 domain containing 1 | RSL1D1 | 15761015 | |
| ARSENIC TRIOXIDE | NM_001005861; NM_002958 | RYK receptor-like tyrosine kinase | RYK | 15761015 | |
| ARSENIC TRIOXIDE | NM_002966 | S100 calcium binding protein A10 | S100A10 | 15949261 | |
| ARSENIC TRIOXIDE | NM_002964 | S100 calcium binding protein A8 | S100A8 | 15761015, 15 | |
| ARSENIC TRIOXIDE | NM_002965 | S100 calcium binding protein A9 | S100A9 | 15725085 | |
| ARSENIC TRIOXIDE | NM_015265 | SATB homeobox 2 | SATB2 | 15761015 | |
| ARSENIC TRIOXIDE | NM_138967 | secretory carrier membrane protein 5 | SCAMP5 | 15761015 | |
| ARSENIC TRIOXIDE | NM_002411 | secretoglobin, family 2A, member 2 | SCGB2A2 | 15761015 | |
| ARSENIC TRIOXIDE | NM_021626 | serine carboxypeptidase 1 | SCPEP1 | 15725085 | |
| ARSENIC TRIOXIDE | NM_021920 | secretin | SCT | 15761015 | |
| ARSENIC TRIOXIDE | NM_002998 | syndecan 2 | SDC2 | 15761015, 12852829, 15725085 | |
| ARSENIC TRIOXIDE | NM_002999 | syndecan 4 | SDC4 | 15761015 | |
| ARSENIC TRIOXIDE | NM_003005 | selectin P (granule membrane protein 140 kDa, antigen CD62) | SELP | 16206674 | |

TABLE 1-continued

| Molecule | RefSeq | Description | Symbol | PMID | Interaction |
|---|---|---|---|---|---|
| ARSENIC TRIOXIDE | NM_030666 | serpin peptidase inhibitor, clade B (ovalbumin), member 1 | SERPINB1 | 15761015 | |
| ARSENIC TRIOXIDE | NM_014755 | SERTA domain containing 2 | SERTAD2 | 15725085 | |
| ARSENIC TRIOXIDE | NM_001039465; NM_006925 | splicing factor, arginine/serine-rich 5 | SFRS5 | 14703492 | |
| ARSENIC TRIOXIDE | NM_003026 | SH3-domain GRB2-like 2 | SH3GL2 | 15761015 | |
| ARSENIC TRIOXIDE | NM_001245; NM_198845; NM_198846 | sialic acid binding Ig-like lectin 6 | SIGLEC6 | 15761015 | |
| ARSENIC TRIOXIDE | NM_007163 | solute carrier family 14 (urea transporter), member 2 | SLC14A2 | 15761015 | |
| ARSENIC TRIOXIDE | NM_005073 | solute carrier family 15 (oligopeptide transporter), member 1 | SLC15A1 | 15761015 | |
| ARSENIC TRIOXIDE | NM_004171 | solute carrier family 1 (glial high affinity glutamate transporter), member 2 | SLC1A2 | 17547211 | |
| ARSENIC TRIOXIDE | NM_002555; NM_183233 | solute carrier family 22, member 18 | SLC22A18 | 15725085 | |
| ARSENIC TRIOXIDE | NM_006516 | solute carrier family 2 (facilitated glucose transporter), member 1 | SLC2A1 | 17064664 | |
| ARSENIC TRIOXIDE | NM_080546 | solute carrier family 44, member 1 | SLC44A1 | 15761015 | |
| ARSENIC TRIOXIDE | NM_017842 | solute carrier family 48 (heme transporter), member 1 | SLC48A1 | 15761015, 16 | |
| ARSENIC TRIOXIDE | NM_178498 | solute carrier family 5 (sodium/glucose cotransporter), member 12 | SLC5A12 | 15761015 | |
| ARSENIC TRIOXIDE | NM_004211 | solute carrier family 6 (neurotransmitter transporter, glycine), member 5 | SLC6A5 | 15761015 | |
| ARSENIC TRIOXIDE | NM_001145044; NM_013272 | solute carrier organic anion transporter family, member 3A1 | SLCO3A1 | 15761015 | |
| ARSENIC TRIOXIDE | NM_001003688; NM_005900 | SMAD family member 1 | SMAD1 | 15761015 | |
| ARSENIC TRIOXIDE | NM_001002800; NM_005496 | structural maintenance of chromosomes 4 | SMC4 | 17547211 | |
| ARSENIC TRIOXIDE | NM_000454 | superoxide dismutase 1, soluble | SOD1 | 16867262 | |
| ARSENIC TRIOXIDE | NM_018419 | SRY (sex determining region Y)-box 18 | SOX18 | 15761015 | |
| ARSENIC TRIOXIDE | NM_007017; NM_178424 | SRY (sex determining region Y)-box 30 | SOX30 | 15761015 | |
| ARSENIC TRIOXIDE | NM_003107 | SRY (sex determining region Y)-box 4 | SOX4 | 15725085 | |
| ARSENIC TRIOXIDE | NM_003109; NM_138473 | Sp1 transcription factor | SP1 | 11714746, 15761015 | |
| ARSENIC TRIOXIDE | NM_001130438; NM_003127 | spectrin, alpha, non-erythrocytic 1 (alpha-fodrin) | SPTAN1 | 12852829 | |
| ARSENIC TRIOXIDE | NM_175039; NM_175040 | ST6 (alpha-N-acetyl-neuraminyl-2,3-beta-galactosyl-1,3)-N-acetylgalactosaminide alpha-2,6-sialyltransferase 4 | ST6GALNAC4 | 17547211 | |
| ARSENIC TRIOXIDE | NM_015136 | stabilin 1 | STAB1 | 15761015 | |

TABLE 1-continued

| Molecule | RefSeq | Description | Symbol | PMID | Interaction |
|---|---|---|---|---|---|
| ARSENIC TRIOXIDE | NM_007315; NM_139266 | signal transducer and activator of transcription 1, 91 kDa | STAT1 | 14668793, 16914093 | |
| ARSENIC TRIOXIDE | NM_001009181; NM_003154 | statherin | STATH | 15761015 | |
| ARSENIC TRIOXIDE | NM_001128204; NM_001128205; NM_001128206; NM_015170 | sulfatase 1 | SULF1 | 15725085 | |
| ARSENIC TRIOXIDE | NM_015551 | sushi domain containing 5 | SUSD5 | 15761015 | |
| ARSENIC TRIOXIDE | NM_001135774; NM_003490; NM_133633 | synapsin III | SYN3 | 15761015 | |
| ARSENIC TRIOXIDE | NM_003898 | synaptojanin 2 | SYNJ2 | 12852829 | |
| ARSENIC TRIOXIDE | NM_001083962; NM_003199 | transcription factor 4 | TCF4 | 15761015 | |
| ARSENIC TRIOXIDE | NR_001566; NR_001566; NR_001566; NR_001566; NR_001566; NR_001566 | telomerase RNA component | TERC | 11714746 | |
| ARSENIC TRIOXIDE | NM_003218; NM_017489 | telomeric repeat binding factor (NIMA-interacting) 1 | TERF1 | 16129045 | |
| ARSENIC TRIOXIDE | NM_005652 | telomeric repeat binding factor 2 | TERF2 | 16129045 | |
| ARSENIC TRIOXIDE | NM_198253; NM_198255 | telomerase reverse transcriptase | TERT | 11714746, 16966277, 15761015, 15761015, 16129045, 11714746, 16966277, 16285558, 15996315 | |
| ARSENIC TRIOXIDE | NM_003222 | transcription factor AP-2 gamma (activating enhancer binding protein 2 gamma) | TFAP2C | 15761015 | |
| ARSENIC TRIOXIDE | NM_003225 | trefoil factor 1 | TFF1 | 12014631 | |
| ARSENIC TRIOXIDE | NM_001024847; NM_003242 | transforming growth factor, beta receptor II (70/80 kDa) | TGFBR2 | 12852829 | |
| ARSENIC TRIOXIDE | NM_003254 | TIMP metallopeptidase inhibitor 1 | TIMP1 | 16624393 | |
| ARSENIC TRIOXIDE | NM_003255 | TIMP metallopeptidase inhibitor 2 | TIMP2 | 16624393 | |
| ARSENIC TRIOXIDE | NM_015444 | transmembrane protein 158 | TMEM158 | 15761015 | |
| ARSENIC TRIOXIDE | NM_000594 | tumor necrosis factor (TNF superfamily, member 2) | TNF | 12560223 | |
| ARSENIC TRIOXIDE | NM_006290 | tumor necrosis factor, alpha-induced protein 3 | TNFAIP3 | 17547211 | |
| ARSENIC TRIOXIDE | NM_001077654; NM_014350 | tumor necrosis factor, alpha-induced protein 8 | TNFAIP8 | 17547211 | |
| ARSENIC TRIOXIDE | NM_001066 | tumor necrosis factor receptor superfamily, member 1B | TNFRSF1B | 15761015 | |
| ARSENIC TRIOXIDE | NM_001039664; NM_003790; NM_148965; NM_148966; NM_148967; NM_148970 | tumor necrosis factor receptor superfamily, member 25 | TNFRSF25 | 15761015 | |
| ARSENIC TRIOXIDE | NM_001561 | tumor necrosis factor receptor superfamily, member 9 | TNFRSF9 | 16010437 | |
| ARSENIC TRIOXIDE | NM_003808; NM_172087; NM_172088 | tumor necrosis factor (ligand) superfamily, member 13 | TNFSF13 | 15761015 | |
| ARSENIC TRIOXIDE | NM_001244 | tumor necrosis factor (ligand) superfamily, member 8 | TNFSF8 | 15761015 | |

TABLE 1-continued

| Molecule | RefSeq | Description | Symbol | PMID | Interaction |
|---|---|---|---|---|---|
| ARSENIC TRIOXIDE | NM_001067 | topoisomerase (DNA) II alpha 170 kDa | TOP2A | 16884364 | |
| ARSENIC TRIOXIDE | NM_000546; NM_001126112; NM_001126113; NM_001126114; NM_001126115; NM_001126116; NM_001126117 | tumor protein p53 | TP53 | 11714746, 14682389, 11714746, 15622746, 11775218, 15979894, 12490120, 16467208 | |
| ARSENIC TRIOXIDE | NM_022112 | tumor protein p53 regulated apoptosis inducing protein 1 | TP53AIP1 | 15031205, 16467208 | |
| ARSENIC TRIOXIDE | NM_001076787; NM_006034 | tumor protein p53 inducible protein 11 | TP53I11 | 12883691, 15225615, 15761015 | |
| ARSENIC TRIOXIDE | NM_001126240; NM_001126241; NM_001126242; NM_005427 | tumor protein p73 | TP73 | 15031205, 16467208 | |
| ARSENIC TRIOXIDE | NM_003295 | tumor protein, translationally-controlled 1 | TPT1 | 15949261 | |
| ARSENIC TRIOXIDE | NM_013293 | transformer 2 alpha homolog (Drosophila) | TRA2A | 15761015 | |
| ARSENIC TRIOXIDE | NM_147200; NM_147686 | TRAF3 interacting protein 2 | TRAF3IP2 | 15761015 | |
| ARSENIC TRIOXIDE | NM_006470 | tripartite motif-containing 16 | TRIM16 | 15725085 | |
| ARSENIC TRIOXIDE | NM_004237 | thyroid hormone receptor interactor 13 | TRIP13 | 17547211 | |
| ARSENIC TRIOXIDE | NM_001136035; NM_001142554; NM_017722 | TRM1 tRNA methyltransferase 1 homolog (S. cerevisiae) | TRMT1 | 15725085 | |
| ARSENIC TRIOXIDE | NM_001015881; NM_004089; NM_198057 | TSC22 domain family, member 3 | TSC22D3 | 17081986 | |
| ARSENIC TRIOXIDE | NM_017931 | tetratricopeptide repeat domain 38 | TTC38 | 15761015 | |
| ARSENIC TRIOXIDE | NM_006472 | thioredoxin interacting protein | TXNIP | 15725085 | |
| ARSENIC TRIOXIDE | NM_001071 | thymidylate synthetase | TYMS | 17547211 | |
| ARSENIC TRIOXIDE | NM_007019; NM_181799; NM_181800; NM_181801; NM_181802; NM_181803 | ubiquitin-conjugating enzyme E2C | UBE2C | 17547211 | |
| ARSENIC TRIOXIDE | NM_003338 | ubiquitin-conjugating enzyme E2D 1 (UBC4/5 homolog, yeast) | UBE2D1 | 15761015 | |
| ARSENIC TRIOXIDE | NM_004181 | ubiquitin carboxyl-terminal esterase L1 (ubiquitin thiolesterase) | UCHL1 | 15725085 | |
| ARSENIC TRIOXIDE | NM_003355 | uncoupling protein 2 (mitochondrial, proton carrier) | UCP2 | 15761015 | |
| ARSENIC TRIOXIDE | NM_001025366; NM_001025367; NM_001025368; NM_001025369; NM_001025370; NM_001033756; NM_003376 | vascular endothelial growth factor A | VEGFA | 12482858, 15949266, 16928304 | |
| ARSENIC TRIOXIDE | NM_004666 | vanin 1 | VNN1 | 15761015 | |
| ARSENIC TRIOXIDE | NM_018256 | WD repeat domain 12 | WDR12 | 15725085 | |
| ARSENIC TRIOXIDE | NM_025222 | WD repeat domain 82 | WDR82 | 15761015 | |
| ARSENIC TRIOXIDE | NM_018639 | WD repeat and SOCS box-containing 2 | WSB2 | 15725085 | |

TABLE 1-continued

| Molecule | RefSeq | Description | Symbol | PMID | Interaction |
|---|---|---|---|---|---|
| ARSENIC TRIOXIDE | NM_000378; NM_024424; NM_024425; NM_024426 | Wilms tumor 1 | WT1 | 16966277 | |
| ARSENIC TRIOXIDE | NM_001167 | X-linked inhibitor of apoptosis | XIAP | 16105982, 16 | |
| ARSENIC TRIOXIDE | NM_001469 | X-ray repair complementing defective repair in Chinese hamster cells 6 | XRCC6 | 15761015 | |
| ARSENIC TRIOXIDE | NM_003407 | zinc finger protein 36, C3H type, homolog (mouse) | ZFP36 | 12749819 | |
| ARSENIC TRIOXIDE | NM_004926 | zinc finger protein 36, C3H type-like 1 | ZFP36L1 | 15725085 | |
| ARSENIC TRIOXIDE | NM_003453; NM_197968 | zinc finger, MYM-type 2 | ZMYM2 | 17027752 | |
| ARSENIC TRIOXIDE | NM_018102; NM_199441 | zinc finger protein 334 | ZNF334 | 15761015 | |
| ARSENIC TRIOXIDE | NM_001007094; NM_003421 | zinc finger protein 37A | ZNF37A | 15761015 | |
| ARSENIC TRIOXIDE | NM_001077349; NM_033196 | zinc finger protein 682 | ZNF682 | 15761015 | |
| ARSENIC TRIOXIDE | NM_001142305; NM_016643 | zinc finger protein 771 | ZNF771 | 15761015 | |
| ARSENIC TRIOXIDE | NM_001005413; NM_007057; NM_032997 | ZW10 interactor | ZWINT | 17547211 | |
| BORTEZOMIB | NM_001014431; NM_001014432; NM_005163 | v-akt murine thymoma viral oncogene homolog 1 | AKT1 | 15781649 | unrelated |
| BORTEZOMIB | NM_001160; NM_013229; NM_181861; NM_181868; NM_181869 | apoptotic peptidase activating factor 1 | APAF1 | 16024631 | death pathway |
| BORTEZOMIB | NM_001188 | BCL2-antagonist/killer 1 | BAK1 | 16024631 | death pathway |
| BORTEZOMIB | NM_004324; NM_138761; NM_138763; NM_138764; NM_138765 | BCL2-associated X protein | BAX | 16024631 | death pathway |
| BORTEZOMIB | NM_000633; NM_000657 | B-cell CLL/lymphoma 2 | BCL2 | 15781649, 16022909, 16024631 | altered by bortezomib |
| BORTEZOMIB | NM_001191; NM_138578 | BCL2-like 1 | BCL2L1 | 12893773, 15543232, 15781649, 16024631 | altered by bortezomib |
| BORTEZOMIB | NM_006538; NM_138621; NM_207002 | BCL2-like 11 (apoptosis facilitator) | BCL2L11 | 16024631 | death pathway |
| BORTEZOMIB | NM_001196; NM_197966; NM_197967 | BH3 interacting domain death agonist | BID | 12893773 | death pathway |
| BORTEZOMIB | NM_001166 | baculoviral IAP repeat-containing 2 | BIRC2 | 12893773, 15543232, 15781649, 16024631 | altered by bortezomib |
| BORTEZOMIB | NM_001165; NM_182962 | baculoviral IAP repeat-containing 3 | BIRC3 | 12893773, 16024631 | altered by bortezomib |
| BORTEZOMIB | NM_001012270; NM_001012271; NM_001168 | baculoviral IAP repeat-containing 5 | BIRC5 | 16373703 | altered by bortezomib |
| BORTEZOMIB | NM_001216 | carbonic anhydrase IX | CA9 | 16061869 | |
| BORTEZOMIB | NM_004346; NM_032991 | caspase 3, apoptosis-related cysteine peptidase | CASP3 | 12893773, 15735676, 16024631, 16675587, 17121930 | death pathway |
| BORTEZOMIB | NM_001227; NM_033338; NM_033339; NM_033340 | caspase 7, apoptosis-related cysteine peptidase | CASP7 | 16024631 | death pathway |
| BORTEZOMIB | NM_001080124; NM_001080125; NM_001228; NM_033355; NM_033356; NM_033358 | caspase 8, apoptosis-related cysteine peptidase | CASP8 | 12893773, 15735676, 16024631 | death pathway |
| BORTEZOMIB | NM_001229; NM_032996 | caspase 9, apoptosis-related cysteine peptidase | CASP9 | 12893773, 15735676, 16024631 | death pathway |
| BORTEZOMIB | NM_053056 | cyclin D1 | CCND1 | 12893773, 15781649 | |
| BORTEZOMIB | NM_000389; NM_078467 | cyclin-dependent kinase inhibitor 1A (p21, Cip1) | CDKN1A | 12893773, 15543232 | death pathway |
| BORTEZOMIB | NM_004064 | cyclin-dependent kinase inhibitor 1B (p27, Kip1) | CDKN1B | 15543232 | sensitivity |

TABLE 1-continued

| Molecule | RefSeq | Description | Symbol | PMID | Interaction |
|---|---|---|---|---|---|
| BORTEZOMIB | NM_001127183; NM_001127184; NM_003879 | CASP8 and FADD-like apoptosis regulator | CFLAR | 12893773, 16024631 | altered by bortezomib |
| BORTEZOMIB | NM_018947 | cytochrome c, somatic | CYCS | 12893773, 16024631 | death pathway |
| BORTEZOMIB | NM_000761 | cytochrome P450, family 1, subfamily A, polypeptide 2 | CYP1A2 | 15764713 | drug metabolism |
| BORTEZOMIB | NM_000769 | cytochrome P450, family 2, subfamily C, polypeptide 19 | CYP2C19 | 15764713 | drug metabolism |
| BORTEZOMIB | NM_000771 | cytochrome P450, family 2, subfamily C, polypeptide 9 | CYP2C9 | 15764713 | drug metabolism |
| BORTEZOMIB | NM_000106; NM_001025161 | cytochrome P450, family 2, subfamily D, polypeptide 6 | CYP2D6 | 15764713 | drug metabolism |
| BORTEZOMIB | NM_017460 | cytochrome P450, family 3, subfamily A, polypeptide 4 | CYP3A4 | 15764713 | drug metabolism |
| BORTEZOMIB | NM_004083 | DNA-damage-inducible transcript 3 | DDIT3 | 16024631 | altered by bortezomib |
| BORTEZOMIB | NM_004401; NM_213566 | DNA fragmentation factor, 45 kDa, alpha polypeptide | DFFA | 15735676 | resistance |
| BORTEZOMIB | NM_019887; NM_138929 | diablo homolog (Drosophila) | DIABLO | 12893773, 16024631 | death pathway |
| BORTEZOMIB | NM_001530; NM_181054 | hypoxia inducible factor 1, alpha subunit (basic helix-loop-helix transcription factor) | HIF1A | 16061869 | altered by bortezomib |
| BORTEZOMIB | — | | HSP27 | — | resistance |
| BORTEZOMIB | NM_005347 | heat shock 70 kDa protein 5 (glucose-regulated protein, 78 kDa) | HSPA5 | 16024631 | altered by bortezomib |
| BORTEZOMIB | NM_013247; NM_145074 | HtrA serine peptidase 2 | HTRA2 | 16024631 | death pathway |
| BORTEZOMIB | NM_002228 | jun oncogene | JUN | 15735676 | altered by bortezomib |
| BORTEZOMIB | NM_002755 | mitogen-activated protein kinase kinase 1 | MAP2K1 | 12893773 | altered by bortezomib |
| BORTEZOMIB | NM_003010 | mitogen-activated protein kinase kinase 4 | MAP2K4 | 15735676 | altered by bortezomib |
| BORTEZOMIB | NM_002745; NM_138957 | mitogen-activated protein kinase 1 | MAPK1 | 12893773 | altered by bortezomib |
| BORTEZOMIB | NM_001315; NM_139012; NM_139013; NM_139014 | mitogen-activated protein kinase 14 | MAPK14 | 12893773 | altered by bortezomib |
| BORTEZOMIB | NM_001040056; NM_001109891; NM_002746 | mitogen-activated protein kinase 3 | MAPK3 | 12893773 | altered by bortezomib |
| BORTEZOMIB | NM_002750; NM_139046; NM_139047; NM_139049 | mitogen-activated protein kinase 8 | MAPK8 | 12893773 | altered by bortezomib |
| BORTEZOMIB | NM_021960; NM_182763 | myeloid cell leukemia sequence 1 (BCL2-related) | MCL1 | 12893773 | resistance |
| BORTEZOMIB | NM_003998 | nuclear factor of kappa light polypeptide gene enhancer in B-cells 1 | NFKB1 | 12893773, 16230421, 17164350 | resistance |
| BORTEZOMIB | NM_020529 | nuclear factor of kappa light polypeptide gene enhancer in B-cells inhibitor, alpha | NFKBIA | 15543232 | altered by bortezomib |
| BORTEZOMIB | NM_001001716; NM_002503 | nuclear factor of kappa light polypeptide gene enhancer in B-cells inhibitor, beta | NFKBIB | 15543232 | altered by bortezomib |
| BORTEZOMIB | NM_004556 | nuclear factor of kappa light polypeptide gene enhancer in B-cells inhibitor, epsilon | NFKBIE | 15543232 | altered by bortezomib |
| BORTEZOMIB | NM_001618 | poly (ADP-ribose) polymerase 1 | PARP1 | 12893773, 15735676 | altered by bortezomib |
| BORTEZOMIB | — | | PDCD8 | 12893773, 16024631 | death pathway |
| BORTEZOMIB | NM_021127 | phorbol-12-myristate-13-acetate-induced protein 1 | PMAIP1 | 16024631 | target |
| BORTEZOMIB | NM_002793 | proteasome (prosome, macropain) subunit, beta type, 1 | PSMB1 | — | resistance |

TABLE 1-continued

| Molecule | RefSeq | Description | Symbol | PMID | Interaction |
|---|---|---|---|---|---|
| BORTEZOMIB | NM_002794 | proteasome (prosome, macropain) subunit, beta type, 2 | PSMB2 | — | target resistance |
| BORTEZOMIB | NM_001130725; NM_001144932; NM_002797 | proteasome (prosome, macropain) subunit, beta type, 5 | PSMB5 | — | target resistance |
| BORTEZOMIB | NM_002807 | proteasome (prosome, macropain) 26S subunit, non-ATPase, 1 | PSMD1 | 12893773 | target ? |
| BORTEZOMIB | NM_002808 | proteasome (prosome, macropain) 26S subunit, non-ATPase, 2 | PSMD2 | | target ? |
| BORTEZOMIB | NM_002880 | v-raf-1 murine leukemia viral oncogene homolog 1 | RAF1 | 12893773 | altered by bortezomib |
| BORTEZOMIB | NM_000321 | retinoblastoma 1 | RB1 | 12893773 | |
| BORTEZOMIB | NM_001145138; NM_021975 | v-rel reticuloendotheliosis viral oncogene homolog A (avian) | RELA | 12893773, 16061869, 16230421, 17164350 | resistance |
| BORTEZOMIB | NM_006142 | stratifin | SFN | 16373703 | |
| BORTEZOMIB | NM_003150; NM_139276; NM_213662 | signal transducer and activator of transcription 3 (acute-phase response factor) | STAT3 | 17164350 | altered by bortezomib |
| BORTEZOMIB | NM_000594 | tumor necrosis factor (TNF superfamily, member 2) | TNF | 16230421 | |
| BORTEZOMIB | NM_000546; NM_001126112; NM_001126113; NM_001126114; NM_001126115; NM_001126116; NM_001126117 | tumor protein p53 | TP53 | 15543232, 16061869, 16373703 | unrelated |
| BORTEZOMIB | NM_021138 | TNF receptor-associated factor 2 | TRAF2 | 16024631 | |
| BORTEZOMIB | NM_001167 | X-linked inhibitor of apoptosis | XIAP | 12893773, 15543232, 16024631 | altered by bortezomib |
| CELECOXIB | NM_001105515; NM_005845 | ATP-binding cassette, sub-family C (CFTR/MRP), member 4 | ABCC4 | 18690847 | |
| CELECOXIB | NM_001023587; NM_005688 | ATP-binding cassette, sub-family C (CFTR/MRP), member 5 | ABCC5 | 18690847 | |
| CELECOXIB | NM_001014431; NM_001014432; NM_005163 | v-akt murine thymoma viral oncogene homolog 1 | AKT1 | 14654083, 16123214, 17270149 | altered by celecoxib |
| CELECOXIB | NM_004324; NM_138761; NM_138763; NM_138764; NM_138765 | BCL2-associated X protein | BAX | 14654083 | altered by celecoxib |
| CELECOXIB | NM_000633; NM_000657 | B-cell CLL/lymphoma 2 | BCL2 | 14654083 | |
| CELECOXIB | NM_001191; NM_138578 | BCL2-like 1 | BCL2L1 | 14654083 | |
| CELECOXIB | NM_001012270; NM_001012271; NM_001168 | baculoviral IAP repeat-containing 5 | BIRC5 | 16004971, 16123214, 17270149, 16707021, 17270149 | altered by celecoxib |
| CELECOXIB | NM_004346; NM_032991 | caspase 3, apoptosis-related cysteine peptidase | CASP3 | 16123214 | death pathway |
| CELECOXIB | NM_053056 | cyclin D1 | CCND1 | 15489888, 17270149 | altered by celecoxib |
| CELECOXIB | NM_001127183; NM_001127184; NM_003879 | CASP8 and FADD-like apoptosis regulator | CFLAR | — | resistance |
| CELECOXIB | NM_001278 | conserved helix-loop-helix ubiquitous kinase | CHUK | 15489888 | |
| CELECOXIB | NM_000103; NM_031226 | cytochrome P450, family 19, subfamily A, polypeptide 1 | CYP19A1 | 15964185 | altered by celecoxib |
| CELECOXIB | NM_001927 | desmin | DES | 18089846 | |
| CELECOXIB | NM_004864 | growth differentiation factor 15 | GDF15 | 18089846 | |
| CELECOXIB | NM_000852 | glutathione S-transferase pi 1 | GSTP1 | 18089846 | |
| CELECOXIB | NM_000576 | interleukin 1, beta | IL1B | 16357062 | |
| CELECOXIB | NM_000600 | interleukin 6 (interferon, beta 2) | IL6 | 16702388 | |
| CELECOXIB | NM_002755 | mitogen-activated protein kinase kinase 1 | MAP2K1 | 16123214 | altered by celecoxib |
| CELECOXIB | NM_030662 | mitogen-activated protein kinase kinase 2 | MAP2K2 | 16123214 | altered by celecoxib |

TABLE 1-continued

| Molecule | RefSeq | Description | Symbol | PMID | Interaction |
|---|---|---|---|---|---|
| CELECOXIB | NM_021960; NM_182763 | myeloid cell leukemia sequence 1 (BCL2-related) | MCL1 | 14654083 | |
| CELECOXIB | NM_002417 | antigen identified by monoclonal antibody Ki-67 | MKI67 | 16507397 | |
| CELECOXIB | NM_003998 | nuclear factor of kappa light polypeptide gene enhancer in B-cells 1 | NFKB1 | 15489888 | |
| CELECOXIB | NM_020529 | nuclear factor of kappa light polypeptide gene enhancer in B-cells inhibitor, alpha | NFKBIA | 15489888 | |
| CELECOXIB | NM_002507 | nerve growth factor receptor (TNFR superfamily, member 16) | NGFR | 17447067 | |
| CELECOXIB | NM_001159995; NM_001159996; NM_001159999; NM_001160001; NM_001160008; NM_004495; NM_013956; NM_013957; NM_013958; NM_013959; NM_013960; NM_013961; NM_013962; NM_013964 | neuregulin 1 | NRG1 | 16357062 | altered by celecoxib |
| CELECOXIB | NM_001618 | poly (ADP-ribose) polymerase 1 | PARP1 | 16123214 | altered by celecoxib |
| CELECOXIB | NM_002613; NM_031268 | 3-phosphoinositide dependent protein kinase-1 | PDPK1 | — | target |
| CELECOXIB | NM_000963 | prostaglandin-endoperoxide synthase 2 (prostaglandin G/H synthase and cyclooxygenase) | PTGS2 | 15489888, 16004971, 16507397, 18089846 | target |
| CELECOXIB | NM_001145138; NM_021975 | v-rel reticuloendotheliosis viral oncogene homolog A (avian) | RELA | 15489888, 16685529, 17097285 | altered by celecoxib |
| CELECOXIB | NM_000351 | steroid sulfatase (microsomal), isozyme S | STS | 16178010 | |
| CELECOXIB | NM_003167 | sulfotransferase family, cytosolic, 2A, dehydroepiandrosterone (DHEA)-preferring, member 1 | SULT2A1 | 15483193, 17239972 | altered by celecoxib |
| CELECOXIB | NM_000594 | tumor necrosis factor (TNF superfamily, member 2) | TNF | 15489888, 16702388 | |
| CELECOXIB | NM_000546; NM_001126112; NM_001126113; NM_001126114; NM_001126115; NM_001126116; NM_001126117 | tumor protein p53 | TP53 | 16507397 | |
| COLCHICINE | NM_000927 | ATP-binding cassette, sub-family B (MDR/TAP), member 1 | ABCB1 | 15342794, 15725475, 16007523 | resistance |
| COLCHICINE | NM_004996; NM_019862; NM_019898; NM_019899; NM_019900 | ATP-binding cassette, sub-family C (CFTR/MRP), member 1 | ABCC1 | 12067707 | resistance |
| COLCHICINE | NM_000611; NM_001127223; NM_001127225; NM_001127226; NM_001127227; NM_203329; NM_203330; NM_203331 | CD59 molecule, complement regulatory protein | CD59 | 17045307 | |
| COLCHICINE | NM_001025076; NM_001025077; NM_001083591; NM_006561 | CUG triplet repeat, RNA binding protein 2 | CUGBP2 | 11478917 | |
| COLCHICINE | NM_017460 | cytochrome P450, family 3, subfamily A, polypeptide 4 | CYP3A4 | 16007523, 16 | drug metabolism |
| COLCHICINE | NM_001556 | inhibitor of kappa light polypeptide gene enhancer in B-cells, kinase beta | IKBKB | 17029595 | |
| COLCHICINE | NM_002228 | jun oncogene | JUN | 12221076 | death pathway/survival |
| COLCHICINE | NM_002750; NM_139046; NM_139047; NM_139049 | mitogen-activated protein kinase 8 | MAPK8 | 12221076 | death pathway/survival |
| COLCHICINE | NM_001135044; NM_002752; NM_139068; NM_139069; NM_139070 | mitogen-activated protein kinase 9 | MAPK9 | 12221076 | death pathway/survival |
| COLCHICINE | NM_000243 | Mediterranean fever | MEFV | — | |
| COLCHICINE | NM_001136022; NM_004554 | nuclear factor of activated T-cells, cytoplasmic, calcineurin-dependent 4 | NFATC4 | 17044076 | |

TABLE 1-continued

| Molecule | RefSeq | Description | Symbol | PMID | Interaction |
|---|---|---|---|---|---|
| COLCHICINE | NM_003998 | nuclear factor of kappa light polypeptide gene enhancer in B-cells 1 | NFKB1 | 15744361 | |
| COLCHICINE | NM_020529 | nuclear factor of kappa light polypeptide gene enhancer in B-cells inhibitor, alpha | NFKBIA | 17029595 | |
| COLCHICINE | NM_000176; NM_001018074; NM_001018075; NM_001018076; NM_001018077; NM_001020825; NM_001024094 | nuclear receptor subfamily 3, group C, member 1 (glucocorticoid receptor) | NR3C1 | 15744361 | |
| COLCHICINE | NM_004103; NM_173174; NM_173175; NM_173176 | PTK2B protein tyrosine kinase 2 beta | PTK2B | 11478917 | |
| COLCHICINE | NM_006788 | ralA binding protein 1 | RALBP1 | 15386349 | unrelated |
| COLCHICINE | NM_001145138; NM_021975 | v-rel reticuloendotheliosis viral oncogene homolog A (avian) | RELA | 15744361 | |
| COLCHICINE | NM_000353 | tyrosine aminotransferase | TAT | 15744361 | altered by colchicine |
| COLCHICINE | NM_000546; NM_001126112; NM_001126113; NM_001126114; NM_001126115; NM_001126116; NM_001126117 | tumor protein p53 | TP53 | 12221076 | cell death |
| COLCHICINE | NM_030773 | tubulin, beta 1 | TUBB1 | — | target |
| COLCHICINE | NM_001069 | tubulin, beta 2A | TUBB2A | — | target |
| OBLIMERSEN | NM_000633; NM_000657 | B-cell CLL/lymphoma 2 | BCL2 | 11095261, 15867202 | target |
| OBLIMERSEN | NM_004346; NM_032991 | caspase 3, apoptosis-related cysteine peptidase | CASP3 | 16675587 | |
| OBLIMERSEN | — | | IGH-6 | 15867202 | |
| TEGAFUR | NM_001785 | cytidine deaminase | CDA | 18537153 | |
| TEGAFUR | NM_000762 | cytochrome P450, family 2, subfamily A, polypeptide 6 | CYP2A6 | 11376561, 12172220, 11376561, 15980104 | target |
| TEGAFUR | NM_000110 | dihydropyrimidine dehydrogenase | DPYD | 18537153 | |
| TIPIFARNIB | NM_000927 | ATP-binding cassette, sub-family B (MDR/TAP), member 1 | ABCB1 | 15122075 | resistance |
| TIPIFARNIB | NM_017460 | cytochrome P450, family 3, subfamily A, polypeptide 4 | CYP3A4 | 15122075 | |
| TIPIFARNIB | NM_000777 | cytochrome P450, family 3, subfamily A, polypeptide 5 | CYP3A5 | 15122075 | |
| TIPIFARNIB | NM_000463 | UDP glucuronosyltransferase 1 family, polypeptide A1 | UGT1A1 | 15122075 | |
| VORINOSTAT | NM_001014431; NM_001014432; NM_005163 | v-akt murine thymoma viral oncogene homolog 1 | AKT1 | 15781658, 16144943 | death pathway |
| VORINOSTAT | NM_001188 | BCL2-antagonist/killer 1 | BAK1 | 15781658, 16144943 | death pathway |
| VORINOSTAT | NM_004324; NM_138761; NM_138763; NM_138764; NM_138765 | BCL2-associated X protein | BAX | 15781658, 15897598 | death pathway |
| VORINOSTAT | NM_000633; NM_000657 | B-cell CLL/lymphoma 2 | BCL2 | 15897598, 16144943, 15897598 | resistance |
| VORINOSTAT | NM_001114735; NM_004049 | BCL2-related protein A1 | BCL2A1 | 15897598 | resistance |
| VORINOSTAT | NM_001191; NM_138578 | BCL2-like 1 | BCL2L1 | 12893773, 16144943, 15897598 | resistance |
| VORINOSTAT | NM_006538; NM_138621; NM_207002 | BCL2-like 11 (apoptosis facilitator) | BCL2L11 | 16144943 | death pathway |
| VORINOSTAT | NM_001196; NM_197966; NM_197967 | BH3 interacting domain death agonist | BID | 12893773, 17410615, 17410615, 15897598 | death pathway |
| VORINOSTAT | NM_001166 | baculoviral IAP repeat-containing 2 | BIRC2 | 12893773, 16377638 | |
| VORINOSTAT | NM_001165; NM_182962 | baculoviral IAP repeat-containing 3 | BIRC3 | 12893773, 15897598, 16377638 | altered by vorinostat |
| VORINOSTAT | NM_001012270; NM_001012271; NM_001168 | baculoviral IAP repeat-containing 5 | BIRC5 | 16144943, 17410615, 17410615, 18156316 | altered by vorinostat |
| VORINOSTAT | NM_032982; NM_032983 | caspase 2, apoptosis-related cysteine peptidase | CASP2 | 15897598 | death pathway |
| VORINOSTAT | NM_004346; NM_032991 | caspase 3, apoptosis-related cysteine peptidase | CASP3 | 12893773, 15781658, 15897598, 17410615 | death pathway |
| VORINOSTAT | NM_001227; NM_033338; NM_033339; NM_033340 | caspase 7, apoptosis-related cysteine peptidase | CASP7 | 15897598 | death pathway |

TABLE 1-continued

| Molecule | RefSeq | Description | Symbol | PMID | Interaction |
|---|---|---|---|---|---|
| VORINOSTAT | NM_001080124; NM_001080125; NM_001228; NM_033355; NM_033356; NM_033358 | caspase 8, apoptosis-related cysteine peptidase | CASP8 | 12893773, 15781658, 15897598, 17410615 | death pathway |
| VORINOSTAT | NM_001229; NM_032996 | caspase 9, apoptosis-related cysteine peptidase | CASP9 | 12893773, 15897598 | death pathway |
| VORINOSTAT | NM_053056 | cyclin D1 | CCND1 | 12893773, 17431121, 12893773 | altered by vorinostat |
| VORINOSTAT | NM_000389; NM_078467 | cyclin-dependent kinase inhibitor 1A (p21, Cip1) | CDKN1A | 12893773, 16144943, 17431121, 15897598, 12893773, 14707268, 17431121 | altered by vorinostat |
| VORINOSTAT | NM_004064 | cyclin-dependent kinase inhibitor 1B (p27, Kip1) | CDKN1B | 16144943, 17431121, 17431121 | resistance |
| VORINOSTAT | NM_001127183; NM_001127184; NM_003879 | CASP8 and FADD-like apoptosis regulator | CFLAR | 12893773, 15897598 | death pathway |
| VORINOSTAT | NM_018947 | cytochrome c, somatic | CYCS | 12893773, 15781658 | altered by vorinostat |
| VORINOSTAT | NM_000499 | cytochrome P450, family 1, subfamily A, polypeptide 1 | CYP1A1 | 15713371 | altered by vorinostat |
| VORINOSTAT | NM_000104 | cytochrome P450, family 1, subfamily B, polypeptide 1 | CYP1B1 | 15713371 | altered by vorinostat |
| VORINOSTAT | NM_019887; NM_138929 | diablo homolog (Drosophila) | DIABLO | 12893773 | death pathway |
| VORINOSTAT | NM_001005862; NM_004448 | v-erb-b2 erythroblastic leukemia viral oncogene homolog 2, neuro/glioblastoma derived oncogene homolog (avian) | ERBB2 | 16144943 | altered by vorinostat |
| VORINOSTAT | NM_004964 | histone deacetylase 1 | HDAC1 | 15930892 | target |
| VORINOSTAT | NM_001527 | histone deacetylase 2 | HDAC2 | — | target |
| VORINOSTAT | NM_003883 | histone deacetylase 3 | HDAC3 | 15930892 | target |
| VORINOSTAT | NM_006044 | histone deacetylase 6 | HDAC6 | 15930892 | target |
| VORINOSTAT | NM_018486 | histone deacetylase 8 | HDAC8 | — | target |
| VORINOSTAT | NM_003493 | histone cluster 3, H3 | HIST3H3 | 17431121 | altered by vorinostat |
| VORINOSTAT | NM_013247; NM_145074 | HtrA serine peptidase 2 | HTRA2 | 16026644 | death pathway |
| VORINOSTAT | NM_002755 | mitogen-activated protein kinase kinase 1 | MAP2K1 | 12893773, 15781658 | altered by vorinostat |
| VORINOSTAT | NM_002745; NM_138957 | mitogen-activated protein kinase 1 | MAPK1 | 12893773, 15781658 | altered by vorinostat |
| VORINOSTAT | NM_001315; NM_139012; NM_139013; NM_139014 | mitogen-activated protein kinase 14 | MAPK14 | 12893773 | altered by vorinostat |
| VORINOSTAT | NM_001040056; NM_001109891; NM_002746 | mitogen-activated protein kinase 3 | MAPK3 | 12893773, 15781658 | altered by vorinostat |
| VORINOSTAT | NM_002750; NM_139046; NM_139047; NM_139049 | mitogen-activated protein kinase 8 | MAPK8 | 12893773, 15781658, 15964800 | altered by vorinostat |
| VORINOSTAT | NM_003998 | nuclear factor of kappa light polypeptide gene enhancer in B-cells 1 | NFKB1 | 12893773 | altered by vorinostat |
| VORINOSTAT | NM_001618 | poly (ADP-ribose) polymerase 1 | PARP1 | 12893773, 16377638, 17431121, 15897598 | altered by vorinostat |
| VORINOSTAT | — | — | PDCD8 | 12893773, 15781658, 16026644 | death pathway |
| VORINOSTAT | NM_002880 | v-raf-1 murine leukemia viral oncogene homolog 1 | RAF1 | 12893773, 16144943, 12893773 | altered by vorinostat |
| VORINOSTAT | NM_000965; NM_016152 | retinoic acid receptor, beta | RARB | 16832676 | altered by vorinostat |
| VORINOSTAT | NM_000321 | retinoblastoma 1 | RB1 | 12893773, 14707268, 15897598 | altered by vorinostat |
| VORINOSTAT | NM_001145138; NM_021975 | v-rel reticuloendotheliosis viral oncogene homolog A (avian) | RELA | 12893773, 15964800 | altered by vorinostat |
| VORINOSTAT | NM_000594 | tumor necrosis factor (TNF superfamily, member 2) | TNF | 16377638 | altered by vorinostat |
| VORINOSTAT | NM_003810 | tumor necrosis factor (ligand) superfamily, member 10 | TNFSF10 | 17410615 | death pathway |
| VORINOSTAT | NM_001167 | X-linked inhibitor of apoptosis | XIAP | 12893773, 15964800, 16144943, 17410615, 17410615 | altered by vorinostat |

TABLE 2

| Chemical | Target Genes | Target Genes List | Found Targets | Found Targets List (with fold-changes) |
|---|---|---|---|---|
| Nucleotides | | | | |
| Nucleotides >> Antimetabolites | | | | |
| Nucleotides >> Antimetabolites >> Folic acid | | | | |
| METHOTREXATE (Abitrexate, Antifolan, Arbitrexate, Emtexate, Folex, Ledertrexate, Metatrexan, Methotrate, Mexate, Rheumatrex, Trexall) | 35 | ABCB1 ABCC1 ABCC2 ABCC4 ABCG2 ALB ALPI ATIC CD4 CD68 CD8A CYP3A4 DHFR DKK1 GSTM1 ICAM1 IL8 MMP3 MTHFR MTR NAT1 ODC1 PARP1 PRC1 RB1 SELE SLC19A1 SLC46A1 TAGLN TIMP1 TYMS UBE2C VDR WISP1 WNT5A | 19 (10 + 9) (54.3%) | ABCC1 (7.70) ABCC2 (4.39, 5.45) ABCC4 (2.34) ATIC (3.75) NAT1 (2.39) PARP1 (2.68) PRC1 (3.44) TYMS (3.69) UBE2C (9.47) WNT5A (28.92) ABCB1 (−3.59) CD68 (−3.38) CYP3A4 (−7.84) DKK1 (−16.44) ICAM1 (−8.24) IL8 (−16.97) SLC19A1 (−3.24) TIMP1 (−4.76) VDR (−6.07) |
| PEMETREXED (Alimta) | 8 | DHFR FPGS GART GGH RBM17 SLC19A1 TYMP TYMS | 4 (2 + 2) (50.0%) | GART (2.18) TYMS (3.69) SLC19A1 (−3.24) TYMP (−3.83, −5.95) |
| Nucleotides >> Antimetabolites >> Purine | | | | |
| FLUDARABINE (Fludara, Fludura) | 25 | ADA AKT1 ARNT BCL2 CCNA2 CCND1 CCNE1 CDKN1B CYCS DIABLO ERK HIF1A HIST3H3 HIST4H4 MAP2K1 MAP2K2 MAPK1 MAPK3 MCL1 PDCD8 POLA1 RRM1 STAT1 VEGFA XIAP | 6 (4 + 2) (24.0%) | CCNA2 (5.27) CCNE1 (5.62) HIST3H3 (2.04) VEGFA (2.60) CCND1 (−2.52) MCL1 (−3.34) |
| Nucleotides >> Antimetabolites >> Pyrimidine | | | | |
| FLUOROURACIL (5 FU, Fluorouracil, Adrucil, Arumel, Carac, Carzonal, Effluderm, Efudex, Efudix, Efurix, FU, Fluoroblastin, Fluoroplex, Fluracil, Fluracilum, Fluri, Fluril, Fluro, Uracil, Ftoruracil, Kecimeton, Phthoruracil, Phtoruracil, Queroplex, Timazin, URF, Ulup) | 132 | ABCB1 ABCC1 ABCG2 ACADL ADSS AIFM1 AMFR AMT ANGPTL2 AREG ATP5O BARX2 BAX BBS4 BCL2 BDH1 BECN1 BIRC5 BNIP3 BNIP3L BOLL BTG3 BUB3 C13ORF34 CA12 CASP2 CASP3 CASP7 CASP8 CASP9 CCND3 CCNE2 CCNF CCNG2 CDCA8 CDKN1A CDKN1C CIDEB CKS2 CTNND2 CTTN CYR61 DPYD DRD5 DTYMK E2F3 EGFR EIF2B2 EIF3S3 EML2 ERBB2 ERBB4 ERCC1 ERCC2 ERP29 F3 F8 FANCG FAS FEN1 FGF7 FOXO3 GADD45A GAMT GFRA1 GOLGA8A GSTP1 GSTT1 HINT1 HIST1H1D HNRPC IGFBP4 IL8RA IRAK1 JMJD2B KIAA1467 KIF3A KPNA2 KRAS LGALS8 LMNB1 LTB4DH M6PR MALT1 MAPK13 MAPT MED13L MELK METRN MKI67 MYC NDUFA10 NKAIN1 NUCKS1 PARP1 PCDHA5 PDAP1 PGR PPP3CA PRC1 PRNP PSCD3 PSG9 PSRC1 RAD23B RAMP1 RNF34 RPL3 RRM2 RTKN SCUBE2 SERPINE2 SFN SNAPC1 TERF2 THNSL2 TMSB4X TMSL8 TNFRSF10B TP53 TYMP TYMS UBE2C UPP1 UPRT UXT WBSCR1 XAF1 ZNF32 ZNF552 ZNF582 ZRSR2 | 64 (35 + 29) (48.5%) | ABCC1 (7.70) ADSS (3.13, 3.02) BECN1 (2.18) CA12 (21.62, 17.07, 11.24, 25.25) CASP2 (2.27) CASP3 (2.14) CASP8 (8.85, 2.67) CCNE2 (3.25) CCNF (2.52) CDCA8 (2.55) CTNND2 (3.12, 2.44) CTTN (2.13) DTYMK (2.69, 2.60) E2F3 (2.71) EML2 (4.55) FEN1 (2.79, 2.41) FOXO3 (2.21) GOLGA8A (8.56) GSTP1 (3.00) KPNA2 (2.49) LTB4DH (18.28) MED13L (6.09) MELK (6.04) MKI67 (5.91) NDUFA10 (2.42) NKAIN1 (22.33) PARP1 (2.68) PCDHA5 (2.75) PRC1 (3.44) RAD23B (2.57, 2.55, 4.15) RNF34 (2.18, 2.49, 2.45) RRM2 (3.30, 3.47) TYMS (3.69) UBE2C (9.47) ZNF552 (8.76, 2.45) ABCB1 (−3.59) ACADL (−19.18) AMFR (−5.37) ANGPTL2 (−2.89, −3.89) AREG (−119.30) BTG3 (−7.01) CDKN1A (−7.85, −4.44) CDKN1C (−7.69) CYR61 (−3.69, −2.81, −3.06) DPYD (−2.82, −4.07, −4.30) EGFR (−12.64) ERBB4 (−3.94, −3.33) F3 (−3.63) F8 (−3.51, −2.90) FAS (−5.93) FGF7 (−2.01, −3.09, −3.61) GAMT (−3.39, −2.43) GFRA1 (−5.66) IGFBP4 (−2.66) IL8RA (−5.26) LGALS8 (−2.28) PGR (−11.29) PPP3CA (−2.42) PRNP (−3.95) TMSB4X (−2.05) TMSL8 (−11.70) TNFRSF10B (−2.25) TYMP (−3.83, −5.95) UPP1 (−3.24, −2.71, −2.28) |

TABLE 2-continued

| | | | | |
|---|---|---|---|---|
| CAPECITABINE (Xeloda) | 5 | CES1 CES2 CES3 DPYD TYMS | 4 (3 + 1) (80.0%) | CES1 (13.90) CES3 (10.19) TYMS (3.69) DPYD (−2.82, −4.07, −4.30) |
| GEMCITABINE (DDFC, DFDC, GEO, Gemcin, Gemcitabina, Gemcitabine, HCl, Gemcitabine hydrochloride, Gemcitabinum, Gemtro, Gemzar) | 12 | BAX BCL2 CASP3 CDKN1A CMPK PARP1 PDPK1 RBM17 RRM1 SLC29A1 TP53 TYMS | 4 (3 + 1) (33.3%) | CASP3 (2.14) PARP1 (2.68) TYMS (3.69) CDKN1A (−7.85, −4.44) |

DNA
DNA >> Alkylating agents
DNA >> Alkylating agents >> Nitrogen mustards

| | | | | |
|---|---|---|---|---|
| CYCLOPHOSPHAMIDE (ASTA, Asta B 518, CP, CPA, CTX, CY, Clafen, Claphene, Cyclophosphamid, Cyclophosphamide Monohydrate, Cyclophosphamide Sterile, Cyclophosphamidum, Cyclophosphan, Cyclophosphane, Cyclophosphoramide, Cyclostin, Cyklofosfamid, Cytophosphan, Cytoxan, Cytoxan, Lyoph, EndoxanEndoxan, R, Endoxan-Asta, Endoxana, Endoxanal, Endoxane, Enduxan, Genoxal, Hexadrin Lyophilized, Cytoxan, Mitoxan, Neosar, Procytox, Rcra, Waste, Number, U058, Revimmune, Semdoxan, Sendoxan, Senduxan, Zyklophosphamid) | 56 | ABCB1 ABCC1 ABCG2 AMFR BAG1 BBS4 BCL2 BECN1 BTG3 BUB3 CA12 CASP3 CASP9 CDKN1B CTNNBIP1 CTNND2 CYP2B6 E2F3 EGFR EIF1AX EIF4EBP1 ERBB2 ERBB4 ESR1 ESR2 GAMT GFRA1 GSTA1 GTF3C1 IGFBP4 ILF3 IRS1 JMJD2B KIAA1467 KIF3A MAPK14 MAPT MED13L MELK METRN MGMT MKI67 NAIP NKAIN1 PGR PLOD1 PLOD3 RAMP1 RRM2 SCUBE2 SRM ST14 STK39 THNSL2 TP53 ZNF552 | 29 (17 + 12) (51.8%) | ABCC1 (7.70) BECN1 (2.18) CA12 (21.62, 17.07, 11.24, 25.25) CASP3 (2.14) CTNND2 (3.12, 2.44) CYP2B6 (10.92, 3.17) E2F3 (2.71) GSTA1 (16.89) ILF3 (3.78) MED13L (6.09) MELK (6.04) MKI67 (5.91) NKAIN1 (22.33) RRM2 (3.30, 3.47) ST14 (2.22) STK39 (6.44, 6.78) ZNF552 (8.76, 2.45) ABCB1 (−3.59) AMFR (−5.37) BTG3 (−7.01) CTNNBIP1 (−7.17) EGFR (−12.64) ERBB4 (−3.94, −3.33) GAMT (−3.39, −2.43) GFRA1 (−5.66) IGFBP4 (−2.66) IRS1 (−13.62) PGR (−11.29) PLOD1 (−2.05) |
| IFOSFAMIDE (Cyfos, Holoxan, 1000, IFEX, Ifex/Mesnex Kit, Ifosfamide/Mesna Kit, Isoendoxan, Mitoxana, Naxamide) | 10 | BCL2 CASP9 CYP2A6 CYP2B6 CYP3A4 CYP3A5 DNMT1 GSTM1 GSTP1 GSTT1 | 5 (3 + 2) (50.0%) | CYP2B6 (10.92, 3.17) DNMT1 (2.20) GSTP1 (3.00) CYP3A4 (−7.84) CYP3A5 (−34.94) |
| MELPHALAN (Alkeran, L-PAM, L-Phenylalanine mustard, L-Sarcolysin, L-Sarcolysine, L-Sarkolysin, Levofalan, Melfalan, Mephalan, Phenylalanine mustard, Phenylalanine nitrogen mustard, Sarcolysine, Sarkolysin) | 9 | ABCC1 BIRC5 CASP2 CASP3 CDA GSTA1 GSTP1 MGMT MGST2 | 5 (5 + 0) (55.6%) | ABCC1 (7.70) CASP2 (2.27) CASP3 (2.14) GSTA1 (16.89) GSTP1 (3.00) |

DNA >> Alkylating agents >> Nitrosoureas

| | | | | |
|---|---|---|---|---|
| CARMUSTINE (Becenun, Bi CNU, BiCNU, Carmubris, Gliadel, Gliadel Wafer, Nitrumon) | 230 | ABCB1 ABCC1 ACTC1 ACTG2 ACTN1 ADAM15 ADAMTS4 ADCYAP1 ADRA1B AGT AGTRL1 AKT2 ALAD ALOX15B AMH APC2 AQP8 ARGBP2 ARPC2 ARTN ASMTL ATP1A3 ATP4B ATP5D ATP6V0C ATXN2L AVPR1A B4GALT5 BAIAP2 BAIAP3 BCL10 BCL2 BCL2L1 BECN1 BICD1 BLK BMP7 BRF1 CA6 CALB2 CCL2 CD151 CD68 CD79A CD80 | 106 (50 + 56) (46.1%) | ABCC1 (7.70) AGT (3.57) AKT2 (2.40, 3.07, 2.01) ALAD (4.21) AMH (2.39) AQP8 (3.03) B4GALT5 (2.55, 2.84) BAIAP3 (2.18) BECN1 (2.18) BICD1 (13.67) BLK (3.63) CDC25C (8.00) CDK8 (2.39) CEACAM3 (2.96, 2.75) CHEK1 (4.69) CKM (20.86) CLTCL1 (5.12) CRABP1 (3.09) CYP19A1 (2.64) DHX16 (2.71) DVL1 (2.75, 2.21) EIF2B1 (2.16) EPHX1 (4.56) EZH2 (4.80) FNTA (3.94) FTH1 (2.42, 2.32, |

TABLE 2-continued

|  |  |  |  |  |
|---|---|---|---|---|
|  |  | CDC25C CDK8 CDKN1A CDX4 CEACAM3 CEBPB CHEK1 CHRM4 CHRNB3 CHRNG CKM CLTCL1 CNTNAP1 COL9A1 COX6A2 CRABP1 CRAT CRYBB1 CST5 CTF1 CTNNAL1 CYP19A1 DHX16 DNASE1L2 DVL1 ECM2 EEF1G EIF2B1 EIF6 EPHX1 ESRRA EZH2 FBN1 FKBP1A FNTA FOXJ1 FTH1 FTL FYN GABRA2 GABRA6 GAMT GAST GCM1 GDI1 GDI2 GFAP GHSR GNRHR GOLGA2 GOLGA4 GP1BB GPR25 GPR32 GPR37 GPR65 GRB7 GRN GSR GSTA1 GSTM1 GSTM3 GSTP1 GTF2F1 H2AFX HADHSC HAGH HCFC1 HMGN2 HNF1A HOXA4 ICAM5 IDS IER3 IKBKG INPPL1 INSIG1 INSL3 IRS1 ISLR ITGA3 ITIH1 KCNH2 KIF5A KRT17 KRT31 LAD1 LAIR1 LAMB3 LMX1B LOXL1 LRCH4 LRMP MAD1L1 MAP4K2 MAPK10 MAT1A MDK MED1 MGAT3 MGMT MSR1 MUC2 MVD MYBPH MYD88 MYOD1 MYOG NDUFC1 NKX2-2 NPAS1 NPBWR2 NRTN OMP PAEP PAX8 PBX2 PCBD1 PCDHGC3 PCOLCE PCYT1A PFKFB2 PFKM PFN1 PIK3R3 PMS2L11 POLR2E PPM1G PRC1 PRL PRM2 PSCD1 PTPN3 PZP RAD23A RAD51 RAD9 RCN1 RGR RIT2 RNASE4 SEPT5 SFPQ SGCA SHMT2 SHOX SIAT1 SLC10A1 SLC16A2 SLC30A3 SLC6A2 SLCO1A2 SMARCD1 SMPD2 SNAPC1 SNAPC3 SNCG SNRPB2 SOCS1 SPEG SPRR2B SRP14 SRY ST8SIA1 STAM STS STX1B STXBP2 TAC1 TCF21 TEGT TLE3 TNFRSF11B TP53 TRAF1 TSPAN4 TUBB TUBG1 UGT8 UPF1 VGF WIPF1 YWHAH ZBTB17 ZYX |  | 2.35) FTL (3.51, 4.41, 3.40) GCM1 (2.70) GOLGA2 (2.44, 2.57) GPR37 (2.96) GRB7 (2.78) GSR (10.75, 10.84) GSTA1 (16.89) GSTP1 (3.00) HNF1A (3.45) INPPL1 (2.26) KCNH2 (4.05) MAP4K2 (2.72) MAPK10 (3.15) MAT1A (6.12) MDK (17.02) MED1 (2.44) NPAS1 (4.81) PRC1 (3.44) PTPN3 (2.46, 2.03) RAD51 (4.60) SLCO1A2 (2.31) SMPD2 (2.55) SNCG (2.23) UGT8 (5.58, 9.40) ABCB1 (−3.59) ACTG2 (−9.33) ACTN1 (−2.46, −2.62) ADAMTS4 (−3.13, −5.12) ADRA1B (−7.78) ALOX15B (−17.05) ATP1A3 (−5.85) BAIAP2 (−4.34, −2.72, −3.14) BCL10 (−2.16, −3.00) BMP7 (−16.37, −4.33) BRF1 (−3.38) CALB2 (−5.76) CCL2 (−8.86) CD151 (−2.41) CD68 (−3.38) CDKN1A (−7.85, −4.44) COX6A2 (−2.12) CRAT (−3.15) CST5 (−2.40) CTNNAL1 (−5.85) FBN1 (−2.95) FKBP1A (−5.05) FOXJ1 (−5.38, −2.05) FYN (−2.59) GAMT (−3.39, −2.43) GDI2 (−2.36) GPR65 (−2.59) GSTM3 (−3.01) HOXA4 (−8.73) IER3 (−4.31) IRS1 (−13.62) KRT17 (−5.21) LAIR1 (−2.82) LAMB3 (−23.74) LOXL1 (−2.57) MAD1L1 (−2.73) MGAT3 (−12.97) MSR1 (−2.93, −2.73) MYBPH (−4.47) MYD88 (−2.51) NRTN (−7.31) PAX8 (−5.65) PCOLCE (−3.31) PZP (−2.82) RCN1 (−2.52, −2.24) RNASE4 (−2.13) SGCA (−17.29) SLC16A2 (−6.80) SNRPB2 (−2.25) SOCS1 (−5.85, −5.20) SPEG (−5.28) ST8SIA1 (−6.37) TCF21 (−20.30) TSPAN4 (−3.44, −3.61) WIPF1 (−2.18, −3.58) ZYX (−3.12) |
| FOTEMUSTINE (Muphoran) | 2 | MGMT TXNRD1 | 1 (1 + 0) (50.0%) | TXNRD1 (12.56) |
| DNA >> Alkylating agents >> Platinum |  |  |  |  |
| CARBOPLATIN (Paraplatin, Paraplatin-AQ) | 11 | ALB BAX BCL2 BCL2L12 BIRC2 CASP3 CASP9 DCT FAS PARP1 RBM17 | 4 (3 + 1) (36.4%) | BCL2L12 (4.27) CASP3 (2.14) PARP1 (2.68) FAS (−5.93) |
| CISPLATIN (Abiplatin, Biocisplatinum, Briplatin, Carboquone, Cis Pt II, Cismaplat, Cisplatine, Cisplatyl, Citoplationo, Lederplatin, Neoplatin, Plastin, Platamine, Platiblastin, Platidiam, | 111 | A2M ABCB1 ABCC1 ABCC2 ABCC5 AKT1 AKT2 AKT3 ALB APEX1 AXL BAX BCL2 BCL2L1 BCL2L12 BIRC2 BIRC3 BIRC5 CASP2 CASP3 CASP8 CASP9 CAT CDKN1A CFLAR CLU CNTF CREBBP CYCS | 54 (27 + 27) (48.6%) | ABCC1 (7.70) ABCC2 (4.39, 5.45) ABCC5 (4.30, 6.53) AKT2 (2.40, 3.07, 2.01) BCL2L12 (4.27) CASP2 (2.27) CASP3 (2.14) CASP8 (8.85, 2.67) CREBBP (2.11, 2.52) ETV4 (2.09) GSTP1 (3.00) HSPE1 (5.96) KRT4 (8.00) LASS4 (5.10) MCM2 |

TABLE 2-continued

| | | | | |
|---|---|---|---|---|
| Platinex, Platinol, Platinol-AQ, Platinoxan, Randa) | | CYP3A4 DIABLO DPYD EDN2 EGFR EP300 ERBB2 ERCC1 ERCC2 ETV4 FADD FANCG FAS FASLG FGFR3 FOSL1 GDF15 GSTM1 GSTM3 GSTP1 GSTT1 GUK1 HIF1A HSPE1 HTRA2 IFITM1 IGFBP3 IL4R ITGA9 ITGB4 JUN KRT19 KRT4 LASS4 MCM2 MED1 MGMT MMP10 MMP15 MMP16 MRPS27 MT1A MT2A MT3 MVP NAIP NCOA3 NOTCH4 NR1I2 NTHL1 PARP1 PCNA PDIA3 PFDN5 PGK1 PMAIP1 PRNP PTEN PTGS2 PTK2 RB1 RHOC RPL36 RPS5 RUNX3 SFN SLC31A1 SOCS1 SPINT2 TF TP53 TP73 TRAM1 TRAP1 TUBA1A TXN TYMS VEGFA XIAP XPA XRCC1 ZFP36L1 | | (3.39) MED1 (2.44) NCOA3 (3.29, 4.36, 3.16) NR1I2 (3.23) PARP1 (2.68) PMAIP1 (12.40) PTK2 (2.54) SLC31A1 (2.02, 2.41) SPINT2 (6.04) TF (9.84, 8.91) TXN (4.58, 5.09) TYMS (3.69) VEGFA (2.60) A2M (−4.77) ABCB1 (−3.59) AKT3 (−3.90, −3.96) BIRC3 (−2.84) CAT (−3.31) CDKN1A (−7.85, −4.44) CYP3A4 (−7.84) DPYD (−2.82, −4.07, −4.30) EDN2 (−3.91) EGFR (−12.64) FAS (−5.93) FGFR3 (−8.75) GSTM3 (−3.01) IL4R (−4.02) ITGA9 (−2.21) JUN (−2.62) MMP10 (−2.05) MT1A (−7.47) MT2A (−8.59, −9.15) MVP (−2.25) NOTCH4 (−2.63, −3.15) PFDN5 (−2.17) PRNP (−3.95) PTEN (−2.30, −2.56) PTGS2 (−36.04, −32.79) SOCS1 (−5.85, −5.20) TRAM1 (−3.53) |
| OXALIPLATIN (DACPLAT, Eloxatin, Elplat, Foloxatine, Transplatin) | 17 | BCL2 BCL2L1 BIRC5 CCNA2 CCNB1 CCNE1 CDC2 CDK2 CDKN1B EGFR ERCC1 ERCC2 GSTP1 IL8RA MYC RB1 TYMS | 8 (6 + 2) (47.1%) | CCNA2 (5.27) CCNB1 (3.17) CCNE1 (5.62) CDC2 (2.92) GSTP1 (3.00) TYMS (3.69) EGFR (−12.64) IL8RA (−5.26) |
| DNA >> Alkylating agents >> Alkyl sulfonates | | | | |
| BUSULFAN (Busulfex, Citosulfan, Leucosulfan, Mablin, Mielevcin, Mielosan, Mielucin, Milecitan, Mileran, Misulban, Mitosan, Mitostan, Myeleukon, Myeloleukon, Myelosan, Mylecytan, Myleran, Myleran Tablets) | 5 | GSTA1 GSTM1 GSTP1 MGMT MGST2 | 2 (2 + 0) (40.0%) | GSTA1 (16.89) GSTP1 (3.00) |
| DNA >> Alkylating agents >> Hydrazines | | | | |
| PROCARBAZINE (Matulane, Nathulane, Natulan, Natulan hydrochloride, Natulanar, Natunalar) | 1 | MGMT | — | — |
| DNA >> Alkylating agents >> Triazenes | | | | |
| DACARBAZINE (Deticene) | 22 | APEX1 BIRC5 CASP3 CASP8 CD38 CD69 CYP1A1 CYP1A2 EPO IFNA1 IFNA2 IL8 IRF1 MAP3K1 MAPK1 MAPK3 MCL1 MGMT POLA2 SLC2A1 TNFSF10 VEGFA | 9 (5 + 4) (40.9%) | CASP3 (2.14) CASP8 (8.85, 2.67) MAP3K1 (2.06, 2.62) SLC2A1 (22.83) VEGFA (2.60) IL8 (−16.97) IRF1 (−2.23) MCL1 (−3.34) TNFSF10 (−7.51) |
| TEMOZOLOMIDE (Temodal, Temodar) | 10 | AGT DCT MGMT MPG PARP1 PMAIP1 POLB POLI POLL TP53 | 3 (3 + 0) (30.0%) | AGT (3.57) PARP1 (2.68) PMAIP1 (12.40) |
| DNA >> Alkylating agents >> Aziridines | | | | |
| THIOTEPA (Thioplex, Thiotepa) | 5 | GSTA1 GSTA2 GSTM1 GSTP1 MGMT | 3 (3 + 0) (60.0%) | GSTA1 (16.89) GSTA2 (15.07, 16.53) GSTP1 (3.00) |
| DNA >> Alkylating agents >> Other | | | | |
| ECTEINASCIDIN 743 (Trabectedin, ET-743, Yondelis) | 4 | CCNA2 CCNB1 CCNB2 E2F1 | 4 (4 + 0) (100.0%) | CCNA2 (5.27) CCNB1 (3.17) CCNB2 (4.19) E2F1 (2.45) |
| DNA >> Spindle poisons/Mitotic inhibitors | | | | |
| DNA >> Spindle poisons/Mitotic inhibitors >> Taxanes | | | | |
| DOCETAXEL (Toxotere) | 33 | ABCB1 ABCC1 ABCC2 BCL2 BCL2L1 BIRC5 CASP3 CFLAR CYP19A1 | 15 (7 + 8) (45.5%) | ABCC1 (7.70) ABCC2 (4.39, 5.45) CASP3 (2.14) CYP19A1 (2.64) GSTP1 |

TABLE 2-continued

| | | | | |
|---|---|---|---|---|
| | | CYP1B1 CYP3A4 ERBB2 GSTP1 HIF1A HRAS IL6 MAPK1 MAPK3 MDM2 PAR1 PARP1 PGR POR PTGS2 RAF1 RB1 SKP2 TNF TNFRSF10B TP53 TUBB TUBB1 VEGFA | | (3.00) PARP1 (2.68) VEGFA (2.60) ABCB1 (−3.59) CYP1B1 (−3.87) CYP3A4 (−7.84) HRAS (−2.10) IL6 (−39.79) PGR (−11.29) PTGS2 (−36.04, −32.79) TNFRSF10B (−2.25) |
| PACLITAXEL (Epitaxol, LipoPac, Onxol, Paxceed, Paxene, Taxol, Taxol A, Vascular Wrap, Xorane) | 129 | ABCB1 ABCC1 ABCC2 AIFM1 AKR1C2 AKT1 AKT2 AKT3 AMFR APAF1 ARR3 ASPM AURKA BAD BAX BBS4 BCL2 BCL2L1 BECN1 BID BIRC2 BIRC3 BIRC5 BMP7 BTG3 C7ORF23 CA12 CALCA CASP3 CASP7 CASP8 CASP9 CAV1 CCNB1 CCND1 CD46 CD47 CDKN1A CFLAR CLU CTCF CTNND2 CTSL1 CXCR4 CXCR6 CXCR7 CYCS CYP19A1 CYP2C8 CYP3A4 DIABLO E2F3 EGFR ERBB4 FAS FASLG FDPS FTH1 FTL FURIN FXYD3 GADD45A GAMT GFRA1 GSTM1 GSTM5 GSTP1 GSTT1 HIF1A ICAM1 IFI30 IGFBP4 ITGB5 JMJD2B JUN KIAA1467 KIF3A KRT13 MAPK1 MAPK14 MAPK3 MAPK8 MAPK9 MAPT MCL1 MDM2 MED1 MED13L MELK METRN MMP9 MT1E MT2A MYC NAT1 NCOA3 NFKB1 NFKBIA NKAIN1 NR1I2 PARP1 PDPK1 PMP22 POR PRC1 PTEN PTGS2 RAMP1 RB1 RBL2 RELA RFX5 RPL23A RPLP1 RRM2 RTKN S100P SCUBE2 TFF1 THNSL2 TNFRSF10B TOP2A TP53 TUBB TUBB1 TYMS VEGFA XIAP ZNF552 | 65 (31 + 34) (50.4%) | ABCC1 (7.70) ABCC2 (4.39, 5.45) AKT2 (2.40, 3.07, 2.01) ASPM (5.55, 8.12) AURKA (4.00) BECN1 (2.18) CA12 (21.62, 17.07, 11.24, 25.25) CASP3 (2.14) CASP8 (8.85, 2.67) CCNB1 (3.17) CTNND2 (3.12, 2.44) CYP19A1 (2.64) E2F3 (2.71) FTH1 (2.42, 2.32, 2.35) FTL (3.51, 4.41, 3.40) GSTP1 (3.00) MED1 (2.44) MED13L (6.09) MELK (6.04) NAT1 (2.39) NCOA3 (3.29, 4.36, 3.16) NKAIN1 (22.33) NR1I2 (3.23) PARP1 (2.68) PRC1 (3.44) RRM2 (3.30, 3.47) S100P (41.69) TOP2A (5.88) TYMS (3.69) VEGFA (2.60) ZNF552 (8.76, 2.45) ABCB1 (−3.59) AKT3 (−3.90, −3.96) AMFR (−5.37) BIRC3 (−2.84) BMP7 (−16.37, −4.33) BTG3 (−7.01) CAV1 (−22.26, −24.68) CCND1 (−2.52) CD47 (−6.41, −16.99) CDKN1A (−7.85, −4.44) CXCR4 (−2.72) CXCR6 (−2.50) CYP3A4 (−7.84) EGFR (−12.64) ERBB4 (−3.94, −3.33) FAS (−5.93) FURIN (−2.72) FXYD3 (−2.65) GAMT (−3.39, −2.43) GFRA1 (−5.66) GSTM5 (−3.70, −6.54) ICAM1 (−8.24) IGFBP4 (−2.66) JUN (−2.62) MAPK8 (−2.06) MCL1 (−3.34) MMP9 (−10.90) MT1E (−15.67) MT2A (−8.59, −9.15) NFKBIA (−4.00) PMP22 (−6.22) PTEN (−2.30, −2.56) PTGS2 (−36.04, −32.79) TNFRSF10B (−2.25) |
| DNA >> Spindle poisons/Mitotic inhibitors >> Vinca Alkaloids | | | | |
| VINBLASTINE (Nincaluicolflastine, Rozevin, Velban, Velbe Vinblastin, Vinblastina, Vinblastine Sulfate, Vinblastinum, Vincaleucoblastin, Vincaleucoblastine, Vincaleukoblastine, Vincoblastine) | 13 | ABCB1 ABCC1 ABCC2 CASP2 IKBKB JUN MAPK8 MAPK9 NFATC4 NFKBIA TNFRSF10B TP53 TUBB2A | 9 (4 + 5) (69.2%) | ABCC1 (7.70) ABCC2 (4.39, 5.45) CASP2 (2.27) IKBKB (2.08, 2.59, 3.48) ABCB1 (−3.59) JUN (−2.62) MAPK8 (−2.06) NFKBIA (−4.00) TNFRSF10B (−2.25) |
| VINCRISTINE (Marqibo, Onco TCS, Oncovin, Vincasar, Vincasar PFS, Vincrex, Vincristine Sulfate PFS, Vinkristin) | 70 | ABCB1 ABCC1 ABCC2 AKT1 APAF1 APOA1 ASPM AURKA BAD BAX BCL2 CASP1 CASP10 CASP2 CASP3 CASP4 CASP5 CASP6 CASP7 CASP8 CASP9 CAT CEBPB CES1 CFTR CYC1 E2F1 EGFR FADD FAIM2 GAPDH GSTM1 GULP1 HRAS IAPP IGF1 IGF1R IL6 LMNA LMNB1 MAP2K4 MAP3K7 MAPK1 MDM2 MEF2A MGMT MYC NFKB1 P11 PCAF PRC1 PRNP PTK2B PTPN13 RARB RBM17 | 31 (16 + 15) (44.3%) | ABCC1 (7.70) ABCC2 (4.39, 5.45) ASPM (5.55, 8.12) AURKA (4.00) CASP2 (2.27) CASP3 (2.14) CASP8 (8.85, 2.67) CES1 (13.90) E2F1 (2.45) GULP1 (21.16, 15.15) MAP3K7 (3.78) PRC1 (3.44) RARB (2.96) SLC2A1 (22.83) TYMS (3.69) XBP1 (2.26) ABCB1 (−3.59) CASP1 (−4.93) CASP4 (−2.29, −2.55) CASP5 (−2.47) CAT (−3.31) EGFR (−12.64) HRAS (−2.10) IGF1 (−5.82, −4.31, −5.16, −5.25) IL6 (−39.79) LMNA (−2.45) PCAF (−4.52, −6.85) PRNP (−3.95) PTPN13 (−3.49) |

TABLE 2-continued

| | | | | |
|---|---|---|---|---|
| | | RELA ROS1 RUNX3 SLC2A1 SOS1 STAT1 STAT2 STAT3 TNF TP53 TUBB2A TYMS VDR XBP1 | | ROS1 (−5.49) VDR (−6.07) |
| VINFLUNINE | 1 | TUBB1 | — | — |
| VINDESINE (DAVA, Eldesine, Eldisine) | 1 | TUBB1 | — | — |
| VINORELBINE (Navelbine, Navelbine Base) | 3 | RBM17 SLC29A1 TUBB2A | — | — |
| | DNA >> Spindle poisons/Mitotic inhibitors >> Other | | | |
| EPOTHILONES | 17 | BAX BCL2 BCL2L1 BIRC3 MCL1 TUBA1 TUBA2 TUBA3 TUBA6 TUBA8 TUBB1 TUBB2A TUBB2C TUBB3 TUBB4 TUBB4Q XIAP | 3 (0 + 3) (17.6%) | BIRC3 (−2.84) MCL1 (−3.34) TUBB4 (−4.81) |
| | DNA >> Cytotoxic/Antitumor antibiotics | | | |
| | DNA >> Cytotoxic/Antitumor antibiotics >> Anthracyclines | | | |
| DOXORUBICIN (ADM, Adriablastin, Adriamycin, Adriamycin PFS, Adriamycin RDF, Adriamycin Semiquinone, Adriblastin, Adriblastina, Caelyx, DM2, Doxil, Doxo, Myocet, RDF Rubex, Resmycin, Rubex) | 444 | ABCB1 ABCB1A ABCB4 ABCB5 ABCC1 ABCC3 ABCG2 ADAM19 ADAMTS5 AHCY AIFM1 AKR1A1 AKR1C2 AKR1C3 AKT1 AKT2 AKT3 ALB AMFR ANGPT1 AP4E1 APAF1 API5 APOA1 APP ARHGEF1 ARHGEF17 ARL6IP5 ATF4 ATM ATP6V0E1 AZGP1 B4GALT1 BACH1 BAD BAG1 BAK1 BAX BBS12 BBS4 BCL2 BCL2A1 BCL2L1 BCL2L11 BCL2L12 BECN1 BID BIK BIRC2 BIRC3 BIRC5 BIRC6 BIRC7 BIRC8 BTG1 BTG2 BTG3 BUB1B BUB3 C21ORF87 C5ORF13 C7ORF23 CA12 CABC1 CALD1 CAPN6 CASP1 CASP10 CASP2 CASP3 CASP4 CASP5 CASP6 CASP7 CASP8 CASP9 CBR1 CCL2 CCNA2 CCNB1 CCND1 CCND2 CCNE1 CD44 CDC2 CDC25C CDK10 CDK2 CDKN1A CDKN1B CDKN2A CEBPB CENPA CES1 CFLAR CFTR CHEK1 CHEK2 CHUK CISH CLDN1 CLIP1 CLPTM1 CLU COL18A1 COX2 CPT1A CREBBP CRISP2 CRYAA CRYAB CSPG4 CTGF CTNNBIP1 CTNND2 CTSB CTSD CTSG CXCL6 CYC1 CYCS CYP1A1 CYP27B1 CYP2B6 DDEF1 DDIT3 DEK DGKI DHPS DIABLO DKK2 DNAJA1 DNMT1 DPP4 DSPP DTYMK E2F1 E2F3 ECHS1 ECOP EDN1 EFNB3 EGF EGFR EGR1 EHMT2 EIF1AX EIF2A EIF4EBP1 EP300 EPHA2 ERAP1 ERBB2 ERBB3 ERBB4 ESR1 ESR2 ETV6 F3 F7 FADD FAIM2 FAS FASLG FCGR3A FDFT1 FHL2 FKBP5 FKBP8 FN1 FOLR1 FOS FOXJ1 FOXO1 FOXO3 FSHB FTL FTMT FUT4 G6PD GADD45G GAMT GAPDH | 198 (97 + 101) (44.6%) | ABCC1 (7.70) ABCC3 (8.66) AKR1C3 (3.54) AKT2 (2.40, 3.07, 2.01) ATM (2.79) BCL2L11 (3.13) BCL2L12 (4.27) BECN1 (2.18) BIK (3.06) BUB1B (12.77) CA12 (21.62, 17.07, 11.24, 25.25) CABC1 (3.10) CASP2 (2.27) CASP3 (2.14) CASP8 (8.85, 2.67) CBR1 (6.01) CCNA2 (5.27) CCNB1 (3.17) CCNE1 (5.62) CDC2 (2.92) CDC25C (8.00) CDKN2A (18.18, 9.22) CENPA (3.86) CES1 (13.90) CHEK1 (4.69) CHEK2 (2.55) CLIP1 (2.08) CPT1A (2.21) CREBBP (2.11, 2.52) CTNND2 (3.12, 2.44) CYP2B6 (10.92, 3.17) DEK (2.71) DNMT1 (2.20) DTYMK (2.69, 2.60) E2F1 (2.45) E2F3 (2.71) EGF (16.93) EHMT2 (4.08, 2.31, 2.75) ERBB3 (2.54, 3.81, 4.45) ETV6 (2.09) FOXO3 (2.21) FTL (3.51, 4.41, 3.40) G6PD (5.12) GSTA1 (16.89) GSTP1 (3.00) GULP1 (21.16, 15.15) HCRTR1 (2.33) HDAC1 (6.44) HFE (3.86, 3.08) HSAJ2425 (2.32) HSPA9 (2.34) HSPB1 (4.23, 3.70, 3.27) HSPD1 (3.65, 5.01) IKBKB (2.08, 2.59, 3.48) ILF3 (3.78) KCNH2 (4.05) KRT18 (3.49, 2.64, 3.00, 2.48) LY75 (4.92) MAD2L1 (3.87) MAP3K7 (3.78) MDK (17.02) MED13L (6.09) MELK (6.04) MLL (2.05, 2.04) MME (3.38, 4.93) MRPS18A (2.34) NKAIN1 (22.33) NOLC1 (2.54, 2.56) OXTR (4.19) PARP1 (2.68) PDCD5 (3.33) PMAIP1 (12.40) PRKDC (2.47, 2.93) PROC (27.80) PSMB7 (2.15) PTK2 (2.54) PTPRH (42.24) RAD51 (4.60) RARB (2.96) RHCG (3.15) RRM2 (3.30, 3.47) SMAD3 (4.63, 3.78) SOD1 (2.68, 2.37) SSH3 (3.00, 3.18) ST14 (2.22) STK39 (6.44, 6.78) TCF3 (4.52, 3.83) TERT (3.67) TNFRSF25 (7.01) TOP2A (5.88) TRIM28 (2.33) TUBA4A (2.16) TYMS (3.69) UQCRH (3.18, 3.28) VEGFA |

TABLE 2-continued

GATA1 GDF15 GFI1B
GFRA1 GLO1 GNRHR
GP9 GPX1 GSK3B GSTA1
GSTA4 GSTP1 GTF3C1
GULP1 H2AFX HBG2
HCRTR1 HDAC1 HFE
HGF HIF1A HIST1H2BC
HLA-DQB1 HLA-DRB4
HMP19 HNRNPM HRAS
HS3ST1 HSAJ2425
HSP90AA1 HSPA4 HSPA5
HSPA8 HSPA9 HSPB1
HSPD1 HTRA1 HUWE1
IAPP IFNA1 IGF1 IGF1R
IGFBP4 IKBKB IKBKG IL6
IL8 ILF3 IRS1 JAG2
JMJD2B JUN KCNH2
KCNJ13 KCNJ16 KDSR
KHSRP KIAA1467 KIF3A
KLF2 KRT18 LGALS3
LIG4 LIMA1 LMNA LMNB1
LY75 MAD2L1 MAP2K1
MAP2K2 MAP2K3
MAP2K4 MAP2K6
MAP3K7 MAP3K8 MAPK1
MAPK14 MAPK3 MAPK8
MAPK9 MAPT MCL1
MDH2 MDK MDM2
MED13L MEF2A MELK
METAP2 METRN MFGE8
MGMT MLL MLLT3 MME
MMP1 MMP2 MRPS18A
MSH6 MT1G MT1L MT2A
MTR MTSS1 MVP MYC
NAIP NBN NDUFB7
NFKB1 NFKB2 NFKBIA
NID1 NKAIN1 NMBR
NOLC1 NOS2 NR4A1
OR12D2 OR2F1 OXTR
P11 P2RX2 P2RY6
PARP1 PAX6 PCAF PCNA
PDCD5 PDPK1 PITX1
PLAU PLOD1 PLOD3
PMAIP1 POLD4 POMT2
POR PPARD PPT2
PRKACA PRKCA PRKCD
PRKDC PRL PRNP PROC
PROCR PSMA1 PSMA2
PSMA3 PSMA4 PSMA5
PSMA6 PSMA7 PSMB2
PSMB3 PSMB7 PTEN
PTGS2 PTK2 PTK2B
PTPN13 PTPRH RAD51
RALBP1 RAMP1 RARB
RB1 RBL1 RBL2 RBM17
RBPMS REL RELA RELB
RGS13 RHCG ROS1
RRM2 RUNX1 RUNX3
SAT SCNN1G SCUBE2
SEC22B SERPINE1
SERPINH1 SKP2
SLC22A16 SLC22A5
SLC29A1 SLC38A2
SLC5A5 SLC9A1 SLIT3
SMAD2 SMAD3 SMAD4
SMAD7 SMC1A SOD1
SOD2 SOS1 SP1 SPARC
SPHK2 SRM SSH3 ST14
STAT1 STAT2 STAT3
STK39 STMN1 STX3
TAGLN TCF3 TERT TFF1
TGFB1 TGM2 THBD
THBS1 THNSL2 TIA1
TLX3 TMSB4X TNF
TNFRSF10A TNFRSF10B
TNFRSF1A TNFRSF1B
TNFRSF25 TNFSF10
TOMM20 TOP2A TOP2B
TP53 TP73 TRAP1
TRIM23 TRIM28 TRIM34

(2.60) ZMYM2 (3.03, 4.70)
ZNF552 (8.76, 2.45)
ABCB1 (−3.59) ADAMTS5 (−3.42)
AKT3 (−3.90, −3.96)
AMFR (−5.37) ANGPT1 (−13.77,
−19.66) APP (−3.45)
ARL6IP5 (−3.81, −3.50)
ATP6V0E1 (−4.06) BCL2A1 (−18.59,
−2.78) BIRC3 (−2.84)
BTG2 (−3.68) BTG3 (−7.01)
CAPN6 (−3.15) CASP1 (−4.93)
CASP4 (−2.29, −2.55)
CASP5 (−2.47) CCL2 (−8.86)
CCND1 (−2.52) CCND2 (−7.50,
−3.63, −13.98) CD44 (−5.46)
CDKN1A (−7.85, −4.44)
CISH (−6.49, −6.90) CRISP2
(−3.03) CRYAB (−3.91)
CSPG4 (−4.23) CTGF (−2.88)
CTNNBIP1 (−7.17) CTSB (−2.39)
CTSD (−2.66) CTSG (−8.64)
CXCL6 (−7.14) DKK2 (−2.84,
−19.13) DPP4 (−21.02)
EDN1 (−4.13) EFNB3 (−4.49)
EGFR (−12.64) EGR1 (−6.04)
ERBB4 (−3.94, −3.33) F3 (−3.63)
FAS (−5.93) FCGR3A (−2.85)
FN1 (−3.36, −3.49, −4.91)
FOXJ1 (−5.38, −2.05)
FOXO1 (−2.47, −3.13) GAMT
(−3.39, −2.43) GFRA1 (−5.66)
GP9 (−2.54) HGF (−2.73, −6.54)
HLA-DQB1 (−3.19, −3.83)
HLA-DRB4 (−4.14)
HRAS (−2.10) HSPA5 (−2.00)
IGF1 (−5.82, −4.31, −5.16, −5.25)
IGFBP4 (−2.66) IL6 (−39.79)
IL8 (−16.97) IRS1 (−13.62)
JUN (−2.62) KCNJ16 (−14.12)
KDSR (−2.45) KLF2 (−3.43,
−2.31) LMNA (−2.45)
MAP2K3 (−3.18, −3.56)
MAP2K6 (−4.53) MAPK8 (−2.06)
MCL1 (−3.34) MMP1 (−58.24)
MMP2 (−4.48) MT1G (−11.42,
−6.38) MT1L (−11.08)
MT2A (−8.59, −9.15) MTSS1
(−2.60) MVP (−2.25) NFKBIA
(−4.00) NR4A1 (−5.37) PCAF
(−4.52, −6.85) PLOD1 (−2.05)
PRKCA (−3.26) PRNP (−3.95)
PROCR (−2.63) PTEN (−2.30,
−2.56) PTGS2 (−36.04, −32.79)
PTPN13 (−3.49) RELB
(−2.34) ROS1 (−5.49)
SERPINE1 (−2.71)
SLC22A16 (−13.33) SLIT3 (−4.84)
SMAD2 (−2.15, −3.51)
SMAD7 (−2.99) TGM2 (−6.85,
−4.62) THBD (−5.54) THBS1
(−2.30, −3.06) TMSB4X (−2.05)
TNFRSF10B (−2.25)
TNFSF10 (−7.51) TRIM34 (−3.03)
TUBB4 (−4.81) UPP1 (−3.24,
−2.71, −2.28) VDR (−6.07)
ZFP36L2 (−2.99)

TABLE 2-continued

| | | | | |
|---|---|---|---|---|
| | | TRP53 TTPA TUBA4A TUBB TUBB4 TYMS UGCG UGT2B4 UPP1 UQCRH VDR VEGFA XIAP ZFP36L2 ZMYM2 ZNF22 ZNF552 | | |
| EPIRUBICIN (Ellence, Epi-Dx, Epiadriamycin, Epidoxorubicin, Epirubicina, Epirubicine, Epirubicinum, IMI 28, Pharmorubicin Pfs, Pidorubicina, Pidorubicine, Pidorubicinum, Ridorubicin) | 7 | ABCB1 ABCC1 ABCG2 BIRC5 CASP3 CHD1 TOP2A | 4 (3 + 1) (57.1%) | ABCC1 (7.70) CASP3 (2.14) TOP2A (5.88) ABCB1 (−3.59) |

DNA >> Cytotoxic/Antitumor antibiotics >> Anthracenediones

| | | | | |
|---|---|---|---|---|
| MITOXANTRONE (Mitox, Novantron, Novantrone) | 25 | ABCB1 ABCG2 AMOTL1 BIRC2 CASC3 CASP2 ELAVL4 ELOVL5 EPB41L2 FAM130A1 IRX1 LAMA2 LEMD2 MAFF MDM2 PACRGL RARB RASA1 RBM17 RRAGD SFRP4 SYTL2 TMEM99 TOP2A XIAP | 11 (6 + 5) (44.0%) | CASP2 (2.27) ELAVL4 (8.24, 12.95) RARB (2.96) SYTL2 (10.42, 7.94) TMEM99 (2.94) TOP2A (5.88) ABCB1 (−3.59) AMOTL1 (−9.67, −12.72) IRX1 (−2.23) LAMA2 (−5.62) MAFF (−3.57) |

DNA >> Cytotoxic/Antitumor antibiotics >> Streptomyces

| | | | | |
|---|---|---|---|---|
| BLEOMYCIN (Bleo, Bleonexane) | 7 | BIRC2 BLMH CAT LIG1 LIG3 SOCS1 XRCC1 | 4 (2 + 2) (57.1%) | LIG1 (3.03) LIG3 (2.27) CAT (−3.31) SOCS1 (−5.85, −5.20) |
| MITOMYCIN (Ametycin, Ametycine, Mit-C, Mito-C, Mitocin-C, Mitomycin C, Mitomycin-C, Mitomycinum, Mitomycinum C, Mitomycyna C, Mitozytrex, Muamycin, Mutamycin, Mytomycin, Mytozytrex) | 25 | ALDH3A1 APP ATF4 BMP4 CCNB1 CD59 EGR1 EPHA2 GSTP1 HLA-C LIG1 MAPRE1 MGMT MMP14 NFYA NQO1 POR PRNP RB1 RBBP7 RFC4 RPS3A RUNX3 SUB1 TP53 | 13 (8 + 5) (52.0%) | ALDH3A1 (12.05) BMP4 (3.33) CCNB1 (3.17) GSTP1 (3.00) LIG1 (3.03) NFYA (2.84) NQO1 (18.75) RFC4 (2.95) APP (−3.45) CD59 (−8.71, −4.89, −4.77, −7.00) EGR1 (−6.04) PRNP (−3.95) RPS3A (−2.73, −2.31, −2.81, −2.51, −2.45, −2.68) |

DNA >> Cytotoxic/Antitumor antibiotics >> Other

| | | | | |
|---|---|---|---|---|
| HYDROXYUREA (Biosupressin, Droxia, Hidrix, Hydrea, Hydreia, Hydura, Hydurea, Litaler, Litalir, Onco-Carbide, Oxyurea, Ureaphil) | 21 | BAX C13ORF34 CASP3 CCNA2 CCNB1 CCND1 CCND2 CCND3 CCNE1 CCNG1 CDCA8 CDKN1A CKS2 EDN3 FAS KPNA2 PRC1 PSRC1 RRM1 TP53 UBE2C | 13 (8 + 5) (61.9%) | CASP3 (2.14) CCNA2 (5.27) CCNB1 (3.17) CCNE1 (5.62) CDCA8 (2.55) KPNA2 (2.49) PRC1 (3.44) UBE2C (9.47) CCND1 (−2.52) CCND2 (−7.50, −3.63, −13.98) CCNG1 (−3.23) CDKN1A (−7.85, −4.44) FAS (−5.93) |

DNA >> Topoisomerase inhibitors
DNA >> Topoisomerase inhibitors >> Camptotheca

| | | | | |
|---|---|---|---|---|
| CAMPTOTHECIN | 47 | ABCB1 AGRN ALB ANXA4 BAX BCL2 BIRC5 CAB39 CASP2 CASP3 CCNB1 CDK2 CDKN1A CEACAM1 CEBPZ CTSB EI24 EPM2AIP1 FDXR GSTP1 HNRNPC IL1B IL8 JUN MAP2K3 MAP3K5 MAPK9 MDM2 NCK2 PARP1 PLK3 PPP1R1B PRC1 RB1 RBL1 RBL2 SDC1 TAP1 TAX1BP3 THBS1 TNFSF9 TOP1 TP53 TP53I3 TP53TG1 VEGFA XIAP | 20 (8 + 12) (42.6%) | CASP2 (2.27) CASP3 (2.14) CCNB1 (3.17) CEACAM1 (2.43, 2.23) GSTP1 (3.00) PARP1 (2.68) PRC1 (3.44) VEGFA (2.60) ABCB1 (−3.59) CDKN1A (−7.85, −4.44) CTSB (−2.39) IL1B (−12.47) IL8 (−16.97) JUN (−2.62) MAP2K3 (−3.18, −3.56) PLK3 (−2.94) PPP1R1B (−5.77) SDC1 (−2.52) THBS1 (−2.30, −3.06) TNFSF9 (−2.43) |
| TOPOTECAN (Hycamptamine, Hycamptin, Hycamtin) | 7 | ABCG2 ARNT H2AFX HIF1A TOP1 TOP1MT VEGFA | 1 (1 + 0) (14.3%) | VEGFA (2.60) |
| IRINOTECAN (CP0, Camptosar, IRINOTECAN, CPT-11) | 204 | ABCB1 ABCC1 ABCC2 ABCC4 ABCG2 ADD3 AKAP10 ALAS2 ALDH1A1 ANGPTL2 ANXA6 APC ARAF AREG ARHGAP5 ARID4A ATF3 ATG10 | 104 (53 + 51) (51.0%) | ABCC1 (7.70) ABCC2 (4.39, 5.45) ABCC4 (2.34) AURKB (2.61) BCL9 (5.39) BUB1 (2.75) CCNA2 (5.27) CCNB2 (4.19) CCNF (2.52) CCR6 (2.28) CDC2 (2.92) CDKN3 |

TABLE 2-continued

| | | | | |
|---|---|---|---|---|
| | | ATP5O AURKB BCL7A BCL9 BIRC5 BMP8A BOLL BUB1 CASP4 CCNA2 CCNB2 CCNF CCR1 CCR6 CD70 CD80 CDC2 CDC25B CDC2L5 CDK5R2 CDKN1A CDKN3 CENPE CENPF CES1 CES2 CES3 CHD1 COL6A1 COMMD6 CREBBP CYP1A2 CYP2A6 CYP2B6 CYP2C19 CYP2C8 CYP2C9 CYP2D6 CYP2E1 CYP3A4 CYP3A5 DCLRE1A DDB2 DEFA1 DENND4A DMWD DNMT2 DPYD DRD5 DRG1 DUSP2 DYRK1A DYRK2 EBI2 EGFR EGR1 EML2 EP300 ERBB4 ETS2 ETV6 F8 FANCG FASLG FGF2 FN1 FOS FOSB GATA3 GDF15 GOLGA8A GPR109B GPX3 H2AFX HBEGF HIST1H2AC HMMR HRG HSPA4L ID2 IGF1 IL1B IL8 ITGAV ITGAX ITGB3BP JUN KLF9 KRT5 LGALS8 LTF MAD2L1 MAL MALL MAP3K5 MCF2L MCM4 MDM2 MEF2B MGMT MMP9 MPO MSH2 MTHFS MX2 NCK1 NCOA1 NEK2 NID1 OSMR PCDHGC3 PDE4B PLEKHH3 PLK1 PLK2 PLK3 PMAIP1 POR PPP3CB PRKCA PRKCB PRKCD PRKCI PROM1 PSG9 PTGES PTPN13 PTPN22 PTPRD PTPRN RAC3 RAD23B RB1 RBBP5 RBL1 RELA RFC3 RGS1 RUNX1 SDC4 SERPINE2 SESN2 SFN SGK SLC16A4 SLC9A3R2 SNAG1 SPIB STK38 STK4 SULT1A4 TAF2 TBCC TGFA THY1 TMEM41B TMSB4X TNFAIP6 TOB1 TOB2 TOP1 TOP1MT TOP2A TOPORS TP53 TPX2 TRADD TRAF1 TTK TYMP TYMS UBE2C UCHL5 UGT1A1 UGT1A10 UGT1A6 UGT1A7 UGT1A8 UGT1A9 XRCC4 YES1 ZFP36L2 ZFX ZNF32 ZNF582 ZRSR2 | | (5.50) CENPF (7.39, 8.14) CES1 (13.90) CES3 (10.19) CREBBP (2.11, 2.52) CYP2B6 (10.92, 3.17) CYP2C9 (3.97) CYP2D6 (3.52, 3.15) DENND4A (2.86, 2.30) DYRK2 (3.69, 2.90, 2.19, 2.26) EML2 (4.55) ETV6 (2.09) GATA3 (6.10) GOLGA8A (8.56) MAD2L1 (3.87) MCM4 (4.63) MX2 (2.64) NEK2 (23.93, 26.08) PLEKHH3 (2.59) PLK1 (2.97, 2.70) PMAIP1 (12.40) PROM1 (4.29) PTGES (9.53) RAC3 (2.23) RAD23B (2.57, 2.55, 4.15) RBBP5 (2.08, 2.99) RFC3 (4.94, 4.23) SPIB (4.00) STK38 (4.45, 4.62) STK4 (2.65) TAF2 (2.17, 2.48) TBCC (2.21, 2.21) TOB1 (2.20) TOP2A (5.88) TPX2 (5.74) TTK (20.36) TYMS (3.69) UBE2C (9.47) UGT1A6 (35.81, 53.16) UGT1A8 (30.25) YES1 (2.33) ZFX (2.61) ABCB1 (−3.59) ALAS2 (−5.81, −8.89) ANGPTL2 (−2.89, −3.89) ANXA6 (−3.31) AREG (−119.30) CASP4 (−2.29, −2.55) CCR1 (−2.53, −4.69) CDKN1A (−7.85, −4.44) COL6A1 (−3.54) CYP3A4 (−7.84) CYP3A5 (−34.94) DPYD (−2.82, 4.07, −4.30) EBI2 (−5.77) EGFR (−12.64) EGR1 (−6.04) ERBB4 (−3.94, −3.33) ETS2 (−3.94 −5.62, −5.40) F8 (−3.51, −2.90) FGF2 (−9.80) FN1 (−3.36, −3.49, −4.91) GPX3 (−4.85) HBEGF (−5.28, −5.37) HSPA4L (−2.34) ID2 (−2.96, −3.38) IGF1 (−5.82, −4.31, −5.16, −5.25) IL1B (−12.47) IL8 (−16.97) ITGAX (−2.53, −2.13) ITGB3BP (−2.46) JUN (−2.62) KLF9 (4.25) KRT5 (−12.89) LGALS8 (−2.28) LTF (−20.86) MAL (−7.99) MALL (−2.75, −2.73) MMP9 (−10.90) OSMR (−5.11, −3.52) PDE4B (−5.96) PLK3 (−2.94) PPP3CB (−2.30) PRKCA (−3.26) PTPN13 (−3.49) PTPRD (−6.35) SESN2 (−2.98) SLC16A4 (−7.88) TMEM41B (−2.16) TMSB4X (−2.05) TNFAIP6 (−22.06) TYMP (−3.83, −5.95) ZFP36L2 (−2.99) | |
| | | DNA >> Topoisomerase inhibitors >> Podophyllum | | |
| ETOPOSIDE (Eposin, Etopophos, Lastet, Toposar, Vepesid, Vepesid J, Zuyeyidal) | 102 | ABCB1 ABCC1 ABCC2 ABCC3 AGRN AKT1 ALDH3A1 ANXA4 AREG ATF4 BAK1 BCL2 BCL2L1 BCL2L2 BIK BIRC2 BIRC3 BIRC5 BRCA1 BTC CAB39 CALCA CASP2 CASP3 CASP7 CASP9 CCNA2 CD44 CDK2 CDKN1A CDKN1B CEACAM1 CEBPZ CFLAR CYP27B1 CYP2A6 CYP2B6 CYP2C8 CYP2C9 CYP3A4 CYP3A5 DDIT3 EGF EGFR EI24 EPM2AIP1 ERBB2 ERBB3 ERBB4 EREG ETV6 FDXR | 53 (27 + 26) (52.0%) | ABCC1 (7.70) ABCC2 (4.39, 5.45) ABCC3 (8.66) ALDH3A1 (12.05) BIK (3.06) BRCA1 (3.05) CASP2 (2.27) CASP3 (2.14) CCNA2 (5.27) CEACAM1 (2.43, 2.23) CYP2B6 (10.92, 3.17) CYP2C9 (3.97) EGF (16.93) ERBB3 (2.54, 3.81, 4.45) ETV6 (2.09) FOXO3 (2.21) GSTP1 (3.00) PARP1 (2.68) PRC1 (3.44) RAD52 (7.35) RAD54L (8.38) TOP2A (5.88) TYMS (3.69) UBE2C (9.47) UGT1A8 (30.25) WRN (3.29) XRCC2 (5.72) ABCB1 (−3.59) AREG (−119.30) |

TABLE 2-continued

| | | | | |
|---|---|---|---|---|
| | | FOXO1 FOXO3 GSTM1 GSTP1 HBEGF HSPA5 MAP2K3 MAP2K7 MAP3K5 MCL1 MDM2 NCK2 NFKBIA PARP1 PLK3 PRC1 PRNP PTEN RAD52 RAD54L RBM17 RUNX1 RUNX3 SDC1 TAP1 TAX1BP3 TGFA TMSB4X TNFRSF10A TNFRSF10B TNFSF10 TNFSF9 TOP2A TOP2B TP53 TP53I3 TP53TG1 TP73 TYMS UBE2C UGT1A1 UGT1A3 UGT1A8 VDR WRN XAF1 XIAP XRCC2 XRCC3 XRCC4 | | BIRC3 (−2.84) BTC (−3.47, −22.42) CD44 (−5.46) CDKN1A (−7.85, −4.44) CYP3A4 (−7.84) CYP3A5 (−34.94) EGFR (−12.64) ERBB4 (−3.94, −3.33) EREG (−25.83) FOXO1 (−2.47, −3.13) HBEGF (−5.28, −5.37) HSPA5 (−2.00) MAP2K3 (−3.18, −3.56) MCL1 (−3.34) NFKBIA (−4.00) PLK3 (−2.94) PRNP (−3.95) PTEN (−2.30, −2.56) SDC1 (−2.52) TMSB4X (−2.05) TNFRSF10B (−2.25) TNFSF10 (−7.51) TNFSF9 (−2.43) VDR (−6.07) |
| | | DNA >> Other | | |
| | | DNA >> Other >> All | | |
| BEXAROTENE (Targret, Targretin, Targretin-gel, Targretyn, Targrexin) | 68 | ADD3 ADRB2 AKR1C1 AKR1C3 AMOTL2 ARL6IP5 ASNS BNIP2 C10ORF10 C10ORF116 CEBPG COX2 CTH CTSH CYCS CYP26A1 CYR61 DDIT4 DHRS3 DKK1 DUSP1 DUSP5 EGR3 EIF1 EPHA2 GARS GPM6B HERPUD1 ID1 IER2 IGFBP6 IL15 ITGB6 ITM2A ITPR1 KLF10 KRT15 KRT17 LOXL2 MAF MAFF MLLT11 MMP1 MTHFD2 ODC1 PER2 PLAT PLAUR PLOD2 PNO1 PNRC1 RARB RB1 RXRB S100A9 SCD SFRS2 SIAH2 SLC7A1 SLC7A5 SMAD5 SPARC TGM2 TM4SF1 TSC22D3 UAP1 VAMP8 XBP1 | 39 (12 + 27) (57.4%) | AKR1C1 (31.20, 14.60, 19.24, 4.57) AKR1C3 (3.54) CYP26A1 (99.46) KRT15 (2.99) PER2 (3.13) PNO1 (3.43) RARB (2.96) RXRB (2.45) SLC7A1 (3.17) SLC7A5 (2.98) UAP1 (2.13) XBP1 (2.26) ADRB2 (−10.39) AMOTL2 (−2.31) ARL6IP5 (−3.81, −3.50) ASNS (−3.65) CTH (−4.18) CTSH (−3.47) CYR61 (−3.69, −2.81, −3.06) DDIT4 (−2.17) DKK1 (−16.44) DUSP1 (−5.64) GPM6B (−11.99) ID1 (−2.07) IGFBP6 (−3.88) IL15 (−2.46) ITGB6 (−21.40) ITM2A (−3.63) ITPR1 (−2.44) KLF10 (−2.47) KRT17 (−5.21) MAF (−2.53, −3.02) MAFF (−3.57) MMP1 (−58.24) PLAUR (−5.48) PLOD2 (−2.46) S100A9 (−2.26) SCD (−8.09, −15.46, −10.15) TGM2 (−6.85, −4.62) |
| | | Cellular | | |
| | | Cellular >> CI monoclonal antibodies | | |
| | | Cellular >> CI monoclonal antibodies >> Receptor tyrosine kinase | | |
| CETUXIMAB (Erbitux) | 1 | EGFR | 1 (0 + 1) (100.0%) | EGFR (−12.64) |
| TRASTUZUMAB (Herceptin) | 2 | EGFR ERBB2 | 1 (0 + 1) (50.0%) | EGFR (−12.64) |
| | | Cellular >> CI monoclonal antibodies >> Anti-CD20 | | |
| RITUXIMAB (Rituxan) | 1 | MS4A1 | 1 (1 + 0) (100.0%) | MS4A1 (7.61) |
| TOSITUMOMAB (Bexxar) | 1 | MS4A1 | 1 (1 + 0) (100.0%) | MS4A1 (7.61) |
| | | Cellular >> CI monoclonal antibodies >> Other | | |
| ALEMTUZUMAB (Campath, MabCampath) | 1 | CD52 | 1 (0 + 1) (100.0%) | CD52 (−5.80) |
| BEVACIZUMAB (Avastin) | 1 | VEGFA | 1 (1 + 0) (100.0%) | VEGFA (2.60) |
| EDRECOLOMAB (Panorex) | 1 | TACSTD1 | — | — |
| GEMTUZUMAB (Mylotarg) | 1 | CD33 | 1 (0 + 1) (100.0%) | CD33 (−3.02, −3.56) |

TABLE 2-continued

Cellular >> Tyrosine kinase inhibitors
Cellular >> Tyrosine kinase inhibitors >> All

| | | | | |
|---|---|---|---|---|
| AXITINIB | 6 | FLT1 FLT4 KDR KIT PDGFRA PDGFRB | 5 (0 + 5) (83.3%) | FLT1 (−2.68) FLT4 (−2.80) KDR (−2.85, −2.51) KIT (−38.04) PDGFRA (−4.21, −4.58) |
| BOSUTINIB | 3 | ABL1 BCR SRC | 3 (2 + 1) (100.0%) | ABL1 (3.58) SRC (2.09) BCR (−2.40) |
| CEDIRANIB (Recentin) | 2 | FLT1 FLT4 | 2 (0 + 2) (100.0%) | FLT1 (−2.68) FLT4 (−2.80) |
| DASATINIB (Sprycel) | 11 | ABL1 ABL2 BCR EPHA2 FYN KIT LCK PDGFRB SRC STAT5B YES1 | 6 (3 + 3) (54.5%) | ABL1 (3.58) SRC (2.09) YES1 (2.33) BCR (−2.40) FYN (−2.59) KIT (−38.04) |
| ERLOTINIB (Tarceva) | 1 | EGFR | 1 (0 + 1) (100.0%) | EGFR (−12.64) |
| GEFITINIB (Iressa, Irressat, Tarceva) | 48 | ABCG2 ADORA1 AREG AVEN CGRRF1 COL4A3BP CORO1C CYP1A2 CYP2C19 CYP2C9 CYP2D6 CYP2F1 CYP3A4 CYP3A5 DUSP3 DUSP9 EGF EGFR EPOR EPS15 ERBB2 ESR1 FGF6 GADD45A GADD45G GARS GCLC GNB2 GUCY2D HBEGF IFI6 IL8 LEPR MAPK1 MAPK3 MLH1 NFKB1 NPTX2 NRL OSMR PHLDA2 QSOX1 RBM7 RPA1 SFN SKI TGFA TNFRSF1B | 22 (5 + 17) (45.8%) | CYP2C9 (3.97) CYP2D6 (3.52, 3.15) EGF (16.93) GCLC (7.00, 3.83) NRL (2.45) ADORA1 (−2.74) AREG (−119.30) COL4A3BP (−2.58) CORO1C (−3.41, −5.23) CYP2F1 (−2.63) CYP3A4 (−7.84) CYP3A5 (−34.94) EGFR (−12.64) HBEGF (−5.28, −5.37) IFI6 (−7.89) IL8 (−16.97) LEPR (−22.59, −4.51) NPTX2 (−11.45) OSMR (−5.11, −3.52) PHLDA2 (−3.07) QSOX1 (−4.99) SKI (−4.75, −2.71, −3.52) |
| IMATINIB (Gleevec, Glivec) | 29 | ABCB1 ABCG2 ABL1 AKT1 BCL2L1 BCR BIRC5 CCND3 CD69 CSF1R DDR1 FGFR3 FRAP1 HMOX1 IGF1 IL2RA KIT LCK MAPK1 MAPK3 NFKB1 NTRK1 PDGFRA PDGFRB RB1 RELA RET VEGFA WT1 | 11 (3 + 8) (37.9%) | ABL1 (3.58) DDR1 (3.07, 2.69, 3.21) VEGFA (2.60) ABCB1 (−3.59) BCR (−2.40) FGFR3 (−8.75) IGF1 (−5.82, −4.31, −5.16, −5.25) IL2RA(−2.77, −4.16) KIT (−38.04) PDGFRA (−4.21, −4.58) WT1 (−2.49) |
| LAPATINIB (Tycerb, Tykerb) | 11 | AKT1 BIRC5 CCND1 CCNE1 CDK2 CDKN1B EGFR ERBB2 ESR1 MAPK1 MAPK3 | 3 (1 + 2) (27.3%) | CCNE1 (5.62) CCND1 (−2.52) EGFR (−12.64) |
| LESTAURTINIB | 1 | FLT3 | 1 (0 + 1) (100.0%) | FLT3 (−8.47) |
| NILOTINIB (Ketek) | 5 | ABL1 BCR KIT PDGFRA PDGFRB | 4 (1 + 3) (80.0%) | ABL1 (3.58) BCR (−2.40) KIT (−38.04) PDGFRA (−4.21, −4.58) |
| SEMAXANIB | 1 | KDR | 1 (0 + 1) (100.0%) | KDR (−2.85, −2.51) |
| SORAFENIB (Nexavar) | 18 | BAK1 BAX BCL2 BCL2L1 BCL2L11 BID BRAF CASP3 CASP8 CYCS FLT3 FLT4 KDR KIT MCL1 PDGFRB RAF1 XIAP | 9 (4 + 5) (50.0%) | BCL2L11 (3.13) BRAF (2.27) CASP3 (2.14) CASP8 (8.85, 2.67) FLT3 (−8.47) FLT4 (−2.80) KDR (−2.85, −2.51) KIT (−38.04) MCL1 (−3.34) |
| SUNITINIB (SU-11248, Sutent) | 11 | BRAF CSF1R FLT1 FLT3 FLT4 KDR KIT PDGFRA PDGFRB RAF1 RET | 7 (1 + 6) (63.6%) | BRAF (2.27) FLT1 (−2.68) FLT3 (−8.47) FLT4 (−2.80) KDR (−2.85, −2.51) KIT (−38.04) PDGFRA (−4.21, −4.58) |
| VANDETANIB (Zactima) | 2 | EGFR KDR | 2 (0 + 2) (100.0%) | EGFR (−12.64) KDR (−2.85, −2.51) |

Cellular >> mTOR inhibitors
Cellular >> mTOR inhibitors >> All

| | | | | |
|---|---|---|---|---|
| TEMSIROLIMUS (Torisel) | 6 | CCND1 EIF4EBP1 ESR1 FRAP1 RB1 RPS6KB1 | 2 (1 + 1) (33.3%) | RPS6KB1 (2.20, 2.29) CCND1 (−2.52) |

TABLE 2-continued

| | | | | |
|---|---|---|---|---|
| EVEROLIMUS (Certican) | 11 | AKT1 CCND1 CCND2 CCND3 EIF4E EIF4EBP1 EIF4G1 FRAP1 RB1 RPS6 RPS6KB1 | 3 (1 + 2) (27.3%) | RPS6KB1 (2.20, 2.29) CCND1 (−2.52) CCND2 (−7.50, −3.63, −13.98) |

Cellular >> Cyclin-dependant kinase inhibitors
Cellular >> Cyclin-dependant kinase inhibitors >> All

| | | | | |
|---|---|---|---|---|
| FLAVOPIRIDOL (HMR-1275, Alvocidib) | 35 | BAG1 BAX BCL2 BCL2L1 BID BIRC3 BIRC5 CASP3 CASP8 CASP9 CCNB1 CCND1 CDC2 CDK2 CDK4 CDK5 CDK6 CDK7 CDK8 CDK9 CDKN1A CDKN1B CYCS DIABLO EGFR H2AFX HTRA2 MAPK14 MAPK8 MCL1 PARP1 PYGM RB1 TP53 XIAP | 13 (7 + 6) (37.1%) | CASP3 (2.14) CASP8 (8.85, 2.67) CCNB1 (3.17) CDC2 (2.92) CDK6 (2.18, 2.25) CDK8 (2.39) PARP1 (2.68) BIRC3 (−2.84) CCND1 (−2.52) CDKN1A (−7.85, −4.44) EGFR (−12.64) MAPK8 (−2.06) MCL1 (−3.34) |
| ROSCOVITINE (Seliciclib) | 17 | BAX BIRC5 CASP3 CASP9 CDC2 CDK4 CDK5 CDK6 CDKN1A CYCS DIABLO MCL1 PDCD8 RB1 SP1 TP53 XIAP | 5 (3 + 2) (29.4%) | CASP3 (2.14) CDC2 (2.92) CDK6 (2.18, 2.25) CDKN1A (−7.85, −4.44) MCL1 (−3.34) |

Cellular >> Other
Cellular >> Other >> All

| | | | | |
|---|---|---|---|---|
| AFLIBERCEPT (VEGF Trap) | 1 | VEGFA | 1 (1 + 0) (100.0%) | VEGFA (2.60) |
| DENILEUKIN DIFTITOX (Ontak) | 3 | IL2RA IL2RB IL2RG | 1 (0 + 1) (33.3%) | IL2RA (−2.77, −4.16) |

Other/Ungrouped
Other/Ungrouped >> Other
Other/Ungrouped >> Other >> Other

| | | | | |
|---|---|---|---|---|
| ARSENIC TRIOXIDE (Arsenite, Arsenolite, Arsodent, Claudelite, Claudetite, Trisenox) | 496 | ABCB1 ABCG2 ABL1 ACAA2 ADCY9 AFAP1 AKAP12 AKR1B1 AKT1 ALAS1 ALDH6A1 ALDOC ALG13 ALOX5AP ANK3 ANKRD12 ANPEP ANXA2 AP3S1 AQP9 ARL6IP1 ARL6IP5 ARL7 ARMC9 ASNS ASS1 ATP1B1 ATP2B1 ATP2C1 ATP5A1 ATP6 ATP8A1 ATR AZGP1 BACH2 BAMBI BAX BCL2 BCL2A1 BCL2L1 BCMO1 BCR BECN1 BHLHB2 BID BIRC5 BLVRB BLZF1 BNIP3 BNIP3L BPI BRDG1 BTBD2 BTBD3 C14ORF105 C16ORF58 C5ORF13 C6ORF48 C8ORF4 CACNA2D2 CAPN10 CAPZB CARS CASP10 CASP3 CASP8 CASP9 CAV1 CAV2 CCDC102B CCDC52 CCL15 CCL2 CCL23 CCNA1 CCNB1 CCNB2 CCND1 CD1D CD44 CD52 CD70 CD86 CDC42BPA CDC73 CDKN1A CDKN2A CDKN2B CDKN3 CEBPE CEP57 CFB CFLAR CHEK1 CHEK2 CHGB CHI3L1 CHST6 CIDEB CITED2 CKAP4 CLC CLEC7A CLGN CMTM8 CNOT2 COBLL1 COLEC10 COPS5 CREB5 CRH CRIM1 CSF2RB CSH1 CSPP1 CSRP3 CST3 CTNNA1 CTSH CX3CL1 CYB5R3 CYBA CYBRD1 CYCS CYLD CYP1A1 CYP39A1 | 246 (91 + 154 + 1) (49.6%) | ABL1 (3.58) AKAP12 (4.65, 2.82) AKR1B1 (18.32) ATP8A1 (3.45) ATR (2.33) BACH2 (2.04) BAMBI (2.21) BECN1 (2.18) BLVRB (2.08) BLZF1 (2.70) CAPN10 (2.13, 7.15, 2.57) CASP3 (2.14) CASP8 (8.85, 2.67) CCNB1 (3.17) CCNB2 (4.19) CDC42BPA (2.48) CDKN2A (18.18, 9.22) CDKN3 (5.50) CHEK1 (4.69) CHEK2 (2.55) CHGB (3.36, 6.71) CLGN (3.78) CMTM8 (3.87) DNMT1 (2.20) DNMT3B (4.55) DUSP4 (2.60) EPHX1 (4.56) ERC2 (7.66, 17.63) FGFR1 (6.81, 6.75, 7.28, 9.06, 5.07, 6.12) FOXRED2 (2.33) FRK (20.73) FTH1 (2.42, 2.32, 2.35) GABPB2 (3.34, 5.13) GCLM (38.53) GSTA1 (16.89) GSTP1 (3.00) HCG18 (2.45, 2.85, 2.24) HCRTR1 (2.33) HIG2 (9.01) HIST3H3 (2.04) HMGA1 (2.56, 6.05) HSPA1A (4.07, 2.39) HSPB1 (4.23, 3.70, 3.27) IFRD1 (6.54, 6.75) IGFBP2 (2.42) IKBKB (2.08, 2.59, 3.48) IQCH (2.10) KCNH2 (4.05) KLF5 (2.46) KYNU (2.22, 2.53) LAT (2.44) MAFG (3.54, 5.15) MAP7 (4.36, 4.74) MCM2 (3.39) ME1 (8.79, 22.62, 9.07) NPAS1 (4.81) NUP107 (2.16) ORC4L (2.05) PAQR6 (2.43) PARP1 (2.68) PAWR (2.19) PIR (2.63) PTRH2 (2.31) RNF24 (2.24) RPL23 (5.58) RPS6KB1 (2.20, 2.29) RSL1D1 (2.55) SCPEP1 (2.35) SLC2A1 (22.83) |

TABLE 2-continued

CYP3A43 CYTL1 DAXX
DAZ4 DBC1 DDIT3 DEFA1
DEFA4 DKK1 DNAJB4
DNAJC9 DNMT1 DNMT3A
DNMT3B DUSP4
DYNC1H1 DYRK1B EBI2
EGFR EGR1 ELA2A
ENDOGL1 EP300
EPB41L2 EPHX1 EPX
ERC2 ERGIC2 ESR1
ESR2 EVL F3 FAM110B
FAM46C FANCC FAS
FASLG FBLN5 FBXL7
FGFR1 FGFR2 FGR
FNBP1L FOS FOXRED2
FRK FSCN1 FTH1 FYB
GABBR2 GABPB2
GADD45A GBA GCLM
GIMAP6 GIT2 GJA1 GLA
GNAL GPM6A GPR30
GPR44 GPRC5D GPX1
GRAMD3 GRK4 GSTA1
GSTP1 GSTZ1 H2AFX
HCG18 HCRTR1 HGF
HIF1A HIG2 HIST1H2BM
HIST1H4C HIST3H3 HK1
HLA-B HLA-C HLA-DRA
HLA-F HLA-G HMGA1
HMGB2 HMGN2 HMOX1
HSD17B2 HSF1 HSP27
HSPA1A HSPA4 HSPA5
HSPA6 HSPB1 HTATIP2
ICAM3 ID1 ID2 IDS IER2
IFI16 IFIH1 IFNA2 IFNG
IFRD1 IGFBP2 IGFBP7
IKBKB IL12RB2 IL24 IL6
IL8RB INPP5B INSM1
IQCH IRF1 ITGA2B
ITGAM ITGB1 ITGB3BP
ITGB7 ITM2A JUN JUND
KCNH2 KCTD12
KIAA0087 KIAA1609
KIF21B KITLG KLF11
KLF5 KRT6A KYNU
LAMC1 LAT LGALS9
LGMN LHFP LHX6 LSP1
LTC4S MAFF MAFG
MAFK MAN1A1 MAOA
MAP2K3 MAP2K4
MAP2K6 MAP7 MAPK1
MAPK14 MAPK3 MAPK7
MAPK8 MAPK9 MARCH2
MASK MCF2L MCM2 ME1
MKI67IP MMP1 MMP2
MMP28 MMP9 MPL MPO
MRPS16 MSC MSRB2
MT1E MT1G MT1H MT1L
MT1X MT2A MTA1
MXRA7 MYBL1 MYC
MYCN MYO1B MYST4
N4BP1 N4BP2L1 NAB2
NAV3 NCF1 NCF2 ND4
NEU3 NFE2L1 NFKBIA
NFKBIE NME1 NPAS1
NPTX2 NR3C1 NUCB2
NUDT18 NUP107 OBSL1
ORC4L OS9 P4HA1
P53AIP1 PAFAH2 PAOX
PAQR6 PARP1 PAWR
PCNA PCSK5 PDCD4
PDE4A PDE4B PDE4DIP
PDLIM7 PDPK1 PDZD2
PECAM1 PEX3 PGC PGF
PHLDA2 PIGO PIK4CA
PIR PKNOX1 PLAUR
PLEKHO1 PLXNC1 PML
PPGB PPIH PPP1CB
PRG3 PRKCB PRR16
PRSS1 PSMB6 PSMB8
PTGFR PTRH2 PTTG1

SLC44A1 (2.84) SLC5A12
(6.44, 4.94) SMC4 (2.40)
SOD1 (2.68, 2.37) SOX4
(2.17) SYNJ2 (4.91, 9.38)
TERT (3.67) TFAP2C (3.61)
TNFRSF25 (7.01) TOP2A
(5.88) TP53I11 (2.08, 2.00)
TRIP13 (8.20) TRMT1 (2.04)
TYMS (3.69) UBE2C (9.47)
UCHL1 (26.51) VEGFA
(2.60) WDR12 (4.78) ZMYM2
(3.03, 4.70) ZNF334 (12.87)
ZNF682 (3.69, 7.03) ZWINT
(6.72)
ABCB1 (−3.59) ACAA2 (−2.69)
ADCY9 (−2.46)
ALDH6A1 (−2.90) ALDOC (−4.73)
ALOX5AP (−5.07, −7.13)
ANK3 (−9.06, −7.92, −7.43)
ANPEP (−5.41) AQP9 (−13.82)
ARL6IP5 (−3.81, −3.50)
ARMC9 (−5.30, −5.49) ASNS
(−3.65) ASS1 (−2.76) BCL2A1
(−18.59, −2.78) BCR (−2.40)
BHLHB2 (−2.28) BTBD3 (−2.40,
−2.31) CACNA2D2 (−17.47)
CAV1 (−22.26, −24.68)
CAV2 (−14.35, −7.56)
CCDC102B (−2.74, −2.50)
CCL15 (−4.50) CCL2 (−8.86)
CCL23 (−15.78, −18.04)
CCND1 (−2.52) CD44 (−5.46)
CD52 (−5.80) CD86 (−5.13, −2.01)
2.01) CDKN1A (−7.85, −4.44)
CFB (−9.87) CHI3L1 (−3.97, −12.11)
CHST6 (−15.14)
CITED2 (−2.04) CKAP4 (−3.35)
CLEC7A (−2.69, −3.19)
COBLL1 (−3.44) CREB5 (−9.32,
9.32, −11.86) CSF2RB (−2.47)
CST3 (−2.29) CTSH (−3.47)
CX3CL1 (−3.73, −9.86, −4.60)
CYB5R3 (−2.89, −2.40, −2.01)
CYBRD1 (−2.20) CYTL1 (−6.17)
DBC1 (−3.01) DKK1 (−16.44)
EBI2 (−5.77) EGFR (−12.64)
EGR1 (−6.04) ELA2A
(−4.13) EVL (−2.26) F3 (−3.63)
FAM110B (−3.73) FAM46C (−2.08)
FAS (−5.93) FBLN5 (−2.08)
FBXL7 (−4.06) FGFR2
(−31.03, −2.09, −16.52) FGR (−6.72,
−9.45, −8.54) FYB (−2.23)
GIMAP6 (−2.66) GJA1
(−9.56) GPM6A (−34.94)
GRAMD3 (−2.12) HGF (−2.73,
−6.54) HLA-DRA (−4.55)
HSD17B2 (−17.74) HSPA5 (−2.00)
HSPA6 (−4.66) ID1 (−2.07)
ID2 (−2.96, −3.38) IFI16
(−3.75, −3.71) IL6 (−39.79)
IL8RB (−3.46) IRF1 (−2.23)
ITGAM (−3.25) ITGB3BP (−2.46)
ITM2A (−3.63) JUN (−2.62)
KCTD12 (−4.62) KITLG
(−2.48, −3.23, −6.48) KRT6A (−11.07)
LGALS9 (−2.05)
LGMN (−2.41) LHFP (−3.42)
LSP1 (−2.10) LTC4S (−2.70)
MAFF (−3.57) MAN1A1 (−2.01)
MAOA (−3.11) MAP2K3
(−3.18, −3.56) MAP2K6 (−4.53)
MAPK8 (−2.06) MARCH2 (−3.34,
−3.08) MMP1 (−58.24)
MMP2 (−4.48) MMP28 (−8.08,
−14.29) MMP9 (−10.90) MT1E
(−15.67) MT1G (−11.42, −6.38)
MT1H (−8.15, −8.00) MT1L (−11.08)
MT1X (−8.45, −9.49)
MT2A (−8.59, −9.15) MXRA7

TABLE 2-continued

| | | | | |
|---|---|---|---|---|
| | | PURG PXDN RAB27B RACGAP1 RAPGEF4 RARA RASSF8 RBMX RELA RERE RFC2 RGS2 RNASEH2A RNF144A RNF24 RNF6 ROBO1 RPL17 RPL18A RPL23 RPL7 RPS15A RPS6KB1 RRBP1 RSL1D1 RYK S100A10 S100A8 S100A9 SATB2 SCAMP5 SCGB2A2 SCPEP1 SCT SDC2 SDC4 SELP SERPINB1 SERTAD2 SFRS5 SH3GL2 SIGLEC6 SLC14A2 SLC15A1 SLC1A2 SLC22A18 SLC2A1 SLC44A1 SLC5A12 SLC6A5 SLCO3A1 SMAD1 SMC4 SOD1 SOX18 SOX30 SOX4 SP1 SPTAN1 ST6GALNAC4 STAB1 STAT1 STATH SULF1 SUSD5 SYN3 SYNJ2 TCF4 TERC TERF1 TERF2 TERT TFAP2C TFF1 TGFBR2 TIMP1 TIMP2 TMEM158 TNF TNFAIP3 TNFAIP8 TNFRSF1B TNFRSF25 TNFRSF9 TNFSF13 TNFSF8 TOP2A TP53 TP53I11 TP73 TPT1 TRA2A TRAF3IP2 TRIM16 TRIP13 TRMT1 TSC22D3 TTC38 TXNIP TYMS UBE2C UBE2D1 UCHL1 UCP2 VEGFA VNN1 WDR12 WDR82 WSB2 WT1 XIAP XRCC6 ZFP36 ZFP36L1 ZMYM2 ZNF334 ZNF37A ZNF682 ZNF771 ZWINT | | (−2.88, 4.06, −3.93, −3.20) MYO1B (−3.04, −2.30, −2.61) NAV3 (−6.48, −8.99) NCF1 (−3.16, −3.30) NCF2 (−3.56) NFKBIA (−4.00) NPTX2 (−11.45) NUCB2 (−3.02, −3.50) NUDT18 (−4.22) OBSL1 (−5.40, −4.33) P4HA1 (−2.49) PDE4B (−5.96) PDE4DIP (−6.65, −2.11, −2.32, −2.90) PDLIM7 (−2.16) PDZD2 (−33.94) PECAM1 (−4.62) PGC (−3.76, −25.02) PGF (−2.56) PHLDA2 (−3.07) PLAUR (−5.48) PLEKHO1 (−2.69) PML (−2.88, −3.32, −3.67, −3.53) PPP1CB (−5.15, −2.92) PRR16 (−16.52) PTGFR (−7.80) PXDN (−3.39, −3.20) RASSF8 (−5.90, −17.88, −2.19, −10.81) RGS2 (−9.73) RNF144A (−2.56) RPL17 (−3.08, −2.59, −2.80) RPL7 (−2.15, −2.41) S100A8 (−10.28) S100A9 (−2.26) SDC2 (−3.99) SELP (−4.50) SERPINB1 (−2.41 SH3GL2 (−5.52) SMAD1 (−3.04) SUSD5 (−2.47) TCF4 (−3.68, −2.69) TGFBR2 (−3.67, −4.16) TIMP1 (−4.76) TIMP2 (−3.34) TNFAIP3 (−3.78, −3.05) TNFAIP8 (−3.52) TNFSF13 (−4.94) TPT1 (−2.57, −2.61, −2.20) UBE2D1 (−2.48) VNN1 (−2.97, −2.90) WT1 (−2.49) DNMT3A (2.41, −2.89) |
| BORTEZOMIB (Velcade) | 61 | AKT1 APAF1 BAK1 BAX BCL2 BCL2L1 BCL2L11 BID BIRC2 BIRC3 BIRC5 CA9 CASP3 CASP7 CASP8 CASP9 CCND1 CDKN1A CDKN1B CFLAR CYCS CYP1A2 CYP2C19 CYP2C9 CYP2D6 CYP3A4 DDIT3 DFFA DIABLO HIF1A HSPA5 HTRA2 JUN MAP2K1 MAP2K4 MAPK1 MAPK14 MAPK3 MAPK8 MCL1 NFKB1 NFKBIA NFKBIB NFKBIE PARP1 PDCD8 PMAIP1 PSMB1 PSMB2 PSMB5 PSMD1 PSMD2 RAF1 RB1 RELA SFN STAT3 TNF TP53 TRAF2 XIAP | 18 (9 + 9) (29.5%) | BCL2L11 (3.13) CASP3 (2.14) CASP8 (8.85, 2.67) CYP2C9 (3.97) CYP2D6 (3.52, 3.15) NFKBIB (2.90, 2.95, 2.86) PARP1 (2.68) PMAIP1 (12.40) PSMB5 (2.22) BIRC3 (−2.84) CCND1 (−2.52) CDKN1A (−7.85, −4.44) CYP3A4 (−7.84) HSPA5 (−2.00) JUN (−2.62) MAPK8 (−2.06) MCL1 (−3.34) NFKBIA (−4.00) |
| CELECOXIB (Celebra, Celebrex) | 17 | AKT1 BIRC5 CASP3 CCND1 CYP19A1 ILB IL6 MAP2K1 MAP2K2 NRG1 PARP1 PDPK1 PTGS2 RELA STS SULT2A1 TNF | 8 (4 + 4) (47.1%) | CASP3 (2.14) CYP19A1 (2.64) NRG1 (2.37) PARP1 (2.68) CCND1 (−2.52) IL1B (−12.47) IL6 (−39.79) PTGS2 (−36.04, −32.79) |
| COLCHICINE (Col-probenecid, Colbenemid, Condylon, Proben-C) | 21 | ABCB1 ABCC1 CD59 CUGBP2 CYP3A4 IKBKB JUN MAPK8 MAPK9 MEFV NFATC4 NFKB1 NFKBIA NR3C1 PTK2B RALBP1 RELA TAT TP53 TUBB1 TUBB2A | 9 (2 + 7) (42.9%) | ABCC1 (7.70) IKBKB (2.08, 2.59, 3.48) ABCB1 (−3.59) CD59 (−8.71, −4.89, −4.77, −7.00) CUGBP2 (−7.53, −8.05) CYP3A4 (−7.84) JUN (−2.62) MAPK8 (−2.06) NFKBIA (−4.00) |
| OBLIMERSEN (Genasense, Augmerosen) | 2 | BCL2 IGH-6 | — | — |
| TEGAFUR (UFT) | 1 | CYP2A6 | — | — |

TABLE 2-continued

| | | | | |
|---|---|---|---|---|
| TIPIFARNIB (Zarnestra) | 4 | ABCB1 CYP3A4 CYP3A5 UGT1A1 | 3 (0 + 3) (75.0%) | ABCB1 (−3.59) CYP3A4 (−7.84) CYP3A5 (−34.94) |
| VORINOSTAT (Zolinza) | 47 | AKT1 BAK1 BAX BCL2 BCL2A1 BCL2L1 BCL2L11 BID BIRC2 BIRC3 BIRC5 CASP2 CASP3 CASP7 CASP8 CASP9 CCND1 CDKN1A CDKN1B CFLAR CYCS CYP1A1 CYP1B1 DIABLO ERBB2 HDAC1 HDAC2 HDAC3 HDAC6 HDAC8 HIST3H3 HTRA2 MAP2K1 MAPK1 MAPK14 MAPK3 MAPK8 NFKB1 PARP1 PDCD8 RAF1 RARB RB1 RELA TNF TNFSF10 XIAP | 17 (10 + 7) (36.2%) | BCL2L11 (3.13) CASP2 (2.27) CASP3 (2.14) CASP8 (8.85, 2.67) HDAC1 (6.44) HDAC2 (4.18) HDAC6 (2.00) HIST3H3 (2.04) PARP1 (2.68) RARB (2.96) BCL2A1 (−18.59, −2.78) BIRC3 (−2.84) CCND1 (−2.52) CDKN1A (−7.85, −4.44) CYP1B1 (−3.87) MAPK8 (−2.06) TNFSF10 (−7.51) |

| Chemical | Avg Abs(FC) | Avg Abs(FC) UP-REG | Score |
|---|---|---|---|
| Nucleotides | | | |
| Nucleotides >> Antimetabolites | | | |
| Nucleotides >> Antimetabolites >> Folic acid | | | |
| METHOTREXATE (Abitrexate, Antifolan, Arbitrexate, Emtexate, Folex, Ledertrexate, Metatrexan, Methotrate, Mexate, Rheumatrex, Trexall) | 7.36 | 6.93 | 197 |
| PEMETREXED (Alimta) | 3.50 | 2.94 | 73 |
| Nucleotides >> Antimetabolites >> Purine | | | |
| FLUDARABINE (Fludara, Fludura) | 3.56 | 3.88 | 62 |
| Nucleotides >> Antimetabolites >> Pyrimidine | | | |
| FLUOROURACIL (5 FU, Fluorouracil, Adrucil, Arumel, Carac, Carzonal, Effluderm, Efudex, Efudix, Efurix, FU, Fluoroblastin, Fluoroplex, Fluracil, Fluracilum, Fluri, Fluril, Fluro, Uracil, Ftoruracil, Kecimeton, Phthoruracil, Phtoruracil, Queroplex, Timazin, URF, Ulup) | 7.06 | 5.18 | 137 |
| CAPECITABINE (Xeloda) | 7.88 | 9.26 | 5.55 |
| GEMCITABINE (DDFC, DFDC, GEO, Gemcin, Gemcitabina, Gemcitabine, HCl, Gemcitabine hydrochloride, Gemcitabinum, Gemtro, Gemzar) | 3.66 | 2.84 | 70 |
| DNA | | | |
| DNA >> Alkylating agents | | | |
| DNA >> Alkylating agents >> Nitrogen mustards | | | |
| CYCLOPHOSPHAMIDE (ASTA, Asta B 518, CP, CPA, CTX, CY, Clafen, Claphene, Cyclophosphamid, Cyclophosphamide Monohydrate, Cyclophosphamide Sterile, Cyclophosphamidum, Cyclophosphan, Cyclophosphane, Cyclophosphoramide, | 6.89 | 7.19 | 218 |

TABLE 2-continued

| | | | |
|---|---|---|---|
| Cyclostin, Cyklofosfamid, Cytophosphan, Cytoxan, Cytoxan, Lyoph, EndoxanEndoxan, R, Endoxan-Asta, Endoxana, Endoxanal, Endoxane, Enduxan, Genoxal, Hexadrin Lyophilized, Cytoxan, Mitoxan, Neosar, Procytox, Rcra, Waste, Number, U058, Revimmune, Semdoxan, Sendoxan, Senduxan, Zyklophosphamid) | | | |
| IFOSFAMIDE (Cyfos, Holoxan, 1000, IFEX, Ifex/Mesnex Kit, Ifosfamide/Mesna Kit, Isoendoxan, Mitoxana, Naxamide) | 11.00 | 4.08 | 122 |
| MELPHALAN (Alkeran, L-PAM, L-Phenylalanine mustard, L-Sarcolysin, L-Sarcolysine, L-Sarkolysin, Levofalan, Melfalan, Mephalan, Phenylalanine mustard, Phenylalanine nitrogen mustard, Sarcolysine, Sarkolysin) | 6.40 | 6.40 | 355 |
| DNA >> Alkylating agents >> Nitrosoureas | | | |
| CARMUSTINE (Becenun, Bi CNU, BiCNU, Carmubris, Gliadel, Gliadel Wafer, Nitrumon) | 5.24 | 4.73 | 102 |
| FOTEMUSTINE (Muphoran) | 12.56 | 12.56 | 627 |
| DNA >> Alkylating agents >> Platinum | | | |
| CARBOPLATIN (Paraplatin, Paraplatin-AQ) | 3.76 | 3.03 | 82 |
| CISPLATIN (Abiplatin, Biocisplatinum, Briplatin, Carboquone, Cis Pt II, Cismaplat, Cisplatine, Cisplatyl, Citoplationo, Lederplatin, Neoplatin, Plastin, Platamine, Platiblastin, Platidiam, Platinex, Platinol, Platinol-AQ, Platinoxan, Randa) | 5.10 | 4.46 | 108 |
| OXALIPLATIN (DACPLAT, Eloxatin, Elplat, Foloxatine, Transplatin) | 5.20 | 3.95 | 139 |
| DNA >> Alkylating agents >> Alkyl sulfonates | | | |
| BUSULFAN (Busulfex, Citosulfan, Leucosulfan, Mablin, Mielevcin, Mielosan, Mielucin, Milecitan, Mileran, Misulban, Mitosan, Mitostan, Myeleukon, Myeloleukon, Myelosan, Mylecytan, Myleran, Myleran Tablets) | 9.95 | 9.95 | 397 |

TABLE 2-continued

| | | | |
|---|---|---|---|
| DNA >> Alkylating agents >> Hydrazines | | | |
| PROCARBAZINE (Matulane, Nathulane, Natulan, Natulan hydrochloride, Natunalar, Natunalar) | — | — | — |
| DNA >> Alkylating agents >> Triazenes | | | |
| DACARBAZINE (Deticene) | 7.30 | 7.13 | 162 |
| TEMOZOLOMIDE (Temodal, Temodar) | 6.21 | 6.21 | 186 |
| DNA >> Alkylating agents >> Aziridines | | | |
| THIOTEPA (Thioplex, Thiotepa) | 11.90 | 11.90 | 713 |
| DNA >> Alkylating agents >> Other | | | |
| ECTEINASCIDIN 743 (Trabectedin, ET-743, Yondelis) | 3.77 | 3.77 | 376 |
| DNA >> Spindle poisons/Mitotic inhibitors | | | |
| DNA >> Spindle poisons/Mitotic inhibitors >> Taxanes | | | |
| DOCETAXEL (Toxotere) | 8.72 | 3.67 | 77 |
| PACLITAXEL (Epitaxol, LipoPac, Onxol, Paxceed, Paxene, Taxol, Taxol A, Vascular Wrap, Xorane) | 6.54 | 6.14 | 147 |
| DNA >> Spindle poisons/Mitotic inhibitors >> Vinca Alkaloids | | | |
| VINBLASTINE (Nincaluicolflastine, Rozevin, Velban, Velbe Vinblastin, Vinblastina, Vinblastine Sulfate, Vinblastinum, Vincaleucoblastin, Vincaleucoblastine, Vincaleukoblastine, Vincoblastine) | 3.57 | 4.40 | 135 |
| VINCRISTINE (Marqibo, Onco TCS, Oncovin, Vincasar, Vincasar PFS, Vincrex, Vincristine Sulfate PFS, Vinkristin) | 6.79 | 6.69 | 152 |
| VINFLUNINE | — | — | — |
| VINDESINE (DAVA, Eldesine, Eldisine) | — | — | — |
| VINORELBINE (Navelbine, Navelbine Base) | — | — | — |
| DNA >> Spindle poisons/Mitotic inhibitors >> Other | | | |
| EPOTHILONES | 3.66 | 0.00 | 0 |
| DNA >> Cytotoxic/Antitumor antibiotics | | | |
| DNA >> Cytotoxic/Antitumor antibiotics >> Anthracyclines | | | |
| DOXORUBICIN (ADM, Adriablastin, Adriamycin, Adriamycin PFS, Adriamycin RDF, Adriamycin Semiquinone, Adriblastin, Adriblastina, Caelyx, DM2, Doxil, Doxo, Myocet, RDF Rubex, Resmycin, Rubex) | 5.97 | 5.64 | 123 |
| EPIRUBICIN (Ellence, Epi-Dx, Epiadriamycin, Epidoxorubicin, Epirubicina, Epirubicine, Epirubicinum, IMI 28, | 4.83 | 5.24 | 224 |

TABLE 2-continued

Pharmorubicin Pfs,
Pidorubicina,
Pidorubicine,
Pidorubicinum,
Ridorubicin)

DNA >> Cytotoxic/Antitumor antibiotics >> Anthracenediones

| | | | |
|---|---|---|---|
| MITOXANTRONE (Mitox, Novantron, Novantrone) | 5.46 | 5.64 | 135 |

DNA >> Cytotoxic/Antitumor antibiotics >> Streptomyces

| | | | |
|---|---|---|---|
| BLEOMYCIN (Bleo, Bleonexane) | 3.53 | 2.65 | 75 |
| MITOMYCIN (Ametycin, Ametycine, Mit-C, Mito-C, Mitocin-C, Mitomycin C, Mitomycin-C, Mitomycinum, Mitomycinum C, Mitomycyna C, Mitozytrex, Muamycin, Mutamycin, Mytomycin, Mytozytrex) | 5.50 | 6.14 | 196 |

DNA >> Cytotoxic/Antitumor antibiotics >> Other

| | | | |
|---|---|---|---|
| HYDROXYUREA (Biosupressin, Droxia, Hidrix, Hydrea, Hydreia, Hydura, Hydurea, Litaler, Litalir, Onco-Carbide, Oxyurea, Ureaphil) | 4.64 | 4.27 | 162 |

DNA >> Topoisomerase inhibitors
DNA >> Topoisomerase inhibitors >> Camptotheca

| | | | |
|---|---|---|---|
| CAMPTOTHECIN | 4.28 | 2.70 | 46 |
| TOPOTECAN (Hycamptamine, Hycamptin, Hycamtin) | 2.60 | 2.60 | 37 |
| IRINOTECAN (CP0, Camptosar, IRINOTECAN, CPT-11) | 7.59 | 6.54 | 169 |

DNA >> Topoisomerase inhibitors >> Podophyllum

| | | | |
|---|---|---|---|
| ETOPOSIDE (Eposin, Etopophos, Lastet, Toposar, Vepesid, Vepesid J, Zuyeyidal) | 8.65 | 6.31 | 167 |

DNA >> Other
DNA >> Other >> All

| | | | |
|---|---|---|---|
| BEXAROTENE (Targret, Targretin, Targretin-gel, Targretyn, Targrexin) | 8.93 | 12.16 | 214 |

Cellular
Cellular >> CI monoclonal antibodies
Cellular >> CI monoclonal antibodies >> Receptor tyrosine kinase

| | | | |
|---|---|---|---|
| CETUXIMAB (Erbitux) | 12.64 | 0.00 | 0 |
| TRASTUZUMAB (Herceptin) | 12.64 | 0.00 | 0 |

Cellular >> CI monoclonal antibodies >> Anti-CD20

| | | | |
|---|---|---|---|
| RITUXIMAB (Rituxan) | 7.61 | 7.61 | 761 |
| TOSITUMOMAB (Bexxar) | 7.61 | 7.61 | 761 |

Cellular >> CI monoclonal antibodies >> Other

| | | | |
|---|---|---|---|
| ALEMTUZUMAB (Campath, MabCampath) | 5.80 | 0.00 | 0 |
| BEVACIZUMAB (Avastin) | 2.60 | 2.60 | 259 |

TABLE 2-continued

| | | | |
|---|---|---|---|
| EDRECOLOMAB (Panorex) | — | — | — |
| GEMTUZUMAB (Mylotarg) | 3.29 | 0.00 | 0 |

Cellular >> Tyrosine kinase inhibitors
Cellular >> Tyrosine kinase inhibitors >> All

| | | | |
|---|---|---|---|
| AXITINIB | 10.12 | 0.00 | 0 |
| BOSUTINIB | 2.69 | 2.84 | 189 |
| CEDIRANIB (Recentin) | 2.74 | 0.00 | 0 |
| DASATINIB (Sprycel) | 8.51 | 2.67 | 72 |
| ERLOTINIB (Tarceva) | 12.64 | 0.00 | 0 |
| GEFITINIB (Iressa, Irressat, Tarceva) | 13.20 | 6.42 | 66 |
| IMATINIB (Gleevec, Glivec) | 7.04 | 3.06 | 31 |
| LAPATINIB (Tycerb, Tykerb) | 6.93 | 5.62 | 51 |
| LESTAURTINIB | 8.47 | 0.00 | 0 |
| NILOTINIB (Ketek) | 12.11 | 3.58 | 71 |
| SEMAXANIB | 2.68 | 0.00 | 0 |
| SORAFENIB (Nexavar) | 7.63 | 3.32 | 73 |
| SUNITINIB (SU-11248, Sutent) | 8.76 | 2.27 | 20 |
| VANDETANIB (Zactima) | 7.66 | 0.00 | 0 |

Cellular >> mTOR inhibitors
Cellular >> mTOR inhibitors >> All

| | | | |
|---|---|---|---|
| TEMSIROLIMUS (Torisel) | 2.38 | 2.25 | 37 |
| EVEROLIMUS (Certican) | 4.38 | 2.25 | 20 |

Cellular >> Cyclin-dependant kinase inhibitors
Cellular >> Cyclin-dependant kinase inhibitors >> All

| | | | |
|---|---|---|---|
| FLAVOPIRIDOL (HMR-1275, Alvocidib) | 3.91 | 3.04 | 60 |
| ROSCOVITINE (Seliciclib) | 3.35 | 2.43 | 42 |

Cellular >> Other
Cellular >> Other >> All

| | | | |
|---|---|---|---|
| AFLIBERCEPT (VEGF Trap) | 2.60 | 2.60 | 259 |
| DENILEUKIN DIFTITOX (Ontak) | 3.47 | 0.00 | 0 |

Other/Ungrouped
Other/Ungrouped >> Other
Other/Ungrouped >> Other >> Other

| | | | |
|---|---|---|---|
| ARSENIC TRIOXIDE (Arsenite, Arsenolite, Arsodent, Claudelite, Claudetite, Trisenox) | 6.01 | 5.42 | 99 |
| BORTEZOMIB (Velcade) | 3.99 | 4.28 | 63 |
| CELECOXIB (Celebra, Celebrex) | 12.38 | 2.46 | 57 |
| COLCHICINE (Col-probenecid, Colbenemid, Condylon, Proben-C) | 4.96 | 5.21 | 49 |
| OBLIMERSEN (Genasense, Augmerosen) | — | — | — |
| TEGAFUR (UFT) | — | — | — |
| TIPIFARNIB (Zarnestra) | 15.46 | 0.00 | 0 |
| VORINOSTAT (Zolinza) | 4.07 | 3.36 | 71 |

What is claimed:

1. A method for treating a patient having lung cancer, the method comprising:
   a) characterizing molecular anomalies of a lung cancer sample from the patient in comparison to a normal sample from the same patient which is a normal histological counterpart of the lung cancer sample, said molecular anomalies characterization comprising determining genes differentially expressed in the lung cancer sample in comparison to the normal sample by oligonucleotide array and optionally determining the gain or loss of gene copy number in the lung cancer sample in comparison to the normal sample by Comparative Genomic Hybridization and determining deregulated genes in the lung cancer sample based on the genes differentially expressed and optionally the gain or loss of gene copy number;
   b) providing a drug database comprising target genes associated with a plurality of drugs disclosed in Table 1;
   c) determining a score for each drug of said plurality of drugs comprising calculating, for each drug of the plurality of drugs, a percentage of deregulated genes in the lung cancer sample from the patient as characterized in step (a) that are target genes for each drug of the plurality of drugs as provided in step (b) and determining the score for each drug of the plurality of drugs based on the percentage of deregulated genes among the target genes in the lung cancer sample from the patient, wherein a higher score is predictive of a higher relative efficacy of the drug for treating the lung cancer in the patient and wherein the step of characterizing molecular anomalies of the lung cancer sample comprises determining a fold change for the differentially expressed genes and optionally for the gain or loss of gene copy number; and
   d) selecting a drug with a high score for treating the patient, wherein the score (W) for a given drug is determined by the following algorithm:

$$W = Pz \frac{(\Sigma_C F_{c>2})}{n_C F_{c>2}}$$

wherein:
W is the score for the given drug;
P is the percentage of target genes for the given drug which are deregulated in the lung cancer of the patient;
Σ is sum;
$F_{c>2}$ is the Fold Change of each deregulated target gene for the given drug with a Fold Change higher than 2; and
$n_C F_{c>2}$ refers to the number of target genes for the given drug with a Fold Change higher than 2.

2. The method according to claim 1, wherein the target genes for each drug are classified in the database into:
   major target genes (CM) which have been demonstrated to have a clear cause and effect link with the drug's mechanism of action;
   minor target genes (Cm), the level of regulation of which is modified in the presence of the drug, without a direct link with the drug's mechanism of action; and
   resistance genes (CR) which induce a direct resistance to the drug or are associated with a major toxicity.

3. The method according to claim 1, wherein $F_{c>2}$ is the Fold Change of each over-expressed target gene for the given drug with a Fold Change higher than 2 and $n_C F_{c>2}$ is either the number of target genes for the given drug with a Fold Change higher than 2, or the number of over-expressed target genes for the given drug with a Fold Change higher than 2.

4. The method according to claim 1, wherein said plurality of drugs are Axitinib, Capecitabine, Trastuzumab, Erlotinib, Gefitinib, Lapatinib, Bevacizumab, Imatinib, Temsirolimus, Dasatinib, Sorafenib, Nilotinib, Bosutinib, Sunitinib, Cetuximab, Vinorelbine, Dacarbazine, Docetaxel, Paclitaxel, Pemetrexed, Gemcitabine, Irinotecan and Topotecan.

5. The method according to claim 1, wherein the molecular anomalies of said lung cancer sample are determined by northern analysis, mRNA microarrays, cDNA microarrays or RT-PCR.

6. The method according to claim 1, wherein the step of characterizing molecular anomalies of the lung cancer sample further comprises determining the intensity of the gene transcription (Int) for the differentially expressed genes.

7. The method according to claim 1, wherein the patient has lung cancer.

8. A method for treating a patient having lung cancer the method comprising:
   a) characterizing molecular anomalies of a lung cancer sample from the patient in comparison to a normal sample from the same patient which is a normal histological counterpart of the lung cancer sample, said molecular anomalies characterization comprising determining genes differentially expressed in the lung cancer sample in comparison to the normal sample by oligonucleotide array and optionally determining the gain or loss of gene copy number in the lung cancer sample in comparison to the normal sample by Comparative Genomic Hybridization and determining deregulated genes in the lung cancer sample based on the genes differentially expressed and optionally the gain or loss of gene copy number;
   b) providing a drug database comprising target genes associated with a plurality of drugs disclosed in Table 1;
   c) determining a score for each drug of said plurality of drugs comprising calculating, for each drug of the plurality of drugs, a percentage of deregulated genes in the lung cancer sample from the patient as characterized in step (a) that are target genes for each drug of the plurality of drugs as provided in step (b) and determining the score for each drug of the plurality of drugs based on the percentage of deregulated genes among the target genes in the lung cancer sample from the patient, wherein a higher score is predictive of a higher relative efficacy of the drug for treating the lung cancer in the patient and wherein the step of characterizing molecular anomalies of the lung cancer sample comprises determining a fold change for the differentially expressed genes and optionally for the gain or loss of gene copy number; and
   d) selecting a drug with a high score for treating the patient, and
   wherein the method further comprises in step a) the detection of the presence of a mutation in a gene in the lung cancer sample in comparison to the normal sample by sequencing and wherein the score (W) for a given drug is determined by the following algorithm:

$$W = P\left(\frac{(\Sigma_{CM} F_{CM})}{n_1 CM} q_1 z_1 + \frac{(\Sigma_{Cm} F_{Cm})}{n_2 Cm} q_2 z_2 - \frac{(\Sigma_{CR} F_{CR})}{n_3 CR} q_3 z_3\right)$$

wherein:
W is the score for the given drug;
P is the percentage of target genes for the given drug which are deregulated in the lung cancer of the patient;
Σ is sum;

CM refers to major target genes for the given drug;
Cm refers to minor target genes for the given drug;
CR refers to resistance genes for the given drug;
$n_1CM$, $n_2Cm$ and $n_3CR$ are respectively the number of deregulated target genes with a defined threshold for major target genes, minor target genes and resistance genes;
$F_{CM}$, $F_{Cm}$ and $F_{CR}$ are the Fold Change of each gene higher than the defined threshold for major target genes, minor target genes and resistance genes, respectively;
$q_1$, $q_2$ and $q_3$ are multiplication coefficients for major target genes, minor target genes and resistance genes, respectively; and
$z_1$, $z_2$ and $z_3$ are multiplication coefficients associated with the presence of a mutation in a major target gene, a minor target gene and a resistance gene, respectively.

9. The method according to claim 8, wherein $F_{CM}$, $F_{Cm}$ and $F_{CR}$ are the Fold Change of each over-expressed target gene for the given drug with the defined threshold and wherein $n_1CM$, $n_2Cm$ and $n_3CR$ are either the number of target genes for the given drug with the defined threshold or the number of over-expressed target genes for the given drug with the defined threshold.

10. The method according to claim 9, wherein the defined threshold is a Fold Change of at least 2.

11. The method according to claim 8, wherein the multiplication coefficients for the target genes are between 10 and 1,000 for major target genes ($q_1$), between 0.1 and 10 for minor target genes ($q_2$) and between 10 to 1,000 for resistance genes ($q_3$).

12. The method according to claim 8, wherein the multiplication coefficients associated with a mutation $z_1$, $z_2$ and $z_3$ are 1 when no mutation exists and, depending on the functional impact of the mutation, are between 10 and 1,000.

13. The method according to claim 8, wherein $z_1$, $z_2$, $z_3$, $q_1$, $q_2$ and $q_3$ are equal to 1.

14. A method for treating a patient having lung cancer the method comprising:
a) characterizing molecular anomalies of a lung cancer sample from the patient in comparison to a normal sample from the same patient which is a normal histological counterpart of the lung cancer sample, said molecular anomalies characterization comprising determining genes differentially expressed in the lung cancer sample in comparison to the normal sample by oligonucleotide array and optionally determining the gain or loss of gene copy number in the lung cancer sample in comparison to the normal sample by Comparative Genomic Hybridization and determining deregulated genes in the lung cancer sample based on the genes differentially expressed and optionally the gain or loss of gene copy number;
b) providing a drug database comprising target genes associated with a plurality of drugs disclosed in Table 1;
c) determining a score for each drug of said plurality of drugs comprising calculating, for each drug of the plurality of drugs, a percentage of deregulated genes in the lung cancer sample from the patient as characterized in step (a) that are target genes for each drug of the plurality of drugs as provided in step (b) and determining the score for each drug of the plurality of drugs based on the percentage of deregulated genes among the target genes in the lung cancer sample from the patient, wherein a higher score is predictive of a higher relative efficacy of the drug for treating the lung cancer in the patient and wherein the step of characterizing molecular anomalies of the lung cancer sample comprises determining a fold change for the differentially expressed genes and optionally for the gain or loss of gene copy number; and
d) selecting a drug with a high score for treating the patient, and
wherein the method further comprises in step a) the detection of the presence of a mutation in a gene in the lung cancer sample in comparison to the normal sample by sequencing and wherein the score (W) for a given drug is determined by the following algorithm:

$$W = \frac{P_{CM}(\Sigma_{CM} F_{CM})}{n_1 CM} q_1 z_1 + \frac{P_{Cm}(\Sigma_{Cm} F_{Cm})}{n_2 Cm} q_2 z_2 - \frac{P_{CR}(\Sigma_{CR} F_{CR})}{n_3 CR} q_3 z_3$$

wherein W is the score for the given drug;
$\Sigma$ is sum;
CM refers to major target genes for the given drug;
Cm refers to minor target genes for the given drug;
CR refers to resistance genes for the given drug;
$n_1CM$, $n_2Cm$ and $n_3CR$ are respectively the number of deregulated target genes with a defined threshold for major target genes, minor target genes and resistance genes;
$F_{CM}$, $F_{Cm}$ and $F_{CR}$ are the Fold Change of each gene higher than the defined threshold for major target genes, minor target genes and resistance genes, respectively;
$q_1$, $q_2$ and $q_3$ are multiplication coefficients for major target genes, minor target genes and resistance genes, respectively;
$z_1$, $z_2$ and $z_3$ are multiplication coefficients associated with the presence of a mutation in a major target gene, a minor target gene and a resistance gene, respectively; and $P_{CM}$, $P_{Cm}$ and $P_{CR}$ are the percentage of target genes for the given drug which are deregulated in the lung cancer of the patient for major target genes, minor target genes and resistance genes, respectively.

15. The method according to claim 14, wherein $F_{CM}$, $F_{Cm}$ and $F_{CR}$ are the Fold Change of each over-expressed target gene for the given drug with the defined threshold and wherein $n_1CM$, $n_2Cm$ and $n_3CR$ are either the number of target genes for the given drug with the defined threshold or the number of over-expressed target genes for the given drug with the defined threshold.

16. The method according to claim 15, wherein the defined threshold is a Fold Change of at least 2.

17. The method according to claim 14, wherein $z_1$, $z_2$, $z_3$, $q_1$, $q_2$ and $q_3$ are equal to 1.

18. The method according to claim 14, wherein the multiplication coefficients for the target genes are between 10 and 1,000 for major target genes ($q_1$), between 0.1 and 10 for minor target genes ($q_2$) and between 10 to 1,000 for resistance genes ($q_3$).

19. The method according to claim 14, wherein the multiplication coefficients associated with a mutation $z_1$, $z_2$ and $z_3$ are 1 when no mutation exists and, depending on the functional impact of the mutation, are between 10 and 1,000.

20. A method for treating a patient having lung cancer the method comprising:
a) characterizing molecular anomalies of a lung cancer sample from the patient in comparison to a normal sample from the same patient which is a normal histological counterpart of the lung cancer sample, said molecular anomalies characterization comprising determining genes differentially expressed in the lung cancer sample in comparison to the normal sample by oligonucleotide array and optionally determining the gain or loss of gene copy number in the lung cancer sample in comparison to the normal sample by Comparative Genomic Hybridization and determining deregulated genes in the lung cancer sample based on the genes differentially expressed and optionally the gain or loss of gene copy number;

b) providing a drug database comprising target genes associated with a plurality of drugs disclosed in Table 1;

c) determining a score for each drug of said plurality of drugs comprising calculating, for each drug of the plurality of drugs, a percentage of deregulated genes in the lung cancer sample from the patient as characterized in step (a) that are target genes for each drug of the plurality of drugs as provided in step (b) and determining the score for each drug of the plurality of drugs based on the percentage of deregulated genes among the target genes in the lung cancer sample from the patient, wherein a higher score is predictive of a higher relative efficacy of the drug for treating the lung cancer in the patient and wherein the step of characterizing molecular anomalies of the lung cancer sample comprises determining a fold change for the differentially expressed genes and optionally for the gain or loss of gene copy number; and d) selecting a drug with a high score for treating the patient, and wherein the method further comprises in step a) the detection of the presence of a mutation in a gene in the lung cancer sample in comparison to the normal sample by sequencing and wherein the score (W) for a given drug is determined by the following algorithms:

$$W = P\left(\frac{(\Sigma_{CM} F_{CM} \times Int_{CM})}{n_1 CM} q_1 z_1 + \frac{(\Sigma_{Cm} F_{Cm} \times Int_{Cm})}{n_2 Cm} q_2 z_2 - \frac{(\Sigma_{CR} F_{CR} \times Int_{CR})}{n_3 CR} q_3 z_3\right)$$

or $$W = \frac{P_{CM}(\Sigma_{CM} F_{CM} \times Int_{CM})}{n_1 CM} q_1 z_1 + \frac{P_{Cm}(\Sigma_{Cm} F_{Cm} \times Int_{Cm})}{n_2 Cm} q_2 z_2 - \frac{P_{CR}(\Sigma_{CR} F_{CR} \times Int_{CR})}{n_3 CR} q_3 z_3$$

wherein

W is the score for the given drug;

P is the percentage of target genes for the given drug which are deregulated in the lung cancer of the patient;

Σ is sum;

CM refers to major target genes for the given drug;

Cm refers to minor target genes for the given drug;

CR refers to resistance genes for the given drug;

$n_1 CM$, $n_2 Cm$ and $n_3 CR$ are respectively the number of deregulated target genes with a defined threshold for major target genes, minor target genes and resistance genes;

$F_{CM}$, $F_{Cm}$ and $F_{CR}$ are the Fold Change of each gene higher than the defined threshold for major target genes, minor target genes and resistance genes, respectively;

$q_1$, $q_2$ and $q_3$ are multiplication coefficients for major target genes, minor target genes and resistance genes, respectively;

$z_1$, $z_2$ and $z_3$ are multiplication coefficients associated with the presence of a mutation in a major target gene, a minor target gene and a resistance gene, respectively;

$P_{CM}$, $P_{Cm}$ and $P_{CR}$ are the percentage of target genes for the given drug which are deregulated in the lung cancer of the patient for major target genes, minor target genes and resistance genes, respectively; and $Int_{CM}$, $Int_{Cm}$ and $Int_{CR}$ are the intensity for major target genes, minor target genes and resistance genes, respectively.

21. The method according to claim 20, wherein $F_{CM}$, $F_{Cm}$ and $F_{CR}$ are the Fold Change of each over-expressed target gene for the given drug with the defined threshold and wherein $n_1 CM$, $n_2 Cm$ and $n_3 CR$ are either the number of target genes for the given drug with the defined threshold or the number of over-expressed target genes for the given drug with the defined threshold.

22. The method according to claim 21, wherein the defined threshold is a Fold Change of at least 2.

23. The method according to claim 20, wherein $z_1$, $z_2$, $z_3$, $q_1$, $q_2$ and $q_3$ are equal to 1.

24. The method according to claim 20, wherein the multiplication coefficients for the target genes are between 10 and 1,000 for major target genes ($q_1$), between 0.1 and 10 for minor target genes ($q_2$) and between 10 to 1,000 for resistance genes ($q_3$).

25. The method according to claim 20, wherein the multiplication coefficients associated with a mutation $z_1$, $z_2$ and $z_3$ are 1 when no mutation exists and, depending on the functional impact of the mutation, are between 10 and 1,000.

26. A method for treating a patient having lung cancer the method comprising:

a) characterizing molecular anomalies of a lung cancer sample from the patient in comparison to a normal sample from the same patient which is a normal histological counterpart of the lung cancer sample, said molecular anomalies characterization comprising determining genes differentially expressed in the lung cancer sample in comparison to the normal sample by oligonucleotide array and optionally determining the gain or loss of gene copy number in the lung cancer sample in comparison to the normal sample by Comparative Genomic Hybridization and determining deregulated genes in the lung cancer sample based on the genes differentially expressed and optionally the gain or loss of gene copy number;

b) providing a drug database comprising target genes associated with a plurality of drugs disclosed in Table 1;

c) determining a score for each drug of said plurality of drugs comprising calculating, for each drug of the plurality of drugs, a percentage of deregulated genes in the lung cancer sample from the patient as characterized in step (a) that are target genes for each drug of the plurality of drugs as provided in step (b) and determining the score for each drug of the plurality of drugs based on the percentage of deregulated genes among the target genes in the lung cancer sample from the patient, wherein a higher score is predictive of a higher relative efficacy of the drug for treating the lung cancer in the patient and wherein the step of characterizing molecular anomalies of the lung cancer sample comprises determining a fold change for the differentially expressed genes and optionally for the gain or loss of gene copy number; and d) selecting a drug with a high score for treating the patient, and wherein the method further comprises in step a) the detection of the presence of a mutation in a gene in the lung cancer sample in comparison to the normal sample by sequencing and wherein the score (W) for a given drug is determined by one of the following algorithms:

$$W = P\left(\frac{(\Sigma_{CM} F_{CM})}{n_1 CM} q_1 z_1 - \frac{(\Sigma_{CR} F_{CR})}{n_3 CR} q_3 z_3\right)$$

or $$W = \frac{P_{CM}(\Sigma_{CM} F_{CM})}{n_1 CM} q_1 z_1 - \frac{P_{CR}(\Sigma_{CR} F_{CR})}{n_3 CR} q_3 z_3$$

or $$W = P\left(\frac{(\Sigma_{CM} F_{CM} \times Int_{CM})}{n_1 CM} q_1 z_1 - \frac{(\Sigma_{CR} F_{CR} \times Int_{CR})}{n_3 CR} q_3 z_3\right)$$

or $$W = \frac{P_{CM}(\Sigma_{CM} F_{CM} \times Int_{CM})}{n_1 CM} q_1 z_1 - \frac{P_{CR}(\Sigma_{CR} F_{CR} \times Int_{CR})}{n_3 CR} q_3 z_3$$

wherein

W is the score for the given drug;

P is the percentage of target genes for the given drug which are deregulated in the lung cancer of the patient;

$\Sigma$ is sum;

CM refers to major target genes for the given drug;

CR refers to resistance genes for the given drug;

$n_1 CM$ and $n_3 CR$ are respectively the number of deregulated target genes with a defined threshold for major target genes and resistance genes;

$F_{CM}$ and $F_{CR}$ are the Fold Change of each gene higher than the defined threshold for major target genes and resistance genes, respectively;

$q_1$ and $q_3$ are multiplication coefficients for major target genes and resistance genes, respectively;

$z_1$ and $z_3$ are multiplication coefficients associated with the presence of a mutation in a major target gene and a resistance gene, respectively;

$P_{CM}$ and $P_{CR}$ are the percentage of genes for the given drug which are deregulated in the lung cancer of the patient for major target genes and resistance genes, respectively; and $Int_{CM}$ and $Int_{CR}$ are the intensity for major target genes and resistance genes, respectively.

27. The method according to claim 26, wherein $F_{CM}$ and $F_{CR}$ are the Fold Change of each over-expressed target gene for the given drug with the defined threshold and wherein $n_1 CM$ and $n_3 CR$ are either the number of target genes for the given drug with the defined threshold or the number of over-expressed target genes for the given drug with the defined threshold.

28. The method according to claim 27, wherein the defined threshold is a Fold Change of at least 2.

29. The method according to claim 26, wherein $z_1$, $z_3$, $q_1$ and $q_3$ are equal to 1.

30. The method according to claim 26, wherein the multiplication coefficients for the target genes are between 10 and 1,000 for major target genes ($q_1$) and between 10 to 1,000 for resistance genes ($q_3$).

31. The method according to claim 26, wherein the multiplication coefficients associated with a mutation $z_1$ and $z_3$ are 1 when no mutation exists and, depending on the functional impact of the mutation, are between 10 and 1,000.

32. A method for treating a patient having lung cancer the method comprising:

a) characterizing molecular anomalies of a lung cancer sample from the patient in comparison to a normal sample from the same patient which is a normal histological counterpart of the lung cancer sample, said molecular anomalies characterization comprising determining genes differentially expressed in the lung cancer sample in comparison to the normal sample by oligonucleotide array, and optionally determining the gain or loss of gene copy number in the lung cancer sample in comparison to the normal sample by Comparative Genomic Hybridization in the lung cancer sample in comparison to the normal sample by sequencing and determining deregulated genes in the lung cancer sample based on the genes differentially expressed and optionally the gain or loss of gene copy number;

b) providing a drug database comprising target genes associated with a plurality of drugs disclosed in Table 1;

c) determining a score for each drug of said plurality of drugs comprising calculating, for each drug of the plurality of drugs, a percentage of deregulated genes in the lung cancer sample from the patient as characterized in step (a) that are target genes for each drug of the plurality of drugs as provided in step (b) and determining the score for each drug of the plurality of drugs based on the percentage of deregulated genes among the target genes in the lung cancer sample from the patient, wherein a higher score is predictive of a higher relative efficacy of the drug for treating lung cancer in the patient;

d) selecting a drug with a high score for treating the patient; and e) administering the drug with the high score to the patient and treating the patient's lung cancer, wherein the score (W) for a given drug is determined by the following algorithm:

$$W = P z \frac{(\Sigma_C F_{c>2})}{n_C F_{c>2}}$$

wherein:

W is the score for the given drug;

P is the percentage of target genes for the given drug which are deregulated in the lung cancer of the patient;

$\Sigma$ is sum;

$F_{c>2}$ is the Fold Change of each deregulated target gene for the given drug with a Fold Change higher than 2; and $n_C F_{c>2}$ refers to the number of target genes for the given drug with a Fold Change higher than 2.

* * * * *